US007943137B2

(12) United States Patent
Hinuma et al.

(10) Patent No.: US 7,943,137 B2
(45) Date of Patent: May 17, 2011

(54) FPRL1 LIGANDS AND USE THEREOF

(75) Inventors: Shuji Hinuma, Tsukuba (JP); Makoto Kobayashi, Osaka (JP); Yugo Habata, Tsukuba (JP); Masataka Harada, Tsukuba (JP); Shoichi Ohkubo, Osaka (JP); Hiromi Yoshida, Tsukuba (JP); Kazunori Nishi, Tsukuba (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 273 days.

(21) Appl. No.: 10/534,082

(22) PCT Filed: Nov. 6, 2003

(86) PCT No.: PCT/JP03/14138
§ 371 (c)(1),
(2), (4) Date: Dec. 12, 2005

(87) PCT Pub. No.: WO2004/041850
PCT Pub. Date: May 21, 2004

(65) Prior Publication Data
US 2007/0065819 A1   Mar. 22, 2007

(30) Foreign Application Priority Data

Nov. 7, 2002 (JP) ................. 2002-324189
Dec. 18, 2002 (JP) ................. 2002-367119
Mar. 5, 2003 (JP) ................. 2003-059073
Jul. 3, 2003 (JP) ................. 2003-191359

(51) Int. Cl.
*A61K 39/00* (2006.01)
*A61K 39/38* (2006.01)
*G01N 33/53* (2006.01)

(52) U.S. Cl. .... 424/185.1; 424/9.1; 424/9.2; 424/130.1; 424/139.1; 424/184.1; 435/4; 435/7.1

(58) Field of Classification Search ............ 424/9.1, 424/9.2, 130.1, 139.1, 184.1, 185.1; 435/4, 435/7.1
See application file for complete search history.

(56) References Cited

FOREIGN PATENT DOCUMENTS

| WO | WO 00/31261 | | 6/2000 |
|---|---|---|---|
| WO | WO 01/57074 | | 8/2001 |
| WO | WO0166734 | * | 9/2001 |
| WO | WO 03/106683 | | 12/2003 |
| WO | WO 2004/008141 A1 | | 1/2004 |

OTHER PUBLICATIONS

McFadden, E.R., et al "Asthma", in, "Harrison's Priniciples of internal medicine", tenth edition, Petersdorf et al, eds., McGraw-Hill Book Company, New York, New York, USA, 1983, pp. 1512-1519.*
"Multiple Sclerosis", in "Cecil Textbook of medicine", fifteenth edition, Beeson et al, eds., W.B. Saunders Company, Philadelphia, PA, USA, 1979, pp. 845-848.*

Klein, C. et al, "Identification of surrogate agonists for the human FPRL-1 receptor by autocrine selection in yeast," *Nature Biotechnology*, (Dec 1998), vol. 16, No. 13, pp. 1334-1337.
Li, B-Q. et al., "The synthetic peptide WKYMVm attenuates the function of the chemokine receptor CCR5 and CXCR4 through activation of formyl peptide receptor-like 1," *Blood*, (May 2001), vol. 97, No. 10, pp. 2941-2947.
P.M. Murphy, et al., "A Structural Homologue of the N-Formyl Peptide Receptor", The Journal of Biological Chemistry, (1992), pp. 7637-7643, vol. 267, No. 11.
Y. Le, et al., "Receptors for Chemotactic Formyl Peptides as Pharmacological Targets", International Immunopharmacology, (2002), pp. 1-13, vol. 2.
Y. Le, et al., "Amyloid Beta42 Activates a G-Protein-Coupled Chemoattractant Receptor, FPR-Like-1", The Journal of Neuroscience, (2001), RC123, 1 of 5, vol. 21.
H. Yazawa, et al., "Beta Amyloid Peptide (AlphaBeta42) is Internalized via the G-Protein-Coupled Receptor FLPL1 and Forms Fibrillar Aggregates in Macrophages", The FASEB Journal, (2001), pp. 2454-2462, vol. 15.
T. Christophe, et al., "The Synthethetic Peptide Trp-Lys-Tyr-Met-NH2 Specifically Activates Neutrophils . . . ", The Journal of Biological Chemistry, (2001), pp. 21585-21593, vol. 276, No. 24.
A. Betten, et al., "A Proinflammatory Peptide fro Helicobacter Pylori Activates Monocytes to Induce Lymphocyte Dysfunction and Apoptosis", The Journal of Clinical Investigation, (2001), pp. 1221-1228, vol. 108, No. 8.
De Yang, et al., "Human Dendritic Cells Express Functional Formyl Peptide Receptor-Like-2 (FPRL2) Throughout Maturation", Journal of Leukocyte Biology, (2002), pp. 598-607, vol. 72.
M. Perretti, et al., "Endogenous Lipid-and Peptide-Derviced Anti-Inflammatory Pathways Generated with Glucocorticoid and Aspirin Treatment Activate the Lipoxin A4 Receptor", Nature Medicine, (2002), pp. 1296-1302, vol. 8, No. 11.
Y. Cui, et al., "Potential Role of the Formyl Peptide Receptor-Like 1 (FPRL 1) in Inflammatory Aspects of Alzheimer's Disease", Journal of Leukocyte Biology, (2002), pp. 628-635, vol. 72.
S.M. Shawar, et al., "Peptides From the Amino-Terminus of Mouse Mitochondrially Encoded NADH Dehydrogenase Subunit 1 are Potent Chemoattractants", Biochemical and Biophysical Research Communications, (1995), pp. 812-818, vol. 211, No. 3.
H. Carp, "Mitochondrial N-Formylmethionyl Proteins as Chemoattractants for Neutrophils", J. Exp. Med., (1982), pp. 264-275, vol. 155.
S. Anderson, et al., "Sequence and Organization of the Human Mitochondrial Genome", Nature, (1981), pp. 457-465, vol. 290.
Y. Le, et al., "Formyl-Peptide Receptors Revisited", Trends in Immunology, (2002), pp. 541-548, vol. 23, No. 11.
Michael W. Vaughn, Rita J. Proske and David L. Haviland Identification, Cloning, and Functional Characterization of a Murine Lipoxin A4 Receptor Homologue Gene; J. Immunol., 2002, 169(6), pp. 3363-3369.

(Continued)

*Primary Examiner* — Rodney P. Swartz
(74) *Attorney, Agent, or Firm* — Edwards Angell Palmer & Dodge LLP; David G. Conlin; Amy DeCloux

(57) ABSTRACT

By using FPRL1 ligand, which comprises the same or substantially the same amino acid sequence as the amino acid sequence represented by SEQ ID NO: 1, SEQ ID NO: 17 or SEQ ID NO: 21, and FPRL1, an efficient screening for FPRL1 agonist or FPRL1 antagonist can be performed.

26 Claims, 24 Drawing Sheets

OTHER PUBLICATIONS

Takano T, Fiore S, Maddox JF, Brady HR, Petasis NA, Serhan CN: Aspirin-triggered 15-epi-lipoxin A4 and LXA4 stable analogs are potent inhibitors of acute inflammation: evidence for anti-inflammatory receptors. J Exp Med 1997, 185:1693-1704.

Hay, D.W.P., Sarau, H.M. Interleukin-8 receptor antagonists in pulmonary diseases. Curr. Opin. Pharmacol.(2001) 1:242-247.

Mahler DA, Huang S, Tabrizi M, Bell GM. Efficacy and safety of a monoclonal antibody recognizing interleukin-8 in COPD: a pilot study; Chest. 2004 126(3):926-34.

* cited by examiner

US 7,943,137 B2

SEQUENCE LISTING

```
<160> NUMBER OF SEQ ID NOS: 24

<210> SEQ ID NO 1
<211> LENGTH: 13
<212> TYPE: PRT
<213> ORGANISM: Porcine

<400> SEQUENCE: 1

Met Phe Val Asn Arg Trp Leu Tyr Ser Thr Asn His Lys
1               5                   10

<210> SEQ ID NO 2
<211> LENGTH: 351
<212> TYPE: PRT
<213> ORGANISM: Homo sapiens

<400> SEQUENCE: 2

Met Glu Thr Asn Phe Ser Thr Pro Leu Asn Glu Tyr Glu Glu Val Ser
1               5                   10                  15

Tyr Glu Ser Ala Gly Tyr Thr Val Leu Arg Ile Leu Pro Leu Val Val
                20                  25                  30

Leu Gly Val Thr Phe Val Leu Gly Val Leu Gly Asn Gly Leu Val Ile
            35                  40                  45

Trp Val Ala Gly Phe Arg Met Thr Arg Thr Val Thr Thr Ile Cys Tyr
        50                  55                  60

Leu Asn Leu Ala Leu Ala Asp Phe Ser Phe Thr Ala Thr Leu Pro Phe
65                  70                  75                  80

Leu Ile Val Ser Met Ala Met Gly Glu Lys Trp Pro Phe Gly Trp Phe
                85                  90                  95

Leu Cys Lys Leu Ile His Ile Val Val Asp Ile Asn Leu Phe Gly Ser
            100                 105                 110

Val Phe Leu Ile Gly Phe Ile Ala Leu Asp Arg Cys Ile Cys Val Leu
```

```
                115                 120                 125
    His Pro Val Trp Ala Gln Asn His Arg Thr Val Ser Leu Ala Met Lys
        130                 135                 140

Val Ile Val Gly Pro Trp Ile Leu Ala Leu Val Leu Thr Leu Pro Val
    145                 150                 155                 160

Phe Leu Phe Leu Thr Thr Val Thr Ile Pro Asn Gly Asp Thr Tyr Cys
                    165                 170                 175

Thr Phe Asn Phe Ala Ser Trp Gly Gly Thr Pro Glu Glu Arg Leu Lys
                180                 185                 190

Val Ala Ile Thr Met Leu Thr Ala Arg Gly Ile Ile Arg Phe Val Ile
                195                 200                 205

Gly Phe Ser Leu Pro Met Ser Ile Val Ala Ile Cys Tyr Gly Leu Ile
            210                 215                 220

Ala Ala Lys Ile His Lys Lys Gly Met Ile Lys Ser Ser Arg Pro Leu
    225                 230                 235                 240

Arg Val Leu Thr Ala Val Val Ala Ser Phe Phe Ile Cys Trp Phe Pro
                    245                 250                 255

Phe Gln Leu Val Ala Leu Leu Gly Thr Val Trp Leu Lys Glu Met Leu
                260                 265                 270

Phe Tyr Gly Lys Tyr Lys Ile Ile Asp Ile Leu Val Asn Pro Thr Ser
                275                 280                 285

Ser Leu Ala Phe Phe Asn Ser Cys Leu Asn Pro Met Leu Tyr Val Phe
            290                 295                 300

Val Gly Gln Asp Phe Arg Glu Arg Leu Ile His Ser Leu Pro Thr Ser
    305                 310                 315                 320

Leu Glu Arg Ala Leu Ser Glu Asp Ser Ala Pro Thr Asn Asp Thr Ala
                    325                 330                 335

Ala Asn Ser Ala Ser Pro Pro Ala Glu Thr Glu Leu Gln Ala Met
                340                 345                 350

<210> SEQ ID NO 3
<211> LENGTH: 1053
<212> TYPE: DNA
<213> ORGANISM: Homo sapiens
<220> FEATURE:
<221> NAME/KEY: CDS
<222> LOCATION: (1)..(1053)

<400> SEQUENCE: 3 atg gaa acc aac ttc tcc act cct ctg aat gaa tat gaa gaa gtg tcc      48
Met Glu Thr Asn Phe Ser Thr Pro Leu Asn Glu Tyr Glu Glu Val Ser
1               5                   10                  15 tat gag tct gct ggc tac act gtt ctg cgg atc ctc cca ttg gtg gtg      96
Tyr Glu Ser Ala Gly Tyr Thr Val Leu Arg Ile Leu Pro Leu Val Val
            20                  25                  30 ctt ggg gtc acc ttt gtc ctc ggg gtc ctg ggc aat ggg ctt gtg atc     144
Leu Gly Val Thr Phe Val Leu Gly Val Leu Gly Asn Gly Leu Val Ile
        35                  40                  45 tgg gtg gct gga ttc cgg atg aca cgc aca gtc acc acc atc tgt tac     192
Trp Val Ala Gly Phe Arg Met Thr Arg Thr Val Thr Thr Ile Cys Tyr
    50                  55                  60 ctg aac ctg gcc ctg gct gac ttt tct ttc acg gcc aca tta cca ttc     240
Leu Asn Leu Ala Leu Ala Asp Phe Ser Phe Thr Ala Thr Leu Pro Phe
65                  70                  75                  80 ctc att gtc tcc atg gcc atg gga gaa aaa tgg cct ttt ggc tgg ttc     288
Leu Ile Val Ser Met Ala Met Gly Glu Lys Trp Pro Phe Gly Trp Phe
                85                  90                  95 ctg tgt aag tta att cac atc gtg gtg gac atc aac ctc ttt gga agt     336
```

-continued

| | | | | | | | | | | | | | | | | |
|---|---|---|---|---|---|---|---|---|---|---|---|---|---|---|---|---|
| Leu | Cys | Lys | Leu | Ile | His | Ile | Val | Val | Asp | Ile | Asn | Leu | Phe | Gly | Ser | |
| | | | 100 | | | | | 105 | | | | 110 | | | | |

| gtc | ttc | ttg | att | ggt | ttc | att | gca | ctg | gac | cgc | tgc | att | tgt | gtc | ctg | 384 |
|---|---|---|---|---|---|---|---|---|---|---|---|---|---|---|---|---|
| Val | Phe | Leu | Ile | Gly | Phe | Ile | Ala | Leu | Asp | Arg | Cys | Ile | Cys | Val | Leu | |
| | | | 115 | | | | | 120 | | | | 125 | | | | |

| cat | cca | gtc | tgg | gcc | cag | aac | cac | cgc | act | gtg | agt | ctg | gcc | atg | aag | 432 |
|---|---|---|---|---|---|---|---|---|---|---|---|---|---|---|---|---|
| His | Pro | Val | Trp | Ala | Gln | Asn | His | Arg | Thr | Val | Ser | Leu | Ala | Met | Lys | |
| | | | 130 | | | | | 135 | | | | 140 | | | | |

| gtg | atc | gtc | gga | cct | tgg | att | ctt | gct | cta | gtc | ctt | acc | ttg | cca | gtt | 480 |
|---|---|---|---|---|---|---|---|---|---|---|---|---|---|---|---|---|
| Val | Ile | Val | Gly | Pro | Trp | Ile | Leu | Ala | Leu | Val | Leu | Thr | Leu | Pro | Val | |
| 145 | | | | | 150 | | | | | 155 | | | | | 160 | |

| ttc | ctc | ttt | ttg | act | aca | gta | act | att | cca | aat | ggg | gac | aca | tac | tgt | 528 |
|---|---|---|---|---|---|---|---|---|---|---|---|---|---|---|---|---|
| Phe | Leu | Phe | Leu | Thr | Thr | Val | Thr | Ile | Pro | Asn | Gly | Asp | Thr | Tyr | Cys | |
| | | | | 165 | | | | | 170 | | | | | 175 | | |

| act | ttc | aac | ttt | gca | tcc | tgg | ggt | gga | acc | cct | gag | gag | agg | ctg | aag | 576 |
|---|---|---|---|---|---|---|---|---|---|---|---|---|---|---|---|---|
| Thr | Phe | Asn | Phe | Ala | Ser | Trp | Gly | Gly | Thr | Pro | Glu | Glu | Arg | Leu | Lys | |
| | | | 180 | | | | | 185 | | | | 190 | | | | |

| gtg | gcc | att | acc | atg | ctg | aca | gcc | aga | ggg | att | atc | cgg | ttt | gtc | att | 624 |
|---|---|---|---|---|---|---|---|---|---|---|---|---|---|---|---|---|
| Val | Ala | Ile | Thr | Met | Leu | Thr | Ala | Arg | Gly | Ile | Ile | Arg | Phe | Val | Ile | |
| | | | 195 | | | | | 200 | | | | 205 | | | | |

| ggc | ttt | agc | ttg | ccg | atg | tcc | att | gtt | gcc | atc | tgc | tat | ggg | ctc | att | 672 |
|---|---|---|---|---|---|---|---|---|---|---|---|---|---|---|---|---|
| Gly | Phe | Ser | Leu | Pro | Met | Ser | Ile | Val | Ala | Ile | Cys | Tyr | Gly | Leu | Ile | |
| | | 210 | | | | | 215 | | | | | 220 | | | | |

| gca | gcc | aag | atc | cac | aaa | aag | ggc | atg | att | aaa | tcc | agc | cgt | ccc | tta | 720 |
|---|---|---|---|---|---|---|---|---|---|---|---|---|---|---|---|---|
| Ala | Ala | Lys | Ile | His | Lys | Lys | Gly | Met | Ile | Lys | Ser | Ser | Arg | Pro | Leu | |
| 225 | | | | | 230 | | | | | 235 | | | | | 240 | |

| cgg | gtc | ctc | act | gct | gtg | gtg | gct | tct | ttc | ttc | atc | tgt | tgg | ttt | ccc | 768 |
|---|---|---|---|---|---|---|---|---|---|---|---|---|---|---|---|---|
| Arg | Val | Leu | Thr | Ala | Val | Val | Ala | Ser | Phe | Phe | Ile | Cys | Trp | Phe | Pro | |
| | | | | 245 | | | | | 250 | | | | | 255 | | |

| ttt | caa | ctg | gtt | gcc | ctt | ctg | ggc | acc | gtc | tgg | ctc | aaa | gag | atg | ttg | 816 |
|---|---|---|---|---|---|---|---|---|---|---|---|---|---|---|---|---|
| Phe | Gln | Leu | Val | Ala | Leu | Leu | Gly | Thr | Val | Trp | Leu | Lys | Glu | Met | Leu | |
| | | | 260 | | | | | 265 | | | | 270 | | | | |

| ttc | tat | ggc | aag | tac | aaa | atc | att | gac | atc | ctg | gtt | aac | cca | acg | agc | 864 |
|---|---|---|---|---|---|---|---|---|---|---|---|---|---|---|---|---|
| Phe | Tyr | Gly | Lys | Tyr | Lys | Ile | Ile | Asp | Ile | Leu | Val | Asn | Pro | Thr | Ser | |
| | | | 275 | | | | | 280 | | | | 285 | | | | |

| tcc | ctg | gcc | ttc | ttc | aac | agc | tgc | ctc | aac | ccc | atg | ctt | tac | gtc | ttt | 912 |
|---|---|---|---|---|---|---|---|---|---|---|---|---|---|---|---|---|
| Ser | Leu | Ala | Phe | Phe | Asn | Ser | Cys | Leu | Asn | Pro | Met | Leu | Tyr | Val | Phe | |
| | | 290 | | | | | 295 | | | | | 300 | | | | |

| gtg | ggc | caa | gac | ttc | cga | gag | aga | ctg | atc | cac | tcc | ctg | ccc | acc | agt | 960 |
|---|---|---|---|---|---|---|---|---|---|---|---|---|---|---|---|---|
| Val | Gly | Gln | Asp | Phe | Arg | Glu | Arg | Leu | Ile | His | Ser | Leu | Pro | Thr | Ser | |
| 305 | | | | | 310 | | | | | 315 | | | | | 320 | |

| ctg | gag | agg | gcc | ctg | tct | gag | gac | tca | gcc | cca | act | aat | gac | acg | gct | 1008 |
|---|---|---|---|---|---|---|---|---|---|---|---|---|---|---|---|---|
| Leu | Glu | Arg | Ala | Leu | Ser | Glu | Asp | Ser | Ala | Pro | Thr | Asn | Asp | Thr | Ala | |
| | | | | 325 | | | | | 330 | | | | | 335 | | |

| gcc | aat | tct | gct | tca | cct | cct | gca | gag | act | gag | tta | cag | gca | atg | | 1053 |
|---|---|---|---|---|---|---|---|---|---|---|---|---|---|---|---|---|
| Ala | Asn | Ser | Ala | Ser | Pro | Pro | Ala | Glu | Thr | Glu | Leu | Gln | Ala | Met | | |
| | | | 340 | | | | | 345 | | | | 350 | | | | |

<210> SEQ ID NO 4
<211> LENGTH: 351
<212> TYPE: PRT
<213> ORGANISM: Rat

<400> SEQUENCE: 4

| | | | | | | | | | | | | | | | |
|---|---|---|---|---|---|---|---|---|---|---|---|---|---|---|---|
| Met | Glu | Ala | Asn | Tyr | Ser | Ile | Pro | Leu | Asn | Val | Ser | Glu | Val | Val | Val |
| | | | | 5 | | | | | 10 | | | | | 15 | |

| | | | | | | | | | | | | | | | |
|---|---|---|---|---|---|---|---|---|---|---|---|---|---|---|---|
| Tyr | Asp | Ser | Thr | Ile | Ser | Arg | Val | Leu | Trp | Ile | Leu | Thr | Met | Val | Val |
| | | | 20 | | | | | 25 | | | | | 30 | | |

| | | | | | | | | | | | | | | | |
|---|---|---|---|---|---|---|---|---|---|---|---|---|---|---|---|
| Leu | Ser | Ile | Thr | Phe | Val | Leu | Gly | Val | Leu | Gly | Asn | Gly | Leu | Val | Ile |
| | | | 35 | | | | | 40 | | | | | 45 | | |

```
Trp Val Ala Gly Phe Arg Met Val His Thr Val Thr Thr Cys Phe
 50                  55                  60
Leu Asn Leu Ala Leu Ala Asp Phe Ser Phe Thr Val Thr Leu Pro Phe
 65                  70                  75                  80
Phe Val Ile Ser Ile Ala Met Lys Glu Lys Trp Pro Phe Gly Trp Phe
                 85                  90                  95
Leu Cys Lys Leu Val His Ile Val Asp Ile Asn Leu Phe Gly Ser
            100                 105                 110
Val Phe Leu Ile Ala Leu Ile Ala Leu Asp Arg Cys Ile Cys Val Leu
        115                 120                 125
His Pro Val Trp Ala Gln Asn His Arg Thr Val Ser Leu Ala Arg Lys
    130                 135                 140
Val Val Val Gly Pro Trp Ile Leu Ala Leu Ile Leu Thr Leu Pro Ile
145                 150                 155                 160
Phe Ile Phe Met Thr Thr Val Arg Ile Pro Gly Gly Asn Val Tyr Cys
                165                 170                 175
Thr Phe Asn Phe Ala Ser Trp Gly Asn Thr Ala Glu Glu Leu Leu Asn
            180                 185                 190
Ile Ala Asn Thr Phe Val Thr Val Arg Gly Ser Ile Arg Phe Ile Ile
        195                 200                 205
Gly Phe Ile Met Pro Met Ser Ile Val Ala Ile Cys Tyr Gly Leu Ile
    210                 215                 220
Ala Val Lys Ile His Arg Arg Ala Leu Val Asn Ser Ser Arg Pro Leu
225                 230                 235                 240
Arg Val Leu Thr Ala Val Val Ala Ser Phe Phe Ile Cys Trp Phe Pro
                245                 250                 255
Phe Gln Leu Val Ala Leu Leu Gly Thr Ile Trp Phe Lys Glu Ser Leu
            260                 265                 270
Phe Ser Gly Arg Tyr Lys Ile Leu Asp Met Trp Val His Pro Thr Ser
        275                 280                 285
Ser Leu Ala Tyr Phe Asn Ser Cys Leu Asn Pro Met Leu Tyr Ala Phe
    290                 295                 300
Met Gly Gln Asp Phe His Glu Arg Leu Ile His Ser Leu Pro Ser Ser
305                 310                 315                 320
Leu Glu Arg Ala Leu Ser Glu Asp Ser Gly Gln Thr Ser Asp Thr Gly
                325                 330                 335
Ile Ser Ser Ala Leu Pro Pro Val Asn Ile Asp Ile Lys Ala Ile
            340                 345                 350

<210> SEQ ID NO 5
<211> LENGTH: 1053
<212> TYPE: DNA
<213> ORGANISM: Rat

<400> SEQUENCE: 5
atggaagcca actattccat ccctctgaat gtatcagaag tggttgtcta tgattctacc      60
atctccagag ttttgtggat cctcacaatg gtggttctct ccatcacctt tgtcctgggt     120
gtgctgggta tggactagt gatctgggta gctggattcc ggatggtaca cactgtcacc     180
actacctgtt ttctgaatct agctttggct gacttctctt tcacagtgac tctaccattc     240
tttgtcatct caattgctat gaagaaaaaa tggccttttg gatggttcct gtgtaaatta     300
gttcacattg tagtagacat aaacctcttt ggaagtgtct tcctgattgc tttaattgcc     360
ttggaccgct gcatttgtgt cctgcatcca gtctgggctc agaaccaccg cactgtgagc     420
ctggctagga aggtggttgt tgggccctgg attttagctc tgattctcac tttgcccatt     480
```

```
tttattttca tgactacagt tagaattcct ggaggcaatg tgtactgtac attcaacttc    540
gcatcctggg gtaacactgc tgaagaacta ttgaacatag ctaacacttt tgtaacagtt    600
agagggagca tcaggttcat tattggcttc ataatgccta tgtccattgt tgccatctgc    660
tatggactca tcgctgtcaa gatccacaga agagcacttg ttaattccag ccgtccatta    720
agagtcctta cagcagttgt ggcttccttc tttatctgtt ggtttccctt tcaactggtg    780
gcccttttag gtacaatctg gtttaaagag tcattgttta gtggtcgtta caaaattctt    840
gacatgtggg ttcacccaac cagctcattg gcctacttca atagttgcct caatccaatg    900
ctctatgctt tcatgggcca ggactttcat gaaagactga ttcattccct gccttccagt    960
ctggagagag ccctgagtga ggactctggc caaaccagtg atacaggcat cagttctgct   1020
ttacctcctg taaacattga tataaaagca ata                                1053
```

<210> SEQ ID NO 6
<211> LENGTH: 351
<212> TYPE: PRT
<213> ORGANISM: Mouse

<400> SEQUENCE: 6

```
Met Glu Ser Asn Tyr Ser Ile His Leu Asn Gly Ser Glu Val Val
                 5                  10                  15

Tyr Asp Ser Thr Ile Ser Arg Val Leu Trp Ile Leu Ser Met Val Val
                20                  25                  30

Val Ser Ile Thr Phe Phe Leu Gly Val Leu Gly Asn Gly Leu Val Ile
            35                  40                  45

Trp Val Ala Gly Phe Arg Met Pro His Thr Val Thr Thr Ile Trp Tyr
    50                  55                  60

Leu Asn Leu Ala Leu Ala Asp Phe Ser Phe Thr Ala Thr Leu Pro Phe
65                  70                  75                  80

Leu Leu Val Glu Met Ala Met Lys Glu Lys Trp Pro Phe Gly Trp Phe
                85                  90                  95

Leu Cys Lys Leu Val His Ile Val Val Asp Val Asn Leu Phe Gly Ser
            100                 105                 110

Val Phe Leu Ile Ala Leu Ile Ala Leu Asp Arg Cys Ile Cys Val Leu
        115                 120                 125

His Pro Val Trp Ala Gln Asn His Arg Thr Val Ser Leu Ala Arg Lys
    130                 135                 140

Val Val Val Gly Pro Trp Ile Phe Ala Leu Ile Leu Thr Leu Pro Ile
145                 150                 155                 160

Phe Ile Phe Leu Thr Thr Val Arg Ile Pro Gly Gly Asp Val Tyr Cys
                165                 170                 175

Thr Phe Asn Phe Gly Ser Trp Ala Gln Thr Asp Glu Glu Lys Leu Asn
            180                 185                 190

Thr Ala Ile Thr Phe Val Thr Arg Gly Ile Ile Arg Phe Leu Ile
        195                 200                 205

Gly Phe Ser Met Pro Met Ser Ile Val Ala Val Cys Tyr Gly Leu Ile
    210                 215                 220

Ala Val Lys Ile Asn Arg Arg Asn Leu Val Asn Ser Ser Arg Pro Leu
225                 230                 235                 240

Arg Val Leu Thr Ala Val Val Ala Ser Phe Phe Ile Cys Trp Phe Pro
                245                 250                 255

Phe Gln Leu Val Ala Leu Leu Gly Thr Val Trp Phe Lys Glu Thr Leu
            260                 265                 270
```

-continued

| | | | | | | | | | | | | | | |
|---|---|---|---|---|---|---|---|---|---|---|---|---|---|---|
|Leu|Ser|Gly|Ser|Tyr|Lys|Ile|Leu|Asp|Met|Phe|Val|Asn|Pro|Thr|Ser|
| |275| | | |280| | | |285| | | | | |

Ser Leu Ala Tyr Phe Asn Ser Cys Leu Asn Pro Met Leu Tyr Val Phe
    290                       295                   300

Met Gly Gln Asp Phe Arg Glu Arg Phe Ile His Ser Leu Pro Tyr Ser
305                    310                     315                   320

Leu Glu Arg Ala Leu Ser Glu Asp Ser Gly Gln Thr Ser Asp Ser Ser
           325                     330                   335

Thr Ser Ser Thr Ser Pro Pro Ala Asp Ile Glu Leu Lys Ala Pro
          340                     345                   350

<210> SEQ ID NO 7
<211> LENGTH: 1053
<212> TYPE: DNA
<213> ORGANISM: Mouse

<400> SEQUENCE: 7

| | | | | | |
|---|---|---|---|---|---|
|atggaatcca|actactccat|ccatctgaat|ggatcagaag|tggtggttta|tgattctacc|60|
|atctccagag|ttctgtggat|cctctcaatg|gtggttgtct|ccatcacttt|cttccttggt|120|
|gtgctgggca|atggactagt|gatttgggta|gctggattcc|ggatgccaca|cactgtcacc|180|
|actatctggt|atctgaatct|agcattggct|gacttttctt|tcacagcaac|tctaccattc|240|
|cttcttgttg|aaatggctat|gaaagaaaaa|tggccttttg|ctggttcct|gtgtaaatta|300|
|gttcacattg|tggtagatgt|aaacctgttt|ggaagtgtct|tcttgattgc|tctcattgcc|360|
|ttggaccgct|gcatttgtgt|tctgcatcca|gtctgggctc|agaaccaccg|cactgtgagc|420|
|ctggctagga|aggtggttgt|tgggccctgg|atttttgctc|tgattctcac|tttgcccatt|480|
|tttatttct|tgactactgt|tagaattcct|ggaggagatg|tgtattgtac|attcaacttt|540|
|ggatcctggg|ctcaaactga|tgaagaaaag|ttgaacacag|ctatcacttt|tgtaacaact|600|
|agagggatca|tcaggttcct|tattggtttc|agcatgccca|tgtcaattgt|tgctgtttgc|660|
|tatggactca|ttgctgtcaa|gatcaacaga|agaaaccttg|ttaattccag|ccgtccttta|720|
|cgagtcctta|cagcagttgt|ggcttccttc|tttatctgct|ggtttccctt|tcagcttgtg|780|
|gccctttggg|gcacagtctg|gtttaaagag|acattgctta|gtggtagtta|taaaattctt|840|
|gacatgtttg|ttaacccaac|aagctcattg|gcttacttca|atagttgtct|caatccgatg|900|
|ctctatgttt|tcatgggcca|ggactttcgt|gagagattta|ttcattccct|gccttatagt|960|
|cttgagagag|ccctgagtga|ggattctggt|caaaccagtg|attcaagcac|cagttctact|1020|
|tcacctcctg|cagacattga|gttaaaggcc|cca| | |1053|

<210> SEQ ID NO 8
<211> LENGTH: 42
<212> TYPE: DNA
<213> ORGANISM: Artificial Sequence
<220> FEATURE:
<223> OTHER INFORMATION: Primer

<400> SEQUENCE: 8
aaacagtcga ccaccatgga atccaactac tccatccatc tg                       42

<210> SEQ ID NO 9
<211> LENGTH: 33
<212> TYPE: DNA
<213> ORGANISM: Artificial Sequence
<220> FEATURE:
<223> OTHER INFORMATION: Primer

<400> SEQUENCE: 9

```
ctttctagat catgggcct ttaactcaat gtc                          33
```

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10

```
atctgggtag ctggattccg gatg                                   24
```

<210> SEQ ID NO 11
<211> LENGTH: 27
<212> TYPE: DNA
<213> ORGANISM: Artificial Sequence
<220> FEATURE:
<223> OTHER INFORMATION: Primer

<400> SEQUENCE: 11

```
tctttcatga aagtcctggc ccatgaa                                27
```

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12

```
aggaattcta actgtagtca tgaa                                   24
```

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13

```
acagttagag ggagcatcag gttc                                   24
```

<210> SEQ ID NO 14
<211> LENGTH: 43
<212> TYPE: DNA
<213> ORGANISM: Artificial Sequence
<220> FEATURE:
<223> OTHER INFORMATION: Primer

<400> SEQUENCE: 14

```
ataaagtcga ccaccatgga agccaactat tccatccctc tga              43
```

<210> SEQ ID NO 15
<211> LENGTH: 37
<212> TYPE: DNA
<213> ORGANISM: Artificial Sequence
<220> FEATURE:
<223> OTHER INFORMATION: Primer

<400> SEQUENCE: 15

```
aaatctagat catattgctt ttatatcaat gtttaca                     37
```

<210> SEQ ID NO 16
<211> LENGTH: 13
<212> TYPE: PRT
<213> ORGANISM: Human

```
<400> SEQUENCE: 16

Met Phe Ala Asp Arg Trp Leu Phe Ser Thr Asn His Lys
 1               5                  10

<210> SEQ ID NO 17
<211> LENGTH: 15
<212> TYPE: PRT
<213> ORGANISM: Porcine

<400> SEQUENCE: 17

Met Thr Asn Ile Arg Lys Ser His Pro Leu Met Lys Ile Ile Asn
 1               5                  10                  15

<210> SEQ ID NO 18
<211> LENGTH: 16
<212> TYPE: PRT
<213> ORGANISM: Porcine

<400> SEQUENCE: 18

Met Thr Asn Ile Arg Lys Ser His Pro Leu Met Lys Ile Ile Asn Asn
 1               5                  10                  15

<210> SEQ ID NO 19
<211> LENGTH: 15
<212> TYPE: PRT
<213> ORGANISM: Human

<400> SEQUENCE: 19

Met Thr Pro Met Arg Lys Ile Asn Pro Leu Met Lys Leu Ile Asn
 1               5                  10                  15

<210> SEQ ID NO 20
<211> LENGTH: 16
<212> TYPE: PRT
<213> ORGANISM: Human

<400> SEQUENCE: 20

Met Thr Pro Met Arg Lys Ile Asn Pro Leu Met Lys Leu Ile Asn His
 1               5                  10                  15

<210> SEQ ID NO 21
<211> LENGTH: 15
<212> TYPE: PRT
<213> ORGANISM: Porcine

<400> SEQUENCE: 21

Met Phe Val Asn Arg Trp Leu Tyr Ser Thr Asn His Lys Asp Ile
 1               5                  10                  15

<210> SEQ ID NO 22
<211> LENGTH: 15
<212> TYPE: PRT
<213> ORGANISM: Human

<400> SEQUENCE: 22

Met Phe Ala Asp Arg Trp Leu Phe Ser Thr Asn His Lys Asp Ile
 1               5                  10                  15

<210> SEQ ID NO 23
<211> LENGTH: 18
<212> TYPE: PRT
<213> ORGANISM: Porcine

<400> SEQUENCE: 23
```

```
Met Thr Asn Ile Arg Lys Ser His Pro Leu Met Lys Ile Ile Asn Asn Ala Phe
1               5                   10                  15
```

<210> SEQ ID NO 24
<211> LENGTH: 18
<212> TYPE: PRT
<213> ORGANISM: Human

<400> SEQUENCE: 24

```
Met Thr Pro Met Arg Lys Ile Asn Pro Leu Met Lys Leu Ile Asn His Ser Phe
1               5                   10                  15
```

FPRL1 LIGANDS AND USE THEREOF

This application is a 371 National Stage Entry of PCT/JP03/14138 filed Nov. 6, 2003, which claims the benefit of JAPAN 2003-191359 filed Jul. 3, 2003, JAPAN 2003-59073 filed Mar. 5, 2003, JAPAN 2002-367119 filed Dec. 18, 2002 and JAPAN 2002-324189, filed Nov. 7, 2002.

TECHNICAL FIELD

The present invention relates to a novel intrinsic ligand for FPRL1, the G protein-coupled receptor protein, and use thereof.

BACKGROUND ART

Physiologically active substances such as various hormones and neurotransmitters regulate the biological function via specific receptor proteins present on cell membranes. Many of these receptor proteins are coupled with guanine nucleotide-binding protein (hereinafter sometimes simply referred to as G protein) and mediate the intracellular signal transduction via activation of G protein. These receptor proteins possess the common structure containing seven transmembrane domains and are thus collectively referred to as G protein-coupled receptors or seven-transmembrane receptors (7TMR).

G protein-coupled receptor proteins present on the cell surface of each functional cell and organ in the body, and play important physiological roles as the target of the molecules that regulate the functions of the cells and organs, e.g., hormones, neurotransmitters, physiologically active substances and the like. Receptor proteins transmit signals to cells via binding with physiologically active substances, and the signals induce various reactions such as activation and inhibition of the cells.

To clarify the relationship between substances that regulate complex functions in various cells and organs, and their specific receptor proteins, in particular, G protein-coupled receptor proteins, would elucidate the functional mechanisms in various cells and organs in the body to provide a very important means for development of drugs closely associated with the functions.

For example, in various organs, their physiological functions are controlled in vivo through regulation by many hormones, hormone-like substances, neurotransmitters or physiologically active substances. In particular, physiologically active substances are found in numerous sites of the body and regulate the physiological functions through their corresponding receptor proteins. It is supposed that many unknown hormones, neurotransmitters or many other physiologically active substances still exist in the body, and many of structures of the receptor proteins have not yet been reported. In addition, it is still unknown if there are subtypes of known receptor proteins.

It is very important for development of drugs to clarify the relationship between substances that regulate elaborated functions in vivo and their specific receptor proteins. For efficient screening of agonists and antagonists to receptor proteins in development of drugs, it is required to clarify functional mechanisms of receptor protein genes expressed in vivo and express the genes in an appropriate expression system.

In recent years, random analysis of cDNA sequences has been actively studied as a means for analyzing genes expressed in vivo. The sequences of cDNA fragments thus obtained have been registered on and published to databases as Expressed Sequence Tag (EST). However, since many ESTs contain sequence information only, it is difficult to predict their functions from the information.

As one of G protein-coupled receptor proteins, FPRL1s such as human FPRL1 (J. Biol. Chem. 267(11), 7637-7643 (1992)) and mouse FPRL2 (J. Immunol. 169, 3363-3369 (2002)) are known.

Agonists of FPRL1 which have been reported include bacterium-derived FMLF, a partial peptide of HIV-derived gp41 or gp120, a partial peptide of prion, intrinsic substances such as Aβ42, a partial peptide of Annexin I and partial peptides of acute phase protein, hCAP18 and NADH dehydrogenase, and lipoxin A4 as lipid (Int. Immunopharmacol. 2, 1-13, 2002).

In addition, it has been reported that FPRL1 (lipoxin $A_4$ receptor protein) contributes to anti-inflammatory effects (Nature Medicine, 2002 November: 8(11): 1296-1302.) It has been reported that Aβ42 is fibrous as a consequence of binding to monocyte- or microglia-derived FPRL1 and uptake (Journal of Leukocyte Biology, Vol. 72, 628, (2002).)

It has been reported that N-terminus of mitochondrial protein is a chemotactic factor of polymorphonuclear leukocyte, and the mitochondrial protein released from injured cells causes inflammation (Biochem Biophys Res Commun. 1995 Jun 26: 211 (3): 812-818.)

Mitochondrial protein (NADH dehydrogenase), wherein N-terminus thereof is formylated, is reported to be a chemotactic factor of neutrophil (J Exp Med. 1982 Jan 1: 155 (1): 264-275.)

The present invention intends to provide a novel intrinsic ligand for FPRL1, the G protein-coupled receptor protein, a method for screening a compound or a salt thereof that alters binding property between the ligand and FPRL1 (antagonist and agonist) and the like.

DISCLOSURE OF THE INVENTION

As a result of extensive investigations, the present inventors have succeeded at isolation and purification of a novel intrinsic ligand, which can bind to FPRL1, from stomach extracts of swine. In addition, they have succeeded at cloning of the DNA encoding rat-derived novel FPRL1. Based on these findings, the present inventors have continued further extensive studies and as a result, have come to accomplish the present invention.

That is, the present invention provides:

[1] A peptide consisting of the same or substantially the same amino acid sequence as the amino acid sequence represented by SEQ ID NO: 1 or SEQ ID NO: 21, its amide or ester, or salts thereof, wherein a methionine residue at the N-terminus is optionally formylated;

[2] The peptide consisting of the same or substantially the same amino acid sequence as the amino acid sequence represented by SEQ ID NO: 1 according to [1], its amide or ester, or salts thereof, wherein a methionine residue at the N-terminus is optionally formylated;

[3] The peptide consisting of the same or substantially the same amino acid sequence as the amino acid sequence represented by SEQ ID NO: 1 or SEQ ID NO: 16 according to [1], its amide or ester, or salts thereof, wherein a methionine residue at the N-terminus is formylated;

[4] The peptide consisting of the same or substantially the same amino acid sequence as the amino acid sequence represented by SEQ ID NO: 21 or SEQ ID NO: 22 according to [1], its amide or ester, or salts thereof, wherein a methionine residue at the N-terminus is formylated;

[5] The peptide consisting of the same or substantially the same amino acid sequence as the amino acid sequence represented by SEQ ID NO: 21 or SEQ ID NO: 22 according to [1], its amide or ester, or salts thereof, wherein a methionine residue at the N-terminus is formylated and an isoleucine residue at the C-terminus is modified;

[6] A peptide consisting of the same or substantially the same amino acid sequence as the amino acid sequence represented by SEQ ID NO: 17 or SEQ ID NO: 23, its amide or ester, or salts thereof, wherein a methionine residue at the N-terminus is optionally formylated;

[7] The peptide consisting of the same or substantially the same amino acid sequence as the amino acid sequence represented by SEQ ID NO: 17 according to [6], its amide or ester, or salts thereof, wherein a methionine residue at the N-terminus is optionally formylated;

[8] The peptide consisting of the same or substantially the same amino acid sequence as the amino acid sequence represented by SEQ ID NO: 17, SEQ ID NO: 18, SEQ ID NO: 19 or SEQ ID NO: 20 according to [6], its amide or ester, or salts thereof, wherein a methionine residue at the N-terminus is formylated;

[9] The peptide consisting of the same or substantially the same amino acid sequence as the amino acid sequence represented by SEQ ID NO: 23 or SEQ ID NO: 24 according to [6], its amide or ester, or salts thereof, wherein a methionine residue at the N-terminus is formylated;

[10] A medicament comprising the peptide, its amide or ester, or salts thereof, according to [1];

[11] A medicament comprising the peptide, its amide or ester, or salts thereof, according to [6].

[12] The medicament according to [10] or [11], which is a cell migration irritant;

[13] The medicament according to [10] or [11], which is an anti-inflammatory agent;

[14] The medicament according to [10] or [11], which is a prophylactic/therapeutic agent for asthma, allergosis, inflammation, inflammatory eye diseases, Assison's disease, autoimmune hemolytic anemia, systemic lupus erythematosus, psoriasis, rheumatism, brain hemorrhage, brain infarction, head injury, cord injury, brain edema, multiple sclerosis, Alzheimer's disease, Parkinson's disease, amyotrophic lateral sclerosis (ALS), encephalopathy associated with AIDS, cerebral meningitis, diabetes mellitis, arthritis rheumatoides, osteoarthritis, rheumatoid spondylitis, gouty arthritis, synovial inflammation, blood poisoning, Crohn's disease, ulcerative colitis, chronic pneumonia, pulmonary silicosis, pulmonary sarcoidosis, lung tuberculosis, cachexia, arterial sclerosis, Creutzfeldt-Jakob disease, viral infection, angina cordis, cardiac infarction, congestive failure, hepatitis, exaggerated immune response after medical transplantation, dialysis hypotension, diffuse intravascular coagulation syndrome, or immunodeficiency;

[15] An antibody against the peptide, its amide or ester, or salts thereof, according to [1];

[16] An antibody against the peptide, its amide or ester, or salts thereof, according to [6];

[17] A diagnostic agent comprising the antibody according to [15];

[18] A diagnostic agent comprising the antibody according to [16];

[19] The diagnostic agent according to [17] or [18], which is a diagnostic agent for asthma, allergosis, inflammation, inflammatory eye diseases, Assison's disease, autoimmune hemolytic anemia, systemic lupus erythematosus, psoriasis, rheumatism, brain hemorrhage, brain infarction, head injury, cord injury, brain edema, multiple sclerosis, Alzheimer's disease, Parkinson's disease, amyotrophic lateral sclerosis (ALS), encephalopathy associated with AIDS, cerebral meningitis, diabetes mellitis, arthritis rheumatoides, osteoarthritis, rheumatoid spondylitis, gouty arthritis, synovial inflammation, blood poisoning, Crohn's disease, ulcerative colitis, chronic pneumonia, pulmonary silicosis, pulmonary sarcoidosis, lung tuberculosis, cachexia, arterial sclerosis, Creutzfeldt-Jakob disease, viral infection, angina cordis, cardiac infarction, congestive failure, hepatitis, exaggerated immune response after medical transplantation, dialysis hypotension, diffuse intravascular coagulation syndrome, or immunodeficiency;

[20] A medicament comprising the antibody according to [15];

[21] A medicament comprising the antibody according to [16];

[22] The medicament according to [20] or [21], which is a cell migration depressant;

[23] The medicament according to [20] or [21], which is a prophylactic/therapeutic agent for infectious disease;

[24] A method for screening a compound or a salt thereof that alters a binding property or a signal transduction between a G protein-coupled receptor protein or salts thereof, and the peptide according to [1], its amide or ester, or salts thereof, which comprises using (1) the receptor protein comprising the same or substantially the same amino acid sequence as the amino acid sequence represented by SEQ ID NO: 2, a partial peptide of the receptor protein or salts thereof, and (2) (i) the peptide according to [1], its amide or ester, or salts thereof, or (ii) the compound or a salt thereof that alters a binding property between the receptor protein or a salt thereof, and the peptide according to [1], its amide or ester, or salts thereof;

[25] A method for screening a compound or a salt thereof that alters a binding property or a signal transduction between a G protein-coupled receptor protein or salts thereof, and the peptide according to [6], its amide or ester, or salts thereof, which comprises using (1) the receptor protein comprising the same or substantially the same amino acid sequence as the amino acid sequence represented by SEQ ID NO: 2, a partial peptide of the receptor protein or salts thereof, and (2) (i) the peptide according to [6], its amide or ester, or salts thereof, or (ii) the compound or a salt thereof that alters a binding property between the receptor protein or a salt thereof, and the peptide according to [6], its amide or ester, or salts thereof,

[26] The screening method according to [24] or [25], wherein the G protein-coupled receptor protein comprising the same or substantially the same amino acid sequence as the amino acid sequence represented by SEQ ID NO: 2 is a G protein-coupled receptor protein consisting of the amino acid sequence represented by SEQ ID NO: 2, SEQ ID NO: 4 or SEQ ID NO: 6;

[27] A kit for screening a compound or a salt thereof that alters a binding property or a signal transduction between a G protein-coupled receptor protein or salts thereof, and the peptide according to [1], its amide or ester, or salts thereof, which comprises using (1) the receptor protein comprising the same or substantially the same amino acid sequence as the amino acid sequence represented by SEQ ID NO: 2, a partial peptide of the receptor protein or salts thereof, and (2) (i) the peptide according to [1], its amide or ester, or salts thereof, or (ii) the compound or a salt thereof that alters a binding property between the receptor protein or a salt thereof, and the peptide according to [1], its amide or ester, or salts thereof;

[28] A kit for screening a compound or a salt thereof that alters a binding property or a signal transduction between a G protein-coupled receptor protein or salts thereof, and the peptide according to [6], its amide or ester, or salts thereof, which comprises using (1) the receptor protein comprising the same or substantially the same amino acid sequence as the amino acid sequence represented by SEQ ID NO: 2, a partial peptide of the receptor protein or salts thereof, and (2) (i) the peptide according to [6], its amide or ester, or salts thereof, or (ii) the compound or a salt thereof that alters a binding property between the receptor protein or a salt thereof, and the peptide according to [6], its amide or ester, or salts thereof;

[29] A compound or a salt thereof that alters binding property or signal transduction between the peptide, its amide or ester, or salts thereof according to [1] or [6], which is obtained by using the screening method according to [24] or [25], or the screening kit according to [27] or [28], and a G protein-coupled receptor protein comprising the same or substantially the same amino acid sequence as the amino acid sequence represented by SEQ ID NO: 2, or a salt thereof;

[30] The compound according to [29], which is an agonist;

[31] The compound according to [29], which is an antagonist;

[32] A medicament comprising a compound or a salt thereof that alters binding property or signal transduction between the peptide, its amide or ester, or salts thereof according to [1], and a G protein-coupled receptor protein comprising the same or substantially the same amino acid sequence as the amino acid sequence represented by SEQ ID NO: 2, or a salt thereof;

[33] A medicament comprising a compound or a salt thereof that alters binding property or signal transduction between the peptide, its amide or ester, or salts thereof according to [6], and a G protein-coupled receptor protein comprising the same or substantially the same amino acid sequence as the amino acid sequence represented by SEQ ID NO: 2, or a salt thereof,

[34] A cell migration irritant comprising the agonist according to [30];

[35] An anti-inflammatory agent comprising the agonist according to [30];

[36] A prophylactic/therapeutic agent comprising the agonist according to [30] for asthma, allergosis, inflammation, inflammatory eye diseases, Assison's disease, autoimmune hemolytic anemia, systemic lupus erythematosus, psoriasis, rheumatism, brain hemorrhage, brain infarction, head injury, cord injury, brain edema, multiple sclerosis, Alzheimer's disease, Parkinson's disease, amyotrophic lateral sclerosis (ALS), encephalopathy associated with AIDS, cerebral meningitis, diabetes mellitus, arthritis rheumatoides, osteoarthritis, rheumatoid spondylitis, gouty arthritis, synovial inflammation, blood poisoning, Crohn's disease, ulcerative colitis, chronic pneumonia, pulmonary silicosis, pulmonary sarcoidosis, lung tuberculosis, cachexia, arterial sclerosis, Creutzfeldt-Jakob disease, viral infection, angina cordis, cardiac infarction, congestive failure, hepatitis, exaggerated immune response after medical transplantation, dialysis hypotension, diffuse intravascular coagulation syndrome, or immunodeficiency;

[37] A cell migration depressant comprising the antagonist according to [31];

[38] A prophylactic/therapeutic agent for infectious disease according to [31];

[39] A G protein-coupled receptor protein, which comprises comprising the same or substantially the same amino acid sequence as the amino acid sequence represented by SEQ ID NO: 4, its partial peptide, or salts thereof;

[40] A G protein-coupled receptor protein consisting of the amino acid sequence represented by SEQ ID NO: 4, or a salt thereof;

[41] A polynucleotide comprising a polynucleotide encoding the G protein-coupled receptor protein or its partial peptide according to [39];

[42] A DNA consisting of the base sequence represented by SEQ ID NO: 5;

[43] A recombinant vector comprising the polynucleotide according to [41];

[44] A transformant, which is transformed by the recombinant vector according to [43];

[45] A method for manufacturing the G protein-coupled receptor protein or a salt thereof according to [39], which comprises culturing the transformant according to [44], and producing the G protein-coupled receptor protein according to [39];

[46] An antibody against the G protein-coupled receptor protein, its partial peptide or salts thereof according to [39];

[47] A polynucleotide comprising a base sequence or a portion thereof, which is complement to the polynucleotide according to [41];

[48] A medicament comprising the G protein-coupled receptor protein, its partial peptide or salts thereof according to [39];

[49] The medicament according to [48], which is a cell migration irritant;

[50] The medicament according to [48], which is an anti-inflammatory agent;

[51] The medicament according to [48], which is a prophylactic/therapeutic agent for asthma, allergosis, inflammation, inflammatory eye diseases, Assison's disease, autoimmune hemolytic anemia, systemic lupus erythematosus, psoriasis, rheumatism, brain hemorrhage, brain infarction, head injury, cord injury, brain edema, multiple sclerosis, Alzheimer's disease, Parkinson's disease, amyotrophic lateral sclerosis (ALS), encephalopathy associated with AIDS, cerebral meningitis, diabetes mellitus, arthritis rheumatoides, osteoarthritis, rheumatoid spondylitis, gouty arthritis, synovial inflammation, blood poisoning, Crohn's disease, ulcerative colitis, chronic pneumonia, pulmonary silicosis, pulmonary sarcoidosis, lung tuberculosis, cachexia, arterial sclerosis, Creutzfeldt-Jakob disease, viral infection, angina cordis, cardiac infarction, congestive failure, hepatitis, exaggerated immune response after medical transplantation, dialysis hypotension, diffuse intravascular coagulation syndrome, or immunodeficiency;

[52] A medicament comprising the polynucleotide according to [41];

[53] The medicament according to [52], which is a cell migration irritant;

[54] The medicament according to [52], which is an anti-inflammatory agent;

[55] The medicament according to [52], which is a prophylactic/therapeutic agent for asthma, allergosis, inflammation, inflammatory eye diseases, Assison's disease, autoimmune hemolytic anemia, systemic lupus erythematosus, psoriasis, rheumatism, brain hemorrhage, brain infarction, head injury, cord injury, brain edema, multiple sclerosis, Alzheimer's disease, Parkinson's disease, amyotrophic lateral sclerosis (ALS), encephalopathy associated with AIDS, cerebral meningitis, diabetes mellitus, arthritis rheumatoides, osteoarthritis, rheumatoid spondylitis, gouty arthritis, synovial inflammation, blood poisoning, Crohn's disease, ulcerative colitis, chronic pneumonia, pulmonary silicosis, pulmonary sarcoidosis, lung tuberculosis, cachexia, arterial sclerosis, Creutzfeldt-Jakob disease, viral infection, angina cordis, cardiac infarction, congestive failure, hepatitis, exaggerated immune response after medical transplantation, dialysis hypotension, diffuse intravascular coagulation syndrome, or immunodeficiency;

[56] A diagnostic agent comprising the polynucleotide according to [41];

[57] The diagnostic agent according to [56] for asthma, allergosis, inflammation, inflammatory eye diseases, Assison's disease, autoimmune hemolytic anemia, systemic lupus erythematosus, psoriasis, rheumatism, brain hemorrhage, brain infarction, head injury, cord injury, brain edema, multiple sclerosis, Alzheimer's disease, Parkinson's disease, amyotrophic lateral sclerosis (ALS), encephalopathy associated with AIDS, cerebral meningitis, diabetes mellitis, arthritis rheumatoides, osteoarthritis, rheumatoid spondylitis, gouty arthritis, synovial inflammation, blood poisoning, Crohn's disease, ulcerative colitis, chronic pneumonia, pulmonary silicosis, pulmonary sarcoidosis, lung tuberculosis, cachexia, arterial sclerosis, Creutzfeldt-Jakob disease, viral infection, angina cordis, cardiac infarction, congestive failure, hepatitis, exaggerated immune response after medical transplantation, dialysis hypotension, diffuse intravascular coagulation syndrome, or immunodeficiency;

[58] A diagnostic agent comprising the antibody according to [46];

[59] The diagnostic agent according to [58], which is a diagnostic agent for asthma, allergosis, inflammation, inflammatory eye diseases, Assison's disease, autoimmune hemolytic anemia, systemic lupus erythematosus, psoriasis, rheumatism, brain hemorrhage, brain infarction, head injury, cord injury, brain edema, multiple sclerosis, Alzheimer's disease, Parkinson's disease, amyotrophic lateral sclerosis (ALS), encephalopathy associated with AIDS, cerebral meningitis, diabetes mellitis, arthritis rheumatoides, osteoarthritis, rheumatoid spondylitis, gouty arthritis, synovial inflammation, blood poisoning, Crohn's disease, ulcerative colitis, chronic pneumonia, pulmonary silicosis, pulmonary sarcoidosis, lung tuberculosis, cachexia, arterial sclerosis, Creutzfeldt-Jakob disease, viral infection, angina cordis, cardiac infarction, congestive failure, hepatitis, exaggerated immune response after medical transplantation, dialysis hypotension, diffuse intravascular coagulation syndrome, immunodeficiency, or infectious diseases;

[60] A medicament comprising the antibody according to [46];

[61] The medicament according to [60], which is a cell migration depressant;

[62] The medicament according to [60], which is a prophylactic/therapeutic agent for infectious diseases;

[63] A medicament comprising the polynucleotide according to [47];

[64] The medicament according to [63], which is a cell migration depressant;

[65] The medicament according to [63], which is a prophylactic/therapeutic agent for infectious diseases;

[66] A method for screening a compound or a salt thereof that alters an expression level of the G protein-coupled receptor protein according to [39], which comprises using the polynucleotide according to [41];

[67] A kit for screening a compound or a salt thereof that alters an expression level of the G protein-coupled receptor protein according to [1], which comprises the polynucleotide according to [41];

[68] A compound or a salt thereof that alters an expression level of the G protein-coupled receptor protein according to [39], which is obtained by using the screening method according to [66] or the screening kit according to [67];

[69] A compound or a salt thereof that increases an expression level of the G protein-coupled receptor protein according to [39], which is obtained by using the screening method according to [66] or the screening kit according to [67];

[70] A compound or a salt thereof that reduces an expression level of the G protein-coupled receptor protein according to [39], which is obtained by using the screening method according to [66] or the screening kit according to [67];

[71] A medicament comprising a compound or a salt thereof that alters an expression level of the G protein-coupled receptor protein according to [39], which is obtained by using the screening method according to [66] or the screening kit according to [67];

[72] A medicament comprising a compound or a salt thereof that increases an expression level of the G protein-coupled receptor protein according to [39], which is obtained by using the screening method according to [66] or the screening kit according to [67];

[73] The medicament according to [72], which is a cell migration irritant;

[74] The medicament according to [72], which is an anti-inflammatory agent;

[75] The medicament according to [72], which is a prophylactic/therapeutic agent for asthma, allergosis, inflammation, inflammatory eye diseases, Assison's disease, autoimmune hemolytic anemia, systemic lupus erythematosus, psoriasis, rheumatism, brain hemorrhage, brain infarction, head injury, cord injury, brain edema, multiple sclerosis, Alzheimer's disease, Parkinson's disease, amyotrophic lateral sclerosis (ALS), encephalopathy associated with AIDS, cerebral meningitis, diabetes mellitis, arthritis rheumatoides, osteoarthritis, rheumatoid spondylitis, gouty arthritis, synovial inflammation, blood poisoning, Crohn's disease, ulcerative colitis, chronic pneumonia, pulmonary silicosis, pulmonary sarcoidosis, lung tuberculosis, cachexia, arterial sclerosis, Creutzfeldt-Jakob disease, viral infection, angina cordis, cardiac infarction, congestive failure, hepatitis, exaggerated immune response after medical transplantation, dialysis hypotension, diffuse intravascular coagulation syndrome, or immunodeficiency;

[76] A medicament comprising a compound or a salt thereof that reduces an expression level of the G protein-coupled receptor protein according to [39], which is obtained by using the screening method according to [66] or the screening kit according to [67];

[77] The medicament according to [76], which is a cell migration depressant;

[78] The medicament according to [76], which is a prophylactic/therapeutic agent for infectious diseases;

[79] A method for stimulating a cell migration, or a method for preventing/treating asthma, allergosis, inflammation, inflammatory eye diseases, Assison's disease, autoimmune hemolytic anemia, systemic lupus erythematosus, psoriasis, rheumatism, brain hemorrhage, brain infarction, head injury, cord injury, brain edema, multiple sclerosis, Alzheimer's disease, Parkinson's disease, amyotrophic lateral sclerosis (ALS), encephalopathy associated with AIDS, cerebral meningitis, diabetes mellitis, arthritis rheumatoides, osteoarthritis, rheumatoid spondylitis, gouty arthritis, synovial inflammation, blood poisoning, Crohn's disease, ulcerative colitis, chronic pneumonia, pulmonary silicosis, pulmonary sarcoidosis, lung tuberculosis, cachexia, arterial sclerosis, Creutzfeldt-Jakob disease, viral infection, angina cordis, cardiac infarction, congestive failure, hepatitis, exaggerated immune response after medical transplantation, dialysis hypotension, diffuse intravascular coagulation syndrome, or immunodeficiency, which comprises administrating to a mammal an effective dose of (i) the peptide, its amide or ester, or salts thereof, according to [1], (ii) the peptide, its amide or ester, or salts thereof, according to [6], (iii) the G protein-coupled receptor protein, its partial peptide, or salts thereof, according to [39], or (iv) the polynucleotide according to [41];

[80] Use of (i) the peptide, its amide or ester, or salts thereof, according to [1], (ii) the peptide, its amide or ester, or salts thereof, according to [6], (iii) the G protein-coupled receptor protein, its partial peptide, or salts thereof, according to [39], or (iv) the polynucleotide according to [41], for manufacturing a cell migration irritant or a prophylactic/therapeutic agent for asthma, allergosis, inflammation, inflammatory eye diseases, Assison's disease, autoimmune hemolytic anemia, systemic lupus erythematosus, psoriasis, rheumatism, brain hemorrhage, brain infarction, head injury, cord injury, brain edema, multiple sclerosis, Alzheimer's disease, Parkinson's disease, amyotrophic lateral sclerosis (ALS), encephalopathy associated with AIDS, cerebral meningitis, diabetes mellitis, arthritis rheumatoides, osteoarthritis, rheumatoid spondylitis, gouty arthritis, synovial inflammation, blood poisoning, Crohn's disease, ulcerative colitis, chronic pneumonia, pulmonary silicosis, pulmonary sarcoidosis, lung tuberculosis, cachexia, arterial sclerosis, Creutzfeldt-Jakob disease, viral infection, angina cordis, cardiac infarction, congestive failure, hepatitis, exaggerated immune response after medical transplantation, dialysis hypotension, diffuse intravascular coagulation syndrome, or immunodeficiency;

[81] A method for inhibiting a cell stimulation, or a method for preventing/treating infectious disease, which comprises administrating to a mammal an effective dose of (i) the antibody according to [15], (ii) the antibody according to [16], (iii) the antibody according to [46], or (iv) the polynucleotide according to [47];

[82] Use of (i) the antibody according to [15], (ii) the antibody according to [16], (iii) the antibody according to [46], or (iv) the polynucleotide according to [47], for manufacturing a cell migration depressant or a prophylactic/therapeutic agent for infectious disease.

Further, the present invention provides:

[83] A method for quantifying a mRNA encoding the G protein-coupled receptor protein according to [39], which comprises using the polynucleotide according to [41] or a portion thereof;

[84] A method for quantifying a mRNA encoding the G protein-coupled receptor protein according to [39], which comprises using the antibody according to [46];

[85] The screening method according to [24], which comprises comparing between (i) the case where FPRL1, its partial peptide, or salts thereof is contacted with (a) the peptide according to [1], its amide or ester, or salts thereof, or (b) a compound or a salt thereof that alters binding property between the receptor protein or a salt thereof and the peptide according to [1], its amide or ester, or salts thereof, and (ii) the case where FPRL1, its partial peptide, or salts thereof is contacted with (a) the peptide according to [1], its amide or ester, or salts thereof, or (b) a compound or a salt thereof that alters binding property between the receptor protein or a salt thereof and the peptide according to [1], its amide or ester, or salts thereof, and a test compound;

[86] The screening method according to [24], which comprises measuring and comparing binding amount of the labeled peptide according to [1], its amide or ester, or salts thereof to FPRL1, its partial peptide, or salts thereof, between (i) the case where (a) the labeled peptide according to [1], its amide or ester, or salts thereof, or (b) a labeled compound or a salt thereof that alters binding property between FPRL1 or a salt thereof and the peptide according to [1], its amide or ester, or salts thereof, is contacted with FPRL1, its partial peptide, or salts thereof, and (ii) the case where (a) the labeled peptide according to [1], its amide or ester, or salts thereof, or (b) a labeled compound or a salt thereof that alters binding property between FPRL1 or a salt thereof and the peptide according to [1], its amide or ester, or salts thereof, and a test compound are contacted with FPRL1, its partial peptide, or salts thereof,

[87] The screening method according to [24], which comprises measuring and comparing binding amount of the labeled peptide according to [1], its amide or ester, or salts thereof to cells comprising FPRL1, between (i) the case where (a) the labeled peptide according to [1], its amide oe ester, or salts thereof, or (b) a labeled compound or a salt thereof that alters binding property between FPRL1 or a salt thereof and the peptide according to [1], its amide or ester, or salts thereof, is contacted with the cells comprising FPRL1, and (ii) the case where (a) the labeled peptide according to [1], its amide oe ester, or salts thereof, or (b) a labeled compound or a salt thereof that alters binding property between FPRL1 or a salt thereof and the peptide according to [1], its amide or ester, or salts thereof, and a test compound are contacted with the cells comprising FPRL1;

[88] The screening method according to [24], which comprises measuring and comparing binding amount of the labeled peptide according to [1], its amide or ester, or salts thereof to cells comprising FPRL1, between (i) the case where (a) the labeled peptide according to [1], its amide or ester, or salts thereof, or (b) a labeled compound or a salt thereof that alters binding property between FPRL1 or a salt thereof and the peptide according to [1], its amide or ester, or salts thereof, is contacted with the cells comprising FPRL1, and (ii) the case where (a) the labeled peptide according to [1], its amide or ester, or salts thereof, or (b) a labeled compound or a salt thereof that alters binding property between FPRL1 or a salt thereof and the peptide according to [1], its amide or ester, or salts thereof, and a test compound are contacted with the cells comprising FPRL1;

[89] The screening method according to [24], which comprises measuring and comparing binding amount of the labeled peptide according to [1], its amide or ester, or salts thereof to FPRL1, between (i) the case where (a) the labeled peptide according to [1], its amide oe ester, or salts thereof, or (b) a labeled compound or a salt thereof that alters binding property between FPRL1 or a salt thereof and the peptide according to [1], its amide or ester, or salts thereof, is contacted with FPRL1, which is expressed on cell membrane of transformant that transformed with a recombinant vector comprising a DNA containing the DNA encoding FPRL1 by culturing the transformant, and (ii) the case where (a) the labeled peptide according to [1], its amide oe ester, or salts thereof, or (b) a labeled compound or a salt thereof that alters binding property between FPRL1 or a salt thereof and the peptide according to [1], its amide or ester, or salts thereof, and a test compound are contacted with FPRL1, which is expressed on cell membrane of the transformant by culturing the transformant;

[90] The screening method according to [24], which comprises measuring and comparing FPRL1-mediated cell stimulating activity, between (i) the case where a compound that activates FPRL1 is contacted with a cell comprising FPRL1, and (ii) the case where a compound that activates FPRL1 and a test compound are contacted with a cell comprising FPRL1;

[91] The screening method according to [24], which comprises measuring and comparing FPRL1-mediated cell stimulating activity, between the case where a compound that activates FPRL1 is contacted with FPRL1 expressed on a cell membrane of transformant that is transformed with a recombinant vector harboring a DNA comprising the DNA encoding FPRL1, and (ii) the case where a compound that activates FPRL1 and a test compound are contacted with FPRL1 expressed on a cell membrane of the transformant;

[92] The screening method according to [90] or [91], wherein a compound that activates FPRL1 is (i) the peptide according to [1], its amide or ester, or salts thereof, or (ii) a compound that alters binding property between FPRL1 or a salt thereof and the peptide according to [1], its amide or ester, or salts thereof, or a salt thereof;

[93] The screening kit according to [27], which comprises containing a cell comprising FPRL1 or a membrane fraction thereof;

[94] The screening kit according to [27], which comprises containing FPRL1 expressed on a cell membrane of transformant that is transformed with a recombinant vector harboring a DNA comprising the DNA encoding FPRL1 by culturing the transformant;

[95] The screening method according to [25], which comprises comparing between (i) the case where FPRL1, its partial peptide, or salts thereof is contacted with (a) the peptide according to [6], its amide or ester, or salts thereof, or (b) a compound or a salt thereof that alters binding property between the receptor protein or a salt thereof and the peptide according to [6], its amide or ester, or salts thereof, and (ii) the case where FPRL1, its partial peptide, or salts thereof is contacted with (a) the peptide according to [6], its amide or ester, or salts thereof, or (b) a compound or a salt thereof that alters binding property between the receptor protein or a salt thereof and the peptide according to [6], its amide or ester, or salts thereof, and a test compound;

[96] The screening method according to [25], which comprises measuring and comparing binding amount of the labeled peptide according to [6], its amide or ester, or salts thereof to FPRL1, its partial peptide, or salts thereof, between (i) the case where (a) the labeled peptide according to [6], its amide oe ester, or salts thereof, or (b) a labeled compound or a salt thereof that alters binding property between FPRL1 or a salt thereof and the peptide according to [6], its amide or ester, or salts thereof, is contacted with FPRL1, its partial peptide, or salts thereof, and (ii) the case where (a) the labeled peptide according to [6], its amide oe ester, or salts thereof, or (b) a labeled compound or a salt thereof that alters binding property between FPRL1 or a salt thereof and the peptide according to [6], its amide or ester, or salts thereof, and a test compound are contacted with FPRL1, its partial peptide, or salts thereof;

[97] The screening method according to [25], which comprises measuring and comparing binding amount of the labeled peptide according to [6], its amide or ester, or salts thereof to cells comprising FPRL1, between (i) the case where (a) the labeled peptide according to [6], its amide oe ester, or salts thereof, or (b) a labeled compound or a salt thereof that alters binding property between FPRL1 or a salt thereof and the peptide according to [6], its amide or ester, or salts thereof, is contacted with the cells comprising FPRL1, and (ii) the case where (a) the labeled peptide according to [6], its amide oe ester, or salts thereof, or (b) a labeled compound or a salt thereof that alters binding property between FPRL1 or a salt thereof and the peptide according to [6], its amide or ester, or salts thereof, and a test compound are contacted with the cells comprising FPRL1;

[98] The screening method according to [25], which comprises measuring and comparing binding amount of the labeled peptide according to [6], its amide or ester, or salts thereof to FPRL1, between (i) the case where (a) the labeled peptide according to [6], its amide or ester, or salts thereof, or (b) a labeled compound or a salt thereof that alters binding property between FPRL1 or a salt thereof and the peptide according to [6], its amide or ester, or salts thereof, is contacted with FPRL1, which is expressed on cell membrane of transformant that transformed with a recombinant vector comprising a DNA containing the DNA encoding FPRL1 by culturing the transformant, and (ii) the case where (a) the labeled peptide according to [6], its amide or ester, or salts thereof, or (b) a labeled compound or a salt thereof that alters binding property between FPRL1 or a salt thereof and the peptide according to [6], its amide or ester, or salts thereof, and a test compound are contacted with FPRL1, which is expressed on cell membrane of the transformant by culturing the transformant;

[99] The screening method according to [25], which comprises measuring and comparing binding amount of the labeled peptide according to [6], its amide or ester, or salts thereof to FPRL1, between (i) the case where (a) the labeled peptide according to [6], its amide oe ester, or salts thereof, or (b) a labeled compound or a salt thereof that alters binding property between FPRL1 or a salt thereof and the peptide according to [6], its amide or ester, or salts thereof, is contacted with FPRL1, which is expressed on cell membrane of transformant that transformed with a recombinant vector comprising a DNA containing the DNA encoding FPRL1 by culturing the transformant, and (ii) the case where (a) the labeled peptide according to [6], its amide oe ester, or salts thereof, or (b) a labeled compound or a salt thereof that alters binding property between FPRL1 or a salt thereof and the peptide according to [6], its amide or ester, or salts thereof, and a test compound are contacted with FPRL1, which is expressed on cell membrane of the transformant by culturing the transformant;

[100] The screening method according to [25], which comprises measuring and comparing FPRL1-mediated cell stimulating activity, between (i) the case where a compound that activates FPRL1 is contacted with a cell comprising FPRL1, and (ii) the case where a compound that activates FPRL1 and a test compound are contacted with a cell comprising FPRL1;

[101] The screening method according to [25], which comprises measuring and comparing FPRL1-mediated cell stimulating activity, between the case where a compound that activates FPRL1 is contacted with FPRL1 expressed on a cell membrane of transformant that is transformed with a recombinant vector harboring a DNA comprising the DNA encoding FPRL1, and (ii) the case where a compound that activates FPRL1 and a test compound are contacted with FPRL1 expressed on a cell membrane of the transformant;

[102] The screening method according to [100] or [101], wherein a compound that activates FPRL1 is a compound or a salt thereof that alters binding property between (i) the peptide according to [6], its amide or ester, or salts thereof, or (ii) FPRL1 or a salt thereof, and the peptide according to [3], its amide or ester, or salts thereof;

[103] The screening kit according to [28], which comprises containing a cell or a membrane fraction thereof comprising FPRL1;

[104] The screening kit according to [28], which comprises comprising FPRL1 expressed on cell membrane of transformant transformed with a recombinant vector harboring a DNA comprising the DNA encoding FPRL1 by culturing the transformant;

[105] A method for preventing/treating asthma, allergosis, inflammation, inflammatory eye diseases, Assison's disease, autoimmune hemolytic anemia, systemic lupus erythematosus, psoriasis, rheumatism, brain hemorrhage, brain infarction, head injury, cord injury, brain edema, multiple sclerosis, Alzheimer's disease, Parkinson's disease, amyotrophic lateral sclerosis (ALS), encephalopathy associated with AIDS, cerebral meningitis, diabetes mellitis, arthritis rheumatoides, osteoarthritis, rheumatoid spondylitis, gouty arthritis, synovial inflammation, blood poisoning, Crohn's disease, ulcerative colitis, chronic pneumonia, pulmonary silicosis, pulmonary sarcoidosis, lung tuberculosis, cachexia, arterial sclerosis, Creutzfeldt-Jakob disease, viral infection, angina cordis, cardiac infarction, congestive failure, hepatitis, exaggerated immune response after medical transplantation, dialysis hypotension, diffuse intravascular coagulation syndrome, or immunodeficiency, which comprises administering to a mammal an effective dose of (i) the agonist according to [30] or (ii) the compound according to [69] or a salt thereof;

[106] A method for stimulating a cell migration, which comprises administering to a mammal an effective dose of (i) the agonist according to [30] or (ii) the compound according to [69] or a salt thereof;

[107] Use of (i) the agonist according to [30] or (ii) the compound according to [69] or a salt thereof, for manufacturing a prophylactic/therapeutic agent for asthma, allergosis, inflammation, inflammatory eye diseases, Assison's disease, autoimmune hemolytic anemia, systemic lupus erythematosus, psoriasis, rheumatism, brain hemorrhage, brain infarction, head injury, cord injury, brain edema, multiple sclerosis, Alzheimer's disease, Parkinson's disease, amyotrophic lateral sclerosis (ALS), encephalopathy associated with AIDS, cerebral meningitis, diabetes mellitis, arthritis rheumatoides, osteoarthritis, rheumatoid spondylitis, gouty arthritis, synovial inflammation, blood poisoning, Crohn's disease, ulcerative colitis, chronic pneumonia, pulmonary silicosis, pulmonary sarcoidosis, lung tuberculosis, cachexia, arterial sclerosis, Creutzfeldt-Jakob disease, viral infection, angina cordis, cardiac infarction, congestive failure, hepatitis, exaggerated immune response after medical transplantation, dialysis hypotension, diffuse intravascular coagulation syndrome, or immunodeficiency;

[108] Use of (i) the agonist according to [30] or (ii) the compound according to [69] or a salt thereof, for manufacturing a cell migration irritant;

[109] A method for preventing/treating infectious disease, which comprises administering to a mammal an effective dose of (i) the antagonist according to [31] or (ii) the compound according to [70] or a salt thereof;

[110] A method for inhibiting a cell migration, which comprises administering to a mammal an effective dose of (i) the antagonist according to [31] or (ii) the compound according to [70] or a salt thereof;

[111] Use of (i) the antagonist according to [31] or (ii) the compound according to [70] or a salt thereof, for manufacturing a prophylactic/therapeutic agent for infectious disease; and

[112] Use of (i) the antagonist according to [31] or (ii) the compound according to [70] or a salt thereof, for manufacturing a cell migration depressant.

Analysis result by a series of ions belonging to group including the C-terminal end (y group) is denoted above the spectrum.

Figure 6:
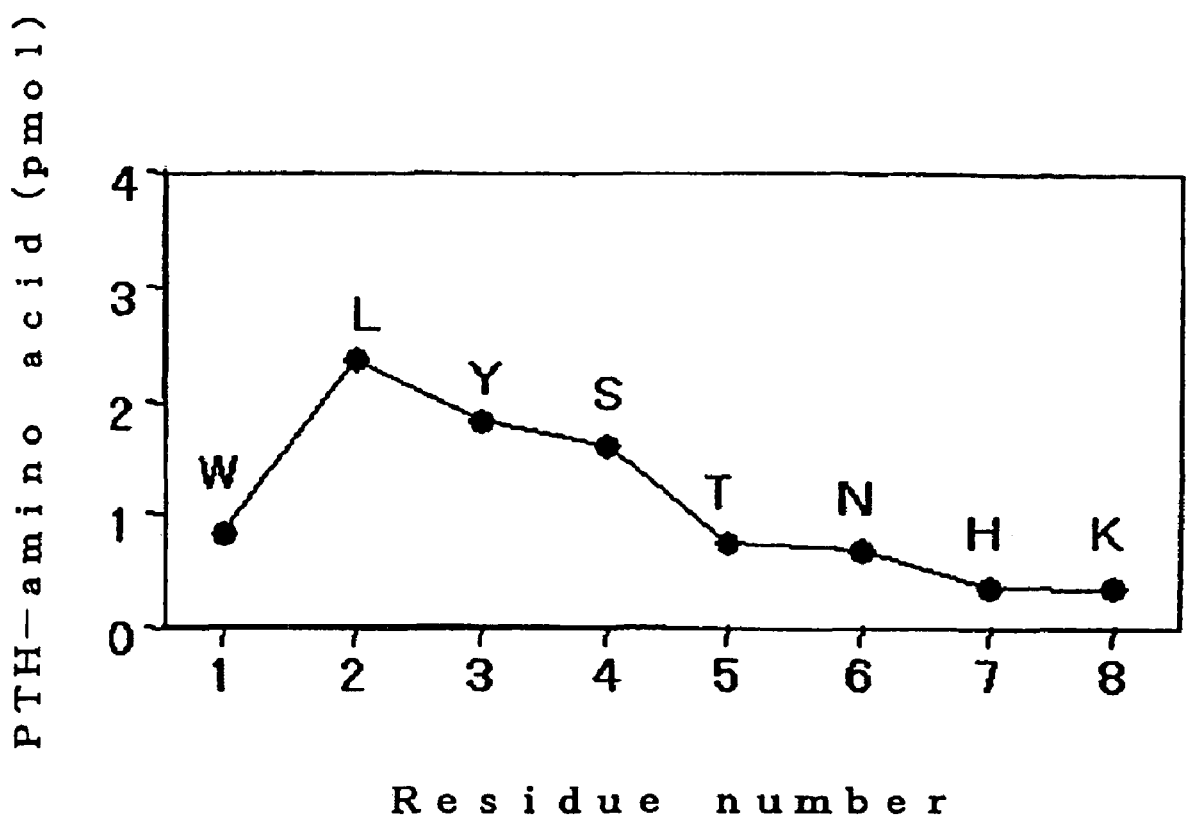

FIG. 6 shows a mass spectrum of porcine intrinsic FPRL1 ligand P3 by electrospray ionization mass spectrometer. A result, of which an internal sequence of porcine intrinsic FPRL1 ligand P3 was analyzed, is indicated. Horizontal axis (Residue number) and vertical axis represent an order of amino acid residues and a level of phenylthiohydantoin (PTH)- amino acid appeared in each cycle, respectively. Alphabets in the figure show one-letter code of amino acid.

Figure 7:
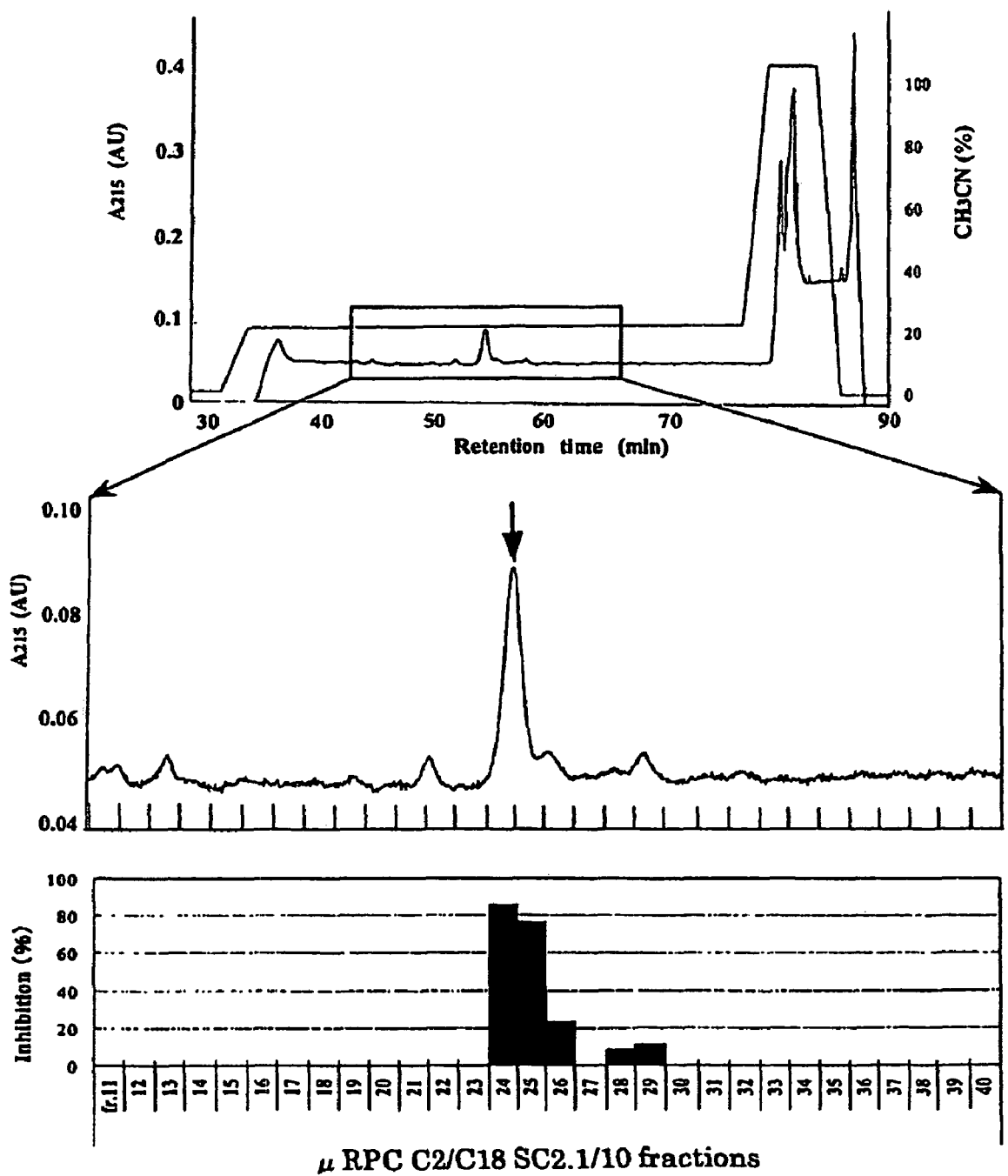

FIG. 7 shows a result for final purification step of intrinsic FPRL1 ligand from porcine stomach by reverse column μRPC C2/C18 SC2.1/10. Upper shows a pattern of chromatogram. Solid line in the figure represents absorbance at 215 nm and a concentration of acetonitrile in eluate. Elution with acetonitrile was carried out at the concentration gradient of 22% to 24%. Middle shows an enlarged view of a portion wherein the eluate having an activity was fractionated in upper column. Absorbance at 215 nm and fractions (Fr.) are represented. In addition, a peak corresponding to activity is marked. Lower shows a human FPRL1-GFP expressing CHO cells-specific inhibitory activity for intracellular cAMP production in each fraction fractionated in middle column.

Figure 8:
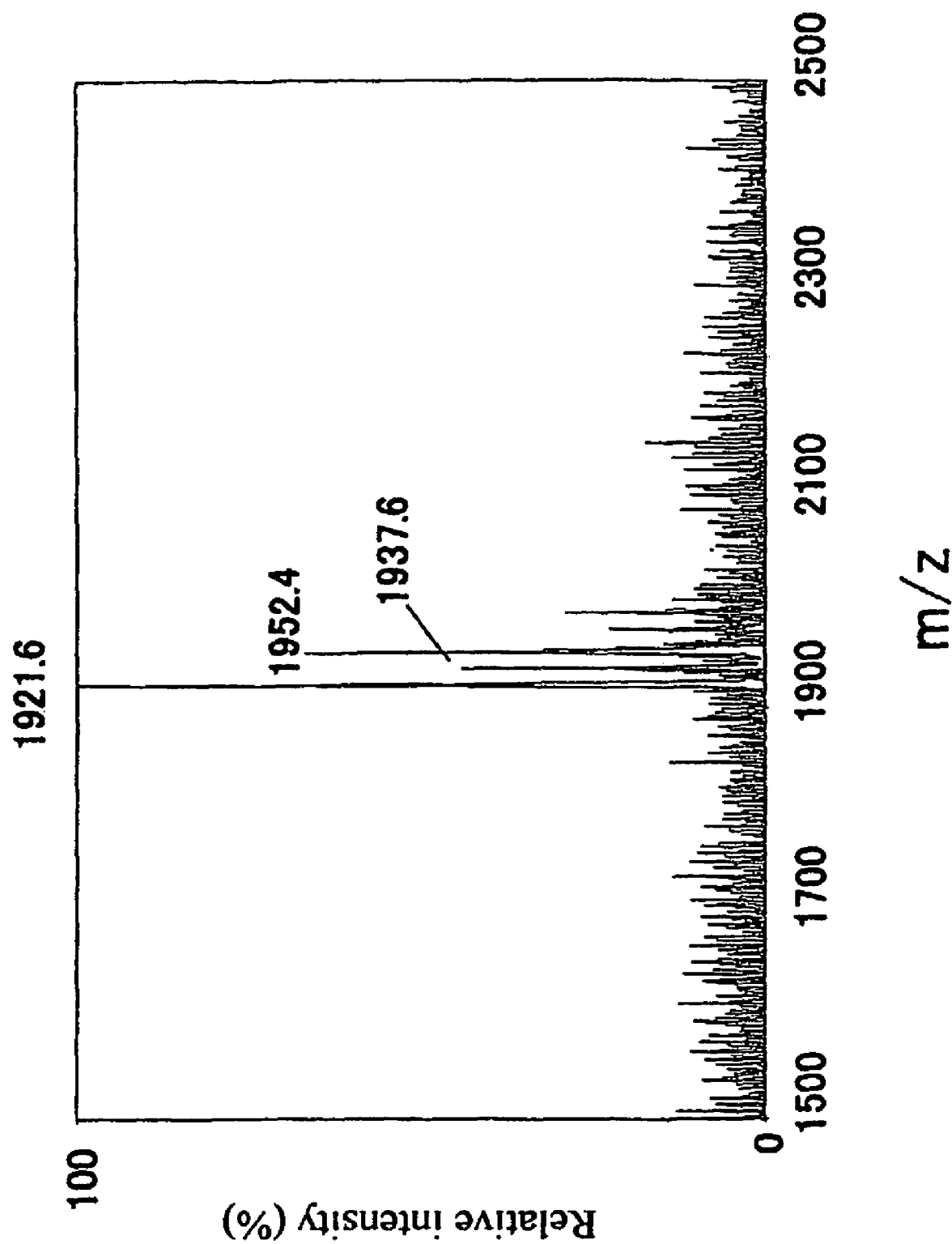

FIG. 8 shows a mass spectrum of porcine intrinsic FPRL1 ligand P1 by matrix assisted laser desorption ionization time-of-flight mass spectrometer. Horizontal axis (Mass) and vertical axis represent mass/electric charge (m/z) and relative intensity in the case where the highest signal is referred to as 100%, respectively. In the figure, numeric value labeled with signal indicates a value of m/z for molecular-associated ion (M+H$^+$) of each signal.

Figure 9:
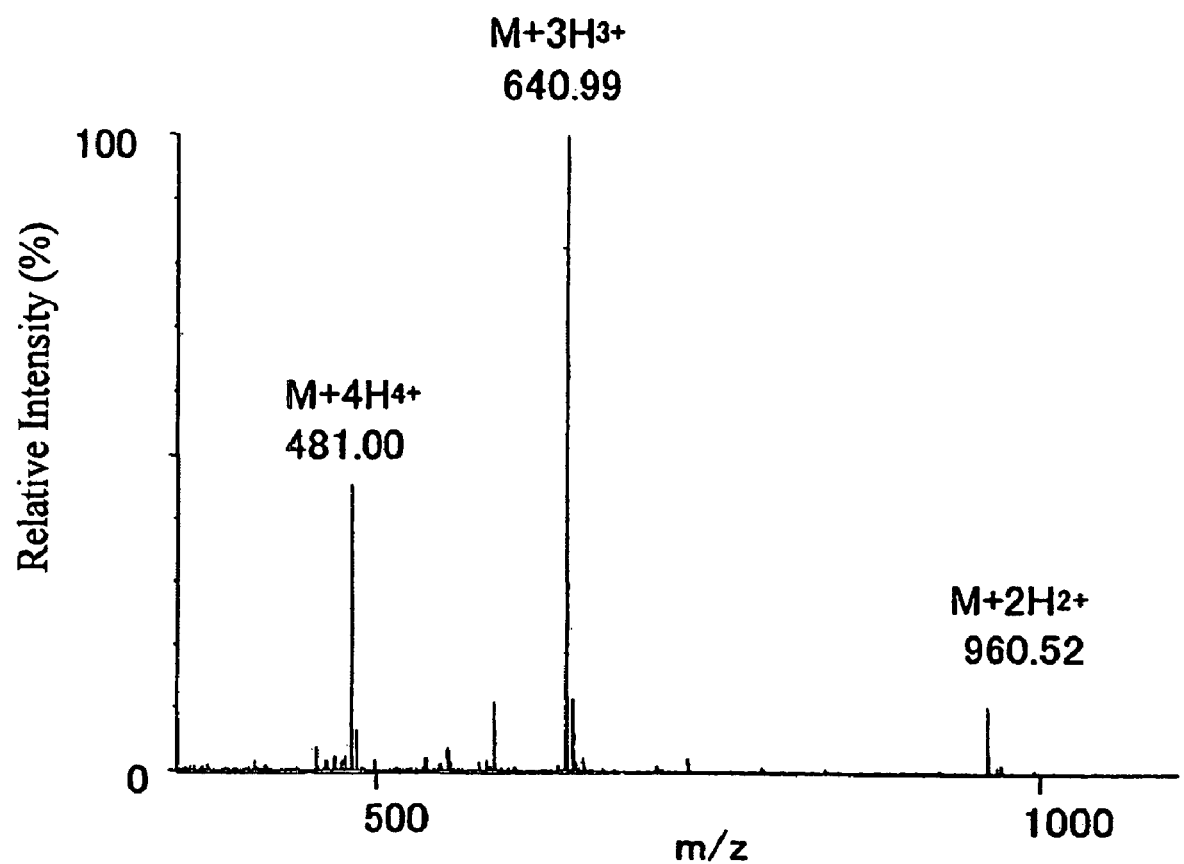

FIG. 9 shows a mass spectrum of porcine intrinsic FPRL1 ligand P1 by electrospray ionization mass spectrometer. Horizontal axis and vertical axis represent mass/electric charge (m/z) and relative intensity in the case where the highest signal is referred to as 100%, respectively. In the figure, numeric value labeled with signal indicates a value of m/z.

Figure 10:
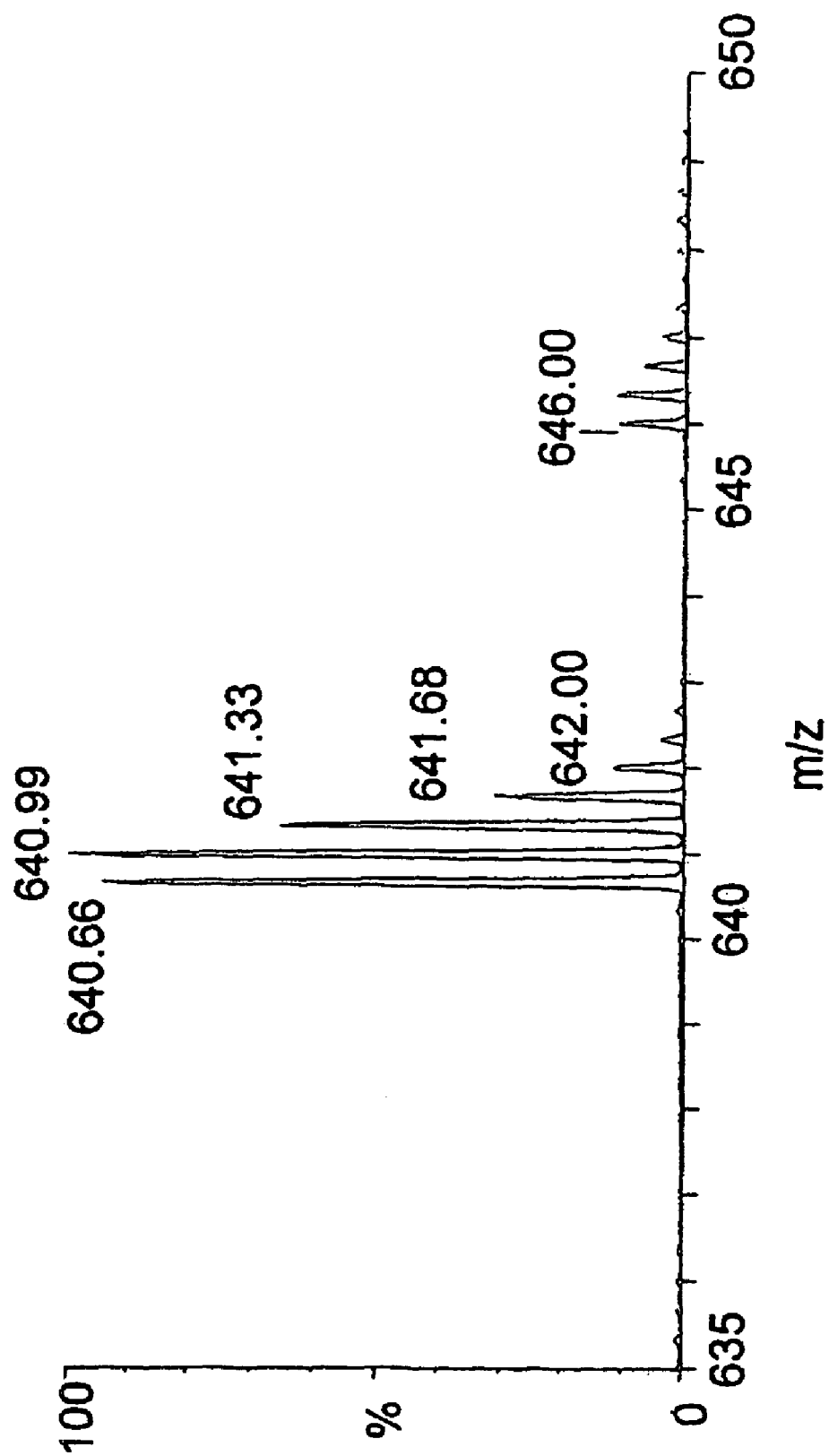

FIG. 10 shows an enlarged view of trivalent molecule-associated ion (M+3H$^{3+}$) in FIG. 9. Horizontal axis and vertical axis represent mass/electric charge (m/z) and relative intensity in the case where the highest signal is referred to as 100%, respectively. In the figure, numeric value labeled with signal indicates a value of m/z.

Figure 11:
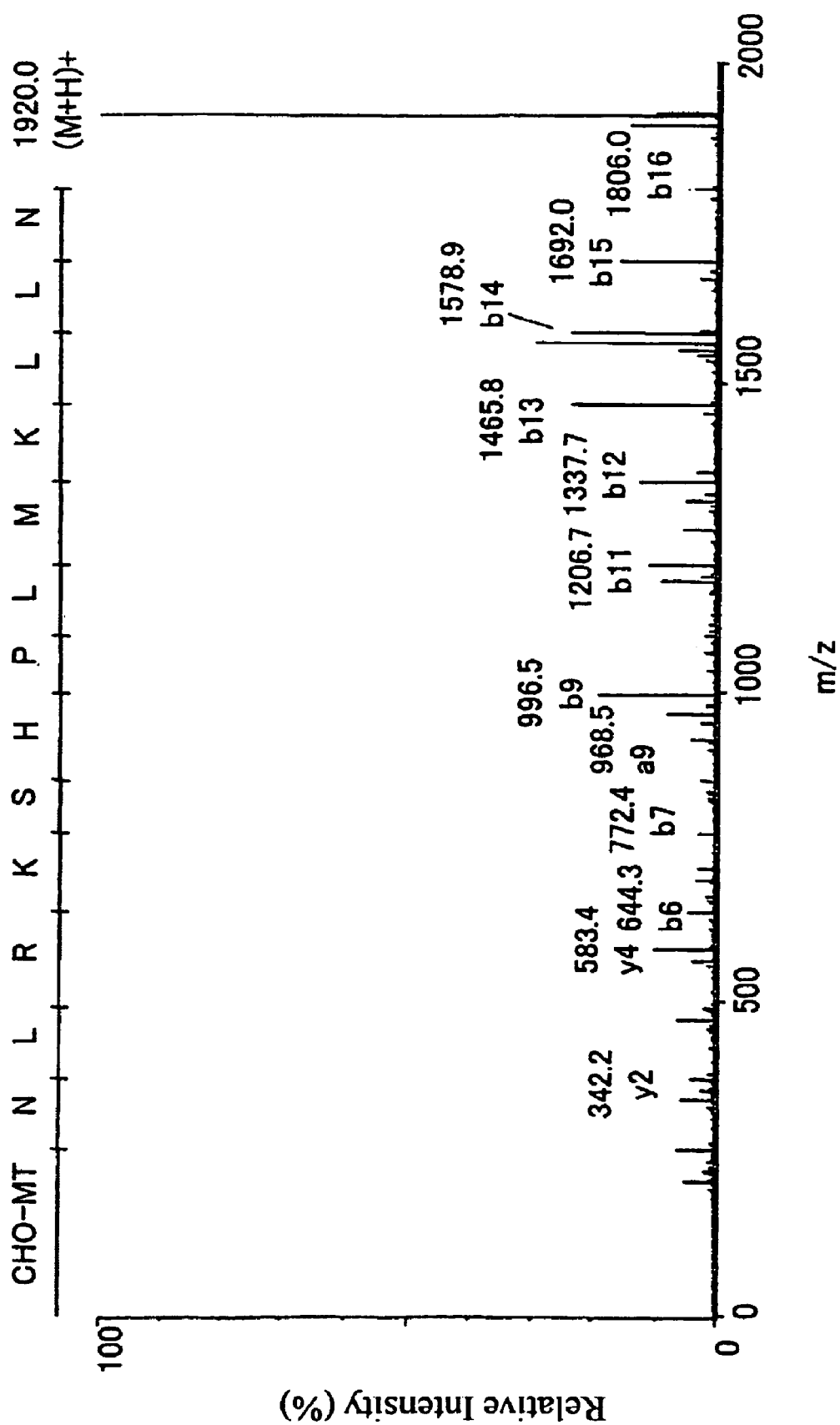

FIG. 11 shows a MS/MS spectrum of porcine intrinsic FPRL1 ligand P1 by electrospray ionization mass spectrometer. MS/MS spectrum wherein divalent ion is a parent ion is shown. Horizontal axis and vertical axis represent mass/electric charge (m/z) and relative intensity in the case where the highest signal is referred to as 100%, respectively. In the figure, numeric value labeled with signal indicates a value of m/z. Analysis result by a series of ions belonging to group including the N-terminal end (y group) is denoted above the spectrum.

Figure 12:
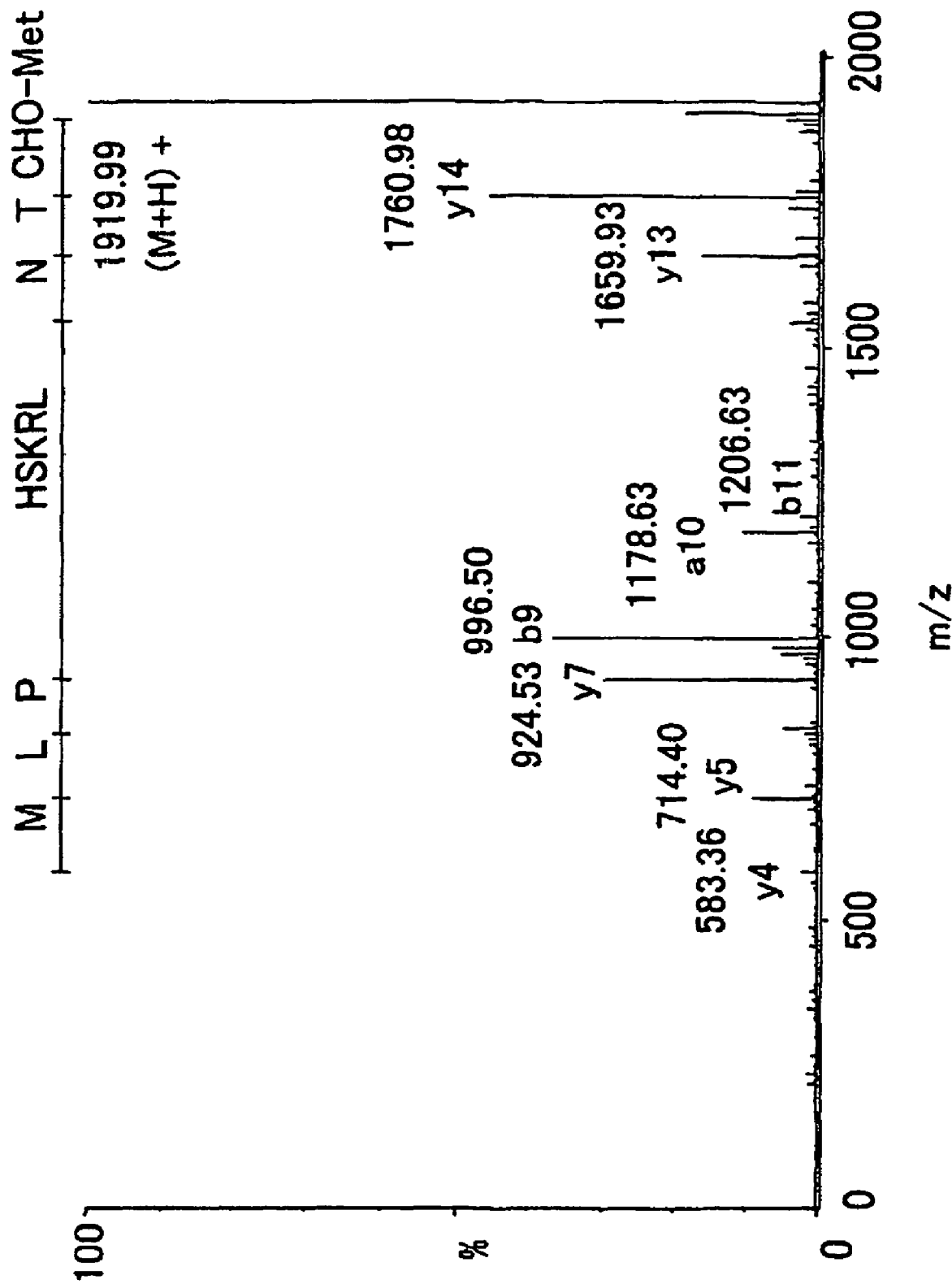

FIG. 12 shows a MS/MS spectrum in the case where tetravalent ion of porcine intrinsic FPRL1 ligand P1 is a parent ion by electrospray ionization mass spectrometer. MS/MS spectrum. Horizontal axis and vertical axis represent mass/electric charge (m/z) and relative intensity in the case where the highest signal is referred to as 100%, respectively. In the figure, numeric value labeled with signal indicates a value of m/z. Analysis result by a series of ions belonging to group including the N-terminal end (b group) is denoted above the spectrum.

Figure 13:
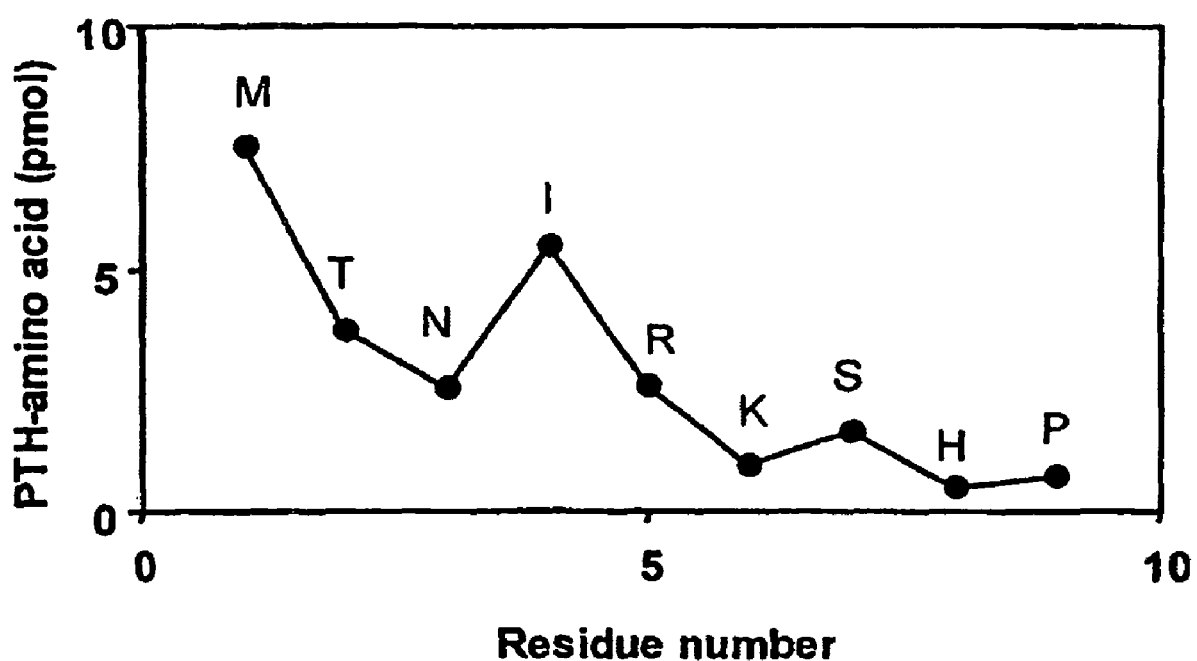

FIG. 13 shows a result, of which a sequence of porcine intrinsic FPRL1 ligand P1 was analyzed, is indicated. Horizontal axis (Residue number) and vertical axis represent an order of amino acid residues and a level of phenylthiohydantoin (PTH)- amino acid appeared in each cycle, respectively. Alphabets in the figure show one-letter code of amino acid.

Figure 14:
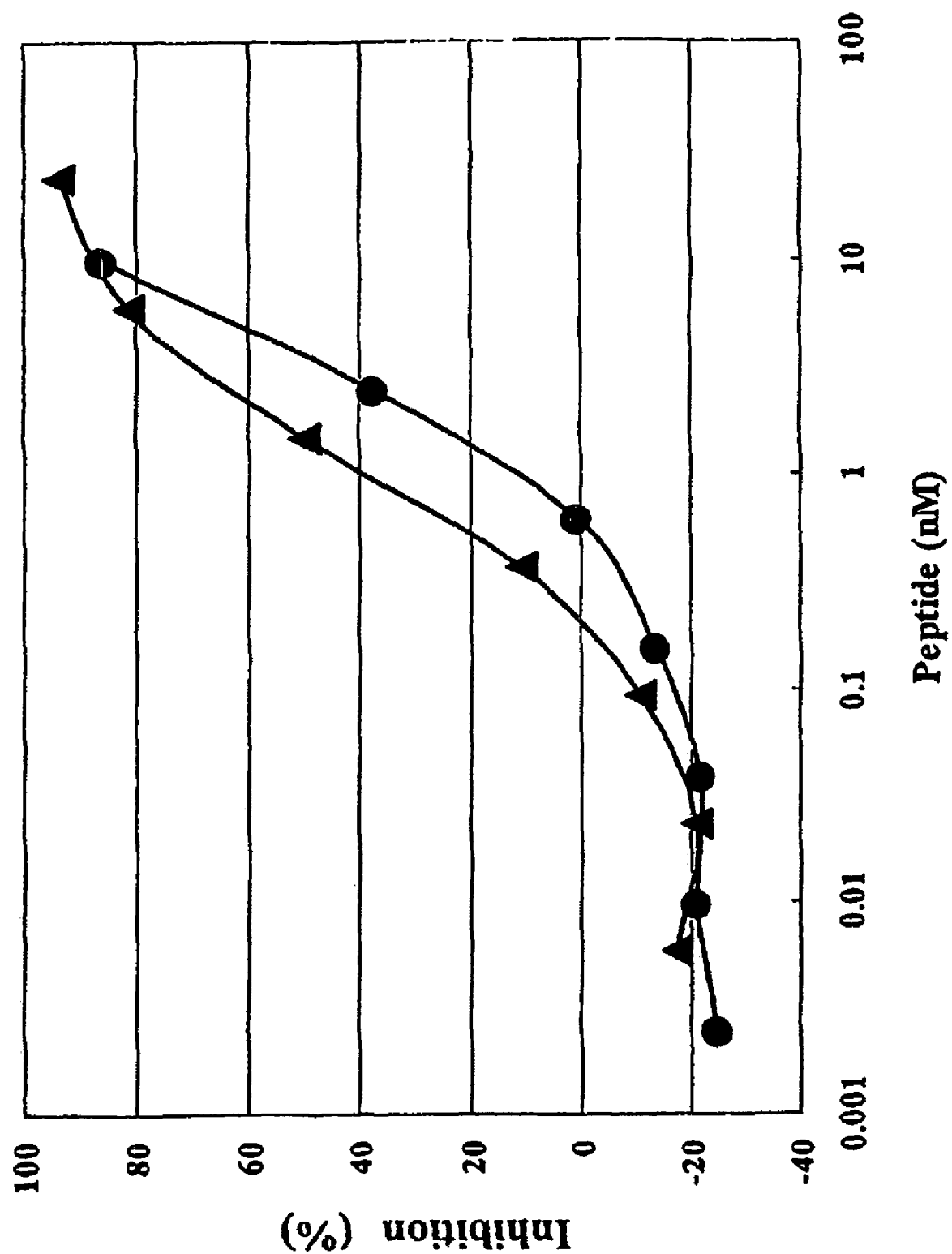

FIG. 14 shows human FPRL1-expressing CHO cell specific inhibiting activity for intracellular cAMP production. The term "Peptide (nM)" on horizontal axis and "Inhibition (5)" on vertical axis means a concentration of peptide (nM) and an inhibiting activity for intracellular cAMP production (Inhibition (%)), respectively. Closed triangle represents an activity of the intrinsic FPRL1 ligand P1, which has been purified in Example 7. It is derived from fr. 24-25 of the final purified preparation uRPC C2/C18 SC2.1/10. The concentration for peptide is deduced from the absorbance at 215 nm of final purification chromatogram. Closed circle indicates an activity of 16 amino acid peptide containing N-terminal fifteen amino acids of porcine cytochrome B, at which synthetic N-terminus is formylated (formyl-MTNIRKSHPLMKI-INN).

Figure 15:
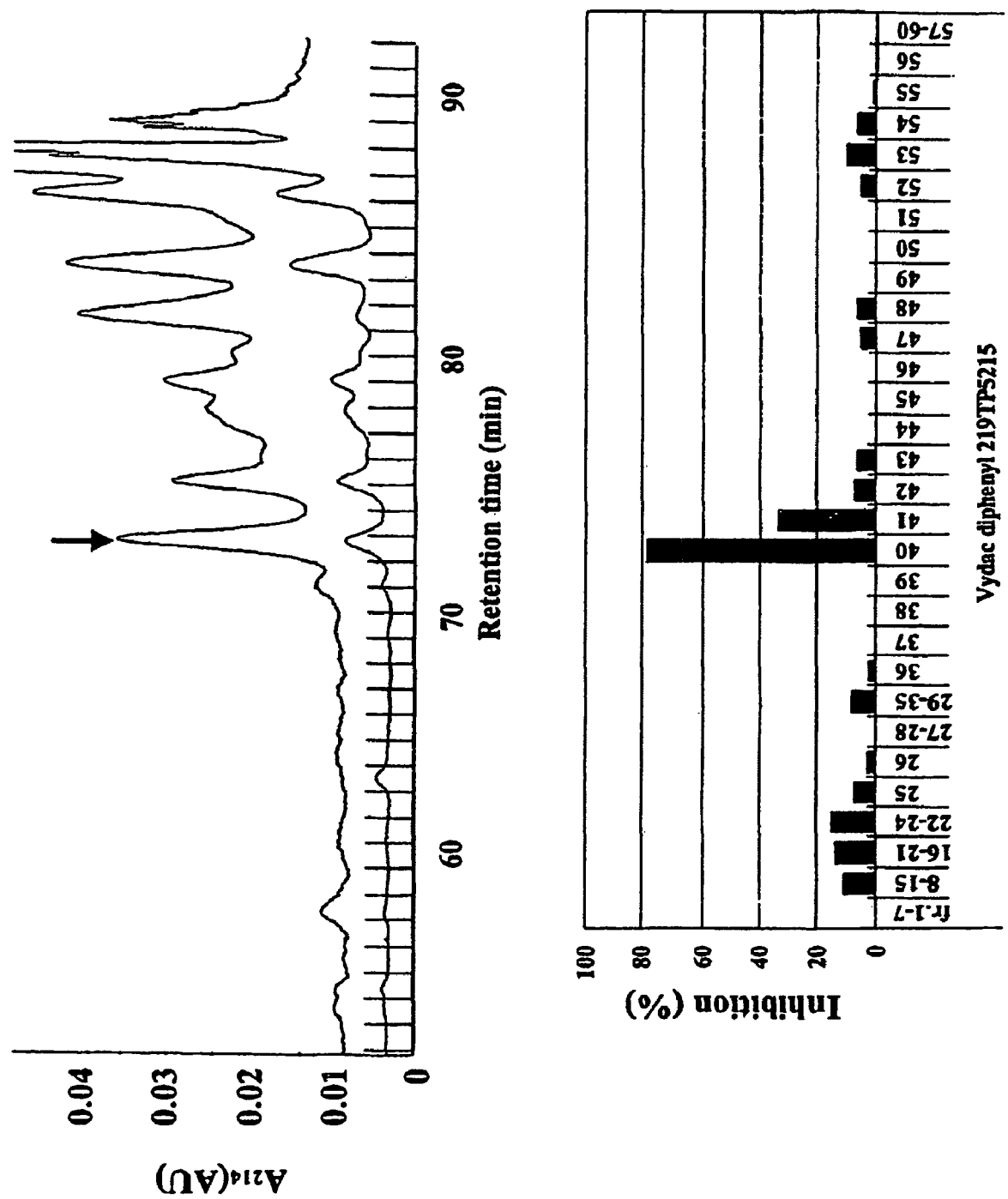

FIG. 15 shows a result for final purification step of intrinsic FPRL1 ligand from porcine stomach by reverse column diphenyl 219TP52 (Vydac). Upper shows a pattern of chromatogram. Solid lines in the figure represent absorbance at 214 nm (upper) and 280 nm (lower), respectively. Arrowhead indicates a peak of the purified FPRL1 ligand P4. The term "Retention time (min)" means elution time (min). The number "21-59" means fraction number. Lower column shows human FPRL1-expressing CHO cell specific inhibiting activity for intracellular cAMP production (Inhibition (%)) in each fraction depicted in upper column (fraction 20-30 of Vydac diphenyl 219TP5215).

Figure 16:
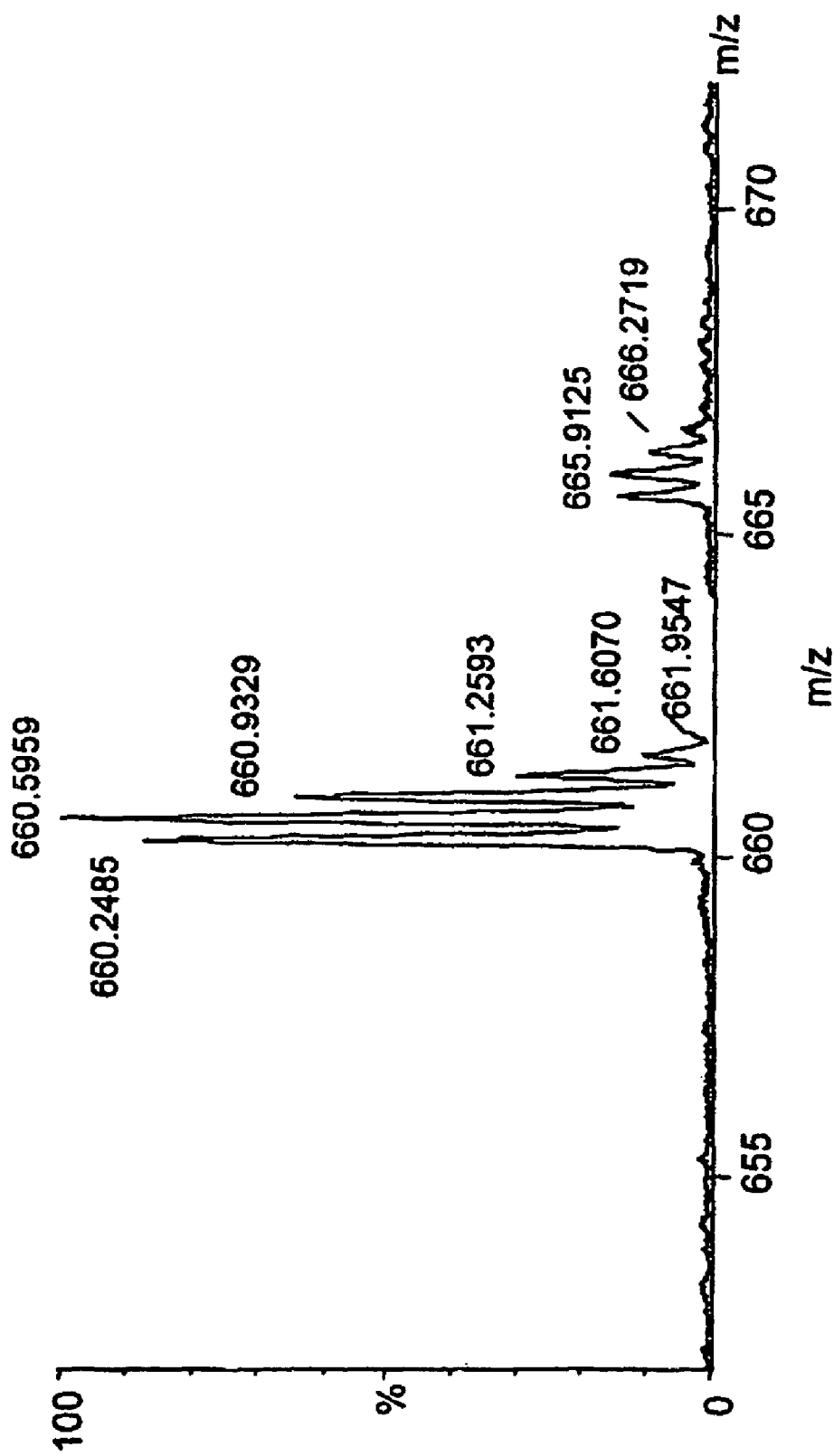

FIG. 16 shows a mass spectrum of porcine intrinsic FPRL1 ligand P4. Horizontal axis and vertical axis represent mass/electric charge (m/z) and relative intensity in the case where the highest signal is referred to as 100%, respectively. Trivalent molecule-associated ion (m/z 660) and its oxidant ion (m/z 665) appear. Thenumeric value in which the signal is labeled indicates a value for m/z.

Figure 17:
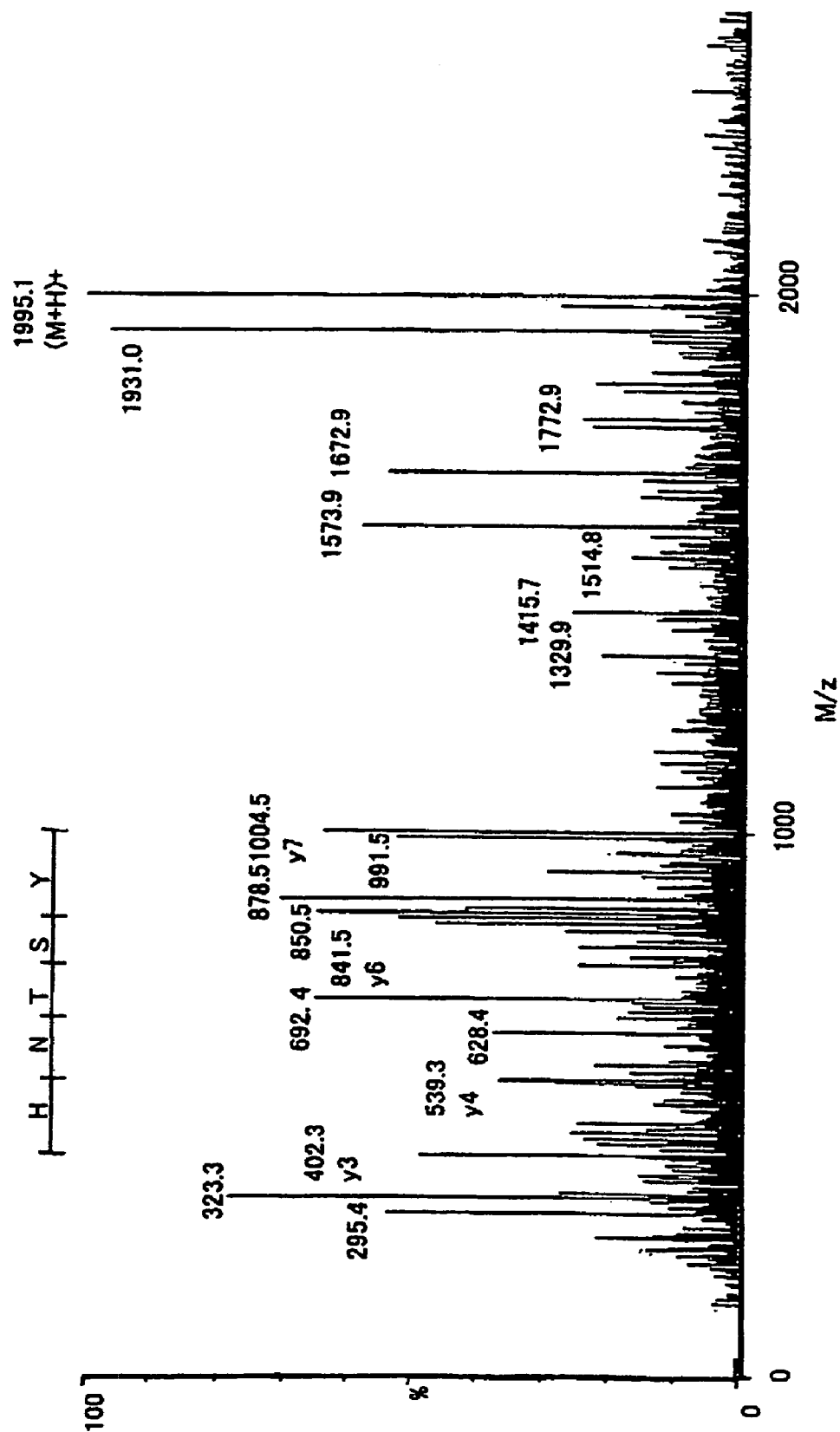

FIG. 17 shows a MS/MS spectrum in the case where trivalent ion m/z 665.60 of porcine intrinsic FPRL1 ligand P4 oxidant is a parent ion by electrospray ionization mass spectrometer. MS/MS spectrum. Horizontal axis and vertical axis represent mass/electric charge (m/z) and relative intensity in the case where the highest signal is referred to as 100%, respectively. In the figure, numeric value labeled with signal indicates a value of m/z. Analysis result by a series of ions belonging to group including the N-terminal end (y group) is denoted above the spectrum.

Figure 18:
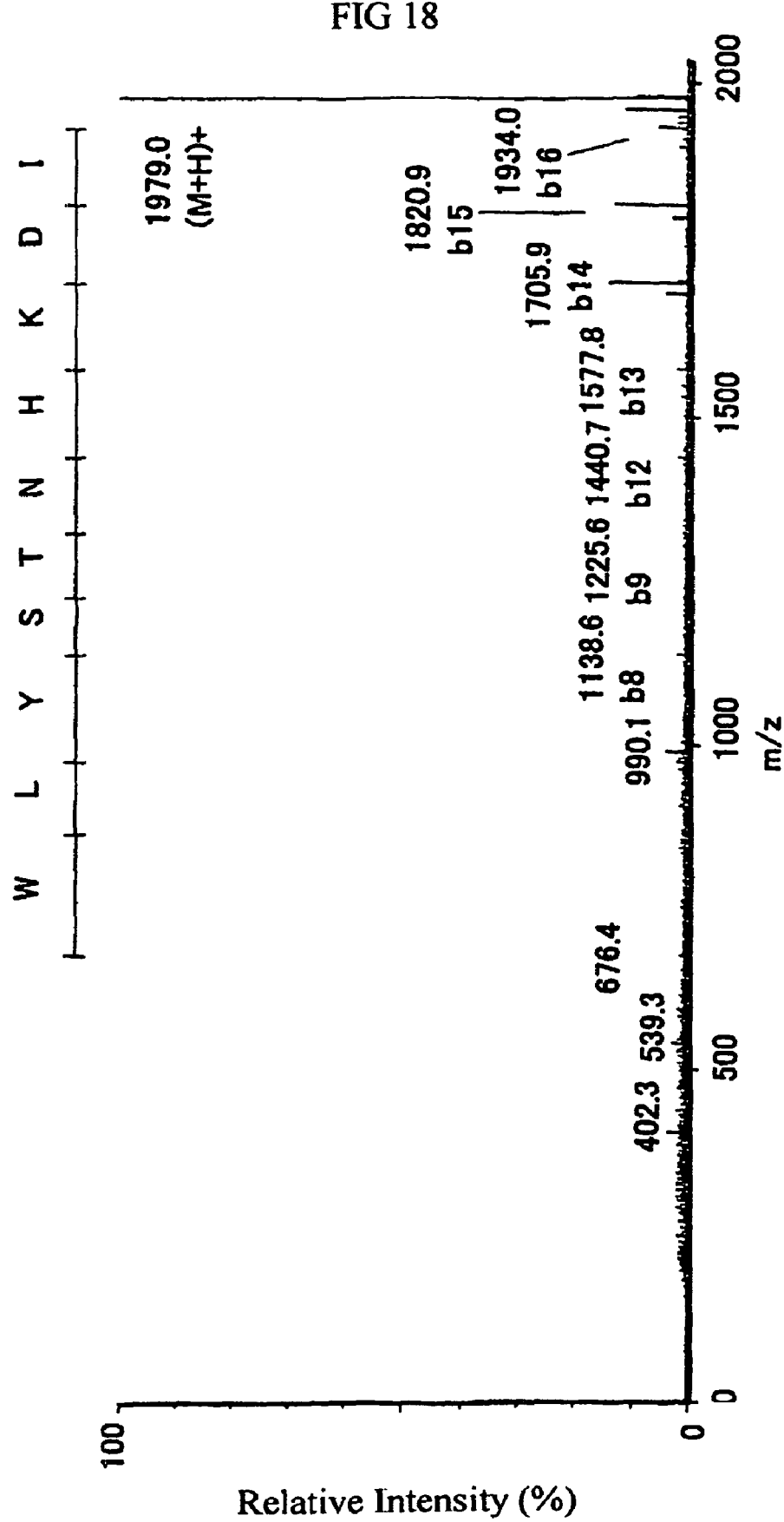

FIG. 18 shows a result of converting a MS/MS spectrum for m/z 989.88 of porcine intrinsic FPRL1 ligand P4 as a parent ion to monovalence by the analysis software MaxEnt 3 attached to mass spectrometer. Horizontal axis and vertical axis represent mass/electric charge (m/z) and relative intensity in the case where the highest signal is referred to as 100%, respectively. In the figure, numeric value labeled with signal indicates a value of m/z. Analysis result by a series of ions belonging to group including the N-terminal end (b group) is denoted above the spectrum.

Figure 19:
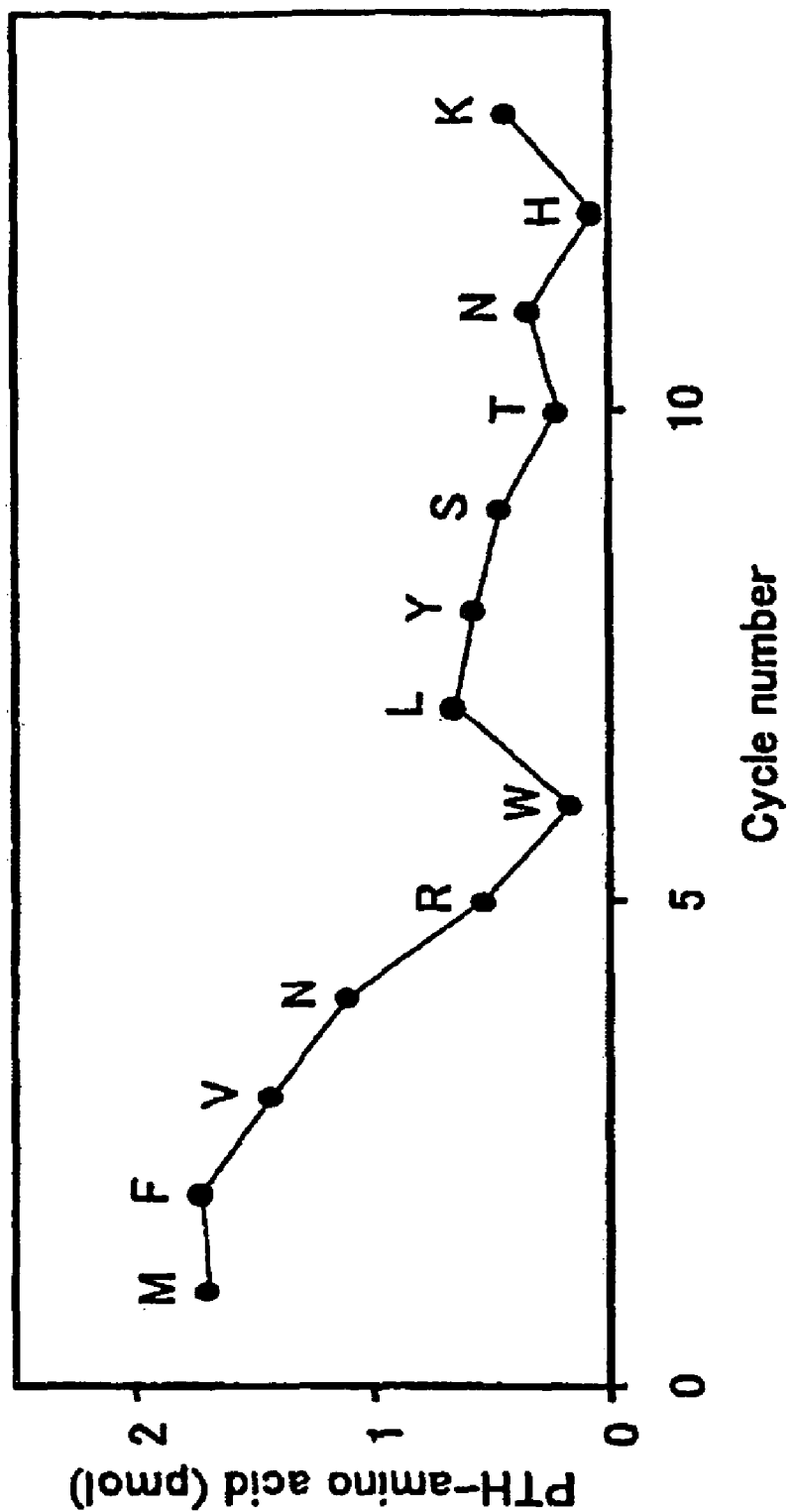

FIG. 19 shows a result, of which a sequence of porcine intrinsic FPRL1 ligand P4 was analyzed, is indicated. Horizontal axis (Residue number) and vertical axis represent an order of amino acid residues and a level of phenylthiohydantoin (PTH)- amino acid appeared in each cycle, respectively. Alphabets in the figure show one-letter code of amino acid.

Figure 20:
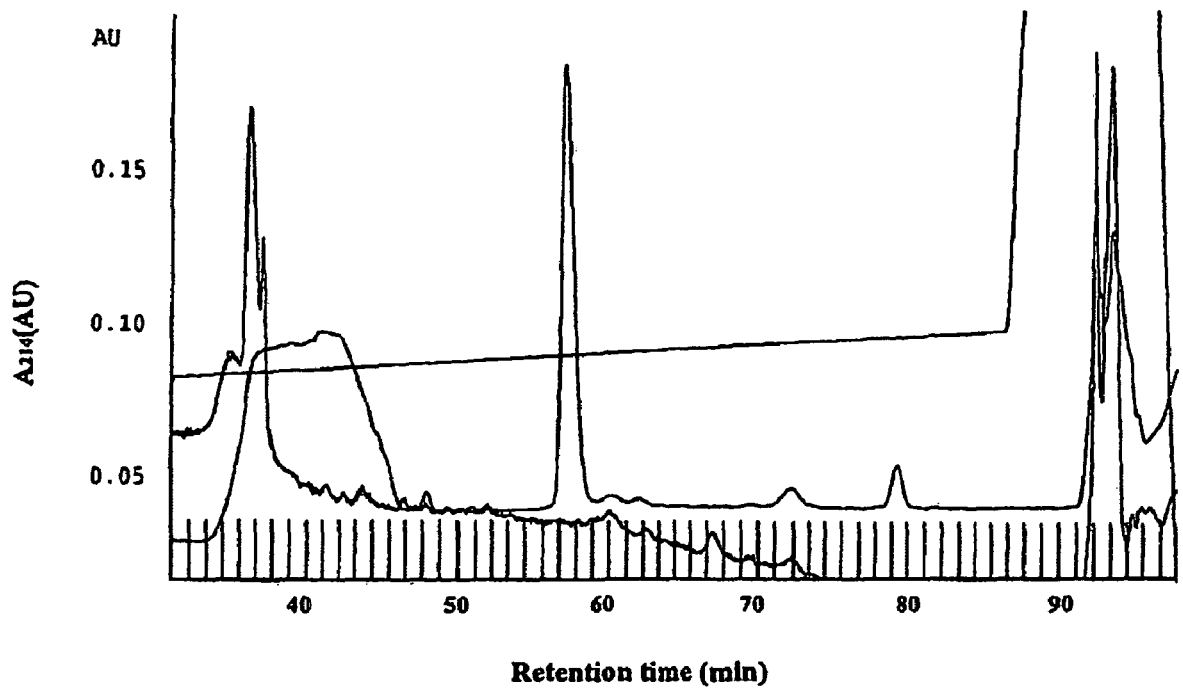
Figure 20:
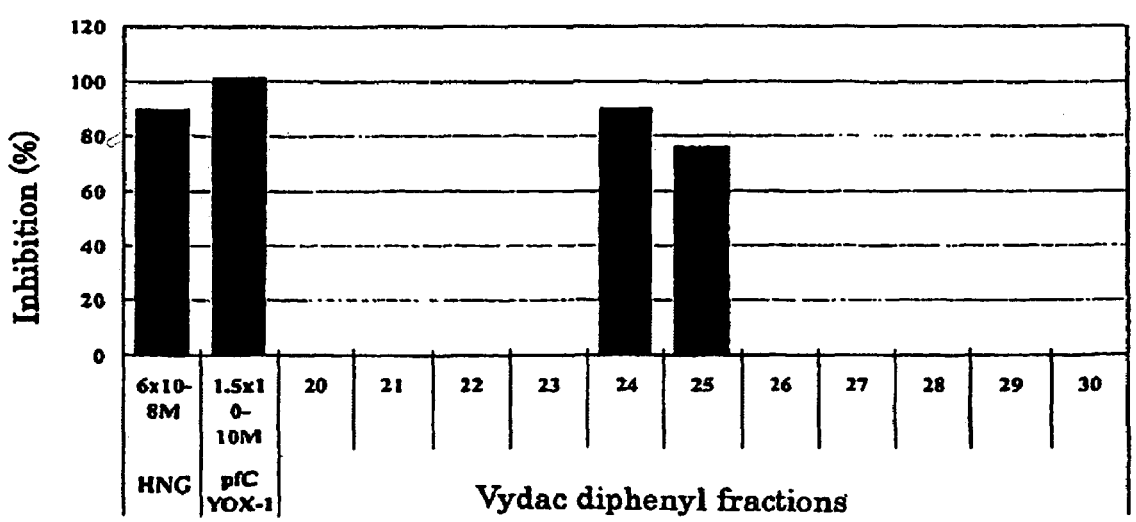

FIG. 20 shows a result for final purification step of intrinsic FPRL1 ligand from porcine stomach by reverse column diphenyl 219TP52 (Vydac). Upper shows a pattern of chromatogram. Solid lines in the figure represent absorbance at 214 nm (upper) and 280 nm (lower), respectively. Arrowhead indicates a peak of the purified FPRL1 ligand P2. The term "Retention time (min)" means elution time (min). The number "1-60" means fraction number. Lower column shows human FPRL1-expressing CHO cell specific inhibiting activity for intracellular cAMP production (Inhibition (%)) in each fraction depicted in upper column (fraction 20-30 of Vydac diphenyl 219TP5215).

Figure 21:
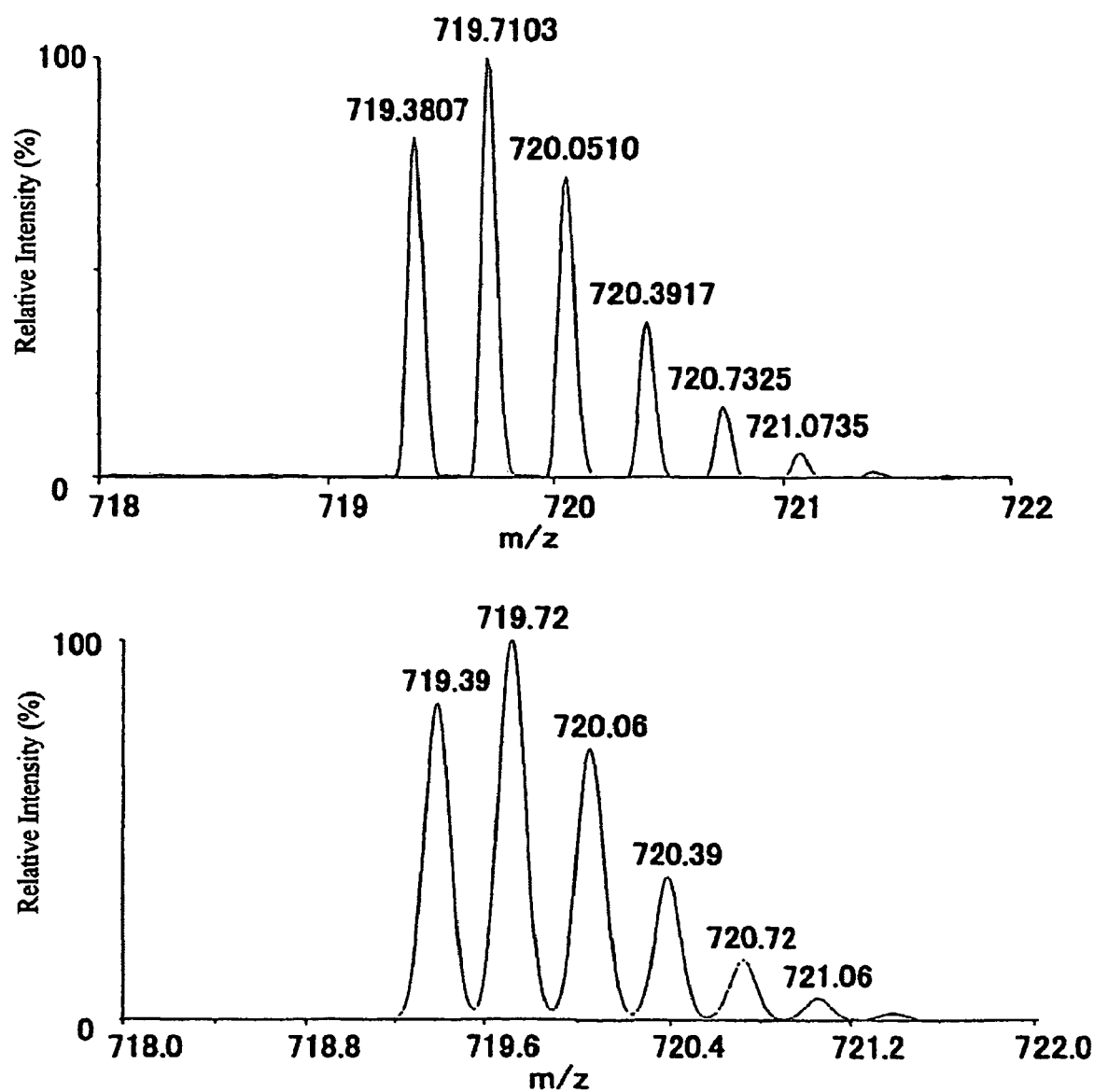

FIG. 21 shows a mass spectrum of porcine intrinsic FPRL1 ligand P3 by electrospray ionization mass spectrometer. Horizontal axis and vertical axis represent mass/electric charge (m/z) and relative intensity in the case where the highest signal is referred to as 100%, respectively. Upper column indicates an enlarged drawing of trivalent molecule associated ion (M+3H$^{3+}$). Thenumeric value in which the signal is labeled indicates a value for m/z. Lower column is theoretical pattern for (M+3H$^{3+}$) ion of porcine formyl-cytochrome b (1-18).

Figure 22:
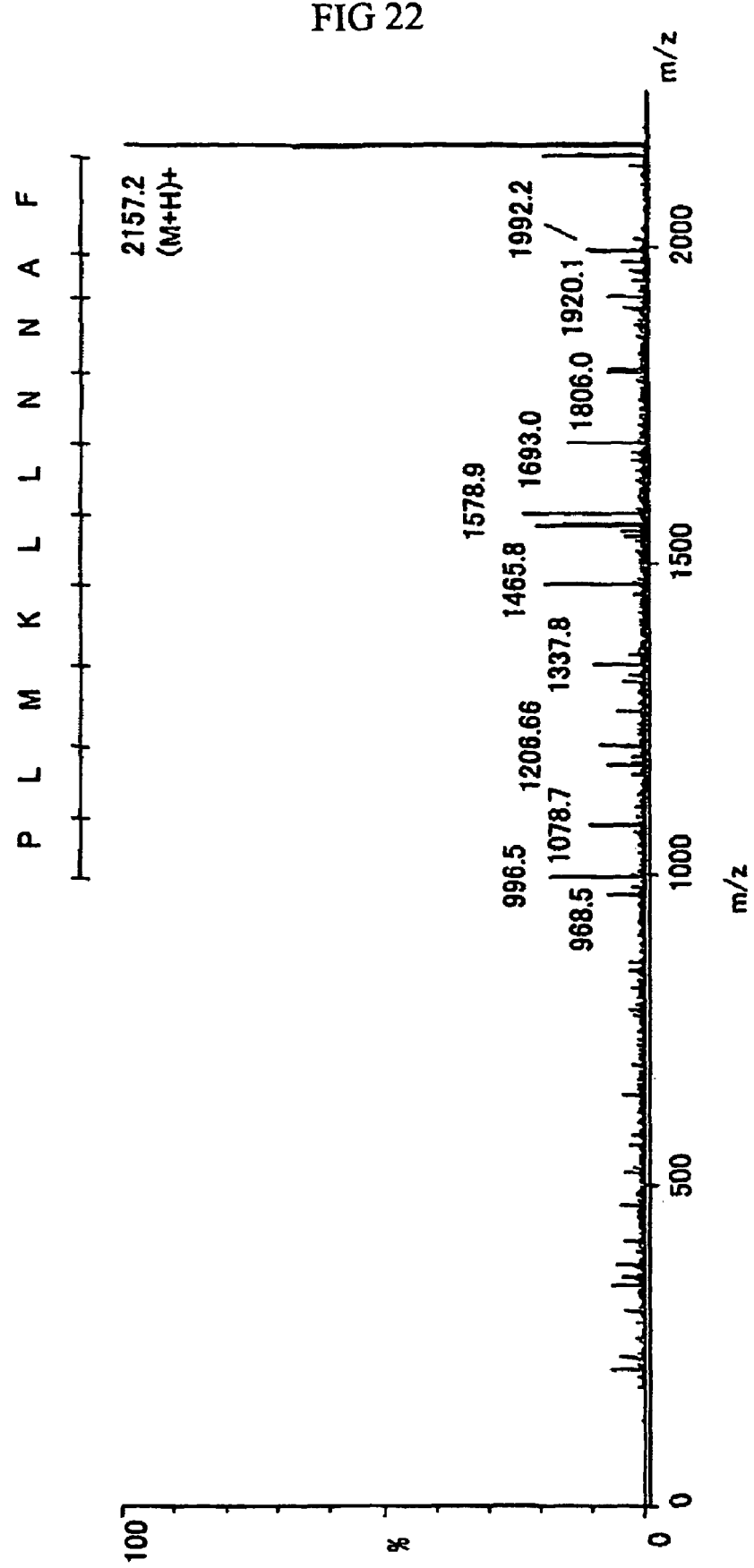

FIG. 22 shows a MS/MS spectrum in the case where tetravalent ion of porcine intrinsic FPRL1 ligand P2 is a parent ion by electrospray ionization mass spectrometer. MS/MS spectrum. MS/Ms spectrum for divalent ion as a parent ion is converted to monovalence by the analysis software MaxEnt 3 attached to mass spectrometer. Horizontal axis and vertical axis represent mass/electric charge (m/z) and relative intensity in the case where the highest signal is referred to as 100%, respectively. In the figure, numeric value labeled with signal indicates a value of m/z. Analysis result by a series of ions belonging to group including the N-terminal end (b group) is denoted above the spectrum.

Figure 23:
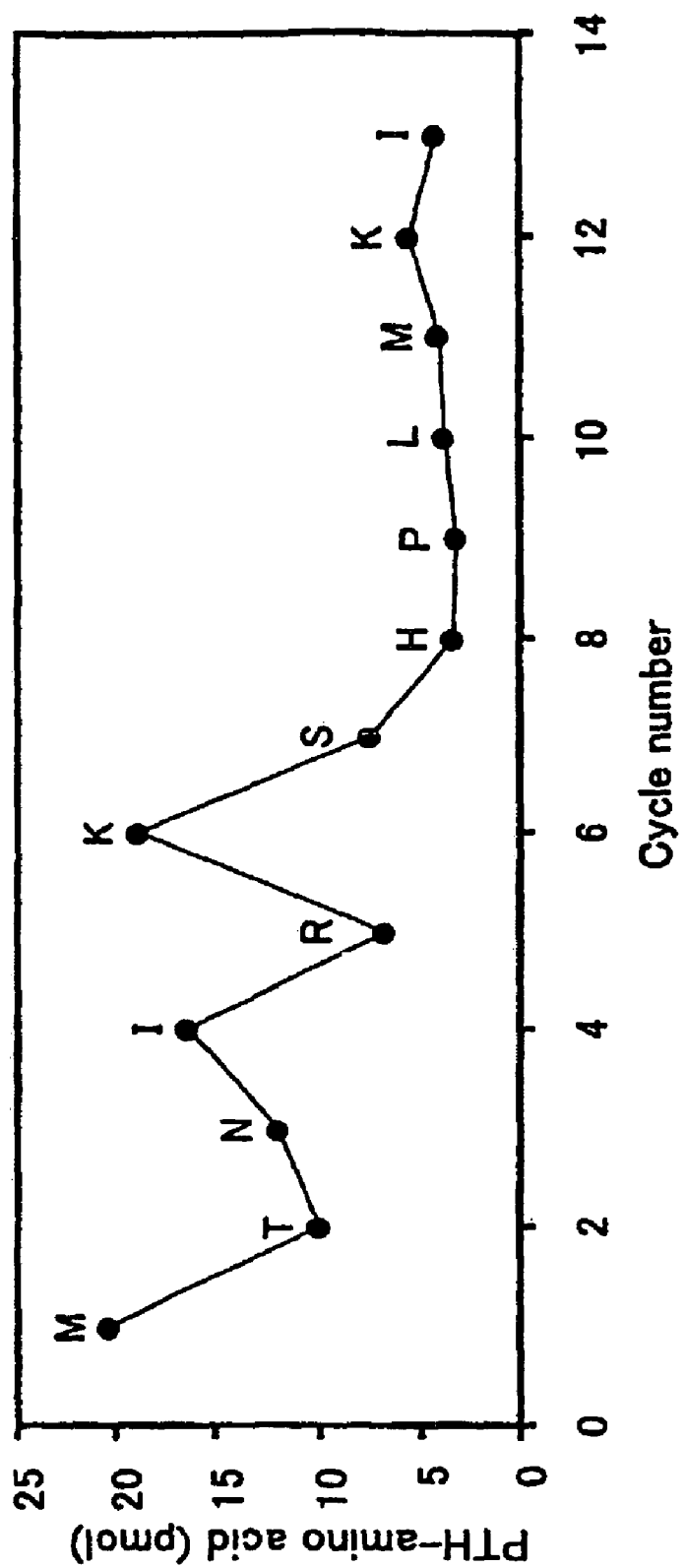

FIG. 23 shows a result, of which a sequence of porcine intrinsic FPRL1 ligand P2 was analyzed, is indicated. Horizontal axis (Cycle number) and vertical axis represent an order of amino acid residues and a level of phenylthiohydantoin (PTH)-amino acid appeared in each cycle, respectively. Alphabets in the figure show one-letter code of amino acid.

Figure 24:
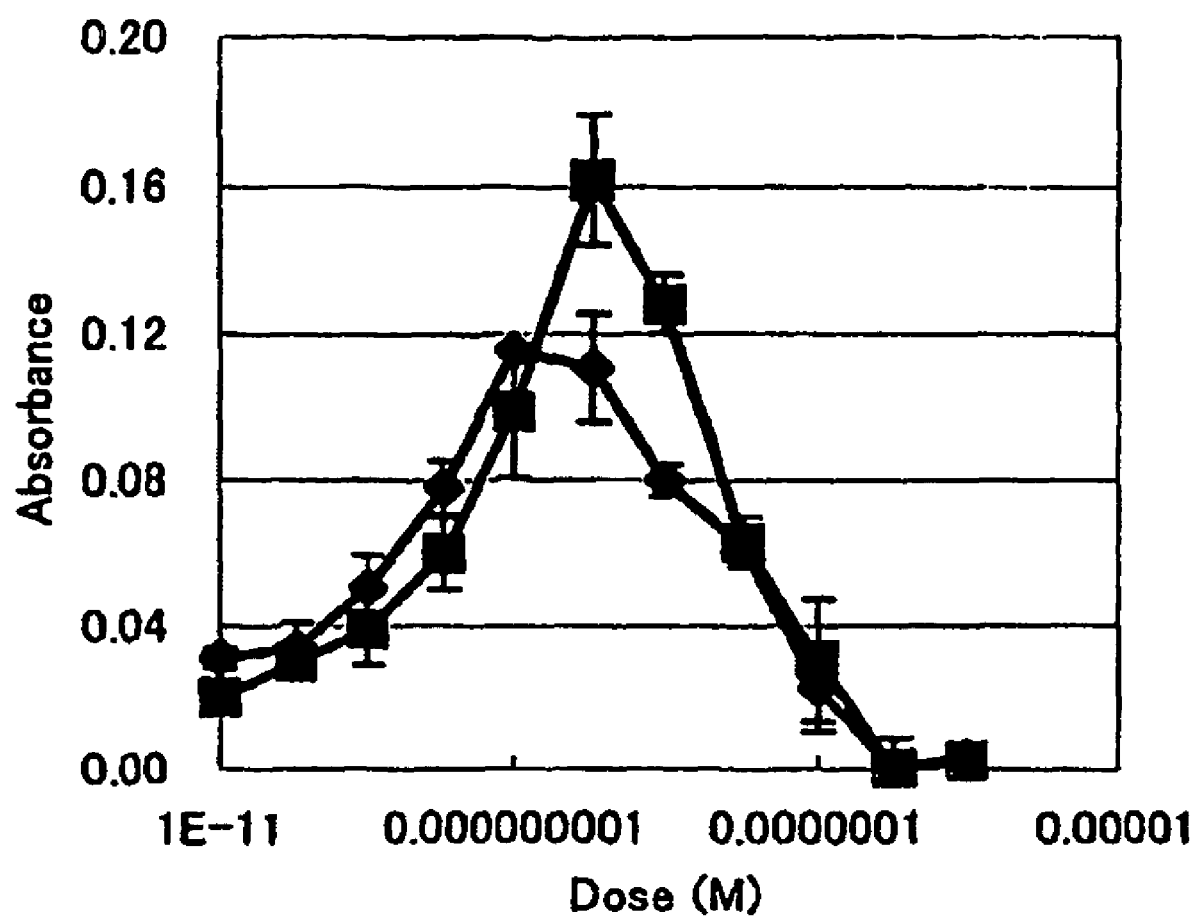

FIG. 24 shows a result of cell migration stimulating activity of various peptides (porcine FPRL1 ligand P3 (pfCYOX-1(1-13)) or human FPRL1 ligand P3 (hfCYOX-1(1-13))) to FPRL1-GFP fusion protein-expressing CHO cells. Horizontal axis (Dose (M)) indicates a value for concentration of peptide by molar concentration. Vertical axis (Absorbance) represents a cell migration activity by absorbance, which reflects cell number stained. Closed rhombus represents pfCYOX-1(1-13). Closed square represents hfCYOX-1(1-13). The examination was triplicated.

BEST MODE FOR CARRYING OUT THE INVENTION

Best Mode for Carrying Out the Invention

FPRL1 used in the present invention is a receptor protein comprising the same or substantially the same amino acid sequence as the amino acid sequence represented by SEQ ID NO: 2.
FPRL1 may be any protein may be any protein derived from any cells (e.g., splenocytes, nerve cells, glial cells, pancreatic β cells, bone marrow cells, mesangial cells, Langerhans' cells, epidermic cells, epithelial cells, endothelial cells, fibroblasts, fibrocytes, myocytes, fat cells, immune cells (e.g., macrophage, T cells, B cells, natural killer cells, mast cells, neutrophil, basophil, eosinophil, monocyte), megakaryocytes, synovial cells, chondrocytes, bone cells, osteoblasts, osteoclasts, mammary gland cells, hepatocytes or interstitial cells, the corresponding precursor cells, stem cells, or cancer cells), hemocyte type cells, or any tissues where such cells are present, e.g., brain or any region of the brain (e.g., olfactory bulb, amygdaloid nucleus, basal ganglia, hippocampus, thalamus, hypothalamus, subthalamic nucleus, cerebral cortex, medulla oblongata, cerebellum, occipital lobe, frontal lobe, temporal lobe, putamen, caudate nucleus, corpus callosum, substantia nigra), spinal cord, hypophysis, stomach, pancreas, kidney, liver, gonad, thyroid, gall-bladder, bone marrow, adrenal gland, skin, muscle, lung, gastrointestinal tract (e.g., large intestine and small intestine), intestinal tract, blood vessel, heart, thymus, spleen, submandibular gland, peripheral blood, peripheral blood cells, prostate, testis, ovary, placenta, uterus, bone, joint, skeletal muscle and the like, from human and mammals (e.g., guinea pigs, rats, mice, rabbits, swine, sheep, bovine, monkeys, etc.). Particularly, the receptor protein may also be a protein derived from immunocompetent organs and immunocompetent cells such as spleen, bone marrow, intestinal tract, monocyte and macrophage or may be a synthetic protein.

Substantially the same amino acid sequence as the amino acid sequence represented by SEQ ID NO: 2 includes, for example, an amino acid sequence having at least about 85% homology, preferably at least about 90% homology and more preferably at least about 95% homology to the amino acid sequence represented by SEQ ID NO: 2.

The homology among the amino acid sequences can be calculated using homology calculation algorism NCBI BLAST (National Center for Biotechnology Information Basic Local Alignment Search Tool) under the following conditions: expected value=10; gap is allowable; matrix=BLOSUM62; filtering=OFF. The protein of the present invention comprising substantially the same amino acid sequence as the amino acid sequence represented by SEQ ID NO: 2 includes, for example, a protein having an amino acid sequence comprising substantially the same amino acid sequence as the amino acid sequence represented by SEQ ID NO: 2 and having a substantially equivalent activity to FPRL1 consisting of the amino acid sequence represented by SEQ ID NO: 2.

The substantially equivalent activity includes, for example, a ligand binding activity, a signal transduction activity, etc. The term "substantially equivalent" is used to mean that the nature of the activity is the same. Therefore, although it is preferred that activities such as the ligand binding and signal transduction activities, etc. be equivalent (e.g., about 0.01- to about 100-fold, preferably about 0.5- to about 20-fold, more preferably about 0.5- to about 2-fold), quantitative factors such as a level of the activity, a molecular weight of the protein, etc. may differ.

The activities such as ligand binding and signal transduction activities or the like can be determined according to a publicly known method, for example, a screening method that will be later described.

As FPRL1, proteins comprising the following amino acid sequences will be used: a) amino acid sequences represented by SEQ ID NO: 2, SEQ ID NO: 4 or SEQ ID NO: 6, wherein 1 or more amino acids (preferably about 1 to 30 amino acids, more preferably about 1 to 10 amino acids, still more preferably several amino acids (1 to 5 amino acids)) are deleted, b) amino acid sequences represented by SEQ ID NO: 2, SEQ ID NO: 4 or SEQ ID NO: 6 to which 1 or more amino acids (preferably about 1 to 30 amino acids, more preferably about 1 to 10 amino acids, still more preferably several amino acids (1 to 5 amino acids)) are added, c) amino acid sequences represented by SEQ ID NO: 2, SEQ ID NO: 4 or SEQ ID NO: 6, wherein 1 or more amino acids (preferably about 1 to 30 amino acids, more preferably about 1 to 10 amino acids, still more preferably several amino acids (1 to 5 amino acids)) are substituted by other amino acids, and d) proteins consisting of a combination of the amino acid sequences described in the above.

Throughout the present specification, FPRL1 is represented in accordance with the conventional way of describing peptides, that is, the N-terminus (amino terminus) at the left hand and the C-terminus (carboxyl terminus) at the right hand. In FPRL1 including FPRL1 comprising the amino acid sequence represented by SEQ ID NO: 1, the C-terminus may be any in the form of a carboxyl group (—COOH), a carboxylate (—COO⁻), an amide (—CONH$_2$) or an ester (—COOR).

The ester group shown by R include, for example, a $C_{1-6}$ alkyl group such as methyl, ethyl, n-propyl, isopropyl, n-butyl; a $C_{3-8}$ cycloalkyl group such as cyclopentyl, cyclohexyl; a $C_{6-12}$ aryl group such as phenyl, α-naphthyl; a $C_{7-14}$ aralkyl group such as a phenyl-$C_{1-2}$-alkyl group, e.g., benzyl, phenethyl, or an α-naphthyl-$C_{1-2}$-alkyl group such as α-naphthylmethyl; and the like. In addition, pivaloyloxymethyl or the like, which is used widely as an ester for oral administration, may also be used.

When FPRL1 has a carboxyl group (or a carboxylate) at a position other than the C-terminus, it may be amidated or esterified, and such an amide or ester is also included within FPRL1 of the present invention. The ester group may be the same group as that described with respect to the C-terminus described above.

Furthermore, examples of FPRL1 include variants of the above proteins, wherein the amino group at the N-terminal methionine residue of the protein supra is protected with a protecting group (for example, a $C_{1-6}$ acyl group such as a $C_{2-6}$ alkanoyl group, formyl group, acetyl group); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{2-6}$ alkanoyl group, formyl group, acetyl group), or conjugated proteins such as glycoproteins bound to sugar chains.

Specific examples of FPRL1 of the present invention which can be used include, for example, human-derived FPRL1 consisting of the amino acid sequence represented by SEQ ID NO: 2 (J. Biol. Chem. 267(11), 7637-7643 (1992)), rat-derived FPRL1 consisting of the amino acid sequence represented by SEQ ID NO: 4, mouse-derived FPRL2 consisting of the amino acid sequence represented by SEQ ID NO: 6 (J. Immunol. 169, 3363-3369 (2002)), or the like.

The rat-derived FPRL1 consisting of the amino acid sequence represented by SEQ ID NO: 4 is a novel protein.

Partial peptides of FPRL1 (hereinafter sometimes simply referred to as the partial peptide of the present invention) may be any partial peptides of FPRL1 described above, and for example, those having a site exposed to the outside of a cell membrane and having a receptor binding activity substantially equivalent to that of FPRL1 can be used.

Specifically, the partial peptide of FPRL1 having the amino acid sequence represented by SEQ ID NO: 1 is a peptide containing the parts analyzed to be extracellular domains (hydrophilic domains) in hydrophobic plotting analysis. A peptide containing a hydrophobic domain in part can be used as well. In addition, the peptide may contain each domain separately or plural domains together.

Preferred partial peptides of the present invention are those having at least 20, preferably at least 50, and more preferably at least 100 amino acids, in the amino acid sequence which constitutes the receptor protein of the present invention.

The term "substantially the same amino acid sequence" refers to an amino acid sequence having at least about 85% homology, preferably at least about 90% homology, more preferably at least about 95% homology, to the amino acid sequences mentioned therein.

The homology among the amino acid sequences can be calculated using homology calculation algorism NCBI BLAST (National Center for Biotechnology Information Basic Local Alignment Search Tool) under the following conditions: expected value=10; gap is allowable; matrix=BLOSUM62; filtering=OFF.

Herein, the term "activity substantially equivalent" refers to the same meaning as defined above. The "substantially equivalent receptor activity" can be assayed in the same manner as given above.

The partial peptide of the present invention includes partial peptides of the amino acid sequence described above, wherein 1 or more amino acids (preferably about 1 to 10 amino acids, more preferably several (1 to 5) amino acids) may be deleted; to which 1 or more amino acids (preferably about 1 to 20 amino acids, more preferably about 1 to 10 amino acids, still more preferably several (1 to 5) amino acids) may be added; or, in which 1 or more amino acids (preferably about 1 to 10 amino acids, more preferably several amino acids, still more preferably about 1 to 5 amino acids) may be substituted by other amino acids.

In the partial peptide of the present invention, the C-terminus may be any in the form of a carboxyl group (—COOH), carboxylate (—COO⁻), amide (—CONH$_2$) or ester (—COOR). Where the partial peptide of the present invention has a carboxyl group (or a carboxylate) at a position other than the C-terminus, it may be amidated or esterified, and such an amide or ester is also included within the partial peptide of the present invention. As the ester group herein, the same esters as those described with respect to the above C-terminal are used.

As in FPRL1 described above, the partial peptide of the present invention further includes those in which the amino group of the N-terminal methionine residue is protected by a protecting group, those in which the N-terminal residue is cleaved in vivo and the produced glutamine residue is pyroglutaminated, those in which substituents on the side chains of amino acids in the molecule are protected by appropriate protecting groups, conjugated peptides such as so-called glycoproteins, to which sugar chains are bound, and the like.

For salts of FPRL1 of the present invention or the partial peptide thereof, preferred are physiologically acceptable salts with acids or bases, especially physiologically acceptable acid addition salts. Examples of the salts include salts with, for example, inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

FPRL1 of the present invention or salts thereof may be manufactured by a publicly known method used to purify a receptor protein from human and mammalian cells or tissues described above, or by culturing a transformant harboring the DNA encoding FPRL1 of the present invention, as will be later described. Furthermore, FPRL1 or its salts may also be manufactured by the methods for synthesizing proteins or by modifications thereof, which will also be described hereinafter.

When FPRL1 is manufactured from human and mammalian tissues or cells, human or mammalian tissues or cells are homogenized, then extracted with an acid or the like, and the extract is isolated and purified by a combination of chromatography techniques such as reverse phase chromatography, ion exchange chromatography, and the like.

To synthesize FPRL1 of the present invention or partial peptides thereof or salts thereof or amides thereof, commercially available resins that are used for protein synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenyl acetamidomethyl resin, polyacrylamide resin, 4-(2',4'-dimethoxyphenylhydroxymethyl)phenoxy resin, 4-(2',4'-dimethoxyphenyl-Fmoc-aminoethyl) phenoxy resin, etc. Using these resins, amino acids in which α-amino groups and functional groups on the side chains are appropriately protected are condensed on the resin in the order of the sequence of the objective protein according to various condensation methods publicly known in the art. At the end of the reaction, the protein is excised from the resin and at the same time, the protecting groups are removed. Then, intramolecular disulfide bond-forming reaction is performed in a highly diluted solution to obtain the objective protein or its amides.

For condensation of the protected amino acids described above, a variety of activation reagents for protein synthesis may be used, and carbodiimides are particularly preferable. Examples of such carbodiimides include DCC, N,N'-diisopropylcarbodiimide, N-ethyl-N'-(3-dimethylaminopropyl) carbodiimide, and the like. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents used to activate the protected amino acids or condense with the resin may be chosen from solvents known to be usable for protein condensation reactions. Examples of such solvents are acid amides such as N,N-dimethylformamide, N,N-dimethylacetamide, and N-methylpyrrolidone; halogenated hydrocarbons such as methylene chloride and chloroform; alcohols such as trifluoroethanol; sulfoxides such as dimethylsulfoxide; ethers such as pyridine, dioxane and tetrahydrofuran; nitriles such as acetonitrile and propionitrile; esters such as methyl acetate and ethyl acetate; and appropriate mixtures of these solvents. The reaction temperature is appropriately chosen from the range known to be applicable to protein binding reactions and is usually selected in the range of approximately −20° C. to 50° C. The activated amino acid derivatives are used generally in an excess of 1.5 to 4 times. The condensation is examined by a test using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole.

Examples of the protecting groups used to protect the amino groups of the starting compounds include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc, and the like.

A carboxyl group can be protected by, e.g., alkyl esterification (in the form of linear, branched or cyclic alkyl esters of the alkyl moiety such as methyl, ethyl, propyl, butyl, tertiary butyl, cyclopentyl, cyclohexyl, cycloheptyl, cyclooctyl, 2-adamantyl, etc.), aralkyl esterification (e.g., esterification in the form of benzyl ester, 4-nitrobenzyl ester, 4-methoxybenzyl ester, 4-chlorobenzyl ester, benzhydryl ester, etc.), phenacyl esterification, benzyloxycarbonyl hydrazidation, tertiary butoxycarbonyl hydrazidation, trityl hydrazidation, or the like.

The hydroxyl group of serine can be protected through, for example, its esterification or etherification. Examples of groups appropriately used for the esterification include a lower alkanoyl group, such as acetyl group, an aroyl group such as benzoyl group, and a group derived from carbonic acid such as benzyloxycarbonyl group, ethoxycarbonyl group, etc. Examples of a group appropriately used for the etherification include benzyl group, tetrahydropyranyl group, t-butyl group, or the like Examples of groups for protecting the phenolic hydroxyl group of tyrosine include Bzl, $Cl_2$-Bzl, 2-nitrobenzyl, Br-Z, tertiary butyl, or the like.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, or the like.

Examples of the activated carboxyl groups in the starting compounds include the corresponding acid anhydrides, azides, activated esters (esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)). As the activated amino acids in which the amino groups are activated in the starting material, the corresponding phosphoric amides are employed.

To eliminate (split off) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethane-sulfonic acid or trifluoroacetic acid, or a mixture solution of these acids; a treatment with a base such as diisopropylethylamine, triethylamine, piperidine or piperazine; and reduction with sodium in liquid ammonia. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol or 1,2-ethanedithiol. Furthermore, 2,4-dinitrophenyl group known as a protecting group for the imidazole of histidine is removed by a treatment with thiophenol. Formyl group used as a protecting group of the indole of tryptophan is eliminated by the aforesaid acid treatment in the presence of 1,2-ethanedithiol or 1,4-butanedithiol, as well as by a treatment with an alkali such as a dilute sodium hydroxide solution and dilute ammonia.

Protection of functional groups that should not be involved in the reaction of the starting materials, protecting groups, elimination of the protecting groups and activation of functional groups involved in the reaction can be appropriately selected from publicly known groups and publicly known means.

In an alternative method for obtaining the amides of the protein, for example, the α-carboxyl group of the carboxy terminal amino acid is first protected by amidation, and the peptide (protein) chain is then extended from the amino group side to a desired length. Thereafter, a protein in which only the protecting group of the N-terminal α-amino group in the peptide chain has been eliminated from the protein, and a protein in which only the protecting group of the C-terminal carboxyl group has been eliminated are prepared. The two proteins are condensed in a mixture of the solvents described above. The details of the condensation reaction are the same as described above. After the protected protein obtained by the condensation is purified, all the protecting groups can be eliminated by the method described above to give the desired crude protein. This crude protein is purified by various known purification means, followed by lyophilization of the major fraction, to give the amide of the desired protein.

To prepare the ester of the protein, for example, the α-carboxyl group of the carboxy terminal amino acid is condensed with a desired alcohol to prepare the amino acid ester, which is followed by procedure similar to the preparation of the amidated protein above to give the ester form of the desired protein.

The partial peptide of FPRL1 of the present invention or salts thereof can be manufactured by publicly known methods for peptide synthesis, or by cleaving FPRL1 of the present invention with an appropriate peptidase. For the methods for peptide synthesis, for example, either solid phase synthesis or liquid phase synthesis may be used. That is, the partial peptide or amino acids that can construct FPRL1 of the present invention are condensed with the remaining part. Where the product has protecting groups, these protecting groups can be removed to give the desired peptide. Publicly known methods for condensation and elimination of the protecting groups are described in (a) to (e) below:
(a) M. Bodanszky & M. A. Ondetti: Peptide Synthesis, Interscience Publishers, New York (1966);
(b) Schroeder & Luebke: The Peptide, Academic Press, New York (1965);
(c) Nobuo Izumiya, et al.: Peptide Gosei-no-Kiso to Jikken (Basics and experiments of peptide synthesis), published by Maruzen Co. (1975);
(d) Haruaki Yajima & Shunpei Sakakibara: Seikagaku Jikken Koza (Biochemical Experiment) 1, Tanpakushitsu no Kagaku (Chemistry of Proteins) IV, 205 (1977); and
(e) Haruaki Yajima, ed.: Zoku Iyakuhin no Kaihatsu (A sequel to Development of Pharmaceuticals), Vol. 14, Peptide Synthesis, published by Hirokawa Shoten.

After completion of the reaction, the product may be purified and isolated by a combination of conventional purification methods such as solvent extraction, distillation, column chromatography, liquid chromatography and recrystallization to give the partial peptide of the present invention. When the partial peptide obtained by the above methods is in a free form, the peptide can be converted into an appropriate salt by a publicly known method; when the partial peptide is obtained in a salt form, it can be converted into a free form by a publicly known method.

The polynucleotide encoding FPRL1 of the present invention may be any polynucleotide so long as it comprises the base sequence (DNA or RNA, preferably DNA) encoding FPRL1 of the present invention described above. Such a polynucleotide may also be any one of DNA encoding FPRL1 of the present invention, RNA such as mRNA, etc., and may be double-stranded or single-stranded. Where the polynucleotide is double-stranded, it may be double-stranded DNA, double-stranded RNA or DNA:RNA hybrid. Where the polynucleotide is single-stranded, it may be a sense strand (i.e., a coding strand) or an antisense strand (i.e., a non-coding strand).

Using the polynucleotide encoding FPRL1 of the present invention, mRNA of FPRL1 of the present invention can be quantified by, for example, the publicly known method published in separate volume of Jikken Igaku 15 (7) "New PCR and its application" (1997), or by its modifications.

The DNA encoding FPRL1 of the present invention may be any of genomic DNA, genomic DNA library, cDNA derived from the cells and tissues described above, cDNA library derived from the cells and tissues described above, and synthetic DNA. The vector to be used for the library may be any of bacteriophage, plasmid, cosmid and phagemid. The DNA may also be directly amplified by reverse transcriptase polymerase chain reaction (hereinafter abbreviated as RT-PCR) using the total RNA or mRNA fraction prepared from the cells and tissues described above.

Specifically, the DNA encoding human FPRL1 of the present invention may be, for example, DNA comprising the base sequence represented by SEQ ID NO: 3, or DNA having a base sequence hybridizable to the base sequence represented by SEQ ID NO: 3, under highly stringent conditions and encoding a receptor protein having the activities substantially equivalent to those (e.g., a ligand binding activity, a signal transduction activity, etc.) of human FPRL1 consisting of the amino acid sequence represented by SEQ ID NO: 2.

Specifically, the DNA encoding rat FPRL1 of the present invention may be, for example, DNA comprising the base sequence represented by SEQ ID NO: 5, or DNA having a base sequence hybridizable to the base sequence represented by SEQ ID NO: 5, under highly stringent conditions and encoding a receptor protein having the activities substantially equivalent to those (e.g., a ligand binding activity, a signal transduction activity, etc.) of rat FPRL1 consisting of the amino acid sequence represented by SEQ ID NO: 4.

Specifically, the DNA encoding mouse FPRL2 of the present invention may be, for example, DNA comprising the base sequence represented by SEQ ID NO: 7, or DNA having a base sequence hybridizable to the base sequence represented by SEQ ID NO: 7, under highly stringent conditions and encoding a receptor protein having the activities substantially equivalent to those (e.g., a ligand binding activity, a signal transduction activity, etc.) of mouse FPRL2 consisting of the amino acid sequence represented by SEQ ID NO: 6.

Specific examples of the DNA hybridizable to the base sequence represented by SEQ ID NO: 3, SEQ ID NO: 5 or SEQ ID NO: 7 include, for example, DNA comprising a base sequence having at least about 85% homology, preferably at least about 90% homology and more preferably at least about 95% homology to the base sequence represented by SEQ ID NO: 3, SEQ ID NO: 5 or SEQ ID NO: 7.

The homology among the base sequences can be calculated using homology calculation algorism NCBI BLAST (National Center for Biotechnology Information Basic Local Alignment Search Tool) under the following conditions: expected value=10; gap is allowable; filtering=ON; match score=1; mismatch score=−3.

The hybridization can be carried out by publicly known methods or by modifications of these methods, for example, according to the method described in Molecular Cloning, 2nd (J. Sambrook et al., Cold Spring Harbor Lab. Press, 1989). A commercially available library may also be used according to the instructions of the attached manufacturer's protocol. Preferably, the hybridization can be carried out under highly stringent conditions.

The highly stringent conditions used herein are, for example, those in a sodium concentration at about 19 mM to about 40 mM, preferably about 19 mM to about 20 mM at a temperature of about 50° C. to about 70° C., preferably about 60° C. to about 65° C. In particular, hybridization conditions in a sodium concentration of about 19 mM at a temperature of about 65° C. are most preferred.

More specifically, DNA consisting of the base sequence represented by SEQ ID NO: 3 or the like is used as the DNA encoding human FPRL1 consisting of the amino acid sequence represented by SEQ ID NO: 2.

DNA consisting of the base sequence represented by SEQ ID NO: 5 or the like is used as the DNA encoding rat FPRL1 consisting of the amino acid sequence represented by SEQ ID NO: 4.

DNA comprising the base sequence represented by SEQ ID NO: 7 or the like is used as the DNA encoding mouse FPRL2 consisting of the amino acid sequence represented by SEQ ID NO: 6.

The polynucleotide comprising a part of the base sequence of the DNA encoding FPRL1 of the present invention or a part of the base sequence complementary to the DNA is used to refer to not only the DNA encoding the partial peptide of the present invention described below but also to RNA.

According to the present invention, the antisense polynucleotide (nucleic acid) that can inhibit replication or expression of the FPRL1 gene can be designed and synthesized based on the base sequence information of the cloned or determined DNA encoding FPRL1. Such a polynucleotide (nucleic acid) is hybridizable with RNA of the FPRL1 gene to inhibit the synthesis or function of the RNA or is capable of modulating/controlling the expression of the FPRL1 gene via interaction with RNA associated with FPRL1. Polynucleotides complementary to the selected sequences of RNA associated with FPRL1 and polynucleotides specifically hybridizable to RNA associated with FPRL1 are useful in modulating/controlling the in vivo and in vitro expression of the FPRL1 gene, and are useful for the treatment or diagnosis of diseases, and the like. The term "corresponding" is used to refer to homologous to or complementary to a particular sequence of the nucleotide including the gene, base sequence or nucleic acid. The term "corresponding" between nucleotides, base sequences or nucleic acids and peptides (proteins) usually refer to amino acids of a peptide (protein) under the order derived from the sequence of nucleotides (nucleic acids) or their complements. In the FPRL1 gene, the 5' end hairpin loop, 5' end 6-base-pair repeats, 5' end untranslated region, polypeptide translation initiation codon, protein coding region, ORF translation termination codon, 3' end untranslated region, 3' end palindrome region, and 3' end hairpin loop, may be selected as preferred target regions, though any other region in the FPRL1 gene may be selected as a target.

The relationship between the target nucleic acids and the polynucleotides complementary to, and hybridizable to, at least a part of the target region, can be denoted to be "antisense" to the polynucleotides in the target region. Examples of the antisense polynucleotides include polydeoxyribonucleotides containing 2-deoxy-D-ribose, polyribonucleotides containing D-ribose, any other type of polynucleotides which are N-glycosides of a purine or pyrimidine base, or other polymers containing non-nucleotide backbones (e.g., commercially available protein nucleic acids and synthetic sequence-specific nucleic acid polymers) or other polymers containing nonstandard linkages (provided that the polymers contain nucleotides having such a configuration that allows base pairing or base stacking, as is found in DNA or RNA), etc. The antisense polynucleotide may be double-stranded DNA, single-stranded DNA, double-stranded RNA, single-stranded RNA or a DNA:RNA hybrid, and may further include unmodified polynucleotides (or unmodified oligonucleotides), those with publicly known types of modifications, for example, those with labels known in the art, those with caps, methylated polynucleotides, those with substitution of one or more naturally occurring nucleotides by their analogue, those with intramolecular modifications of nucleotides such as those with uncharged linkages (e.g., methyl phosphonates, phosphotriesters, phosphoramidates, carbamates, etc.) and those with charged linkages or sulfur-containing linkages (e.g., phosphorothioates, phosphorodithioates, etc.), those having side chain groups such as proteins (nucleases, nuclease inhibitors, toxins, antibodies, signal peptides, poly-L-lysine, etc.), saccharides (e.g., monosaccharides, etc.), those with intercalators (e.g., acridine, psoralen, etc.), those containing chelators (e.g., metals, radioactive metals, boron, oxidative metals, etc.), those containing alkylating agents, those with modified linkages (e.g., a anomeric nucleic acids, etc.), and the like. Herein the terms "nucleoside", "nucleotide" and "nucleic acid" are used to refer to moieties that contain not only the purine and pyrimidine bases, but also other heterocyclic bases, which have been modified. Such modifications may include methylated purines and pyrimidines, acylated purines and pyrimidines and other heterocyclic rings. Modified nucleotides and modified nucleotides also include modifications on the sugar moiety, wherein, for example, one or more hydroxyl groups may optionally be substituted with a halogen atom(s), an aliphatic group(s), etc., or may be converted into the corresponding functional groups such as ethers, amines, or the like.

The antisense polynucleotide (nucleic acid) of the present invention is RNA, DNA or a modified nucleic acid (RNA, DNA). Specific examples of the modified nucleic acid include, but are not limited to, sulfur and thiophosphate derivatives of nucleic acids and those resistant to degradation of polynucleoside amides or oligonucleoside amides. The antisense nucleic acids of the present invention can be modified preferably based on the following design, that is, by increasing the intracellular stability of the antisense nucleic acid, increasing the cell permeability of the antisense nucleic acid, increasing the affinity of the nucleic acid to the targeted sense strand to a higher level, or minimizing the toxicity, if any, of the antisense nucleic acid.

Many of such modifications are known in the art, as disclosed in J. Kawakami, et al., Pharm. Tech. Japan, Vol. 8, p. 247, 1992; Vol. 8, p. 395, 1992; S. T. Crooke, et al. ed., Antisense Research and Applications, CRC Press, 1993; etc.

The antisense nucleic acids of the present invention may contain altered or modified sugars, bases or linkages, may also be provided in a specialized form such as liposomes or microspheres, may be applied to gene therapy, or may be provided in combination with attached moieties. Such attached moieties include polycations such as polylysine that act as charge neutralizers of the phosphate backbone, or hydrophobic moieties such as lipids (e.g., phospholipids, cholesterols, etc.) that enhance the interaction with cell membranes or increase uptake of the nucleic acid. Preferred examples of the lipids to be attached are cholesterols or derivatives thereof (e.g., cholesteryl chloroformate, cholic acid, etc.). These moieties may be attached to the polynucleotide at the 3' or 5' ends thereof and may also be attached thereto through a base, sugar, or intramolecular nucleoside linkage. Other groups may be capping groups specifically placed at the 3' or 5' ends of the nucleic acid to prevent degradation by nucleases such as exonuclease, RNase, etc. Such capping groups include, but are not limited to, hydroxyl protecting groups known in the art, including glycols such as polyethylene glycol, tetraethylene glycol and the like.

The inhibitory activity of the antisense nucleic acid can be examined using the transformant of the present invention, the gene expression system of the present invention in vivo and in vitro, or a translation system of G protein conjugated receptor protein in vivo and in vitro. The nucleic acid itself can be applied to cells by a variety of publicly known methods.

The siRNA to the polynucleotide of the present invention is a double-stranded RNA comprising a part of the RNA encoding FPRL1 and its complementary RNA.

The siRNA can be designed based on the sequence of the polynucleotide of the present invention and manufactured by modifications of publicly known methods (e.g., Nature, 411, 494-498, 2001).

The ribozyme containing a part of the RNA encoding FPRL1 can be designed based on the sequence of the polynucleotide of the present invention and manufactured by modifications of publicly known methods (e.g., Alfred S. Lewin and William W. Hauswirth, TRENDS in Molecular Medicine, Volume 7, Issue 5, Pages 221-228, 2001). For example, it can be manufactured by replacing a part of ribozyme publicly known with a part of the RNA encoding FPRL1. The part of RNA encoding FPRL1 includes a portion in the vicinity of the consensus sequence NUX (wherein N represents all bases and X represents a base other than G), which may be cleaved with by ribozyme publicly known.

The DNA encoding the partial peptide of the present invention may be any DNA insofar as it comprises the base sequence encoding the partial peptide of the present invention described above. The DNA may be any of genomic DNA, genomic DNA library, cDNA derived from the cells and tissues described above, cDNA library derived from the cells and tissues described above, and synthetic DNA. The vector to be used for the library may be any of bacteriophage, plasmid, cosmid and phagemid. The DNA may also be directly amplified by reverse transcriptase polymerase chain reaction (hereinafter abbreviated as RT-PCR) using the mRNA fraction prepared from the cells and tissues described above.

Specifically, the DNA encoding the partial peptide of the present invention may be, for example, (1) DNA having a partial base sequence of DNA having the base sequence represented by SEQ ID NO: 3, SEQ ID NO: 5 or SEQ ID NO: 7, or (2) DNA having a base sequence hybridizable to the base sequence represented by SEQ ID NO: 3, SEQ ID NO: 5 or SEQ ID NO: 7, under highly stringent conditions and having a partial base sequence of DNA encoding a receptor protein having-the activities substantially equivalent to those (e.g., a ligand binding activity, a signal transduction activity, etc.) of FPRL1 (human-derived FPRL1, rat-derived FPRL1 or mouse FPRL2) consisting of the amino acid sequence represented by SEQ ID NO: 2, SEQ ID NO: 4 or SEQ ID NO: 6.

The DNA hybridizable to the base sequence represented by SEQ ID NO: 3, SEQ ID NO: 5 or SEQ ID NO: 7 may be, for example, DNA containing a base sequence having at least about 85% homology, preferably at least about 90% homology and more preferably at least about 95% homology to the base sequence represented by SEQ ID NO: 3, SEQ ID NO: 5 or SEQ ID NO: 7.

The homology among the base sequences can be calculated using homology calculation algorism NCBI BLAST (National Center for Biotechnology Information Basic Local Alignment Search Tool) under the following conditions: expected value=10; gap is allowable; filtering=ON; match score=1; mismatch score=−3.

The method and conditions for hybridization is the same as described above.

For cloning of the DNA that completely encodes FPRL1 of the present invention or its partial peptide (hereinafter sometimes collectively referred to as FPRL1 of the present invention), the DNA may be either amplified by PCR using synthetic DNA primers having a part of the base sequence of FPRL1 of the present invention, or the DNA inserted into an appropriate vector can be selected by hybridization with a labeled DNA fragment or synthetic DNA that encodes a part or entire region of FPRL1 of the present invention. The hybridization can be carried out, for example, according to the method described in Molecular Cloning, 2nd, J. Sambrook et al., Cold Spring Harbor Lab. Press, 1989. The hybridization may also be performed using commercially available library in accordance with the protocol described in the attached instructions.

Conversion of the base sequence of the DNA can be effected by publicly known methods such as the ODA-LA PCR method, the gapped duplex method or the Kunkel method or its modification by using PCR or a publicly known kit available as Mutan™-super Express Km (Takara Shuzo Co., Ltd.) or Mutan™-K (Takara Shuzo Co., Ltd.).

The cloned DNA encoding FPRL1 can be used as it is, depending upon purpose or if desired after digestion with a restriction enzyme or after addition of a linker thereto. The DNA may have ATG as a translation initiation codon at the 5' end thereof and may further have TAA, TGA or TAG as a translation termination codon at the 3' end thereof. These translation initiation and termination codons may also be added by using an appropriate synthetic DNA adapter.

The expression vector for FPRL1 of the present invention can be manufactured, for example, by (a) excising the desired DNA fragment from the DNA encoding FPRL1 of the present invention, and then (b) ligating the DNA fragment with an appropriate expression vector downstream from a promoter in the vector.

Examples of the vector include plasmids derived form *E. coli* (e.g., pBR322, pBR325, pUC12, pUC13), plasmids derived from Bacillus subtilis (e.g., pUB110, pTP5, pC194), plasmids derived from yeast (e.g., pSH19, pSH15), bacteriophages such as λ phage, etc., animal viruses such as retrovirus, vaccinia virus, baculovirus, etc. as well as pA1-11, pXT1, pRc/CMV, pRc/RSV, pcDNAI/Neo, and the like.

The promoter used in the present invention may be any promoter if it matches well with a host to be used for gene expression. In the case of using animal cells as the host, examples of the promoter include SRα promoter, SV40 promoter, LTR promoter, CMV promoter, HSV-TK promoter, or the like.

Among them, CMV promoter or SRα promoter is preferably used. Where the host is bacteria of the genus *Escherichia*, preferred examples of the promoter include trp promoter, lac promoter, recA promoter, $\lambda P_L$ promoter, 1pp promoter and the like. In the case of using bacteria of the genus *Bacillus* as the host, preferred example of the promoter are SPO1 promoter, SPO2 promoter and penP promoter. When yeast is used as the host, preferred examples of the promoter are PHO5 promoter, PGK promoter, GAP promoter and ADH promoter. When insect cells are used as the host, preferred examples of the promoter include polyhedrin prompter and P10 promoter.

In addition to the foregoing examples, the expression vector may further optionally contain an enhancer, a splicing signal, a polyA addition signal, a selection marker, SV40 replication origin (hereinafter sometimes abbreviated as SV40ori) and the like. Examples of the selection marker include dihydrofolate reductase (hereinafter sometimes abbreviated as dhfr) gene [methotrexate (MTX) resistance], ampicillin resistant gene (hereinafter sometimes abbreviated as Amp$^r$), neomycin resistant gene (hereinafter sometimes abbreviated as Neo$^r$, G418 resistance), or the like. In particular, when dhfr gene is used as the selection marker in CHO (dhfr$^-$) cells, selection can also be made on thymidine free media.

If necessary and desired, a signal sequence that matches with a host is added to the N-terminus of the receptor protein of the present invention. Examples of the signal sequence that can be used are PhoA signal sequence, OmpA signal sequence, etc. in the case of using bacteria of the genus *Escherichia* as the host; α-amylase signal sequence, subtilisin signal sequence, etc. in the case of using bacteria of the genus *Bacillus* as the host; MFα signal sequence, SUC2 signal sequence, etc. in the case of using yeast as the host; and insulin signal sequence, α-interferon signal sequence, antibody molecule signal sequence, etc. in the case of using animal cells as the host, respectively.

Using the vector comprising the DNA encoding FPRL1 of the present invention thus constructed, transformants can be manufactured.

Examples of the host, which may be employed, are bacteria belonging to the genus *Escherichia*, bacteria belonging to the genus *Bacillus*, yeast, insect cells, insects and animal cells, etc.

Specific examples of the bacteria belonging to the genus *Escherichia* include *Escherichia coli* K12 DH1 (Proc. Natl. Acad. Sci. U.S.A., 60, 160 (1968)), JM103 (Nucleic Acids Research, 9, 309 (1981)), JA221 (Journal of Molecular Biology, 120, 517 (1978)), HB101 (Journal of Molecular Biology, 41, 459 (1969)), C600 (Genetics, 39, 440 (1954)), etc.

Examples of the bacteria belonging to the genus *Bacillus* include *Bacillus subtilis* MI114 (Gene, 24, 255 (1983)), 207-21 (Journal of Biochemistry, 95, 87 (1984)), etc.

Examples of yeast include *Saccharomyces cereviseae* AH22, AH22R⁻, NA87-11A, DKD-5D, 20B-12, *Schizosaccharomyces pombe* NCYC1913, NCYC2036, *Pichia pastoris*, etc.

Examples of insect cells include, for the virus AcNPV, *Spodoptera frugiperda* cells (Sf cells), MG1 cells derived from mid-intestine of *Trichoplusia ni*, High Five™ cells derived from egg of *Trichoplusia ni*, cells derived from *Mamestra brassicae*, cells derived from Estigmena acrea, etc.; and for the virus BmNPV, Bombyx mori N cells (BmN cells), etc. are used. Examples of the Sf cell which can be used are Sf9 cells (ATCC CRL1711) and Sf21 cells (both cells are described in Vaughn, J. L. et al., In Vivo, 13, 213-217 (1977).

As the insect, for example, a larva of *Bombyx mori* can be used (Maeda, et al., Nature, 315, 592 (1985)).

Examples of animal cells include monkey cells COS-7, Vero, Chinese hamster cells CHO (hereinafter referred to as CHO cells), dhfr gene deficient Chinese hamster cells CHO (hereinafter simply referred to as CHO (dhfr⁻) cell), mouse L cells, mouse AtT-20, mouse myeloma cells, rat GH3, human FL cells, etc.

Bacteria belonging to the genus *Escherichia* can be transformed, for example, by the method described in Proc. Natl. Acad. Sci. U.S.A., 69, 2110 (1972) or Gene, 17, 107 (1982).

Bacteria belonging to the genus *Bacillus* can be transformed, for example, by the method described in Molecular & General Genetics, 168, 111 (1979).

Yeast can be transformed, for example, by the method described in Methods in Enzymology, 194, 182-187 (1991), Proc. Natl. Acad. Sci. U.S.A., 75, 1929 (1978), etc.

Insect cells or insects can be transformed, for example, according to the method described in Bio/Technology, 6, 47-55 (1988), etc.

Animal cells can be transformed, for example, according to the method described in Saibo Kogaku (Cell Engineering), extra issue 8, Shin Saibo Kogaku Jikken Protocol (New Cell Engineering Experimental Protocol), 263-267 (1995), published by Shujunsha, or Virology, 52, 456 (1973).

Thus, the transformant transformed with the expression vector comprising the DNA encoding FPRL1 can be obtained.

Where the host is bacteria belonging to the genus *Escherichia* or the genus *Bacillus*, the transformant can be appropriately incubated in a liquid medium which contains materials required for growth of the transformant such as carbon sources, nitrogen sources, inorganic materials, and so on. Examples of the carbon sources include glucose, dextrin, soluble starch, sucrose, etc. Examples of the nitrogen sources include inorganic or organic materials such as ammonium salts, nitrate salts, corn steep liquor, peptone, casein, meat extract, soybean cake, potato extract, etc. Examples of the inorganic materials are calcium chloride, sodium dihydrogenphosphate, magnesium chloride, etc. In addition, yeast extract, vitamins, growth promoting factors etc. may also be added to the medium. Preferably, pH of the medium is adjusted to about 5 to about 8.

A preferred example of the medium for incubation of the bacteria belonging to the genus *Escherichia* is M9 medium supplemented with glucose and Casamino acids (Miller, Journal of Experiments in Molecular Genetics, 431-433, Cold Spring Harbor Laboratory, New York, 1972). If necessary and desired, a chemical such as 3β-indolylacrylic acid can be added to the medium to activate the promoter efficiently.

Where the bacteria belonging to the genus *Escherichia* are used as the host, the transformant is usually cultivated at about 15° C. to about 43° C. for about 3 hours to about 24 hours. If necessary and desired, the culture may be aerated or agitated.

Where the bacteria belonging to the genus *Bacillus* are used as the host, the transformant is cultivated generally at about 30° C. to about 40° C. for about 6 hours to about 24 hours. If necessary and desired, the culture can be aerated or agitated.

Where yeast is used as the host, the transformant is cultivated, for example, in Burkholder's minimal medium (Bostian, K. L. et al., Proc. Natl. Acad. Sci. U.S.A., 77, 4505 (1980)) or in SD medium supplemented with 0.5% Casamino acids (Bitter, G. A. et al., Proc. Natl. Acad. Sci. U.S.A., 81, 5330 (1984)). Preferably, pH of the medium is adjusted to about 5 to about 8. In general, the transformant is cultivated at about 20° C. to about 35° C. for about 24 hours to about 72 hours. If necessary and desired, the culture can be aerated or agitated.

Where insect cells or insects are used as the host, the transformant is cultivated in, for example, Grace's Insect Medium (Grace, T. C. C., Nature, 195, 788 (1962)) to which an appropriate additive such as inactivated 10% bovine serum is added. Preferably, pH of the medium is adjusted to about 6.2 to about 6.4. Normally, the transformant is cultivated at about 27° C. for about 3 days to about 5 days and, if necessary and desired, the culture can be aerated or agitated.

Where animal cells are employed as the host, the transformant is cultivated in, for example, MEM medium containing about 5% to about 20% fetal bovine serum (Science, 122, 501 (1952)), DMEM medium (Virology, 8, 396 (1959)), RPMI 1640 medium (The Journal of the American Medical Association, 199, 519 (1967)), 199 medium (Proceeding of the Society for the Biological Medicine, 73, 1 (1950)), etc. Preferably, pH of the medium is adjusted to about 6 to about 8. The transformant is usually cultivated at about 30° C. to about 40° C. for about 15 hours to about 60 hours and, if necessary and desired, the culture can be aerated or agitated.

As described above, FPRL1 of the present invention can be produced in the cell, in the cell membrane or out of the cell of the transformant.

FPRL1 of the present invention can be separated and purified from the culture described above by the following procedures.

When FPRL1 of the present invention is extracted from the culture or cells after cultivation, the transformants or cells are collected by a publicly known method and suspended in an appropriate buffer. The transformants or cells are then disrupted by publicly known methods such as ultrasonication, treatment with lysozyme and/or freeze-thaw cycling, followed by centrifugation, filtration, etc. Thus, the crude extract of FPRL1 of the present invention can be obtained. The buffer used for the procedures may contain a protein modifier such as urea or guanidine hydrochloride, or a surfactant such as Triton X-100™, etc. When FPRL1 is secreted in the culture, the supernatant after completion of the cultivation can be separated from the transformants or cells to collect the supernatant by a publicly known method.

FPRL1 contained in the supernatant or the extract thus obtained can be purified by appropriately combining the publicly known methods for separation and purification. Such publicly known methods for separation and purification include a method utilizing difference in solubility such as salting out, solvent precipitation, etc.; a method utilizing mainly difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing electrophoresis; and the like.

When FPRL1 thus obtained is in a free form, it can be converted into the salt by publicly known methods or modifications thereof. On the other hand, when FPRL1 is obtained in the form of a salt, it can be converted into the free form or in the form of a different salt by publicly known methods or modifications thereof.

FPRL1 produced by the recombinant can be treated, prior to or after the purification, with an appropriate protein-modifying enzyme so that FPRL1 can be appropriately modified to partially remove a polypeptide. Examples of the protein-modifying enzyme include trypsin, chymotrypsin, arginyl endopeptidase, protein kinase, glycosidase or the like.

The activity of the thus produced FPRL1 of the present invention or salts thereof can be determined by a test binding to a labeled ligand (FPRL1 ligand), by an enzyme immunoassay using a specific antibody, or the like.

Antibodies against FPRL1 of the present invention may be any of polyclonal antibodies and monoclonal antibodies as long as they are capable of recognizing FPRL1 of the present invention.

The antibodies against FPRL1 of the present invention may be manufactured by publicly known methods for manufacturing antibodies or antisera, using as antigens FPRL1 of the present invention.

[Preparation of Monoclonal Antibody]
(a) Preparation of Monoclonal Antibody-Producing Cells FPRL1 of the present invention is administered to mammals either solely or together with carriers or diluents to the site where the production of antibody is possible by the administration. In order to potentiate the antibody productivity upon the administration, complete Freund's adjuvants or incomplete Freund's adjuvants may be administered. The administration is usually carried out once in every two to six weeks and 2 to 10 times in total. Examples of the mammals used are monkeys, rabbits, dogs, guinea pigs, mice, rats, sheep and goats, with mice and rats being preferred.

In the preparation of monoclonal antibody-producing cells, warm-blooded animals, e.g., mice, immunized with an antigen wherein the antibody titer is noted are selected, then the spleen or lymph node is collected after 2 to 5 days from the final immunization and antibody-producing cells contained therein are fused with myeloma cells from an animal of the same or different species to give monoclonal antibody-producing hybridomas. Measurement of the antibody titer in antisera may be made, for example, by reacting a labeled form of the receptor protein, which will be described later, with the antiserum followed by assaying the binding activity of the labeling agent bound to the antibody. The fusion may be operated, for example, by the known Kohler, and Milstein method (Nature, 256, 495-497, 1975). Examples of the fusion accelerator are polyethylene glycol (PEG), Sendai virus, etc., among which PEG is preferably employed.

Examples of the myeloma cells used include NS-1, P3U1, SP2/0 etc., among which P3U1 is preferably employed. A preferred ratio of the count of the antibody-producing cells used (spleen cells) to the count of myeloma cells is within a range of approximately 1:1 to 20:1. When PEG (preferably, PEG 1000 to PEG 6000) is added in a concentration of approximately 10 to 80% followed by incubation at about 20° C. to about 40° C., preferably at about 30° C. to about 37° C. for about 1 to about 10 minutes, efficient cell fusion can be carried out.

Various methods can be used for screening of a monoclonal antibody-producing hybridoma. Examples of such methods include a method which comprises adding the supernatant of hybridoma to a solid phase (e.g., microplate) adsorbed with the receptor protein as an antigen directly or together with a carrier, adding an anti-immunoglobulin antibody (when mouse cells are used for the cell fusion, anti-mouse immunoglobulin antibody is used) labeled with a radioactive substance or an enzyme, or Protein A and detecting the monoclonal antibody bound to the solid phase, and a method which comprises adding the supernatant of hybridoma to a solid phase adsorbed with an anti-immunoglobulin antibody or Protein A, adding the receptor protein labeled with a radioactive substance or an enzyme and detecting the monoclonal antibody bound to the solid phase.

The monoclonal antibody can be selected by publicly known methods or by modifications of these methods. In general, the selection can be effected in a medium for animal cells supplemented with HAT (hypoxanthine, aminopterin and thymidine). Any selection and growth medium can be employed as far as the hybridoma can grow therein. For example, RPMI 1640 medium containing 1% to 20%, preferably 10% to 20% fetal bovine serum, GIT medium (Wako Pure Chemical Industries, Ltd.) containing 1% to 10% fetal bovine serum, a serum-free medium for cultivation of a hybridoma (SFM-101, Nissui Seiyaku Co., Ltd.) and the like can be used for the selection and growth medium. The cultivation is carried out generally at 20° C. to 40° C., preferably at about 37° C., for 5 days to 3 weeks, preferably 1 to 2 weeks. The cultivation can be conducted normally in 5% $CO_2$. The antibody titer of the culture supernatant of hybridomas can be determined as in the assay for the antibody titer in antisera described above.

(b) Purification of Monoclonal Antibody

Separation and purification of a monoclonal antibody can be carried out by methods applied to conventional separation and purification of immunoglobulins, as in the conventional methods for separation and purification of polyclonal antibodies [e.g., salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with an activated adsorbent such as an antigen-binding solid phase, Protein A, Protein G etc. and dissociating the binding to obtain the antibody].

[Preparation of Polyclonal Antibody]

The polyclonal antibody of the present invention can be manufactured by publicly known methods or modifications thereof. For example, an immunogen (antigen such as FPRL1) itself or a complex prepared from the immunogen and a carrier protein is used to immunize a mammal in a manner similar to the method described above for the manufacture of monoclonal antibodies. The product containing the antibody to FPRL1 of the present invention is collected from the immunized animal followed by separation and purification of the antibody.

In the complex of an immunogen and a carrier protein used to immunize a mammal, the type of carrier protein and the mixing ratio of a carrier to hapten may be any type and in any ratio, as long as the antibody is efficiently produced against the hapten immunized by crosslinking to the carrier. For example, bovine serum albumin, bovine thyroglobulins, keyhole limpet hemocyanin or the like is coupled to hapten in a carrier-to-hapten weight ratio of approximately 0.1 to 20, preferably about 1 to about 5.

A variety of condensing agents can be used for the coupling of a carrier to hapten. Glutaraldehyde, carbodiimide, maleimide-activated ester, activated ester reagents containing thiol group or dithiopyridyl group, etc. are used for the coupling.

The condensation product is administered to warm-blooded animals either solely or together with carriers or diluents to the site in which the antibody can be produce by the administration. In order to potentiate the antibody productivity upon the administration, complete Freund's adjuvant or incomplete Freund's adjuvant may be administered. The administration is usually made once approximately in every 2 to 6 weeks and about 3 to about 10 times in total.

The polyclonal antibody can be collected from the blood, ascites, etc., preferably from the blood of mammals immunized by the method described above.

The polyclonal antibody titer in antiserum can be assayed by the same procedure as that for the determination of serum antibody titer described above. The separation and purification of the polyclonal antibody can be carried out according to the method for the separation and purification of immunoglobulins performed as applied to the separation and purification of monoclonal antibodies described hereinabove.

FPRL1 ligand of the present invention is a peptide comprising the same or substantially the same amino acid sequence as the amino acid sequence represented by SEQ ID NO: 1, SEQ ID NO: 17, SEQ ID NO: 21 or SEQ ID NO: 23, preferably a peptide consisting of the same or substantially the same amino acid sequence as the amino acid sequence represented by SEQ ID NO: 1, SEQ ID NO: 17, SEQ ID NO: 21 or SEQ ID NO: 23.

FPRL1 ligand may be any polypeptide derived from any cells (e.g., liver cells, splenocytes, nerve cells, glial cells, pancreatic β cells, bone marrow cells, mesangial cells, Langerhans' cells, epidermal cells, epithelial cells, endothelial cells, fibroblasts, fibrocytes, myocytes, fat cells, immune cells (e.g., macrophage, T cells, B cells, natural killer cells, mast cells, neutrophil, basophil, eosinophil, monocyte), megakaryocyte, synovial cells, chondrocytes, bone cells, osteoblasts, osteoclasts, mammary gland cells or interstitial cells, the corresponding precursor cells, stem cells, cancer cells, etc.), or any tissues where such cells are present, e.g., brain or any region of the brain (e.g., olfactory bulb, amygdaloid nucleus, basal ganglia, hippocampus, thalamus, hypothalamus, cerebral cortex, medulla oblongata and cerebellum), spinal cord, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, prostate, testis, ovary, placenta, uterus, bone, cartilage, joint, skeletal muscle, etc. from human and non-human warm-blooded animals (e.g., guinea pigs, rats, mice, chickens, rabbits, swine, sheep, bovine, monkeys, etc.). FPRL1 ligand may also be a synthetic polypeptide.

The term "substantially equivalent" means that the polypeptide referred to is substantially equivalent in respect of the activities of FPRL1 ligand, for example physiological properties such as binding activity to FPRL1, intracellular signal transduction or anti-inflammatory action. Insofar as the substitution, deletion, addition or insertion of amino acids does not bring about a significant change in the physiological properties or chemical properties of the polypeptide, the polypeptide subjected to such substitution, deletion, addition or insertion is substantially the same as the peptide not having such substitution, deletion, addition or insertion. Substantially equivalent substituting amino acids in the amino acid sequence can be selected from amino acids in the class to which the amino acids to be substituted belong.

Non-polar (hydrophobic) amino acids include alanine, leucine, isoleucine, valine, proline, phenylalanine, tryptophan, methionine etc. Polar (neutral) amino acids include glycine, serine, threonine, cysteine, tyrosine, asparagine, glutamine etc. Positively charged (basic) amino acids include arginine, lysine, histidine etc. Negatively charged (acidic) amino acids include aspartic acid, glutamic acid etc.

The amino acid sequence having substantially the same amino acid sequence as the amino acid sequence represented by SEQ ID NO: 1, SEQ ID NO: 17, SEQ ID NO: 21 or SEQ ID NO: 23 is not particularly limited insofar as a polypeptide having the amino acid sequence has the activity (property) substantially equivalent to that of FPRL1 ligand consisting of the amino acid sequence represented by SEQ ID NO: 1, SEQ ID NO: 17, SEQ ID NO: 21 or SEQ ID NO: 23, and examples of the above amino acid sequence include an amino acid sequence having at least about 80% homology, preferably at least about 85% homology, more preferably at least about 90% homology, most preferably at least about 95% homology, to the amino acid sequence represented by SEQ ID NO: 1, SEQ ID NO: 17, SEQ ID NO: 21 or SEQ ID NO: 23.

The homology among the amino acid sequences can be calculated using homology calculation algorism NCBI BLAST (National Center for Biotechnology Information Basic Local Alignment Search Tool) under the following conditions: expected value=10; gap is allowable; matrix=BLOSUM62; filtering=OFF.

The substantially equivalent activity (property) described above means that the polypeptide referred to is qualitatively equivalent to FPRL1 ligand consisting of the amino acid sequence represented by SEQ ID NO: 1, SEQ ID NO: 17, SEQ ID NO: 21 or SEQ ID NO: 23 in respect of physiological properties such as binding activity to FPRL1, intracellular signal transduction or anti-inflammatory action.

More specific examples of FPRL1 ligand comprising substantially the same amino acid sequence as the amino acid sequence represented by SEQ ID NO: 1, SEQ ID NO: 17, SEQ ID NO: 21 or SEQ ID NO: 23 include a) amino acid sequences represented by SEQ ID NO: 1, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23 or SEQ ID NO: 24, wherein 1 or more amino acids (for example, 1 to 3 amino acids, preferably 1 or 2 amino acids) are deleted, b) amino acid sequences represented by SEQ ID NO: 1, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23 or SEQ ID NO: 24 to which 1 or more amino acids (for example 1 to 3 amino acids, preferably 1 or 2 amino acids) are added, c) amino acid sequences represented by SEQ ID NO: 1, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23 or SEQ ID NO: 24, wherein 1 or more amino acids (for example 1 to 3 amino acids, preferably 1 or 2 amino acids) are substituted by other amino acids, and d) polypeptides consisting of a combination of the amino acid sequences described in the above. When the amino acid sequence has undergone insertion, deletion or substitution as described above, the position of the insertion, deletion or substitution is not particularly limited.

FPRL1 ligand also includes those wherein a substituent on the side chain of an amino acid in the molecule is protected with a suitable protecting group, or conjugated peptides such as glycopeptides bound to sugar chains.

In addition, FPRL1 ligand includes those wherein an arbitrary extraneous peptide sequence (for example, FLAG, His tag, HA tag, HSV tag etc.) capable of serving as an epitope (antibody recognition site) is added to the N- or C-terminus thereof.

FPRL1 ligand is represented in accordance with the conventional way of describing peptides, that is, the N-terminus (amino terminus) at the left hand and the C-terminus (carboxyl terminus) at the right hand. In FPRL1 ligand including the peptide comprising the amino acid sequence represented by SEQ ID NO: 1, the C-terminus may be in the form of a carboxyl group (—COOH), a carboxylate (—COO$^-$), an amide (—CONH$_2$) or an ester (—COOR).

The ester group shown by R include, for example, a $C_{1-6}$ alkyl group such as methyl, ethyl, n-propyl, isopropyl, or n-butyl; a $C_{3-8}$ cycloalkyl group such as cyclopentyl, or cyclohexyl; a $C_{6-12}$ aryl group such as phenyl, or α-naphthyl; a $C_{7-14}$ aralkyl group such as a phenyl-$C_{1-2}$-alkyl group, e.g., benzyl, phenethyl, etc., or an α-naphthyl-$C_{1-2}$-alkyl group such as α-naphthylmethyl, etc. In addition, a pivaloyloxymethyl group or the like which is used widely as an ester for oral administration may also be used.

Where FPRL1 ligand has a carboxyl group (or a carboxylate) at a position other than the C-terminus, it may be amidated or esterified, and such an amide or ester is also included within FPRL1 ligand in the present specification. As the ester group herein, the same esters as those described with respect to the above C-terminal are used.

Furthermore, examples of FPRL1 ligand include variants of the above proteins, wherein the N-terminal amino group residue (e.g. methionine residue) thereof is protected with a protecting group (for example, a $C_{1-6}$ acyl group such as a $C_{1-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{1-6}$ alkanoyl group, e.g., formyl group, acetyl group, etc.), or conjugated polypeptides such as glycopolypeptides having sugar chains bound thereto. In particular, it is preferred that the amino group of methionine residue at N-terminus is protected by formyl group. In this case, further protection or modification described above may be acceptable.

Specific examples of FPRL1 ligand as follows are preferably used:

(1) Porcine FPRL1 ligand (P3) consisting of the amino acid sequence represented by SEQ ID NO: 1, in which methionine residue at the N-terminus is formylated;

(2) Human FPRL1 ligand (P3) consisting of the amino acid sequence represented by SEQ ID NO: 16, in which methionine residue at the N-terminus is formylated;

(3) Porcine FPRL1 ligand (P1) A consisting of the amino acid sequence represented by SEQ ID NO: 17, in which methionine residue at the N-terminus is formylated;

(4) Porcine FPRL1 ligand (P1) B consisting of the amino acid sequence represented by SEQ ID NO: 18, in which methionine residue at the N-terminus is formylated;

(5) Human FPRL1 ligand (P1) A consisting of the amino acid sequence represented by SEQ ID NO: 19, in which methionine residue at the N-terminus is formylated;

(6) Human FPRL1 ligand (P1) B consisting of the amino acid sequence represented by SEQ ID NO: 20, in which methionine residue at the N-terminus is formylated;

(7) Porcine FPRL1 ligand (P4) consisting of the amino acid sequence represented by SEQ ID NO: 21, in which methionine residue at the N-terminus is formylated;

(8) Human FPRL1 ligand (P4) consisting of the amino acid sequence represented by SEQ ID NO: 22, in which methionine residue at the N-terminus is formylated;

(9) Porcine FPRL1 ligand (P4) consisting of the amino acid sequence represented by SEQ ID NO: 21, in which methionine residue at the N-terminus is formylated and isoleucine residue at C-terminus is modified;

(10) Human FPRL1 ligand (P4) consisting of the amino acid sequence represented by SEQ ID NO: 22, in which methionine residue at the N-terminus is formylated and isoleucine residue at C-terminus is modified;

(11) Porcine FPRL1 ligand (P2) consisting of the amino acid sequence represented by SEQ ID NO: 23, in which methionine residue at the N-terminus is formylated; and

(12) Human FPRL1 ligand (P2) consisting of the amino acid sequence represented by SEQ ID NO: 24, in which methionine residue at the N-terminus is formylated.

P1 and P2 correspond to the N-terminal peptide of cytochrome B. P3 and P4 correspond to the N-terminal peptide of cytochrome c oxidase.

Further, for FPRL1 ligand of the present invention, as with the "peptide comprising the same or substantially the same amino acid sequence as the amino acid sequence represented by SEQ ID NO: 1, SEQ ID NO: 17, SEQ ID NO: 21 or SEQ ID NO: 23" described above, any formylated amino acid or formylated amino acid residue at the N-terminus (in this regard, excluding formylated MLP derived from bacteria, N-terminally formylated NADH dehydrogenase, or partial peptides thereof) may be used. The "peptide" moiety of the "peptide wherein the amino acid residue at the N-terminus is formylated" may be a peptide derived from the living body or synthetic peptide. Number of amino acids for the "peptide" moiety is usually 2-50 residues, preferably 2-20 residues.

As salts of FPRL1 ligand, use is made of salts with physiologically acceptable acids (e.g., inorganic acids or organic acids) or bases (e.g., alkali metal salts), preferably physiologically acceptable acid addition salts. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

FPRL1 ligand may be manufactured from the human and non-human warm-blooded animal tissues or cells described above by a publicly known purification method for polypeptide, or may also be manufactured by the peptide synthesis method, which will be described below.

When FPRL1 ligand is manufactured from human and non-human mammalian tissues or cells, the human or non-human mammalian tissues or cells are homogenized, then extracted with an acid or the like, and the extract is isolated and purified by a combination of chromatography techniques such as reverse phase chromatography, ion exchange chromatography, and the like.

To synthesize FPRL1 ligand or amides thereof, commercially available resins that are used for polypeptide synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenyl acetamidomethyl resin, polyacrylamide resin, 4-(2', 4'-dimethoxyphenylhydroxymethyl)phenoxy resin, 4-(2',4'-dimethoxyphenyl-Fmoc-aminoethyl) phenoxy resin, etc. Using these resins, amino acids in which α-amino groups and functional groups on the side chains are appropriately protected are condensed on the resin in the order of the sequence of the objective polypeptide according to various condensation methods publicly known in the art. At the end of the reaction, the polypeptide is cut out from the resin and at the same time, the protecting groups are removed. Then, intramolecular disulfide bond-forming reaction is performed in a highly diluted solution to obtain the objective polypeptide or its amides.

For condensation of the protected amino acids described above, a variety of activation reagents for polypeptide synthesis may be used, and carbodiimides are particularly preferable. Examples of such carbodiimides include DCC, N,N'-diisopropylcarbodiimide, N-ethyl-N'-(3-dimethylaminopropyl)carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents used to activate the protected amino acids or condense with the resin may be chosen from solvents known to be usable for polypeptide condensation reactions. Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxane, tetrahydrofuran, etc.; nitriles such as acetonitrile, propionitrile, etc.; esters such as methyl acetate, ethyl acetate, etc.; and appropriate mixtures of these solvents. The reaction temperature is appropriately chosen from the range known to be applicable to polypeptide binding reactions and is usually selected in the range of approximately −20° C. to 50° C. The activated amino acid derivatives are used generally in an excess of 1.5 to 4 times. The condensation is examined by a test using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole to cancel any possible adverse effect on the subsequent reaction.

Examples of the protecting groups used to protect the amino groups of the starting compounds include Z, Boc, t-pentyloxycarbonyl, isobomyloxycarbonyl, 4-methoxybenzyloxycarbonyl, Cl—Z, Br—Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (in the form of linear, branched or cyclic alkyl esters of the alkyl moiety such as methyl, ethyl, propyl, butyl, t-butyl, cyclopentyl, cyclohexyl, cycloheptyl, cyclooctyl, 2-adamantyl, etc.), aralkyl esterification (e.g., esterification in the form of benzyl ester, 4-nitrobenzyl ester, 4-methoxybenzyl ester, 4-chlorobenzyl ester, benzhydryl ester, etc.), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups appropriately used for the esterification include a lower ($C_{1-6}$) alkanoyl group, such as acetyl group, an aroyl group such as benzoyl group, and a group derived from carbonic acid, such as benzyloxycarbonyl group, ethoxycarbonyl group, etc. Examples of a group appropriately used for the etherification include benzyl group, tetrahydropyranyl group, t-butyl group, etc.

Examples of groups for protecting the phenolic hydroxyl group of tyrosine include Bzl, $Cl_2$-Bzl, 2-nitrobenzyl, Br—Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups in the starting compounds include the corresponding acid anhydrides, azides, activated esters (esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)). As the activated amino acids in which the amino groups are activated in the starting material, the corresponding phosphoric amides are employed.

To eliminate (split off) the protecting groups, there are used catalytic reduction under hydrogen gas flow in the presence of a catalyst such as Pd-black or Pd-carbon; acid treatment with anhydrous hydrogen fluoride, methanesulfonic acid, trifluoromethanesulfonic acid or trifluoroacetic acid, or a mixture solution of these acids; treatment with a base such as diisopropylethylamine, triethylamine, piperidine or piperazine; and reduction with sodium in liquid ammonia. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol or 1,2-ethanedithiol. Furthermore, 2,4-dinitrophenyl group used as the protecting group for the imidazole of histidine is removed by treatment with thiophenol. Formyl group used as the protecting group of the indole of tryptophan is eliminated by the aforesaid acid treatment in the presence of 1,2-ethanedithiol or 1,4-butanedithiol, as well as by treatment with an alkali such as a dilute sodium hydroxide solution and dilute ammonia.

Protection of functional groups that should not be involved in the reaction of the starting materials, protecting groups, elimination of the protecting groups and activation of functional groups involved in the reaction may be appropriately selected from publicly known groups and publicly known means.

In an alternative method for obtaining the amides of FPRL1 ligand, for example, the α-carboxyl group of the carboxy terminal amino acid is first protected by amidation, and the peptide (polypeptide) chain is then extended from the amino group side to a desired length. Thereafter, a polypeptide in which only the protecting group of the N-terminal α-amino group in the peptide chain has been eliminated from the polypeptide and a polypeptide in which only the protecting group of the C-terminal carboxyl group has been eliminated are prepared. The two polypeptides are condensed in a mixture of the solvents described above. The details of the condensation reaction are the same as described above. After the protected polypeptide obtained by the condensation is purified, all the protecting groups are eliminated by the method described above to give the desired crude polypeptide. This crude polypeptide is purified by various known purification means. Lyophilization of the major fraction gives the amide of desired FPRL1 ligand.

To prepare esterified FPRL1 ligand, for example, the α-carboxyl group of the carboxy terminal amino acid is condensed with a desired alcohol to prepare the amino acid ester, which is followed by procedure similar to the preparation of the amidated FPRL1 ligand above to give the ester form of the desired polypeptide.

Alternatively, FPRL1 ligand can be manufactured by publicly known methods for peptide synthesis. For the methods for peptide synthesis, for example, either solid phase synthesis or liquid phase synthesis may be used. That is, the partial peptide or amino acids that can construct FPRL1 ligand are condensed with the remaining part. Where the product contains protecting groups, these protecting groups are removed to give the desired peptide. Publicly known methods for condensation and elimination of the protecting groups are described in (a) to (e) below:
(a) M. Bodanszky & M. A. Ondetti: Peptide Synthesis, Interscience Publishers, New York (1966);
(b) Schroeder & Luebke: The Peptide, Academic Press, New York (1965);
(c) Nobuo Izumiya, et al.: Peptide Gosei-no-Kiso to Jikken (Basics and experiments of peptide synthesis), published by Maruzen Co. (1975);
(d) Haruaki Yajima & Shunpei Sakakibara: Seikagaku Jikken Koza (Biochemical Experiment) 1, Tanpakushitsu no Kagaku (Chemistry of Proteins) IV, 205 (1977); and
(e) Haruaki Yajima, ed.: Zoku Iyakuhin no Kaihatsu (A sequel to Development of Pharmaceuticals), Vol. 14, Peptide Synthesis, published by Hirokawa Shoten.

After completion of the reaction, the product may be isolated and purified by a combination of conventional purification methods such as solvent extraction, distillation, column chromatography, liquid chromatography and recrystallization to give the polypeptide or the partial peptide of the present invention. When the polypeptide obtained by the above methods is in a free form, the polypeptide can be converted into an appropriate salt by a publicly known method or a modification thereof; when the partial peptide is obtained in a salt form, it can be converted into a free form or another salt by a publicly known method or a modification thereof.

Antibody against FPRL1 ligand can be manufactured in a manner similar to the antibody against FPRL1 of the present invention.

FPRL1 ligand participate in diseases such as inflammation., and thus FPRL1 ligand (or DNA encoding FPRL1 ligand), FPRL1, DNA encoding FPRL1 (hereinafter sometimes referred to as the DNA of the present invention), the antibody against FPRL1 ligand or FPRL1 (hereinafter sometimes referred to as the antibody of the present invention), the antisense DNA to the DNA of the present invention (hereinafter sometimes referred to as the antisense DNA of the present invention) have the following uses.
(1) Prophylactic/Therapeutic Agent for Diseases Associated with Dysfunction of FPRL1 of the Present Invention FPRL1 ligand possesses, for example, a cell migration stimulating activity (e.g., a stimulating activity for migration of cells such as neutrophil, macrophage and microglia). In addition, where FPRL1 ligand, FPRL1 or the polynucleotide (for example, DNA etc.) encoding the same is abnormal or deficient, or where the expression level of the same is abnormally reduced or promoted, there occur a variety of diseases involving asthma, allergosis, inflammation, inflammatory eye diseases, Assison's disease, autoimmune hemolytic anemia, systemic lupus erythematosus, psoriasis, rheumatism, central nervous system damage (e.g., cerebrovascular diseases such as brain hemorrhage and brain infarction, head injury, cord injury, brain edema and multiple sclerosis), neurodegenerative diseases (e.g., Alzheimer's disease, Parkinson's disease, amyotrophic lateral sclerosis (ALS) and encephalopathy associated with AIDS), cerebral meningitis, diabetes mellitus, arthritis (e.g., arthritis rheumatoides, osteoarthritis, rheumatoid spondylitis, gouty arthritis and synovial inflammation), blood poisoning (e.g., sepsis, septic shock, endotoxic shock, gram-negative sepsis and toxic-shock syndrome), inflammatory bowel diseases (e.g., Crohn's disease and ulcerative colitis), inflammatory pulmonary diseases (e.g., chronic pneumonia, pulmonary silicosis, pulmonary sarcoidosis and lung tuberculosis), cachexia (e.g., infectious cachexia, canoerous cachexia and cachexia associated with acquired immunodeficiency syndrome (AIDS)), arterial sclerosis, Creutzfeldt-Jakob disease, viral infection (e.g., viral infection by cytomegalovirus, influenza virus, herpes virus and the like), angina cordis, cardiac infarction, congestive failure, hepatitis, exaggerated immune response after medical transplantation, dialysis hypotension, diffuse intravascular coagulation syndrome, and immunodeficiency.

Accordingly, when the physiological activity of FPRL1 ligand cannot be expected in a patient (deficiency of FPRL1 ligand or FPRL1) due to a decrease in FPRL1 ligand or FPRL1 in the living body, the activity of the FPRL1 ligand can be exhibited by (i) administering FPRL1 ligand or FPRL1 to the patient thereby supplementing the amount of the FPRL1 ligand or FPRL1 or (ii) by increasing the amount of FPRL1 ligand or FPRL1 in the patient through (a) administration of the DNA encoding FPRL1 to express the same in the patient or (b) insertion and expression of the DNA encoding FPRL1 in the objective cells to transplant the cells to the patient, whereby the activity of the FPRL1 ligand can be sufficiently exhibited.

Accordingly, (a) FPRL1 ligand, (b) FPRL1, or (c) the DNA encoding FPRL1 may be use as a medicament such as prophylactic/therapeutic agent for diseases associated with dysfunction of FPRL1 ligand or FPRL1.

Specifically, FPRL1 ligand, FPRL1 or the DNA of the present invention can be used as, for example, a cell migration irritant (or a cell migration accerelator) and an anti-inflammatory agent. Further, they can be used as a low toxic and safe medicament such as a prophylactic/therapeutic agent for diseases involving asthma, allergosis, inflammation, inflammatory eye diseases, Assison's disease, autoimmune hemolytic anemia, systemic lupus erythematosus, psoriasis, rheumatism, central nervous system damage (e.g., cerebrovascular diseases such as brain hemorrhage and brain infarction, head injury, cord injury, brain edema and multiple sclerosis), neurodegenerative diseases (e.g., Alzheimer's disease, Parkinson's disease, amyotrophic lateral sclerosis (ALS) and encephalopathy associated with AIDS), cerebral meningitis, diabetes mellitus, arthritis (e.g., arthritis rheumatoides, osteoarthritis, rheumatoid spondylitis, gouty arthritis and synovial inflammation), blood poisoning (e.g., sepsis, septic shock, endotoxic shock, gram-negative sepsis and toxic-shock syndrome), inflammatory bowel diseases (e.g., Crohn's disease and ulcerative colitis), inflammatory pulmonary diseases (e.g., chronic pneumonia, pulmonary silicosis, pulmonary sarcoidosis and lung tuberculosis), cachexia (e.g., infectious cachexia, canoerous cachexia and cachexia associated with acquired immunodeficiency syndrome (AIDS)), arterial sclerosis, Creutzfeldt-Jakob disease, viral infection (e.g., viral infection by cytomegalovirus, influenza virus, herpes virus and the like), angina cordis, cardiac infarction, congestive failure, hepatitis, exaggerated immune response after medical transplantation, dialysis hypotension, diffuse intravascular coagulation syndrome, and immunodeficiency.

When FPRL1 ligand or FPRL1 is used as the prophylactic/therapeutic agents supra, FPRL1 ligand or FPRL1 can be prepared into a pharmaceutical composition in a conventional manner.

On the other hand, where the DNA of the present invention is used as the prophylactic/therapeutic agents described above, the DNA itself is administered; alternatively, the DNA is inserted into an appropriate vector such as retrovirus vector, adenovirus vector, adenovirus-associated virus vector, etc. and then administered in a conventional manner. The DNA of the present invention may also be administered as naked DNA, or with adjuvants to assist its uptake by gene gun or through a catheter such as a catheter with a hydrogel.

For example, (a) FPRL1 ligand, (b) FPRL1 or (c) the DNA of the present invention can be used orally in the form of tablets which may be sugar coated if necessary and desired, capsules, elixirs, microcapsules etc., or parenterally in the form of injectable preparations such as a sterile solution and a suspension in water or with other pharmaceutically acceptable liquid. These preparations can be manufactured for example by mixing (a) FPRL1 ligand, (b) FPRL1 or (c) the DNA of the present invention with a physiologically acceptable known carrier, a flavoring agent, an excipient, a vehicle, an antiseptic agent, a stabilizer, a binder, etc. in a unit dosage form required in a generally accepted manner that is applied to making pharmaceutical preparations. The active ingredient in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin, alginic acid, etc., a lubricant such as magnesium stearate, a sweetening agent such as sucrose, lactose or saccharin, and a flavoring agent such as peppermint, akamono oil or cherry. When the unit dosage is in the form of capsules, liquid carriers such as oils and fats may further be used together with the additives described above. A sterile composition for injection may be formulated according to a conventional manner used to make pharmaceutical compositions, e.g., by dissolving or suspending the active ingredient in a vehicle such as water for injection, with a naturally occurring vegetable oil such as sesame oil, coconut oil, etc. to prepare the pharmaceutical composition. Examples of an aqueous medium for injection include physiological saline and an isotonic solution containing glucose and other auxiliary agents (e.g., D-sorbitol, D-mannitol, sodium chloride, etc.) and may be used in combination with an appropriate solubilizer such as an alcohol (e.g., ethanol or the like), a polyalcohol (e.g., propylene glycol and polyethylene glycol), a nonionic surfactant (e.g., polysorbate 80™ and HCO-50), etc. Examples of the oily medium include sesame oil, soybean oil, etc., which may also be used in combination with a solubilizer such as benzyl benzoate, benzyl alcohol, etc.

The prophylactic/therapeutic agent may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus prepared liquid for injection is normally filled in an appropriate ampoule.

The thus obtained pharmaceutical preparation is safe and low toxic, and can thus be administered to, for example, humans and mammals (e.g., rat, mouse, rabbit, sheep, swine, bovine, cat, dog, monkey etc.)

The doses of FPRL1 ligand may vary depending on subject to be administered, target organ, symptom, administration method, etc. When the ligand is orally administered, the ligand is administered to a patient with inflammation (as 60 kg) generally in a daily dose of approximately 0.1 to 100 mg, preferably approximately 1.0 to 50 mg, more preferably approximately 1.0 to 20 mg. When the ligand is parenterally administered, a single dose may vary depending on subject to be administered, target organ, symptom, administration method, etc. When the ligand is administered in the form of an injection to a patient with inflammation (as 60 kg), it is convenient to administer the ligand by intravenous injection generally in a daily dose of approximately 0.01 to 30 mg, preferably approximately 0.1 to 20 mg, more preferably approximately 0.1 to 10 mg. For other animal species, the corresponding dose as converted per 60 kg weight can be administered.

The dose of the DNA of the present invention may vary depending on subject to be administered, target organ, symptom, administration method, etc. When the DNA is orally administered, the DNA is administered to a patient with inflammation (as 60 kg) generally in a daily dose of approximately 0.1 to 100 mg, preferably approximately 1.0 to 50 mg, more preferably approximately 1.0 to 20 mg. When the DNA is parenterally administered, a single dose of the DNA may vary depending on subject to be administered, target organ, symptom, administration method, etc. When the DNA is administered in the form of an injection to a patient with inflammation (as 60 kg), it is convenient to administer the protein by intravenous injection generally in a daily dose of approximately 0.01 to 30 mg, preferably approximately 0.1 to 20 mg, more preferably approximately 0.1 to 10 mg. For other animal species, the corresponding dose as converted per 60 kg weight can be administered.

(2) Gene Diagnostic Agent

By using the DNA or antisense DNA of the present invention as a probe, an abnormality (gene abnormality) of the DNA or mRNA encoding FPRL1 of the present invention or its partial peptide in humans or mammals (e.g., rat, mouse, rabbit, sheep, swine, bovine, cat, dog, monkey etc.) can be detected. Therefore, the DNA or antisense DNA of the present invention is useful as a gene diagnostic agent for detecting damages to the DNA or mRNA, its mutation, or decreased expression, increased expression, overexpression, etc. of the DNA or mRNA.

The gene diagnosis described above using the DNA or antisense DNA of the present invention can be performed by, for example, the publicly known Northern hybridization assay or the PCR-SSCP assay (Genomics, 5, 874-879 (1989); Proceedings of the National Academy of Sciences of the United States of America, 86, 2766-2770 (1989)), etc.

When decreased expression of FPRL1 is detected, e.g., by the Northern hybridization or when DNA mutation is detected by the PCR-SSCP assay, it can be diagnosed that he or she suffers from, or is highly likely to suffer from diseases, for example, involving asthma, allergosis, inflammation, inflammatory eye diseases, Assison's disease, autoimmune hemolytic anemia, systemic lupus erythematosus, psoriasis, rheumatism, central nervous system damage (e.g., cerebrovascular diseases such as brain hemorrhage and brain infarction, head injury, cord injury, brain edema and multiple sclerosis), neurodegenerative diseases (e.g., Alzheimer's disease, Parkinson's disease, amyotrophic lateral sclerosis (ALS) and encephalopathy associated with AIDS), cerebral meningitis, diabetes mellitus, arthritis (e.g., arthritis rheumatoides, osteoarthritis, rheumatoid spondylitis, gouty arthritis and synovial inflammation), blood poisoning (e.g., sepsis, septic shock, endotoxic shock, gram-negative sepsis and toxic-shock syndrome), inflammatory bowel diseases (e.g., Crohn's disease and ulcerative colitis), inflammatory pulmonary diseases (e.g., chronic pneumonia, pulmonary silicosis, pulmonary sarcoidosis and lung tuberculosis), cachexia (e.g., infectious cachexia, canoerous cachexia and cachexia associated with acquired immunodeficiency syndrome (AIDS)), arterial sclerosis, Creutzfeldt-Jakob disease, viral infection (e.g., viral infection by cytomegalovirus, influenza virus, herpes virus and the like), angina cordis, cardiac infarction, congestive failure, hepatitis, exaggerated immune response after medical transplantation, dialysis hypotension, diffuse intravascular coagulation syndrome, and immunodeficiency.

Meanwhile, when over-expression of FPRL1 is detected by the Northern hybridization or when DNA mutation is detected by the PCR-SSCP assay, it can be diagnosed that he or she suffers from, or is highly likely to suffer from diseases, for example, diseases caused by over-expression of FPRL1 such as infectious disease.

In addition, when over-expression of FPRL1 is detected by the Northern hybridization or when DNA mutation is detected by the PCR-SSCP assay, it can also be diagnosed that he or she suffers from, or is highly likely to suffer from diseases involving asthma, allergosis, inflammation, inflammatory eye diseases, Assison's disease, autoimmune hemolytic anemia, systemic lupus erythematosus, psoriasis, rheumatism, central nervous system damage (e.g., cerebrovascular diseases such as brain hemorrhage and brain infarction, head injury, cord injury, brain edema and multiple sclerosis), neurodegenerative diseases (e.g., Alzheimer's disease, Parkinson's disease, amyotrophic lateral sclerosis (ALS) and encephalopathy associated with AIDS), cerebral meningitis, diabetes mellitus, arthritis (e.g., arthritis rheumatoides, osteoarthritis, rheumatoid spondylitis, gouty arthritis and synovial inflammation), blood poisoning (e.g., sepsis, septic shock, endotoxic shock, gram-negative sepsis and toxic-shock syndrome), inflammatory bowel diseases (e.g., Crohn's disease and ulcerative colitis), inflammatory pulmonary diseases (e.g., chronic pneumonia, pulmonary silicosis, pulmonary sarcoidosis and lung tuberculosis), cachexia (e.g., infectious cachexia, canoerous cachexia and cachexia associated with acquired immunodeficiency syndrome (AIDS)), arterial sclerosis, Creutzfeldt-Jakob disease, viral infection (e.g., viral infection by cytomegalovirus, influenza virus, herpes virus and the like), angina cordis, cardiac infarction, congestive failure, hepatitis, exaggerated immune response after medical transplantation, dialysis hypotension, diffuse intravascular coagulation syndrome, and immunodeficiency.

(3) Medicament Comprising a Compound or a Salt Thereof that Alters the Expression Level of FPRL1 of the Present Invention The DNA of the present invention can be used as a probe in screening of a compound or its salt that alters the expression level of FPRL1 of the present invention.

That is, the present invention provides, for example, a method of screening a compound or its salt that alters the expression level of FPRL1 of the present invention, which comprises measuring the level of mRNA encoding FPRL1 of the present invention in, for example, (i) (a) blood, (b) specific organs or (c) tissues or cells isolated from organs in non-human mammals or (ii) transformants, etc.

Specifically, the level of mRNA encoding FPRL1 of the present invention is measured in the following manner.

(i) Normal or morbid non-human mammals (for example, mice, rats, rabbits, sheep, swine, bovine, cats, dogs, monkeys etc., specifically rats, mice, rabbits etc. with Alzheimer's disease) are given a chemical (for example, an immune regulator etc.) or physical stress (for example, water immersion stress, electrical shock, brightening/darkening, low temperature, etc.), and after a predetermined time, blood, a specific organ (for example, brain, liver, kidney, etc.) or tissues or cells isolated from organs are obtained.

The mRNA encoding FPRL1 of the present invention contained in the resulting cells can be quantified by techniques such as, for example, TaqMan PCR of the mRNA extracted in a usual manner from the cells, and can be analyzed by Northern blotting by a means known per se.

(ii) The transformant expressing FPRL1 of the present invention is prepared according to the method described above, and the mRNA encoding FPRL1 of the present invention in the transformant can be quantified and analyzed in the same manner as described above.

Screening of the compound or its salt that alters the expression level of FPRL1 of the present invention can be carried out by:

(i) Administering a test compound into normal or morbid non-human mammals before a predetermined time, that is, 30 minutes to 24 hours before, preferably 30 minutes to 12 hours before, more preferably 1 hour to 6 hours before giving chemical or physical stress to the mammals, or after a predetermined time, that is, 30 minutes to 3 days after, preferably 1 hour to 2 days after, more preferably 1 hour to 24 hours after giving chemical or physical stress, or simultaneously with the chemical or physical stress, and quantifying and analyzing the level of mRNA encoding FPRL1 of the present invention in the cells after a predetermined time, that is, 30 minutes to 3 days after, preferably 1 hour to 2 days after, more preferably 1 hour to 24 hours after the administration, or (ii) Mixing a test compound with a medium for culturing the transformant in a usual manner and quantifying and analyzing the level of mRNA encoding FPRL1 of the present invention in the transformant after culture, that is, 1 to 7 days later, preferably 1 to 3 days later, more preferably 2 to 3 days later.

The test compound used includes, for example, peptides, proteins, non-peptide compounds, synthetic compounds, fermentation products, cell extracts, plant extracts, and animal tissue extracts or blood plasma. These compounds may be novel or known compounds.

The test compounds may form salts, and as salts of the test compounds, use is made of salts with physiologically acceptable acids (e.g., inorganic acids etc.) or bases (e.g., organic acids etc.), preferably physiologically acceptable acid addition salts. Examples of such salts are salts with inorganic acids (e.g., hydrochloric acid, phosphoric acid, hydrobromic acid, sulfuric acid etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid etc.) etc.

The compound or its salt obtained using the screening method of the present invention is a compound or its salt having an action of changing the expression level of FPRL1 of the present invention, specifically (a) a compound or its salt that potentiates the expression level of FPRL1 of the present invention thereby increasing the FPRL1-mediated cell-stimulating activity (for example, activities that accelerate or inhibit arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos, pH reduction, a cell migration stimulating activity (or a cell migration accelerating activity), particularly inhibiting activity of intracellular cAMP production and a cell migration stimulating activity (or a cell migration accelerating activity)) or (b) a compound or its salt that attenuates the expression level of FPRL1 of the present invention thereby reducing the cell-stimulating activity.

The compounds, which are obtained using the screening method, include peptides, proteins, non-peptide compounds, synthetic compounds and fermentation products, and these compounds may be novel or known compounds.

As salts of the compounds obtained using the screening method of the present invention, use is made of salts with physiologically acceptable acids (e.g., inorganic acids etc.) or bases (e.g., organic acids etc.), preferably physiologically acceptable acid addition salts. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid etc.) and the like.

The compound or its salt obtained by the screening method described above is:

(1) A compound or its salt preventing/treating diseases associated with dysfunction of FPRL1 of the present invention by increasing the expression level of FPRL1 of the present invention, specifically (i) a compound having a cell migration stimulating activity (or a cell migration accelerating activity), (ii) a compound having an anti-inflammatory action, (iii) a compound preventing/treating asthma, allergosis, inflammation, inflammatory eye diseases, Assison's disease, autoimmune hemolytic anemia, systemic lupus erythematosus, psoriasis, rheumatism, central nervous system damage (e.g., cerebrovascular diseases such as brain hemorrhage and brain infarction, head injury, cord injury, brain edema and multiple sclerosis), neurodegenerative diseases (e.g., Alzheimer's disease, Parkinson's disease, amyotrophic lateral sclerosis (ALS) and encephalopathy associated with AIDS), cerebral meningitis, diabetes mellitus, arthritis (e.g., arthritis rheumatoides, osteoarthritis, rheumatoid spondylitis, gouty arthritis and synovial inflammation), blood poisoning (e.g., sepsis, septic shock, endotoxic shock, gram-negative sepsis and toxic-shock syndrome), inflammatory bowel diseases (e.g., Crohn's disease and ulcerative colitis), inflammatory pulmonary diseases (e.g., chronic pneumonia, pulmonary silicosis, pulmonary sarcoidosis and lung tuberculosis), cachexia (e.g., infectious cachexia, canoerous cachexia and cachexia associated with acquired immunodeficiency syndrome (AIDS)), arterial sclerosis, Creutzfeldt-Jakob disease, viral infection (e.g., viral infection by cytomegalovirus, influenza virus, herpes virus and the like), angina cordis, cardiac infarction, congestive failure, hepatitis, exaggerated immune response after medical transplantation, dialysis hypotension, diffuse intravascular coagulation syndrome, and a compound preventing/treating immunodeficiency, or salts thereof; or (2) A compound or its salt, which decreases the expression level of FPRL1 of the present invention, and (i) a compound having an inhibitory activity for cell migration, or (ii) a compound preventing/treating diseases caused by over-expression of FPRL1 of the present invention such as infectious disease.

Accordingly, the compound or its salt obtained by the screening method described above, which increases the expression level of FPRL1 of the present invention, can be used for example as a low toxic and safe cell migration irritant (or a cell migration accelerator) or an anti-inflammatory agent, further a prophylactic/therapeutic agent for diseases involving asthma, allergosis, inflammation, inflammatory eye diseases, Assison's disease, autoimmune hemolytic anemia, systemic lupus erythematosus, psoriasis, rheumatism, central nervous system damage (e.g., cerebrovascular diseases such as brain hemorrhage and brain infarction, head injury, cord injury, brain edema and multiple sclerosis), neurodegenerative diseases (e.g., Alzheimer's disease, Parkinson's disease, amyotrophic lateral sclerosis (ALS) and encephalopathy associated with AIDS), cerebral meningitis, diabetes mellitus, arthritis (e.g., arthritis rheumatoides, osteoarthritis, rheumatoid spondylitis, gouty arthritis and synovial inflammation), blood poisoning (e.g., sepsis, septic shock, endotoxic shock, gram-negative sepsis and toxic-shock syndrome), inflammatory bowel diseases (e.g., Crohn's disease and ulcerative colitis), inflammatory pulmonary diseases (e.g., chronic pneumonia, pulmonary silicosis, pulmonary sarcoidosis and lung tuberculosis), cachexia (e.g., infectious cachexia, canoerous cachexia and cachexia associated with acquired immunodeficiency syndrome (AIDS)), arterial sclerosis, Creutzfeldt-Jakob disease, viral infection (e.g., viral infection by cytomegalovirus, influenza virus, herpes virus and the like), angina cordis, cardiac infarction, congestive failure, hepatitis, exaggerated immune response after medical transplantation, dialysis hypotension, diffuse intravascular coagulation syndrome, and immunodeficiency.

On the other hand, the compound or its salt that decreases the expression level of FPRL1 of the present invention, which is obtained by the screening method described above, can be used as a cell migration depressant, further a medicament such as a low toxic and safe prophylactic/therapeutic agent for diseases caused by over-expression of FPRL4 of the present invention (e.g., infectious disease).

In addition, the compound or its salt that decreases the expression level of FPRL1 of the present invention, which is obtained by the screening method described above, can also be used as an anti-inflammatory agent, further a prophylactic/therapeutic agent for diseases involving asthma, allergosis, inflammation, inflammatory eye diseases, Assison's disease, autoimmune hemolytic anemia, systemic lupus erythematosus, psoriasis, rheumatism, central nervous system damage (e.g., cerebrovascular diseases such as brain hemorrhage and brain infarction, head injury, cord injury, brain edema and multiple sclerosis), neurodegenerative diseases (e.g., Alzheimer's disease, Parkinson's disease, amyotrophic lateral sclerosis (ALS) and encephalopathy associated with AIDS), cerebral meningitis, diabetes mellitus, arthritis (e.g., arthritis rheumatoides, osteoarthritis, rheumatoid spondylitis, gouty arthritis and synovial inflammation), blood poisoning (e.g., sepsis, septic shock, endotoxic shock, gram-negative sepsis and toxic-shock syndrome), inflammatory bowel diseases (e.g., Crohn's disease and ulcerative colitis), inflammatory pulmonary diseases (e.g., chronic pneumonia, pulmonary silicosis, pulmonary sarcoidosis and lung tuberculosis), cachexia (e.g., infectious cachexia, cancerous cachexia and cachexia associated with acquired immunodeficiency syndrome (AIDS)), arterial sclerosis, Creutzfeldt-Jakob disease, viral infection (e.g., viral infection by cytomegalovirus, influenza virus, herpes virus and the like), angina cordis, cardiac infarction, congestive failure, hepatitis, exaggerated immune response after medical transplantation, dialysis hypotension, diffuse intravascular coagulation syndrome, and immunodeficiency.

When the compound or its salt obtained by the screening method of the present invention is used in a pharmaceutical composition, the compound can be formulated by the conventional methods.

For example, the compound or its salt can be used orally, for example, in the form of tablets which may be sugar coated if necessary and desired, capsules, elixirs, microcapsules etc., or parenterally in the form of injectable preparations such as a sterile solution and a suspension in water or with other pharmaceutically acceptable liquid. These preparations can be manufactured for example by mixing the compound or its salt with a physiologically acceptable known carrier, a flavoring agent, an excipient, a vehicle, an antiseptic agent, a stabilizer, a binder, etc. in a unit dosage form required in a generally accepted manner that is applied to making pharmaceutical preparations. The active ingredient in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin, alginic acid, etc., a lubricant such as magnesium stearate, a sweetening agent such as sucrose, lactose or saccharin, and a flavoring agent such as peppermint, akamono oil or cherry. When the unit dosage is in the form of capsules, liquid carriers such as oils and fats may further be used together with the additives described above. A sterile composition for injection may be formulated according to a conventional manner used to make pharmaceutical compositions, e.g., by dissolving or suspending the active ingredients in a vehicle such as water for injection with a naturally occurring vegetable oil such as sesame oil, coconut oil, etc. to prepare the pharmaceutical composition. Examples of an aqueous medium for injection include physiological saline and an isotonic solution containing glucose and other auxiliary agents (e.g., D-sorbitol, D-mannitol, sodium chloride, etc.) and may be used in combination with an appropriate solubilizer such as an alcohol (e.g., ethanol or the like), a polyalcohol (e.g., propylene glycol and polyethylene glycol), a nonionic surfactant (e.g., polysorbate 80™ and HCO-50), etc. Examples of the oily medium include sesame oil, soybean oil, etc., which may also be used in combination with a solubilizer such as benzyl benzoate, benzyl alcohol, etc.

The prophylactic/therapeutic agent described above may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus prepared liquid for injection is normally filled in an appropriate ampoule.

The thus obtained pharmaceutical preparation is safe and low toxic, and can thus be administered to, for example, human and mammals (e.g., rat, mouse, rabbit, sheep, swine, bovine, cat, dog, monkey, etc.).

The dose of the compound or its salt may vary depending on subject to be administered, target organ, symptom, administration method, etc. When the compound or its salt that increases the expression level of FPRL1 of the present invention is orally administered, the compound is administered to a patient with inflammation (as 60 kg) generally in a daily dose of approximately 0.1 to 100 mg, preferably approximately 1.0 to 50 mg, more preferably approximately 1.0 to 20 mg. When the compound is parenterally administered, a single dose of the compound may vary depending on subject to be administered, target organ, symptom, administration method, etc. When the compound or its salt that increases the expression level of FPRL1 of the present invention is administered to a patient with inflammation (as 60 kg) in the form of injection, it is convenient to administer the compound or its salt by intravenous injection, generally in a daily dose of approximately 0.01 to 30 mg, preferably approximately 0.1 to 20 mg, more preferably approximately 0.1 to 10 mg. For other animal species, the corresponding dose as converted per 60 kg weight can be administered.

(4) Diagnostic Method using the Antibody of the Present Invention

The antibody against FPRL1 ligand is capable of specifically recognizing FPRL1 ligand of the present invention and can thus be used for detection or neutralization of FPRL1 ligand of the present invention in a test sample fluid.

The antibody against FPRL1 is capable of specifically recognizing FPRL1 of the present invention and can thus be used for detection or neutralization of FPRL1 of the present invention in a test sample fluid.

It will be described about a method for quantifying FPRL1 using the antibody against FPRL1 of the present invention below. A method for quantifying FPRL1 ligand using the antibody against FPRL1 ligand of the present invention may be carried out in the same manner.

That is, the present invention provides:

(i) A method for quantifying FPRL1 in a test sample fluid, which comprises competitively reacting the antibody of the present invention, a test sample fluid and a labeled form of FPRL1, and measuring the ratio of the labeled FPRL1 of the present invention bound to said antibody; and.

(ii) A method for quantifying FPRL1 in a test sample fluid, which comprises reacting the test sample fluid simultaneously or continuously with the antibody of the present invention immobilized on a carrier and a labeled form of the antibody of the present invention, and then measuring the activity of the labeling agent on the insoluble carrier.

In the quantification method in the above-mentioned (ii), it is desirable that one antibody is an antibody recognizing the N-terminal region of FPRL1, and the other antibody is an antibody reacting with the C-terminal region of FPRL1.

The monoclonal antibody against FPRL1 may be used to quantify FPRL1. Besides, FPRL1 may also be detected by means of tissue staining. For these purposes, the antibody molecule per se may be used, or $F(ab')_2$, Fab' or Fab fractions of the antibody molecule may be used as well.

There is no particular limitation to the method of quantifying FPRL1 using the antibody of the present invention; any method may be used so far as it relates to a method in which the amount of antibody, antigen or antibody-antigen complex can be detected by a chemical or a physical means, depending on or corresponding to the amount of antigen (e.g., the amount of FPRL1) in a test sample fluid to be assayed, and then calculated using a standard curve prepared by a standard solution containing the known amount of antigen. Advantageously used are, for example, nephrometry, competitive method, immunometric method and sandwich method; in terms of sensitivity and specificity, the sandwich method, which will be later described, is particularly preferred.

Examples of the labeling agent used in the assay method using the labeling substance are radioisotopes, enzymes, fluorescent substances, luminescent substances, etc. Examples of the radioisotope are [$^{125}$I], [$^{131}$I], [$^{3}$H], [$^{14}$C], etc. Preferred examples of the enzyme are those that are stable and have a high specific activity, which include β-galactosidase, β-glucosidase, alkaline phosphatase, peroxidase, malate dehydrogenase, etc. Examples of the fluorescent substance are fluorescamine, fluorescein isothiocyanate, etc. Examples of the luminescent substance are luminol, a luminol derivative, luciferin, lucigenin, etc. Furthermore, the biotin-avidin system may also be used for binding of an antibody or antigen to a labeling agent.

In the immobilization of antigens or antibodies, physical adsorption may be used. Alternatively, chemical binding conventionally used for immobilization of FPRL1 or enzymes may be used as well. Examples of the carrier include insoluble polysaccharides such as agarose, dextran and cellulose; synthetic resins such as polystyrene, polyacrylamide, silicone, etc.; glass; and the like.

In the sandwich method, a test sample fluid is reacted with an immobilized form of the monoclonal antibody of the present invention (primary reaction), then reacted with another labeled form of the monoclonal antibody of the present invention (secondary reaction) and the activity of the labeling agent on the insoluble carrier is assayed, whereby the amount of FPRL1 in the test sample fluid can be quantified. The primary and secondary reactions may be carried out in a reversed order, simultaneously or sequentially with an interval. The type of the labeling agent and the method for immobilization may be effected by modifications of those described hereinabove. In the immunoassay by the sandwich method, it is not always necessary that the antibody used for the labeled antibody and for the solid phase should be one type or one species but a mixture of two or more antibodies may be used as well, for the purpose of improving the measurement sensitivity, etc.

In the method for assaying FPRL1 by the sandwich method according to the present invention, preferred monoclonal antibodies of the present invention used for the primary and the secondary reactions are antibodies whose binding sites to FPRL1 are different from one another. Thus, the antibodies used in the primary and the secondary reactions are those wherein when the antibody used in the secondary reaction recognizes the C-terminal region of FPRL1, the antibody recognizing the site other than the C-terminal region, e.g., recognizing the N-terminal region, is preferably used in the primary reaction.

The monoclonal antibody of the present invention may be used in an assay system other than the sandwich method, such as a competitive method, an immunometric method, nephrometry, etc.

In the competitive method, an antigen in a test sample fluid and a labeled antigen are competitively reacted with an antibody, then the unreacted labeled antigen (F) and the labeled antigen bound to the antibody (B) are separated (i.e., B/F separation) and the labeled amount of either B or F is measured to determine the amount of the antigen in the test sample fluid. In the reactions for such a method, there are a liquid phase method in which a soluble antibody is used as the antibody and the B/F separation is effected by polyethylene glycol while a second antibody to the antibody described above is used, and a solid phase method in which an immobilized antibody is used as the first antibody or a soluble antibody is used as the first antibody while an immobilized antibody is used as the second antibody.

In the immunometric method, an antigen in a test sample fluid and an immobilized antigen are competitively reacted with a given amount of a labeled antibody followed by separating the solid phase from the liquid phase; or an antigen in a test sample fluid and an excess amount of labeled antibody are reacted, then an immobilized antigen is added to bind an unreacted labeled antibody to the solid phase, and the solid phase is separated from the liquid phase. Thereafter, the labeled amount of any of the phases is measured to determine the antigen amount in the test sample fluid.

In the nephrometry, the amount of insoluble sediment, which is produced as a result of the antigen-antibody reaction in a gel or in a solution, is measured. Even when the amount of an antigen in a test sample fluid is small and only a small amount of the sediment is obtained, laser nephrometry utilizing laser scattering can be suitably used.

In applying each of those immunoassays to the quantification method of the present invention, any special conditions or operations are not required to set forth. The assay system for FPRL1 of the present invention may be constructed in addition to conditions or operations conventionally used for each of the methods, taking the technical consideration by one skilled in the art into account.

For the details of such conventional technical means, a variety of reviews, reference books, etc. may be referred to (for example, Hiroshi Irie (ed.): "Radioimmunoassay" (published by Kodansha, 1974); Hiroshi Irie (ed.): "Radioimmunoassay; Second Series" (published by Kodansha, 1979); Eiji Ishikawa, et al. (ed.): "Enzyme Immunoassay" (published by Igaku Shoin, 1978); Eiji Ishikawa, et al. (ed.): "Enzyme Immunoassay" (Second Edition) (published by Igaku Shoin, 1982); Eiji Ishikawa, et al. (ed.): "Enzyme Immunoassay" (Third Edition) (published by Igaku Shoin, 1987); "Methods in Enzymology" Vol. 70 (Immuochemical Techniques (Part A)); ibid., Vol. 73 (Immunochemical Techniques (Part B)); ibid., Vol. 74 (Immunochemical Techniques (Part C)); ibid., Vol. 84 (Immunochemical Techniques (Part D: Selected Immunoassays)); ibid., Vol. 92 (Immunochemical Techniques (Part E: Monoclonal Antibodies and General Immunoassay Methods)); ibid., Vol. 121 (Immunochemical Techniques (Part I: Hybridoma Technology and Monoclonal Antibodies)) (published by Academic Press); etc.)

As described above, FPRL1 of the present invention can be quantified with high sensitivity, using the antibody of the present invention.

Furthermore, when a decrease in the concentration of FPRL1 is detected by quantifying the concentration of FPRL1 using the antibody of the present invention, it can be diagnosed that he or she suffers from, or it is highly likely to suffer from diseases, for example, diseases involving asthma, allergosis, inflammation, inflammatory eye diseases, Assison's disease, autoimmune hemolytic anemia, systemic lupus erythematosus, psoriasis, rheumatism, central nervous system damage (e.g., cerebrovascular diseases such as brain hemorrhage and brain infarction, head injury, cord injury, brain edema and multiple sclerosis), neurodegenerative diseases (e.g., Alzheimer's disease, Parkinson's disease, amyotrophic lateral sclerosis (ALS) and encephalopathy associated with AIDS), cerebral meningitis, diabetes mellitus, arthritis (e.g., arthritis rheumatoides, osteoarthritis, rheumatoid spondylitis, gouty arthritis and synovial inflammation), blood poisoning (e.g., sepsis, septic shock, endotoxic shock, gram-negative sepsis and toxic-shock syndrome), inflammatory bowel diseases (e.g., Crohn's disease and ulcerative colitis), inflammatory pulmonary diseases (e.g., chronic pneumonia, pulmonary silicosis, pulmonary sarcoidosis and lung tuberculosis), cachexia (e.g., infectious cachexia, canoerous cachexia and cachexia associated with acquired immunodeficiency syndrome (AIDS)), arterial sclerosis, Creutzfeldt-Jakob disease, viral infection (e.g., viral infection by cytomegalovirus, influenza virus, herpes virus and the like), angina cordis, cardiac infarction, congestive failure, hepatitis, exaggerated immune response after medical transplantation, dialysis hypotension, diffuse intravascular coagulation syndrome, and immunodeficiency in the future.

Meanwhile, when an increase in the concentration of FPRL1 is detected, it can be diagnosed that he or she suffers from, or it is highly likely to suffer from, for example, a disease caused by over-expression of FPRL1 such as infectious disease in the future.

In addition, when an increase in the concentration of FPRL1 is detected, it can also be diagnosed that he or she suffers from, or it is highly likely to suffer from diseases, for example, diseases involving asthma, allergosis, inflammation, inflammatory eye diseases, Assison's disease, autoimmune hemolytic anemia, systemic lupus erythematosus, psoriasis, rheumatism, central nervous system damage (e.g., cerebrovascular diseases such as brain hemorrhage and brain infarction, head injury, cord injury, brain edema and multiple sclerosis), neurodegenerative diseases (e.g., Alzheimer's disease, Parkinson's disease, amyotrophic lateral sclerosis (ALS) and encephalopathy associated with AIDS), cerebral meningitis, diabetes mellitis, arthritis (e.g., arthritis rheumatoides, osteoarthritis, rheumatoid spondylitis, gouty arthritis and synovial inflammation), blood poisoning (e.g., sepsis, septic shock, endotoxic shock, gram-negative sepsis and toxic-shock syndrome), inflammatory bowel diseases (e.g., Crohn's disease and ulcerative colitis), inflammatory pulmonary diseases (e.g., chronic pneumonia, pulmonary silicosis, pulmonary sarcoidosis and lung tuberculosis), cachexia (e.g., infectious cachexia, canoerous cachexia and cachexia associated with acquired immunodeficiency syndrome (AIDS)), arterial sclerosis, Creutzfeldt-Jakob disease, viral infection (e.g., viral infection by cytomegalovirus, influenza virus, herpes virus and the like), angina cordis, cardiac infarction, congestive failure, hepatitis, exaggerated immune response after medical transplantation, dialysis hypotension, diffuse intravascular coagulation syndrome, and immunodeficiency in the future.

(5) Method for Screening a Compound or Its Salt that Alters Binding Property or Signal Transduction between FPRL1 and FPRL1 Ligand of the Present Invention, and Medicament Comprising a Compound or Its Salt that Alters Binding Property or Signal Transduction between FPRL1 and FPRL1 Ligand of the Present Invention Using FPRL1 of the present invention, or using the receptor binding assay system of the expression system constructed using the recombinant FPRL1, compounds (e.g., peptides, proteins, non-peptide compounds, synthetic compounds, fermentation products, etc.) or salt forms thereof that alter the binding property or signal transduction between FPRL1 ligand and FPRL1 of the present invention can be efficiently screened.

Such compounds include (a) compounds that have FPRL1-mediated cell-stimulating activity (so-called agonists to FPRL1 of the present invention); (b) compounds that inhibit the FPRL1-mediated cell-stimulating activity (so-called antagonists to FPRL1 of the present invention); (c) compounds that potentiate the binding affinity between FPRL1 ligand and FPRL1 of the present invention; or (d) compounds that reduce the binding affinity between FPRL1 ligand and FPRL1 of the present invention.

The cell stimulating activity includes, e.g., activities that promote or suppress arachidonic acid release, acetylcholine release, intracellular $Ca^{2+}$ release, intracellular cAMP production, intracellular cGMP production, inositol phosphate production, changes in cell membrane potential, phosphorylation of intracellular proteins, activation of c-fos, pH reduction, a cell migration stimulating activity (or a cell migration accelerating activity). Among them, an inhibiting activity for intracellular production, and a cell migration stimulating activity (or a cell migration accelerating activity) are preferred.

That is, the present invention provides a method for screening a compound or its salt that alters binding property or signal transduction between FPRL1 and FPRL1 ligand of the present invention, which comprises comparing (i) the case where FPRL1 of the present invention is brought in contact with a FPR1 ligand, with (ii) the case where FPRL1 of the present invention is brought in contact with FPRL1 ligand and a test compound.

The screening method of the present invention comprises measuring, for example, a binding level of FPRL1 ligand to FPRL1, or a cell stimulating activity in (i) and (ii), and comparing the results.

For FPRL1 ligand, as substitute for the aforementioned FPRL1 ligand, a compound that alters binding property between FPRL1 ligand and FPRL1 of the present invention, or a salt thereof (e.g., low-molecular-weight synthetic compound, preferably low-molecular-weight synthetic agonist) can be used. The compound that alters binding property between FPRL1 ligand and FPRL1 of the present invention, or a salt thereof can be obtained using the screening method described later. In the screening method of the present invention, those including the compound that alters binding property between FPRL1 ligand and FPRL1 of the present invention, or a salt thereof refers to as FPRL1 ligand.

More specifically, the present invention provides the following screening methods:

(a) A method of screening a compound or its salt that alters the binding property or signal transduction between FPRL1 ligand and FPRL1 of the present invention, which comprises measuring and comparing the binding level of labeled FPRL1 ligand to FPRL1, when the labeled FPRL1 ligand is brought into contact with FPRL1 of the present invention and when the labeled FPRL1 ligand and a test compound are brought into contact with FPRL1 of the present invention;

(b) A method of screening a compound or its salt that alters the binding property or signal transduction between FPRL1 ligand and FPRL1 of the present invention, which comprises measuring and comparing the binding level of labeled FPRL1 ligand to cells or the membrane fraction of the cells, when the labeled FPRL1 ligand is brought into contact with the cells or cell membrane fraction containing FPRL1 of the present invention and when the labeled FPRL1 ligand and a test compound are brought into contact with the cells or cell membrane fraction containing FPRL1 of the present invention;

(c) A method of screening a compound or its salt that alters the binding property or information transduction between FPRL1 ligand and FPRL1 of the present invention, which comprises measuring and comparing the binding level of labeled FPRL1 ligand to FPRL1, when the labeled FPRL1 ligand is brought into contact with FPRL1 expressed on the cell membrane induced by culturing a transformant containing the DNA of the present invention and when the labeled FPRL1 ligand and a test compound are brought into contact with FPRL1 of the present invention expressed on the cell membrane induced by culturing a transformant containing the DNA of the present invention;

(d) A method of screening a compound or its salt that alters the binding property or information transduction between FPRL1 ligand and FPRL1 of the present invention, which comprises measuring and comparing the FPRL1-mediated cell-stimulating activity, when a compound or its salt (e.g., FPRL1 ligand to FPRL1 of the present invention) that activates FPRL1 of the present invention is brought into contact with cells containing FPRL1 of the present invention and when the compound that activates FPRL1 of the present invention and a test compound are brought into contact with cells containing FPRL1 of the present invention; and (e) A method of screening a compound or its salt that alters the binding property or information transduction between FPRL1 ligand and FPRL1 of the present invention, which comprises measuring and comparing the FPRL1-mediated cell-stimulating activity, when a compound or its salt (e.g., FPRL1 ligand to FPRL1 of the present invention) that activates FPRL1 of the present invention is brought into contact with FPRL1 of the present invention expressed on the cell membrane induced by culturing a transformant containing the DNA of the present invention and when the compound that activates FPRL1 of the present invention and a test compound are brought into contact with FPRL1 of the present invention expressed on the cell membrane induced by culturing a transformant containing the DNA of the present invention.

Hereinafter, the screening methods of the present invention are described more specifically.

As FPRL1 of the present invention used in the screening methods of the present invention, any substance may be used so long as it comprises FPRL1 of the present invention described above. The cell membrane fraction from mammalian organs containing FPRL1 of the present invention is preferred. However, it is very difficult to obtain human organs, and thus human-derived FPRL1 or the like, produced by large-scale expression using recombinants, is preferably used in screening.

FPRL1 of the present invention can be manufactured by the method described above, preferably by expressing the DNA of the present invention in mammalian or insect cells. As DNA fragments encoding the desired portion of the protein, complementary DNA is generally used but not necessarily limited thereto. For example, gene fragments or synthetic DNA may also be used. For introducing a DNA fragment encoding FPRL1 of the present invention into host animal cells and efficiently expressing the same, it is preferred to insert the DNA fragment downstream a polyhedrin promoter of nuclear polyhedrosis virus (NPV), which is a baculovirus having insect hosts, an SV40-derived promoter, a retrovirus promoter, a metallothionein promoter, a human heat shock promoter, a cytomegalovirus promoter, an SRα promoter or the like. The amount and quality of the receptor expressed can be determined by a publicly known method. For example, this determination can be made by the method described in the literature (Nambi, P., et al., J. Biol. Chem., 267, 19555-19559 (1992)).

Accordingly, the subject containing FPRL1 of the present invention in the screening method of the present invention may be FPRL1 purified by publicly known methods, cells containing FPRL1, or membrane fractions of such cells.

Where cells containing FPRL1 of the present invention are used in the screening method of the present invention, the cells may be fixed using glutaraldehyde, formalin, etc. The fixation can be made by a publicly known method.

The cells containing FPRL1 of the present invention are host cells that have expressed the FPRL1, and as the host cells, preferred are *Escherichia coli, Bacillus subtilis*, yeast, insect cells, animal cells, and the like.

The cell membrane fraction refers to a fraction abundant in cell membrane obtained by cell disruption and subsequent fractionation by a publicly known method. Cell disruption methods include cell squashing using a Potter-Elvehjem homogenizer, disruption using a Waring blender or Polytron (manufactured by Kinematica Inc.), disruption by ultrasonication, and disruption by cell spraying through thin nozzles under an increased pressure using a French press or the like. Cell membrane fractionation is effected mainly by fractionation using a centrifugal force, such as centrifugation for fractionation and density gradient centrifugation. For example, cell disruption fluid is centrifuged at a low speed (500 rpm to 3,000 rpm) for a short period of time (normally about 1 to about 10 minutes), the resulting supernatant is then centrifuged at a higher speed (15,000 rpm to 30,000 rpm) normally for 30 minutes to 2 hours. The precipitate thus obtained is used as the membrane fraction. The membrane fraction is rich in FPRL1 expressed and membrane components such as cell-derived phospholipids and membrane proteins.

The amount of FPRL1 in the cells containing FPRL1 and in the membrane fraction is preferably $10^3$ to $10^8$ molecules per cell, more preferably $10^5$ to $10^7$ molecules per cell. As the amount of expression increases, the ligand binding activity per unit of membrane fraction (specific activity) increases so that not only the highly sensitive screening system can be constructed but also large quantities of samples can be assayed with the same lot.

To perform the above-mentioned (a) to (c) for screening the compounds or salts thereof that alter the binding property or signal transduction between FPRL1 ligand and FPRL1 of the present invention, for example, an appropriate FPRL1 fraction and labeled FPRL1 ligand are necessary.

The FPRL1 fraction is preferably a fraction of naturally occurring FPRL1, or a recombinant FPRL1 fraction having an activity equivalent to that of natural FPRL1. Herein, the equivalent activity is intended to mean a ligand binding activity, a signal. information transduction activity or the like that is equivalent to that possessed by naturally occurring FPRL1.

As labeled FPRL1 ligand, for example FPRL1 ligand labeled with [$^3$H], [$^{125}$I], [$^{14}$C], [$^{35}$S] or the like is used.

Specifically, to screen the compounds that alter the binding property or signal transduction between FPRL1 ligand and FPRL1 of the present invention, first, an FPRL1 standard is prepared by suspending cells or cell membrane fraction containing FPRL1 of the present invention in a buffer appropriate for the screening. As the buffer, any buffer that does not interfere with the binding between FPRL1 ligand and FPRL1 is usable and examples of such a buffer are phosphate buffer, Tris-hydrochloride buffer, etc., having pH of 4 to 10 (preferably pH of 6 to 8). To minimize non-specific binding, a surfactant such as CHAPS, Tween-80™ (Kao-Atlas Co.), digitonin, deoxycholate, etc. may be added to the buffer. To inhibit degradation of the receptor and FPRL1 ligand by proteases, protease inhibitors such as PMSF, leupeptin, E-64 (manufactured by Peptide Research Laboratory, Co.), and pepstatin may be added. To 0.01 to 10 ml of the receptor protein solution, a given amount (5,000 to 500,000 cpm) of labeled FPRL1 ligand is added, and $10^{-4}$ M to $10^{-10}$ M of a test compound is simultaneously added to be co-present. To examine non-specific binding (NSB), a reaction tube containing unlabeled humanin in a large excess is also prepared. The reaction is carried out at approximately 0 to 50° C., preferably about 4 to 37° C. for about 20 minutes to about 24 hours, preferably about 30 minutes to about 3 hours. After completion of the reaction, the reaction mixture is filtrated through glass fiber filter paper, etc. and washed with an appropriate volume of the same buffer. The residual radioactivity on the glass fiber filter paper is then measured by means of a liquid scintillation counter or γ-counter. Assuming that the count obtained by subtracting the amount of non-specific binding (NSB) from the count obtained in the absence of any competitive substance ($B_0$) is 100%, the test compound by which the amount of specific binding (B-NSB) is reduced to e.g. 50% or less can be selected as a candidate substance having a potential of competitive inhibition.

To perform the methods (d) to (e) supra of screening the compounds that alter the binding property and signal transduction between FPRL1 ligand and FPRL1 of the present invention, the FPRL1-mediated cell-stimulating activity can be measured using publicly known methods or commercially available kits.

Specifically, the cells containing FPRL1 of the present invention are first cultured on a multi-well plate, etc. Prior to screening, the medium is replaced with fresh medium or with an appropriate non-cytotoxic buffer, followed by incubation for a given period of time in the presence of a test compound, etc. Subsequently, the cells are extracted or the supernatant is recovered and the resulting product is quantified by appropriate procedures. Where it is difficult to detect the production of the index substance (e.g., arachidonic acid, cAMP, etc.) for the cell-stimulating activity due to a degrading enzyme contained in the cells, an inhibitor against such a degrading enzyme may be added prior to the assay. For detecting activities such as the cAMP production suppression activity, the baseline production in the cells is increased by forskolin or the like and the suppressing effect on the increased baseline production may then be detected.

Screening by assaying the cell-stimulating activity requires cells that have expressed appropriate FPRL1. For the cells that have expressed FPRL1 of the present invention, the cell strain possessing naturally occurring FPRL1 of the present invention, the cell strain expressing the recombinant FPRL1 described above and the like are desirable.

For the test compound, for example, peptides, proteins, non-peptide compounds, synthetic compounds, fermentation products, cell extracts, plant extracts, and animal tissue extracts are used. These compounds may be novel or known compounds.

The test compounds may form salts, and as salts of the test compounds, use is made of salts with physiologically acceptable acids (e.g., inorganic acids etc.) or bases (e.g., organic acids etc.), preferably physiologically acceptable acid addition salts. Examples of such salts are salts with inorganic acids (e.g., hydrochloric acid, phosphoric acid, hydrobromic acid, sulfuric acid etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid etc.) and the like.

The test compound used is preferably a compound which on the basis of the atomic coordinates of an FPRL1 active site and the position of a ligand binding pocket, is designed to bind to the ligand binding pocket. The atomic coordinates of the FPRL1 active site and the position of the ligand binding pocket can be measured by a publicly known method or a modification thereof.

The kit for screening the compounds or salts thereof that alter the binding property or signal transduction between FPRL1 ligand and FPRL1 of the present invention comprises FPRL1 of the present invention, cells containing FPRL1 of the present invention, or a membrane fraction of cells containing FPRL1 of the present invention.

For example, the screening kit of the present invention includes:

1. Screening Reagents (a) Buffers for Measurement and Washing

Hanks' balanced salt solution (manufactured by Gibco Co.) supplemented with 0.05% bovine serum albumin (manufactured by Sigma Co.).

The solution is sterilized by filtration through a 0.45 μm filter, and stored at 4° C. or may be prepared at use.

(b) FPRL1 Standard

CHO cells expressing FPRL1 of the present invention are passaged in a 12-well plate at a density of $5 \times 10^5$ cells/well followed by culturing at 37° C. under 5% $CO_2$ and 95% air for 2 days.

(c) Labeled FPRL1 Ligand

Aqueous solutions of FPRL1 ligand labeled with commercially available [$^3$H], [$^{125}$I], [$^{14}$C], [$^{35}$S], etc. are stored at 4° C. or −20° C., and diluted to 1 μM with the measurement buffer just before use.

(d) Standard FPRL1 Ligand Solution

FPRL1 ligand is dissolved in and adjusted to 1 mM with PBS containing 0.1% bovine serum albumin (manufactured by Sigma Co.) and stored at −20° C.

2. Measurement Method (a) CHO cells expressing FPRL1 of the present invention are cultured in a 12-well culture plate and washed twice with 1 ml of the measurement buffer, and 490 μl of the measurement buffer is added to each well.

(b) After adding 5 μl of $10^{-3}$ to $10^{-10}$ M test compound solution, 5 μl of labeled FPRL1 ligand is added to the mixture, and the cells are incubated at room temperature for 1 hour. To determine the amount of the non-specific binding, 5 μl of $10^{-3}$ M FPRL1 ligand is added in place of the test compound.

(c) The reaction solution is removed, and the wells are washed 3 times with 1 ml of the washing buffer. The labeled FPRL1 ligand bound to the cells is dissolved in 0.2 N NaOH-1% SDS, and mixed with 4 ml of liquid scintillator A (manufactured by Wako Pure Chemical Industries, Ltd.).

(d) The radioactivity is measured using a liquid scintillation counter (manufactured by Beckman Co.), and the percent maximum binding (PMB) is calculated by the equation below.

$$PMB = [(B-NSB)/(B_0-NSB)] \times 100$$

PMB: Percent maximum binding
B: Value obtained in the presence of a test compound
NSB: Non-specific binding
$B_0$: Maximum binding To determine if the compound is agonists or antagonists to FPRL1, the following specific procedure (i) or (ii) is available.

(i) The binding assay described in the screening method of (a) through (c) supra is performed to obtain the compound that alters the binding property between FPRL1 ligand and FPRL1 (especially inhibits the binding) followed by assay for the compound to determine if the compound has the cell stimulating activities described above. The compound having the cell stimulating activities, or its salts are agonists to FPRL1 of the present invention, whereas the compound having no such activity or its salts are agonists to FPRL1 of the present invention.

(ii)(a) A test compound is brought into contact with FPRL1-containing cells to assay the above-mentioned cell stimulating activities. The compound having the cell stimulating activities or its salts are agonists to FPRL1 of the present invention.

(b) The FPRL1-mediated cell stimulating activities are assayed both when a compound (e.g., ligand) that activates FPRL1 is brought into contact with the FPRL1-containing cells and when the compound that activates FPRL1 and a test compound are brought into contact with the FPRL1-containing cells and comparison is made on the cell stimulating activities between the two cases. The compound or its salts that can reduce the cell stimulating activities by the FPRL1-activating compound are antagonists to FPRL1 of the present invention.

The compounds or their salts, which are obtained using the screening methods or the screening kits of the present invention, are the compounds that alter the binding property or signal transduction between FPRL1 ligand and FPRL1 of the present invention. Specifically, these compounds include (a) compounds that have the FPRL1-mediated cell-stimulating activity (so-called agonists to FPRL1 of the present invention), (b) compounds having no cell stimulating-activity (so-called antagonists to FPRL1 of the present invention), (c) compounds that potentiate the binding affinity between FPRL1 ligand and FPRL1 of the present invention, and (d) compounds that reduce the binding affinity between FPRL1 ligandand FPRL1 of the present invention.

The compounds which are obtained using the screening methods or the screening kits of the present invention include peptides, proteins, non-peptide compounds, synthetic compounds and fermentation products, and may be novel or publicly known compounds.

The compound obtained by the screening method of the present invention or the screening kit of the present invention may be in the form of salt. As salts of the compounds, use is made of salts with physiologically acceptable acids (e.g., inorganic acids etc.) or bases (e.g., organic acids etc.), preferably physiologically acceptable acid addition salts. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid etc.) and the like.

Since agonists to FPRL1 of the present invention have the same physiological activities as those of FPRL1 ligand, the agonists are useful as safe and low toxic medicament, correspondingly to the physiological activities of FPRL1 ligand.

Since antagonists to FPRL1 of the present invention can suppress the physiological activities of FPRL1 ligand, the antagonists are useful as safe and low toxic medicament that inhibits the physiological activities of FPRL1 ligand.

The compounds or their salts that potentiate the binding affinity between FPRL1 ligand and FPRL1 of the present invention are useful as safe and low toxic medicament to potentiate the physiological activities of FPRL1 ligand.

The compounds that reduce the binding affinity between FPRL1 ligand and FPRL1 of the present invention are useful as safe and low toxic medicament that decreases the physiological activities of FPRL1 ligand.

Specifically, the compound or a salt thereof obtained using the screening method or screening kit of the present invention, particularly the compound or its salt, which potentiates the binding affinity between agonist or FPRL1 ligand and FPRL1 of the present invention, can be used as, for example, a low-toxic and safe cell migration irritant (or a cell migration accelerator), or an anti-inflammatory agent, further a prophylactic/therapeutic agent for diseases involving asthma, allergosis, inflammation, inflammatory eye diseases, Assison's disease, autoimmune hemolytic anemia, systemic lupus erythematosus, psoriasis, rheumatism, central nervous system damage (e.g., cerebrovascular diseases such as brain hemorrhage and brain infarction, head injury, cord injury, brain edema and multiple sclerosis), neurodegenerative diseases (e.g., Alzheimer's disease, Parkinson's disease, amyotrophic lateral sclerosis (ALS) and encephalopathy associated with AIDS), cerebral meningitis, diabetes mellitis, arthritis (e.g., arthritis rheumatoides, osteoarthritis, rheumatoid spondylitis, gouty arthritis and synovial inflammation), blood poisoning (e.g., sepsis, septic shock, endotoxic shock, gram-negative sepsis and toxic-shock syndrome), inflammatory bowel diseases (e.g., Crohn's disease and ulcerative colitis), inflammatory pulmonary diseases (e.g., chronic pneumonia, pulmonary silicosis, pulmonary sarcoidosis and lung tuberculosis), cachexia (e.g., infectious cachexia, canoerous cachexia and cachexia associated with acquired immunodeficiency syndrome (AIDS)), arterial sclerosis, Creutzfeldt-Jakob disease, viral infection (e.g., viral infection by cytomegalovirus, influenza virus, herpes virus and the like), angina cordis, cardiac infarction, congestive failure, hepatitis, exaggerated immune response after medical transplantation, dialysis hypotension, diffuse intravascular coagulation syndrome, and immunodeficiency.

On the other hand, the compound or its salt obtained using the screening method of the present invention, which reduces the binding affinity between the antagonist or FPRL1 ligand and FPRL1 of the present invention, can be used as a medicament such as a cell migration depressant, or a prophylactic/therapeutic agent for diseases caused by over-expression of FPRL1 of the present invention (e.g., infectious disease).

In addition, the compound or its salt obtained using the screening method of the present invention, which reduces the binding affinity between the antagonist or FPRL1 ligand and FPRL1 of the present invention, can also be used as a prophylactic/therapeutic agent for diseases including, e.g., asthma, allergosis, inflammation, inflammatory eye diseases, Assison's disease, autoimmune hemolytic anemia, systemic lupus erythematosus, psoriasis, rheumatism, central nervous system damage (e.g., cerebrovascular diseases such as brain hemorrhage and brain infarction, head injury, cord injury, brain edema and multiple sclerosis), neurodegenerative diseases (e.g., Alzheimer's disease, Parkinson's disease, amyotrophic lateral sclerosis (ALS) and encephalopathy associated with AIDS), cerebral meningitis, diabetes mellitis, arthritis (e.g., arthritis rheumatoides, osteoarthritis, rheumatoid spondylitis, gouty arthritis and synovial inflammation), blood poisoning (e.g., sepsis, septic shock, endotoxic shock, gram-negative sepsis and toxic-shock syndrome), inflammatory bowel diseases (e.g., Crohn's disease and ulcerative colitis), inflammatory pulmonary diseases (e.g., chronic pneumonia, pulmonary silicosis, pulmonary sarcoidosis and lung tuberculosis), cachexia (e.g., infectious cachexia, canoerous cachexia and cachexia associated with acquired immunodeficiency syndrome (AIDS)), arterial sclerosis, Creutzfeldt-Jakob disease, viral infection (e.g., viral infection by cytomegalovirus, influenza virus, herpes virus and the like), angina cordis, cardiac infarction, congestive failure, hepatitis, exaggerated immune response after medical transplantation, dialysis hypotension, diffuse intravascular coagulation syndrome, and immunodeficiency.

When the compound or its salt obtained using the screening method or screening kit of the present invention is used as the pharmaceutical composition supra, it can be prepared into a pharmaceutical composition in a conventional manner.

For example, the compound or its salt can be used orally, for example, in the form of tablets which may be sugar coated if necessary and desired, capsules, elixirs, microcapsules etc., or parenterally in the form of injectable preparations such as a sterile solution and a suspension in water or with other pharmaceutically acceptable liquid. These preparations can be manufactured for example by mixing the compound or its salt with a physiologically acceptable known carrier, a flavoring agent, an excipient, a vehicle, an antiseptic agent, a stabilizer, a binder, etc. in a unit dosage form required in a generally accepted manner that is applied to making pharmaceutical preparations. The active ingredient in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin, alginic acid, etc., a lubricant such as magnesium stearate, a sweetening agent such as sucrose, lactose or saccharin, and a flavoring agent such as peppermint, akamono oil or cherry. When the unit dosage is in the form of capsules, liquid carriers such as oils and fats may further be used together with the additives described above. A sterile composition for injection may be formulated according to a conventional manner used to make pharmaceutical compositions, e.g., by dissolving or suspending the active ingredients in a vehicle such as water for injection with a naturally occurring vegetable oil such as sesame oil, coconut oil, etc. to prepare the pharmaceutical composition. Examples of an aqueous medium for injection include physiological saline and an isotonic solution containing glucose and other auxiliary agents (e.g., D-sorbitol, D-mannitol, sodium chloride, etc.) and may be used in combination with an appropriate solubilizer such as an alcohol (e.g., ethanol), a polyalcohol (e.g., propylene glycol and polyethylene glycol), a nonionic surfactant (e.g., polysorbate 80™ and HCO-50), etc. Examples of the oily medium include sesame oil, soybean oil, etc., which may also be used in combination with a solubilizer such as benzyl benzoate, benzyl alcohol, etc.

The prophylactic/therapeutic agent described above may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus prepared liquid for injection is normally filled in an appropriate ampoule.

The thus obtained pharmaceutical preparation is safe and low toxic, and can thus be administered to, for example, human and mammals (e.g., rat, mouse, rabbit, sheep, swine, bovine, cat, dog, monkey, etc.)

The dose of the compound or its salt may vary depending on subject to be administered, target organ, symptom, administration method, etc. In oral administration, the agonist to FPRL1 is administered to a patient with inflammation (as 60 kg) generally in a daily dose of approximately 0.1 to 100 mg, preferably approximately 1.0 to 50 mg, more preferably approximately 1.0 to 20 mg. In parenteral administration, a single dose of the agonist to FPRL1 may vary depending on subject to be administered, target organ, symptom, administration method, etc. In administration in the form of an injection to e.g. a patient with inflammation (as 60 kg), it is convenient to administer the agonist to FPRL1 by intravenous injection generally in a daily dose of approximately 0.01 to 30 mg, preferably approximately 0.1 to 20 mg, more preferably approximately 0.1 to 10 mg. For other animal species, the corresponding dose as converted per 60 kg weight can be administered.

(6) Medicament Comprising a Compound or its Salt that Alters the Amount of FPRL1 of the Present Invention in Cell Membranes The antibody of the present invention can specifically recognize FPRL1 of the present invention, and can thus be used in screening a compound or its salt that alters the amount of FPRL1 of the present invention in cell membranes.

That is, the present invention provides, for example:

(i) A method of screening a compound or its salt that alters the amount of FPRL1 of the present invention in cell membranes, which comprises disrupting (a) blood, (b) specific organs, or (c) tissues or cells isolated from organs, then isolating a cell membrane fraction and quantifying FPRL1 of the present invention contained in the cell membrane fraction;

(ii) A method of screening a compound or its salt that alters the amount of FPRL1 of the present invention in cell membranes, which comprises disrupting e.g. an transformant expressing FPRL1 of the present invention, then isolating a cell membrane fraction and quantifying FPRL1 of the present invention contained in the cell membrane fraction;

(iii) A method of screening a compound or its salt that alters the amount of FPRL1 of the present invention in cell membranes, which comprises preparing a section of (a) blood, (b) specific organs, or (c) tissues or cells of organs isolated from a non-human mammal and quantifying the degree of staining of the receptor protein on a cell surface layer by immune staining thereby confirming the protein on the cell surface layer; and (iv) A method of screening a compound or its salt that alters the amount of FPRL1 of the present invention in cell membranes, which comprises preparing a section of e.g. a transformant expressing FPRL1 of the present invention and quantifying the degree of staining of the receptor protein on a cell surface layer by immune staining thereby confirming the protein on the cell surface layer.

Specifically, FPRL1 of the present invention contained in the cell membrane fraction is quantified as follows.

(i) Normal or morbid non-human mammals (for example, mice, rats, rabbits, sheep, swine, bovine, cats, dogs, monkeys etc., specifically rats, mice, rabbits etc. with Alzheimer's disease) are given a chemical (for example, an immune regulator etc.) or physical stress (for example, water immersion stress, electrical shock, brightening/darkening, low temperature, etc.), and after a predetermined time, blood, a specific organ (for example, brain, liver, kidney, etc.) or tissues or cells isolated from organs are obtained. The resulting organ, tissues or cells are suspended for example in a suitable buffer (for example, Tris-HCl buffer, phosphate buffer, HEPES buffer etc.) and the organ, tissues or cells are disrupted therein, and a cell membrane fraction is obtained with a surfactant (for example, Triton X100™, Tween 20™ etc.) by techniques such as centrifugation, column fractionation, etc.

The cell membrane fraction is a fraction abundant in cell membrane obtained by cell disruption and subsequent fractionation by a publicly known method. Cell disruption methods include cell squashing using a Potter-Elvehjem homogenizer, disruption using a Waring blender or Polytron (manufactured by Kinematica Inc.), disruption by ultrasonication, and disruption by cell spraying through thin nozzles under an increased pressure using a French press or the like. Cell membrane fractionation is effected mainly by fractionation using a centrifugal force, such as centrifugation for fractionation and density gradient centrifugation. For example, cell disruption fluid is centrifuged at a low speed (500 rpm to 3,000 rpm) for a short period of time (normally about 1 to about 10 minutes), the resulting supernatant is then centrifuged at a higher speed (15,000 rpm to 30,000 rpm) normally for 30 minutes to 2 hours. The precipitate thus obtained is used as the membrane fraction. The membrane fraction is rich in FPRL1 expressed and in membrane components such as cell-derived phospholipids and membrane proteins.

FPRL1 of the present invention contained in the cell membrane fraction can be quantified by, for example, sandwich immunoassays using the antibody of the present invention, Western blotting analysis, etc.

The sandwich immunoassays can be performed in the same manner as in the method described above, and Western blotting can be performed by a means known per se.

(ii) The transformant expressing FPRL1 of the present invention is created according to the method descried above, and FPRL1 of the present invention contained in its cell membrane fraction can be quantified.

Screening of the compound or its salt that alters the amount of FPRL1 of the present invention in the cell membrane can be carried out by:

(i) Administering a test compound into normal or morbid non-human mammals before a predetermined time, that is, 30 minutes to 24 hours before, more preferably 30 minutes to 12 hours before, still more preferably one hour to 6 hours before giving chemical or physical stress to the mammals, or after a predetermined time, that is, 30 minutes to 3 days after, preferably one hour to two days after, more preferably one hour to 24 hours after giving chemical or physical stress, or simultaneously with the chemical or physical stress, and quantifying and analyzing the amount of FPRL1 of the present invention in a cell membrane after a predetermined time, that is, 30 minutes to 3 days after, preferably one hour to two days after, more preferably one hour to 24 hours after the administration, or (ii) Mixing a test compound with a medium for culturing the transformant in a usual manner and quantifying and analyzing the amount of FPRL1 of the present invention in a cell membrane of the transformant after culture, that is, one to 7 days later, preferably one to 3 days later, more preferably two to 3 days later.

Specifically, FPRL1 of the present invention contained in the cell membrane fraction is confirmed in the following manner.

(iii) Normal or morbid non-human mammals (for example, mice, rats, rabbits, sheep, swine, bovine, cats, dogs, monkeys etc., specifically rats, mice, rabbits etc. with Alzheimer's disease) are given a chemical (for example, an immune regulator etc.) or physical stress (for example, water immersion stress, electrical shock, brightening/darkening, low temperature, etc.), and after a predetermined time, blood, a specific organ (for example, brain, liver, kidney, etc.) or tissues or cells isolated from organs are obtained. The resulting organ, tissues or cells are formed in a usual manner into a tissue section, which is then subjected to immune staining with the antibody of the present invention. The degree of staining of the receptor protein in the cell surface layer is quantified to confirm the protein on the cell membrane, whereby the amount of FPRL1 of the present invention on the cell membrane can be quantitatively or qualitatively confirmed.

(iv) FPRL1 of the present invention can also be confirmed in an analogous manner by using e.g. the transformant expressing FPRL1 of the present invention.

Examples of the test compounds include peptides, proteins, non-peptide compounds, synthetic compounds, fermentation products, cell extracts, plant extracts, animal tissue extracts, blood plasma, etc. and these compounds may be novel compounds or publicly known compounds.

The test compounds may form salts, and as salts of the test compounds, use is made of salts with physiologically acceptable acids (e.g., inorganic acids etc.) or bases (e.g., organic acids etc.), preferably physiologically acceptable acid addition salts. Examples of such salts are salts with inorganic acids (e.g., hydrochloric acid, phosphoric acid, hydrobromic acid, sulfuric acid etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid etc.) and the like.

The compound or its salt obtained using the screening method of the present invention is a compound or its salt having an action of changing the expression level of FPRL1 of the present invention in the cell membrane, specifically (a) a compound or its salt that potentiates the expression level of FPRL1 of the present invention in the cell membrane thereby increasing the FPRL1-mediated cell-stimulating activity or (b) a compound or its salt that reduces the expression level of FPRL1 of the present invention in the cell membrane thereby reducing the cell-stimulating activity.

The compounds obtained by the screening methods of the present invention include peptides, proteins, non-peptide compounds, synthetic compounds and fermentation products, and may be novel compounds or publicly known compounds.

The compounds obtained by the screening methods of the present invention may form salts, and as salts of the test compounds, use is made of salts with physiologically acceptable acids (e.g., inorganic acids etc.) or bases (e.g., organic acids etc.), preferably physiologically acceptable acid addition salts. Examples of such salts are salts with inorganic acids (e.g., hydrochloric acid, phosphoric acid, hydrobromic acid, sulfuric acid etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid etc.) and the like.

The compound or its salt that potentiates the cell-stimulating activity by increasing the amount of FPRL1 of the present invention in the cell membrane can be used as a low-toxic and safe medicament such as a prophylactic/therapeutic agent for diseases associated with dysfunction of FPRL1 of the present invention. Specifically, the compound or its salt can be used as, for example, a cell migration irritant (or a cell migration accelerator), an anti-inflammatory agent, or prophylactic/therapeutic agent for asthma, allergosis, inflammation, inflammatory eye diseases, Assison's disease, autoimmune hemolytic anemia, systemic lupus erythematosus, psoriasis, rheumatism, central nervous system damage (e.g., cerebrovascular diseases such as brain hemorrhage and brain infarction, head injury, cord injury, brain edema and multiple sclerosis), neurodegenerative diseases (e.g., Alzheimer's disease, Parkinson's disease, amyotrophic lateral sclerosis (ALS) and encephalopathy associated with AIDS), cerebral meningitis, diabetes mellitus, arthritis (e.g., arthritis rheumatoides, osteoarthritis, rheumatoid spondylitis, gouty arthritis and synovial inflammation), blood poisoning (e.g., sepsis, septic shock, endotoxic shock, gram-negative sepsis and toxic-shock syndrome), inflammatory bowel diseases (e.g., Crohn's disease and ulcerative colitis), inflammatory pulmonary diseases (e.g., chronic pneumonia, pulmonary silicosis, pulmonary sarcoidosis and lung tuberculosis), cachexia (e.g., infectious cachexia, canoerous cachexia and cachexia associated with acquired immunodeficiency syndrome (AIDS)), arterial sclerosis, Creutzfeldt-Jakob disease, viral infection (e.g., viral infection by cytomegalovirus, influenza virus, herpes virus and the like), angina cordis, cardiac infarction, congestive failure, hepatitis, exaggerated immune response after medical transplantation, dialysis hypotension, diffuse intravascular coagulation syndrome, and immunodeficiency.

The compound or its salt that reduces the cell-stimulating activity by decreasing the amount of FPRL1 of the present invention in the cell membrane is useful as, for example, a cell migration depressant, or a safe and low-toxic prophylactic/therapeutic agent for diseases caused by over-expression of FPRL1 of the present invention (e.g., infectious disease).

In addition, the compound or its salt that reduces the cell-stimulating activity by decreasing the amount of FPRL1 of the present invention in the cell membrane can also be used as, for example, an anti-inflammatory agent, or a prophylactic/therapeutic agent for diseases including, e.g., asthma, allergosis, inflammation, inflammatory eye diseases, Assison's disease, autoimmune hemolytic anemia, systemic lupus erythematosus, psoriasis, rheumatism, central nervous system damage (e.g., cerebrovascular diseases such as brain hemorrhage and brain infarction, head injury, cord injury, brain edema and multiple sclerosis), neurodegenerative diseases (e.g., Alzheimer's disease, Parkinson's disease, amyotrophic lateral sclerosis (ALS) and encephalopathy associated with AIDS), cerebral meningitis, diabetes mellitus, arthritis (e.g., arthritis rheumatoides, osteoarthritis, rheumatoid spondylitis, gouty arthritis and synovial inflammation), blood poisoning (e.g., sepsis, septic shock, endotoxic shock, gram-negative sepsis and toxic-shock syndrome), inflammatory bowel diseases (e.g., Crohn's disease and ulcerative colitis), inflammatory pulmonary diseases (e.g., chronic pneumonia, pulmonary silicosis, pulmonary sarcoidosis and lung tuberculosis), cachexia (e.g., infectious cachexia, canoerous cachexia and cachexia associated with acquired immunodeficiency syndrome (AIDS)), arterial sclerosis, Creutzfeldt-Jakob disease, viral infection (e.g., viral infection by cytomegalovirus, influenza virus, herpes virus and the like), angina cordis, cardiac infarction, congestive failure, hepatitis, exaggerated immune response after medical transplantation, dialysis hypotension, diffuse intravascular coagulation syndrome, and immunodeficiency.

When the compound or its salt obtained using the screening kit of the present invention is used as the pharmaceutical composition supra, it can be prepared into a pharmaceutical composition in a conventional manner.

For example, the compound or its salt can be used orally, for example, in the form of tablets which may be sugar coated if necessary and desired, capsules, elixirs, microcapsules etc., or parenterally in the form of injectable preparations such as a sterile solution and a suspension in water or with other pharmaceutically acceptable liquid. These preparations can be manufactured for example by mixing the compound or its salt with a physiologically acceptable known carrier, a flavoring agent, an excipient, a vehicle, an antiseptic agent, a stabilizer, a binder, etc. in a unit dosage form required in a generally accepted manner that is applied to making pharmaceutical preparations. The active ingredient in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin and alginic acid, a lubricant such as magnesium stearate, a sweetening agent such as sucrose, lactose or saccharin, and a flavoring agent such as peppermint, akamono oil or cherry. When the unit dosage is in the form of capsules, liquid carriers such as oils and fats may further be used together with the additives described above. A sterile composition for injection may be formulated according to a conventional manner used to make pharmaceutical compositions, e.g., by dissolving or suspending the active ingredients in a vehicle such as water for injection with a naturally occurring vegetable oil such as sesame oil, coconut oil, etc. to prepare the pharmaceutical composition. Examples of an aqueous medium for injection include physiological saline and an isotonic solution containing glucose and other auxiliary agents (e.g., D-sorbitol, D-mannitol, sodium chloride, etc.) and may be used in combination with an appropriate solubilizer such as an alcohol (e.g., ethanol), a polyalcohol (e.g., propylene glycol and polyethylene glycol), a nonionic surfactant (e.g., polysorbate 80™ and HCO-50), etc. Examples of the oily medium include sesame oil, soybean oil, etc., which may also be used in combination with a solubilizer such as benzyl benzoate, benzyl alcohol, etc.

The prophylactic/therapeutic agent described above may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus prepared liquid for injection is normally filled in an appropriate ampoule.

The thus obtained pharmaceutical preparation is safe and low toxic, and can thus be administered to, for example, human and mammals (e.g., rat, mouse, rabbit, sheep, swine, bovine, cat, dog, monkey, etc.).

The dose of the compound or its salt may vary depending on subject to be administered, target organ, symptom, administration method, etc. When the compound or its salt that increases the amount of FPRL1 of the present invention is orally administered, the compound or its salt is administered to a patient with inflammation (as 60 kg) generally in a daily dose of approximately 0.1 to 100 mg, preferably approximately 1.0 to 50 mg, more preferably approximately 1.0 to 20 mg. When the compound or its salt is parenterally administered, a single dose of the compound or its salt may vary depending on subject to be administered, target organ, symptom, administration method, etc. When the compound or its salt that increases the amount of FPRL1 of the present invention is administered to a patient with inflammation (as 60 kg) in the form of injection, it is convenient to administer the compound or its salt by intravenous injection, generally in a daily dose of approximately 0.01 to 30 mg, preferably approximately 0.1 to 20 mg, more preferably approximately 0.1 to 10 mg. For other animal species, the corresponding dose as converted per 60 kg weight can be administered.

(7) Medicament Comprising the Antibody Against FPRL1 of the Present Invention

The neutralizing activity of the antibody against FPRL1 of the present invention refers to an activity of inactivating the signal transduction function in which FPRL1 is involved. Therefore, when the antibody has the neutralizing activity, the antibody can inactivate the signal transduction in which FPRL1 is involved, for example, inactivate the FPRL1-mediated cell-stimulating activity (e.g., activity that promotes or inhibits arachidonic acid release, acetylcholine release, intracellular $Ca^{2+}$ release, intracellular cAMP production, intracellular cGMP production, inositol phosphate production, changes in cell membrane potential, phosphorylation of intracellular proteins, activation of c-fos, pH reduction, or a cell migration stimulating activity, particularly inhibiting activity of intracellular cAMP production, or a cell migration stimulating activity (or a cell migration accelerating activity)).

Therefore, the antibody against FPRL1 of the present invention (for example, the neutralizing antibody) can be used as a low-toxic and safe medicament such as a cell migration depressant, or a prophylactic/therapeutic agent for diseases caused by over-expression of FPRL1 or an excess of FPRL1 ligand.

In addition, the antibody against FPRL1 of the present invention can also be used as an anti-inflammatory agent, or a prophylactic/therapeutic agent for diseases including, e.g., asthma, allergosis, inflammation, inflammatory eye diseases, Assison's disease, autoimmune hemolytic anemia, systemic lupus erythematosus, psoriasis, rheumatism, central nervous system damage (e.g., cerebrovascular diseases such as brain hemorrhage and brain infarction, head injury, cord injury, brain edema and multiple sclerosis), neurodegenerative diseases (e.g., Alzheimer's disease, Parkinson's disease, amyotrophic lateral sclerosis (ALS) and encephalopathy associated with AIDS), cerebral meningitis, diabetes mellitus, arthritis (e.g., arthritis rheumatoides, osteoarthritis, rheumatoid spondylitis, gouty arthritis and synovial inflammation), blood poisoning (e.g., sepsis, septic shock, endotoxic shock, gram-negative sepsis and toxic-shock syndrome), inflammatory bowel diseases (e.g., Crohn's disease and ulcerative colitis), inflammatory pulmonary diseases (e.g., chronic pneumonia, pulmonary silicosis, pulmonary sarcoidosis and lung tuberculosis), cachexia (e.g., infectious cachexia, canoerous cachexia and cachexia associated with acquired immunodeficiency syndrome (AIDS)), arterial sclerosis, Creutzfeldt-Jakob disease, viral infection (e.g., viral infection by cytomegalovirus, influenza virus, herpes virus and the like), angina cordis, cardiac infarction, congestive failure, hepatitis, exaggerated immune response after medical transplantation, dialysis hypotension, diffuse intravascular coagulation syndrome, and immunodeficiency.

The above prophylactic/therapeutic agent can be produced and used in the same manner as for the medicament comprising FPRL1 of the present invention described above.

(8) Medicament Comprising the Antisense DNA or siRNA of the Present Invention

The antisense DNA or siRNA of the present invention can be used as a low-toxic and safe medicament such as, for example, a cell migration depressant, or a prophylactic/therapeutic agent for diseases caused by over-expression of FPRL1 or an excess of FPRL1 ligand.

In addition, the antisense DNA or siRNA of the present invention can also be used as, for example, an anti-inflammatory agent, or a prophylactic/therapeutic agent for diseases including, e.g., asthma, allergosis, inflammation, inflammatory eye diseases, Assison's disease, autoimmune hemolytic anemia, systemic lupus erythematosus, psoriasis, rheumatism, central nervous system damage (e.g., cerebrovascular diseases such as brain hemorrhage and brain infarction, head injury, cord injury, brain edema and multiple sclerosis), neurodegenerative diseases (e.g., Alzheimer's disease, Parkinson's disease, amyotrophic lateral sclerosis (ALS) and encephalopathy associated with AIDS), cerebral meningitis, diabetes mellitus, arthritis (e.g., arthritis rheumatoides, osteoarthritis, rheumatoid spondylitis, gouty arthritis and synovial inflammation), blood poisoning (e.g., sepsis, septic shock, endotoxic shock, gram-negative sepsis and toxic-shock syndrome), inflammatory bowel diseases (e.g., Crohn's disease and ulcerative colitis), inflammatory pulmonary diseases (e.g., chronic pneumonia, pulmonary silicosis, pulmonary sarcoidosis and lung tuberculosis), cachexia (e.g., infectious cachexia, canoerous cachexia and cachexia associated with acquired immunodeficiency syndrome (AIDS)), arterial sclerosis, Creutzfeldt-Jakob disease, viral infection (e.g., viral infection by cytomegalovirus, influenza virus, herpes virus and the like), angina cordis, cardiac infarction, congestive failure, hepatitis, exaggerated immune response after medical transplantation, dialysis hypotension, diffuse intravascular coagulation syndrome, and immunodeficiency.

Where the antisense DNA or siRNA, for example is used, the antisense DNA or siRNA itself is administered as it is; or it is inserted into an appropriate vector such as retrovirus vector, adenovirus vector, adenovirus-associated virus vector, etc. and then administered in a conventional manner. The antisense DNA or siRNA of the present invention may also be administered as naked DNA, or with adjuvants to assist its uptake by gene gun or through a catheter such as a catheter with a hydrogel.

Further, the antisense DNA can also be used as a diagnostic oligonucleotide probe for examining the presence of the DNA of the present invention in tissues or cells or its expression.

(9) Preparation of an Animal in which the DNA of the Present Invention has been Introduced The present invention provides a non-human mammal having the DNA of the present invention, which is exogenous (hereinafter simply referred to as the exogenous DNA of the present invention) or its mutant DNA (sometimes simply referred to as the exogenous mutant DNA of the present invention).

Thus, the present invention provides:

[1] A non-human mammal having the exogenous DNA of the present invention or its mutant DNA;
[2] The mammal according to [1], wherein the non-human mammal is a rodent;
[3] The mammal according to [2], wherein the rodent is a mouse or rat; and
[4] A recombinant vector comprising the exogenous DNA of the present invention or its mutant DNA and capable of expression in a mammal.

The non-human mammal having the exogenous DNA of the present invention or its mutant DNA (hereinafter simply referred to as the DNA transgenic animal of the present invention) can be prepared by transfecting the desired DNA into an unfertilized egg, a fertilized egg, a spermatozoon, a germinal cell containing a primordial germinal cell thereof, or the like, preferably in the embryogenic stage in the development of a non-human mammal (more preferably in the single cell or fertilized cell stage and generally before the 8-cell phase) by standard means such as the calcium phosphate method, the electric pulse method, the lipofection method, the agglutination method, the microinjection method, the particle gun method, the DEAE-dextran method, etc. Also, it is possible to transfect the exogenous DNA of the present invention into a somatic cell, a living organ, a tissue cell or the like, by the DNA transfection methods, and utilize the transformant for cell culture, tissue culture, etc. In addition, these cells may be fused with the above-described germinal cell by a publicly known cell fusion method to prepare the transgenic animal of the present invention.

Examples of the non-human mammal that can be used include bovine, swine, sheep, goat, rabbits, dogs, cats, guinea pigs, hamsters, mice, rats and the like. Above all, preferred are rodents, especially mice (e.g., C57BL/6 strain, DBA2 strain, etc. for a pure line and for a cross line, B6C3F$_1$ strain, BDF$_1$ strain, B6D2F$_1$ strain, BALB/c strain, ICR strain, etc.) or rats (Wistar, SD, etc.) and the like, since they are relatively short in ontogeny and life cycle from a standpoint of preparing model disease animals, and are easy in breeding.

"Mammals" in a recombinant vector that can be expressed in mammals include human etc. in addition to the aforesaid non-human mammals.

The exogenous DNA of the present invention refers to the DNA of the present invention that is once isolated and extracted from mammals, not the DNA of the present invention inherently possessed by the non-human mammals.

The mutant DNA of the present invention includes mutants resulting from variation (e.g., mutation, etc.) in the base sequence of the original DNA of the present invention, specifically DNAs resulting from base addition, deletion, substitution with other bases, etc. and further including abnormal DNA.

The abnormal DNA is intended to mean the DNA that expresses abnormal FPRL1 of the present invention and exemplified by such a DNA that expresses FPRL1 suppressing the functions of normal FPRL1 of the present invention, or the like.

The exogenous DNA of the present invention may be any one of those derived from a mammal of the same species as, or a different species from, the mammal as the target animal. In transfecting the DNA of the present invention to the target animal, it is generally advantageous to use the DNA as a DNA construct in which the DNA is ligated downstream a promoter capable of expressing the DNA in the target animal. For example, in the case of transfecting the human DNA of the present invention, a DNA transgenic mammal that expresses the DNA of the present invention to a high level can be prepared by microinjecting a DNA construct (e.g., vector, etc.) ligated with the human DNA of the present invention into a fertilized egg of the target mammal, e.g., a fertilized egg of mouse, downstream the various promoters capable of expressing the DNA derived from various mammals (e.g., rabbits, dogs, cats, guinea pigs, hamsters, rats, mice, etc.) having the DNA of the present invention highly homologous to the human DNA.

As expression vectors for FPRL1 of the present invention, there are *Escherichia coli*-derived plasmids, *Bacillus subtilis*-derived plasmids, yeast-derived plasmids, bacteriophages such as λ phage, etc., retroviruses such as Moloney leukemia virus, etc., animal viruses such as vaccinia virus, baculovirus, etc. Of these vectors, *Escherichia coli*-derived plasmids, *Bacillus subtilis*-derived plasmids, yeast-derived plasmids, etc. are preferably used.

Examples of these promoters for regulating the DNA expression include (i) promoters for DNA derived from viruses (e.g., simian virus, cytomegalovirus, Moloney leukemia virus, JC virus, breast cancer virus, poliovirus, etc.), and (ii) promoters derived from various mammals (human, rabbits, dogs, cats, guinea pigs, hamsters, rats, mice, etc.), for example, promoters of albumin, insulin II, uroplakin II, elastase, erythropoietin, endothelin, muscular creatine kinase, glial fibrillary acidic protein glutathione S-transferase, platelet-derived growth factor β, keratins K1, K10 and K14, collagen types I and II, cyclic AMP-dependent protein kinase βI subunit, dystrophin, tartarate-resistant alkaline phosphatase, atrial natriuretic factor, endothelial receptor tyrosine kinase (generally abbreviated as Tie2), sodium-potassium adenosine triphosphorylase (Na, K-ATPase), neurofilament light chain, metallothioneins I and IIA, metalloproteinase 1 tissue inhibitor, MHC class I antigen (H-2L), H-ras, renin, dopamine β-hydroxylase, thyroid peroxidase (TPO), polypeptide chain elongation factor 1α (EF-1α), β actin, α and β myosin heavy chains, myosin light chains 1 and 2, myelin base protein, thyroglobulins, Thy-1, immunoglobulins, H-chain variable region (VNP), serum amyloid component P, myoglobin, troponin C, smooth muscle α actin, preproencephalin A, vasopressin, etc. Among them, cytomegalovirus promoters, human peptide elongation factor 1α (EF-1α) promoters, human and chicken β actin promoters etc., which can achieve high expression in the whole body, are preferred.

It is preferred that the vectors described above have a sequence for terminating the transcription of the desired messenger RNA in the DNA transgenic animal (generally called a terminator); for example, a sequence of each DNA derived from viruses and various mammals. SV40 terminator of the simian virus, etc. is preferably used.

In addition, for the purpose of increasing the expression of the desired exogenous DNA to a higher level, the splicing signal and enhancer region of each DNA, a portion of the intron of an eukaryotic DNA may also be ligated at the 5' upstream of the promoter region, or between the promoter region and the translational region, or at the 3' downstream of the translational region, depending upon purposes.

The normal translational region of FPRL1 of the present invention can be prepared as the whole or a part of genomic DNA from DNA derived from liver, kidney, thyroid cells, fibroblasts etc. derived from humans or mammals (for example, rabbit, dog, cat, guinea pig, hamster, rat, mouse etc.) and a wide variety of commercial DNA libraries, or from complementary DNA as a starting material prepared by a known method from RNA derived from liver, kidney, thyroid cells, fibroblasts etc. As the extraneous abnormal DNA, a translational region can be prepared by point mutation of the normal translational region of FPRL1 obtained from the above cells or tissues.

The translational region can be prepared, as a DNA construct capable of being expressed in the transgenic animal, by a conventional DNA engineering technique, in which the DNA is ligated downstream from the aforesaid promoter and if desired, upstream from the translation termination site.

The exogenous DNA of the present invention is transfected at the fertilized egg cell stage in a manner such that the DNA is certainly present in all the germinal cells and somatic cells of the target mammal. The fact that the exogenous DNA of the present invention is present in the germinal cells of the animal prepared by DNA transfection means that all offspring of the prepared animal will maintain the exogenous DNA of the present invention in all of the germinal cells and somatic cells thereof. The offspring of the animal that inherits the exogenous DNA of the present invention also have the exogenous DNA of the present invention in all of the germinal cells and somatic cells thereof.

The non-human mammal, in which the normal exogenous DNA of the present invention has been transfected, can be passaged as the DNA-bearing animal under ordinary rearing environment, by confirming that the exogenous DNA is stably retained by mating.

By the transfection of the exogenous DNA of the present invention at the fertilized egg cell stage, the DNA is retained to be excess in all of the germinal and somatic cells of the target mammal. The fact that the exogenous DNA of the present invention is excessively present in the germinal cells of the prepared animal after transfection means that all of the offspring of the animal prepared have the exogenous DNA of the present invention excessively in all of the germinal cells and somatic cells thereof. The offspring of the animal of this kind that inherits the exogenous DNA of the present invention excessively have the DNA of the present invention in all of the germinal cells and somatic cells thereof.

By obtaining a homozygotic animal having the transfected DNA in both of homologous chromosomes and mating a male and female of the animal, all offspring can be passaged to excessively retain the DNA.

In a non-human mammal bearing the normal DNA of the present invention, the normal DNA of the present invention is expressed to a high level, and may eventually develop the hyperfunction of FPRL1 of the present invention by promoting the functions of endogenous normal DNA. Therefore, the animal can be utilized as a pathologic model animal for such a disease. Specifically, using the normal DNA transgenic animal of the present invention, it becomes possible to elucidate the hyperfunction of FPRL1 of the present invention and to clarify the pathological mechanism of the disease associated with FPRL1 of the present invention and to determine how to treat these diseases.

Furthermore, since a mammal transfected with the exogenous normal DNA of the present invention exhibits an increasing symptom of FPRL1 of the present invention, the animal is usable for screening of therapeutic agents for the disease associated with FPRL1 of the present invention.

On the other hand, non-human mammal having the exogenous abnormal DNA of the present invention can be passaged under normal breeding conditions as the DNA-bearing animal by confirming the stable retaining of the exogenous DNA via crossing. In addition, the objective exogenous DNA can be utilized as a starting material by inserting the objective exogenous DNA into the plasmid described above. The DNA construct with a promoter can be prepared using conventional DNA engineering techniques. The transfection of the abnormal DNA of the present invention at the fertilized egg cell stage is preserved to be present in all of the germinal and somatic cells of the mammals to be targeted. The fact that the abnormal DNA of the present invention is present in the germinal cells of the animal after DNA transfection means that all of the offspring of the prepared animal have the abnormal DNA of the present invention in all of the germinal and somatic cells. The offspring of such an animal that inherits the exogenous DNA of the present invention has the abnormal DNA of the present invention in all the germinal and somatic cells. A homozygous animal having the introduced DNA on both of homologous chromosomes can be acquired and then by mating these male and female animals, all the offspring can be bred to have the DNA.

Since the non-human mammal having the abnormal DNA of the present invention expresses the abnormal DNA of the present invention at a high level, the animal may cause the function inactive type inadaptability of FPRL1 of the present invention by inhibiting the functions of the endogenous normal DNA, and can be utilized as its disease model animal. For example, using the abnormal DNA-transferred animal of the present invention, it is possible to elucidate the mechanism of the function inactive type inadaptability of FPRL1 of the present invention and to study a method for treatment of this disease.

In its specific applicability, the transgenic animal of the present invention expressing the abnormal DNA of the present invention to a high level is also expected to serve as a model for the elucidation of the mechanism of the functional inhibition (dominant negative effect) of normal FPRL1 by abnormal FPRL1 of the present invention in the function inactive type inadaptability of FPRL1 of the present invention.

A mammal bearing the abnormal exogenous DNA of the present invention is also expected to serve for screening a candidate drug for the treatment of the function inactive type inadaptability of FPRL1 of the present invention, since FPRL1 of the present invention is increased in such an animal.

Other potential applications of two kinds of the DNA transgenic animals of the present invention described above further include:

(1) Use as a cell source for tissue culture;
(2) Elucidation of the relation to FPRL1 that is specifically expressed or activated by FPRL1 of the present invention, by direct analysis of DNA or RNA in tissues of the DNA transgenic animal of the present invention or by analysis of the FPRL1 tissues expressed by the DNA;
(3) Research on the function of cells derived from tissues that are usually cultured only with difficulty, using cells in tissues bearing the DNA cultured by a standard tissue culture technique;
(4) Screening a drug that enhances the functions of cells using the cells described in (3) above; and
(5) Isolation and purification of mutant FPRL1 of the present invention and preparation of an antibody thereto.

Furthermore, clinical conditions of a disease associated with FPRL1 of the present invention, including the function inactive type inadaptability to FPRL1 of the present invention, can be examined by using the DNA transgenic animal of the present invention. Also, pathological findings on each organ in a disease model associated with FPRL1 of the present invention can be obtained in more detail, leading to the development of a new method for treatment as well as the research and therapy of any secondary diseases associated with the disease.

It is also possible to obtain a free DNA-transfected cell by withdrawing each organ from the DNA transgenic animal of the present invention, mincing the organ and degrading with a proteinase such as trypsin, etc., followed by establishing the line of culturing or cultured cells. Furthermore, the DNA transgenic animal of the present invention can serve to identify cells capable of producing FPRL1 of the present invention, and to study in association with apoptosis, differentiation or propagation or on the mechanism of signal transduction in these properties to inspect any abnormality therein. Thus, the DNA transgenic animal can provide an effective research material for FPRL1 of the present invention and for investigation of the function and effect thereof.

To develop a drug for the treatment of diseases associated with FPRL1 or FPRL2 of the present invention, including the function inactive type inadaptability to FPRL1 of the present invention, using the DNA transgenic animal of the present invention, an effective and rapid method for screening a drug for the treatment of the diseases can be provided by using the method for inspection, the method for quantification etc. described above. It is also possible to investigate and develop a method for DNA therapy for the treatment of diseases associated with FPRL1 of the present invention, using the DNA transgenic animal of the present invention or a vector capable of expressing the exogenous DNA of the present invention.

(10) Knockout Animal

The present invention provides a non-human mammalian embryonic stem cell bearing the DNA of the present invention inactivated and a non-human mammal deficient in expressing the DNA of the present invention.

Thus, the present invention provides:

[1] A non-human mammalian embryonic stem cell in which the DNA of the present invention is inactivated;

[2] The embryonic stem cell according to [1], wherein the DNA is inactivated by introducing a reporter gene (e.g., β-galactosidase gene derived from *Escherichia coli*);

[3] The embryonic stem cell according to [1], which is resistant to neomycin;

[4] The embryonic stem cell according to [1], wherein the non-human mammal is a rodent;

[5] The embryonic stem cell according to [4], wherein the rodent is a mouse;

[6] A non-human mammal deficient in expressing the DNA of the present invention, wherein the DNA of the present invention is inactivated;

[7] The non-human mammal according to [6], wherein the DNA is inactivated by inserting a reporter gene (e.g., β-galactosidase derived from *Escherichia coli*), and the reporter gene is capable of being expressed under the control of a promoter for the DNA of the present invention;

[8] The non-human mammal according to [6], which is a rodent;

[9] The non-human mammal according to [8], wherein the rodent is a mouse; and

[10] A method for screening a compound or its salt that promotes or inhibits the promoter activity for the DNA of the present invention, which comprises administering a test compound to the animal of [7] and detecting expression of the reporter gene.

The non-human mammalian embryonic stem cell, in which the DNA of the present invention is inactivated, refers to a non-human mammalian embryonic stem cell that suppresses the ability of the non-human mammalian to express the DNA by artificially mutating the DNA of the present invention possessed in the non-human mammal, or the DNA has no substantial ability to express FPRL1 of the present invention (hereinafter sometimes referred to as the knockout DNA of the present invention) by substantially inactivating the activities of FPRL1 of the present invention encoded by the DNA (hereinafter merely referred to as ES cell).

As the non-human mammalian, the same examples as described above apply.

Techniques for artificially mutating the DNA of the present invention include deletion of a part or all of the DNA sequence and insertion of, or substitution with, other DNA, e.g., by genetic engineering. By these mutations, the knockout DNA of the present invention may be prepared, for example, by shifting the reading frame of a codon or by destroying the function of a promoter or exon.

Specifically, the non-human mammalian embryonic stem cell in which the DNA of the present invention is inactivated (hereinafter merely referred to as the ES cell with the DNA of the present invention inactivated or the knockout ES cell of the present invention) can be obtained by, for example, isolating the DNA of the present invention possessed by the target non-human mammal, inserting a DNA strand (hereinafter simply referred to as targeting vector) having a DNA sequence constructed so as to eventually destroy the gene by inserting into its exon site a chemical resistant gene such as a neomycin resistant gene or a hygromycin resistant gene, or a reporter gene such as lacZ (β-galactosidase gene) or cat (chloramphenicol acetyltransferase gene), etc. thereby destroying the functions of exon, or by inserting into the intron site between exons a DNA sequence which terminates gene transcription (e.g., polyA-added signal, etc.) thereby disabling the synthesis of complete messenger RNA, into a chromosome of the animal cells by, e.g., homologous recombination. The thus obtained ES cells are analyzed by the Southern hybridization using as a probe a DNA sequence on or near the DNA of the present invention, or by PCR using as primers a DNA sequence on the targeting vector and another DNA sequence near the DNA of the present invention which is not included in the targeting vector, and the knockout ES cell of the present invention is selected.

The parent ES cells to inactivate the DNA of the present invention by homologous recombination, etc. may be of a strain already established as described above, or may be originally established in accordance with a modification of the known method by Evans and Kaufman. For example, in the case of mouse ES cells, currently it is common practice to use ES cells of the 129 strain. However, since their immunological background is obscure, the C57BL/6 mouse or the $BDF_1$ mouse ($F_1$ hybrid between C57BL/6 and DBA/2), wherein the low ovum collection per C57BL/6 mouse or C57BL/6 has been improved by crossing with DBA/2, may be preferably used, instead of obtaining a pure line of ES cells with the clear immunological genetic background. The $BDF_1$ mouse is advantageous in that when a pathologic model mouse is generated using ES cells obtained therefrom, the genetic background can be changed to that of the C57BL/6 mouse by back-crossing with the C57BL/6 mouse, since its background is of the C57BL/6 mouse, as well as being advantageous in that ovum availability per animal is high and ova are robust.

In establishing ES cells, blastocytes of 3.5 days after fertilization are commonly used. A large number of early stage embryos may be acquired more efficiently by collecting the embryos of the 8-cell stage and using the same after culturing until the blastocyte stage.

Although the ES cells used may be of either sex, male ES cells are generally more convenient for generation of a germ cell line chimera and are therefore preferred. It is desirable to identify sexes as soon as possible also in order to save painstaking culture time.

As an example of the method for sex identification of the ES cell, mention may be made of a method in which a gene in the sex-determining region on the Y-chromosome is amplified by PCR and detected. When this method is used, ES cells (about 50 cells) corresponding to almost 1 colony are sufficient, whereas karyotype analysis hitherto required about $10^6$ cells; therefore, the first selection of ES cells at the early stage of culture can be based on sex identification, and male cells can be selected early, which saves a significant amount of time at the early stage of culture.

Second selection can be achieved by, for example, chromosome number confirmation by the G-banding method. It is usually desirable that the chromosome number of the obtained ES cells be 100% of the normal number. However, when it is difficult to obtain the cells having the normal number of chromosomes due to physical operation etc. in cell establishment, it is desirable that the ES cell be again cloned to a normal cell (e.g., in mouse cells having the number of chromosomes being 2n=40) after the gene of the ES cells is rendered knockout.

Although the embryonic stem cell line thus obtained shows a very high growth potential, it must be subcultured with great care, since it tends to lose its ontogenic capability. For example, the embryonic stem cell line is cultured at about 37° C. in a carbon dioxide incubator (preferably about 5% carbon dioxide and about 95% air, or about 5% oxygen, about 5% carbon dioxide and about 90% air) in the presence of LIF (1-10000 U/ml) on appropriate feeder cells such as STO fibroblasts, treated with a trypsin/EDTA solution (normally about 0.001 to about 0.5% trypsin/about 0.1 to 5 mM EDTA, preferably about 0.1% trypsin/about 1 mM EDTA) at the time of passage to obtain separate single cells, which are then seeded on freshly prepared feeder cells. This passage is normally conducted every 1 to 3 days; it is desirable that cells be observed at passage and cells found to be morphologically abnormal in culture, if any, be abandoned.

By allowing ES cells to reach a high density in mono-layers or to form cell aggregates in suspension under appropriate conditions, it is possible to differentiate them to various cell types, for example, parietal and visceral muscles, cardiac muscle or the like [M. J. Evans and M. H. Kaufman, Nature, 292, 154, 1981; G. R. Martin, Proc. Natl. Acad. Sci. U.S.A., 78, 7634, 1981; T. C. Doetschman et al., Journal of Embryology Experimental Morphology, 87, 27, 1985]. The cells deficient in expression of the DNA of the present invention, which are obtainable from the differentiated ES cells of the present invention, are useful for studying the functions of FPRL1 of the present invention or FPRL1 of the present invention in vitro cytologically or molecular biologically.

The non-human mammal deficient in expression of the DNA of the present invention can be identified from a normal animal by measuring the amount of mRNA in the subject animal by a publicly known method, and indirectly comparing the levels of expression.

As the non-human mammal, the same examples supra apply.

With respect to the non-human mammal deficient in expression of the DNA of the present invention, the DNA of the present invention can be made knockout by transfecting a targeting vector, prepared as described above, to mouse embryonic stem cells or mouse oocytes thereof, and conducting homologous recombination in which a targeting vector DNA sequence, wherein the DNA of the present invention is inactivated by the transfection, is replaced with the DNA of the present invention on a chromosome of a mouse embryonic stem cell or mouse oocyte.

The cells with the DNA of the present invention in which the DNA of the present invention is rendered knockout can be identified by the Southern hybridization analysis using as a probe a DNA sequence on or near the DNA of the present invention, or by PCR analysis using as primers a DNA sequence on the targeting vector and another DNA sequence which is not included in the DNA of the present invention derived from mouse, which is used as the targeting vector. When non-human mammalian embryonic stem cells are used, the cell line wherein the DNA of the present invention is inactivated is cloned by homologous recombination; the resulting cloned cell line is injected to, e.g., a non-human mammalian embryo or blastocyte, at an appropriate stage such as the 8-cell stage. The resulting chimeric embryos are transplanted to the uterus of the pseudo-pregnant non-human mammal. The resulting animal is a chimeric animal composed of both cells having the normal locus of the DNA of the present invention and those having an artificially mutated locus of the DNA of the present invention.

When some germ cells of the chimeric animal have a mutated locus of the DNA of the present invention, an individual in which all tissues are composed of cells having an artificially mutated locus of the DNA of the present invention can be selected from a series of offspring obtained by crossing between such a chimeric animal and a normal animal, e.g., by coat color identification, etc. The individuals thus obtained are normally deficient in heterozygous expression of FPRL1 of the present invention. The individuals deficient in homozygous expression of FPRL1 of the present invention can be obtained from offspring of the intercross between the heterozygotes.

When an oocyte is used, a DNA solution may be injected, e.g., to the prenucleus by microinjection thereby obtaining a transgenic non-human mammal having a targeting vector introduced into its chromosome. From such transgenic non-human mammals, those having a mutation at the locus of the DNA of the present invention can be obtained by selection based on homologous recombination.

As described above, individuals wherein the DNA of the present invention is rendered knockout permit passage rearing under ordinary rearing conditions, after it is confirmed that in the animal individuals obtained by their crossing, the DNA has been knockout.

Furthermore, the genital system may be obtained and maintained by conventional methods. That is, by crossing male and female animals each having the inactivated DNA, homozygote animals having the inactivated DNA in both loci can be obtained. The homozygotes thus obtained may be reared so that one normal animal and two or more homozygotes are produced from a mother animal to efficiently obtain such homozygotes. By crossing male and female heterozygotes, homozygotes and heterozygotes having the inactivated DNA are proliferated and passaged.

The non-human mammalian embryonic stem cell, in which the DNA of the present invention is inactivated, is very useful for preparing a non-human mammal deficient in expression of the DNA of the present invention.

Since the non-human mammal, in which the DNA of the present invention fails to express, lacks various biological activities induced by FPRL1 of the present invention, such an animal can be a disease model suspected of inactivated biological activities of FPRL1 of the present invention and thus, offers an effective study to investigate causes for and therapy for these diseases.

(10a) Method for Screening a Compound or a Salt Thereof Having Therapeutic/Prophylactic Effects for Diseases Caused by Deficiency, Damages, etc. of the DNA of the Present Invention The non-human mammal deficient in expression of the DNA of the present invention can be used to screen a compound or a salt thereof having therapeutic/prophylactic effects for diseases caused by deficiency, damages, etc. of the DNA of the present invention.

That is, the present invention provides a method for screening of a compound or its salt having therapeutic/prophylactic effects for diseases caused by deficiency, damages, etc. of the DNA of the present invention, which comprises administering a test compound to the non-human mammal deficient in expression of the DNA of the present invention, and observing and measuring a change having occurred in the animal.

As the non-human mammal deficient in expression of the DNA of the present invention used for the screening method, the same examples as given hereinabove apply.

Examples of the test compounds include peptides, proteins, non-peptide compounds, synthetic compounds, fermentation products, cell extracts, plant extracts, animal tissue extracts, blood plasma, etc., and these compounds may be novel compounds or publicly known compounds.

The test compounds may form salts, and as salts of the test compounds, use is made of salts with physiologically acceptable acids (e.g., inorganic acids etc.) or bases (e.g., organic acids etc.), preferably physiologically acceptable acid addition salts. Examples of such salts are salts with inorganic acids (e.g., hydrochloric acid, phosphoric acid, hydrobromic acid, sulfuric acid etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid etc.) and the like.

Specifically, the non-human mammal deficient in the expression of the DNA of the present invention is treated with a test compound, comparison is made with an intact animal for control and a change in each organ, tissue, disease conditions, etc. of the animal is used as an indicator to assess the therapeutic/prophylactic effects of the test compound.

For treating an animal to be tested with a test compound, for example, oral administration, intravenous injection, etc. are applied and the treatment is appropriately selected depending upon conditions of the test animal, properties of the test compound, etc. Furthermore, the amount of a test compound administered can be appropriately selected depending on administration route, nature of the test compound, or the like.

In the screening method, when the Alzheimer's disease symptom of a test animal is ameliorated by about 10% or more, preferably about 30% or more, more preferably about 50% or more by administering a test compound to the test animal, the test compound can be selected as a compound or its salt that has therapeutic/prophylactic effects on the disease.

The compound or its salt obtained by the screening method is a compound or its salt selected from the aforementioned test compounds, and can be used as, for example, a cell migration irritant (or a cell migration accelerator) or an anti-inflammatory agent, further a medicament such as a safe and low toxic prophylactic/therapeutic agent for diseases caused by deficiency in or damage to FPRL1 of the present invention (for example, diseases involving asthma, allergosis, inflammation, inflammatory eye diseases, Assison's disease, autoimmune hemolytic anemia, systemic lupus erythematosus, psoriasis, rheumatism, central nervous system damage (e.g., cerebrovascular diseases such as brain hemorrhage and brain infarction, head injury, cord injury, brain edema and multiple sclerosis), neurodegenerative diseases (e.g., Alzheimer's disease, Parkinson's disease, amyotrophic lateral sclerosis (ALS) and encephalopathy associated with AIDS), cerebral meningitis, diabetes mellitus, arthritis (e.g., arthritis rheumatoides, osteoarthritis, rheumatoid spondylitis, gouty arthritis and synovial inflammation), blood poisoning (e.g., sepsis, septic shock, endotoxic shock, gram-negative sepsis and toxic-shock syndrome), inflammatory bowel diseases (e.g., Crohn's disease and ulcerative colitis), inflammatory pulmonary diseases (e.g., chronic pneumonia, pulmonary silicosis, pulmonary sarcoidosis and lung tuberculosis), cachexia (e.g., infectious cachexia, canoerous cachexia and cachexia associated with acquired immunodeficiency syndrome (AIDS)), arterial sclerosis, Creutzfeldt-Jakob disease, viral infection (e.g., viral infection by cytomegalovirus, influenza virus, herpes virus and the like), angina cordis, cardiac infarction, congestive failure, hepatitis, exaggerated immune response after medical transplantation, dialysis hypotension, diffuse intravascular coagulation syndrome, and immunodeficiency.) Further, a compound derived from the compound obtained by the screening can also be similarly used.

The compound obtained by the screening method may form a salt, and as the salts of the compound, there may be used salts with physiologically acceptable acids (e.g., inorganic acids or organic acids) or bases (e.g., alkali metals), preferably physiologically acceptable acid addition salts. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

A medicament comprising the compound or salts thereof obtained by the above screening method may be manufactured in a manner similar to the above-described method for preparing the medicament comprising the compound or a salt thereof changing the binding property or signal transduction between FPRL1 of the present invention and FPRL1 ligand.

Since the pharmaceutical preparation thus obtained is safe and low toxic, it can be administered to humans or mammals (e.g., rat, mouse, guinea pig, rabbit, sheep, swine, bovine, horse, cat, dog, monkey, etc.)

The dose of the above compound or its salt may vary depending on target disease, subject to be administered, route for administration, etc. When the compound is orally administered, the compound is administered to a patient with inflammation (as 60 kg) generally in a daily dose of approximately 0.1 to 100 mg, preferably approximately 1.0 mg to 50 mg, more preferably approximately 1.0 to 20 mg. When the compound is parenterally administered, a single dose of the compound may vary depending on subject to be administered, target disease, etc. When the compound is administered in the form of an injection to a patient with inflammation (as 60 kg), it is convenient to administer the compound by intravenous injection generally in a daily dose of approximately 0.01 to 30 mg, preferably approximately 0.1 to 20 mg, more preferably approximately 0.1 to 10 mg. For other animal species, the corresponding dose as converted per 60 kg weight can be administered.

(10b) Method of Screening a Compound that Promotes or Inhibits the Activities of a Promoter for the DNA of the Present Invention The present invention provides a method of screening a compound or its salt that promotes or inhibits the activities of a promoter for the DNA of the present invention, which comprises administering a test compound to a non-human mammal deficient in expression of the DNA of the present invention and detecting expression of the reporter gene.

In the screening method described above, the non-human mammal deficient in expression of the DNA of the present invention is selected from the aforesaid non-human mammals deficient in expression of the DNA of the present invention in which the DNA of the present invention is inactivated by introducing a reporter gene and the reporter gene can be expressed under the control of a promoter for the DNA of the present invention.

The same examples given above for the test compound, apply to the test compound.

As the reporter gene, the same specific examples given above apply to the reporter gene, with β-galactosidase (lacZ), soluble alkaline phosphatase gene, luciferase gene, etc. being preferred.

In the non-human mammal deficient in expression of the DNA of the present invention wherein the DNA of the present invention is replaced by a reporter gene, the reporter gene is present under the control of a promoter for the DNA of the present invention. Thus, the activity of the promoter can be detected by tracing the expression of a substance encoded by the reporter gene.

For example, when a part of the DNA region encoding FPRL1 of the present invention is replaced by, e.g., β-galactosidase gene (lacZ) derived from *Escherichia coli*, β-galactosidase is expressed in a tissue where FPRL1 of the present invention should originally be expressed, in place of FPRL1 of the present invention. Thus, the expression state of FPRL1 of the present invention can be readily observed in vivo in an animal, by staining with a reagent, e.g., 5-bromo-4-chloro-3-indolyl-β-galactopyranoside (X-gal), which is a substrate for β-galactosidase. Specifically, a mouse deficient in FPRL1 of the present invention, or its tissue section, is fixed with glutaraldehyde, etc. After washing with phosphate buffered saline (PBS), the system is reacted with a staining solution containing X-gal at room temperature or about 37° C. for approximately 30 minutes to 1 hour. After the β-galactosidase reaction is terminated by washing the tissue preparation with 1 mM EDTA/PBS solution, the color formed is observed. Alternatively, mRNA encoding lacZ may be detected in a conventional manner.

The compound or salts thereof obtained using the screening methods supra are compounds (or their salts) selected from the test compounds described above, which promote or inhibit the promoter activity for the DNA of the present invention.

As the salts of the compounds obtained by the screening methods, use is made of salts with physiologically acceptable acids (e.g., inorganic acids) or bases (e.g., organic acids), and physiologically acceptable acid addition salts are preferred. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The compound or its salt that promotes the promoter activity for the DNA of the present invention can promote the expression of FPRL1 of the present invention to promote the functions of FPRL1, and can thus be used as a low-toxic and safe medicament such as a prophylactic/therapeutic agent for diseases associated with dysfunction of FPRL1 of the present invention. Specifically, the compound or its salt can be used as, for example, a cell migration irritant (or a cell migration accelerator), or an anti-inflammatory agent, further a prophylactic/therapeutic agent for diseases involving asthma, allergosis, inflammation, inflammatory eye diseases, Assison's disease, autoimmune hemolytic anemia, systemic lupus erythematosus, psoriasis, rheumatism, central nervous system damage (e.g., cerebrovascular diseases such as brain hemorrhage and brain infarction, head injury, cord injury, brain edema and multiple sclerosis), neurodegenerative diseases (e.g., Alzheimer's disease, Parkinson's disease, amyotrophic lateral sclerosis (ALS) and encephalopathy associated with AIDS), cerebral meningitis, diabetes mellitus, arthritis (e.g., arthritis rheumatoides, osteoarthritis, rheumatoid spondylitis, gouty arthritis and synovial inflammation), blood poisoning (e.g., sepsis, septic shock, endotoxic shock, gram-negative sepsis and toxic-shock syndrome), inflammatory bowel diseases (e.g., Crohn's disease and ulcerative colitis), inflammatory pulmonary diseases (e.g., chronic pneumonia, pulmonary silicosis, pulmonary sarcoidosis and lung tuberculosis), cachexia (e.g., infectious cachexia, canoerous cachexia and cachexia associated with acquired immunodeficiency syndrome (AIDS)), arterial sclerosis, Creutzfeldt-Jakob disease, viral infection (e.g., viral infection by cytomegalovirus, influenza virus, herpes virus and the like), angina cordis, cardiac infarction, congestive failure, hepatitis, exaggerated immune response after medical transplantation, dialysis hypotension, diffuse intravascular coagulation syndrome, and immunodeficiency.

On the other hand, the compound or its salt that inhibits the promoter activity for the DNA of the present invention can inhibit the expression of FPRL1 of the present invention to inhibit the functions of FPRL1, and is thus useful as a cell migration depressant, further a low-toxic and safe medicament such as a prophylactic/therapeutic agent for diseases associated with over-expression of FPRL1 of the present invention (e.g., infectious disease).

In addition, the compound or its salt that inhibits the promoter activity for the DNA of the present invention can be used as an anti-inflammatory agent, further a prophylactic/therapeutic agent for asthma, allergosis, inflammation, inflammatory eye diseases, Assison's disease, autoimmune hemolytic anemia, systemic lupus erythematosus, psoriasis, rheumatism, central nervous system damage (e.g., cerebrovascular diseases such as brain hemorrhage and brain infarction, head injury, cord injury, brain edema and multiple sclerosis), neurodegenerative diseases (e.g., Alzheimer's disease, Parkinson's disease, amyotrophic lateral sclerosis (ALS) and encephalopathy associated with AIDS), cerebral meningitis, diabetes mellitus, arthritis (e.g., arthritis rheumatoides, osteoarthritis, rheumatoid spondylitis, gouty arthritis and synovial inflammation), blood poisoning (e.g., sepsis, septic shock, endotoxic shock, gram-negative sepsis and toxic-shock syndrome), inflammatory bowel diseases (e.g., Crohn's disease and ulcerative colitis), inflammatory pulmonary diseases (e.g., chronic pneumonia, pulmonary silicosis, pulmonary sarcoidosis and lung tuberculosis), cachexia (e.g., infectious cachexia, canoerous cachexia and cachexia associated with acquired immunodeficiency syndrome (AIDS)), arterial sclerosis, Creutzfeldt-Jakob disease, viral infection (e.g., viral infection by cytomegalovirus, influenza virus, herpes virus and the like), angina cordis, cardiac infarction, congestive failure, hepatitis, exaggerated immune response after medical transplantation, dialysis hypotension, diffuse intravascular coagulation syndrome, and immunodeficiency.

Further, a compound derived from the compound obtained in the above screening can also be used similarly.

The medicament comprising the compound or its salt obtained by the screening method can be produced in a manner similar to the method for preparing the medicament comprising the compound or a salt thereof changing the binding property between FPRL1 of the present invention or a salt thereof and FPRL1 ligand described hereinabove.

The thus obtained pharmaceutical preparation is safe and low toxic, and can thus be administered to, for example, human and mammals (e.g., rat, mouse, guinea pig, rabbit, sheep, swine, bovine, horse, cat, dog, monkey, etc.)

The dose of the compound or its salt may vary depending on target disease, subject to be administered, route for administration, etc. When the compound promoting the promoter activity for the DNA of the present invention is orally administered, the compound is administered to a patient with inflammation (as 60 kg) generally in a daily dose of approximately 0.1 to 100 mg, preferably approximately 1.0 mg to 50 mg, more preferably approximately 1.0 to 20 mg. When the compound is parenterally administered, a single dose of the compound may vary depending on subject to be administered, target disease, etc. When the compound (or its salt) promoting the promoter activity for the DNA of the present invention is administered in the form of an injection to a patient with inflammation (as 60 kg), it is convenient to administer the compound or its salt by intravenous injection in a daily dose of approximately 0.01 to 30 mg, preferably approximately 0.1 to 20 mg, more preferably approximately 0.1 to 10 mg. For other animal species, the corresponding doses as converted per 60 kg weight can be administered.

Thus, the non-human mammal deficient in expression of the DNA of the present invention is extremely useful in screening a compound or its salt that promotes or inhibits the activity of a promoter for the DNA of the present invention, and can contribute significantly to elucidation of causes for various diseases attributable to deficient expression of the DNA of the present invention or development of a prophylactic/therapeutic agent for the diseases.

Further, genes encoding various proteins are ligated downstream from DNA containing a promoter region for FPRL1 of the present invention and injected into a fertilized egg of an animal to create a transgenic animal by which FPRL1 of the present invention can be specifically synthesized and examined for its action in the living body. When a suitable reporter gene is ligated to the promoter region to establish a cell strain expressing the same, the cell strain can be used as a system of searching for a low-molecular-weight compound having an action of specifically promoting or suppressing the ability of the cell strain to produce FPRL1 of the present invention in vivo.

In the specification and drawings, the codes of bases and amino acids are denoted in accordance with the IUPAC-IUB Commission on Biochemical Nomenclature or by the common codes in the art, examples of which are shown below. For amino acids that may have the optical isomer, L form is presented unless otherwise indicated.

DNA: deoxyribonucleic acid
cDNA: complementary deoxyribonucleic acid
A: adenine
T: thymine
G: guanine
C: cytosine
RNA: ribonucleic acid
mRNA: messenger ribonucleic acid
dATP: deoxyadenosine triphosphate
dTTP: deoxythymidine triphosphate
dGTP: deoxyguanosine triphosphate
dCTP: deoxycytidine triphosphate
ATP: adenosine triphosphate
EDTA: ethylenediaminetetraacetic acid
SDS: sodium dodecyl sulfate
Gly: glycine
Ala: alanine
Val: valine
Leu: leucine
Ile: isoleucine
Ser: serine
Thr: threonine
Cys: cysteine
Met: methionine
Glu: glutamic acid
Asp: aspartic acid
Lys: lysine
Arg: arginine
His: histidine
Phe: phenylalanine
Tyr: tyrosine
Trp: tryptophan
Pro: proline
Asn: asparagine
Gln: glutamine
pGlu: pyroglutamic acid
*: corresponding stop codon
Me: methyl group
Et: ethyl group
Bu: butyl group
Ph: phenyl group
TC: thiazolidine-4(R)-carboxamide group The substituents, protective groups and reagents, which are frequently used throughout the specification, are shown by the following abbreviations.

Tos: p-toluenesulfonyl
CHO: formyl
Bzl: benzyl
Cl$_2$Bl: 2,6-dichlorobenzyl
Bom: benzyloxymethyl
z: benzyloxycarbonyl
Cl—Z: 2-chlorobenzyloxycarbonyl
Br—Z: 2-bromobenzyloxycarbonyl
Boc: t-butoxycarbonyl
DNP: dinitrophenol
Trt: trityl
Bum: t-butoxymethyl
Fmoc: N-9-fluorenylmethoxycarbonyl
HOBt: 1-hydroxybenztriazole
HOOBt: 3,4-dihydro-3-hydroxy-4-oxo-1,2,3-benzotriazine
HONB: 1-hydroxy-5-norbornene-2,3-dicarboximide
DCC: N,N'-dicyclohexylcarbodiimide The sequence identification numbers in the sequence listing of the specification indicates the following sequence, respectively.

[SEQ ID NO: 1]
This shows the amino acid sequence of porcine FPRL1 ligand (P3).

[SEQ ID NO: 2]
This shows the amino acid sequence of human-derived FPRL1.

[SEQ ID NO: 3]
This shows the base sequence of cDNA encoding human-derived FPRL1.

[SEQ ID NO: 4]
This shows the amino acid sequence of rat-derived FPRL1.

[SEQ ID NO: 5]
This shows the base sequence of cDNA encoding rat-derived FPRL1.

[SEQ ID NO: 6]
This shows the amino acid sequence of mouse-derived FPRL2.

[SEQ ID NO: 7]
This shows the base sequence of cDNA encoding mouse-derived FPRL2.

[SEQ ID NO: 8]
This shows the base sequence of primer 1 used in Example 5.

[SEQ ID NO: 9]
This shows the base sequence of primer 2 used in Example 5.

[SEQ ID NO: 10]
This shows the base sequence of primer 3 used in Example 5.

[SEQ ID NO: 11]
This shows the base sequence of primer 4 used in Example 5.

[SEQ ID NO: 12]
This shows the base sequence of primer 5 used in Example 5.

[SEQ ID NO: 13]
This shows the base sequence of primer 6 used in Example 5.

[SEQ ID NO: 14]
This shows the base sequence of primer 7 used in Example 5.

[SEQ ID NO: 15]
This shows the base sequence of primer 8 used in Example 5.

[SEQ ID NO: 16]
This shows the amino acid sequence of human FPRL1 ligand (P3) of the present invention.

[SEQ ID NO: 17]
This shows the amino acid sequence of porcine FPRL1 ligand (P1) A of the present invention.

[SEQ ID NO: 18]
This shows the amino acid sequence of porcine FPRL1 ligand (P1) B of the present invention.

[SEQ ID NO: 19]
This shows the amino acid sequence of human FPRL1 ligand (P1) A of the present invention.

[SEQ ID NO: 20]

This shows the amino acid sequence of human FPRL1 ligand (P1) B of the present invention.
[SEQ ID NO:21]
This shows the amino acid sequence of porcine FPRL1 ligand (P4) of the present invention.
[SEQ ID NO: 22]
This shows the amino acid sequence of human FPRL1 ligand (P4) of the present invention.
[SEQ ID NO: 23]
This shows the amino acid sequence of porcine FPRL1 ligand (P2) of the present invention.
[SEQ ID NO: 24]
This shows the amino acid sequence of human FPRL1 ligand (P2) of the present invention.

The transformant *Escherichia coli* JM109/pUC18-rF-PRL1 obtained in Example 5 described below was on deposit with International Patent Organisms Depository, National Institute of Advanced Industrial Science and Technology, located at Central 6, 1-1-1 Higashi, Tsukuba, Ibaraki, 305-8566, Japan, as the Accession Number FERM BP-8274 on Jan. 10, 2003.

EXAMPLES

Hereinafter, the present invention is described in more detail by reference to the Reference Examples and the Examples, which however are not intended to limit the scope of the present invention. The gene manipulation procedures using *Escherichia coli* were performed according to the methods described in the Molecular Cloning.

Example 1

Reduction of a Level of Intracellular cAMP, Which Has Been Increased by Addition of Forskolin, by Fraction of Porcine Stomach Extract in human FPRL1-GFP Expressing CHO Cells Human FPRL1-GFP expressing CHO cells were washed with assay medium (HBSS (GibcoBRL) supplemented with 0.1% bovine serum albumin and 0.2 mM IBMX). Then the cells were incubated at 37° C. for 30 minutes under 5% $CO_2$. Each concentration of fraction of porcine stomach (0.05 g/well and 0.5 g/well) diluted with assay medium was added to the cells, followed by addition of forskolin to be 1 µM. The mixture was incubated at 37° C. for 30 minutes under 5% $CO_2$. After discarding culture supernatant, in accordance with the protocol of cAMP screen kit (Applied Biosystems), a level of intracellular cAMP was measured using plate reader (ARVO sx multilabel counter, Wallac).

Figure 1:
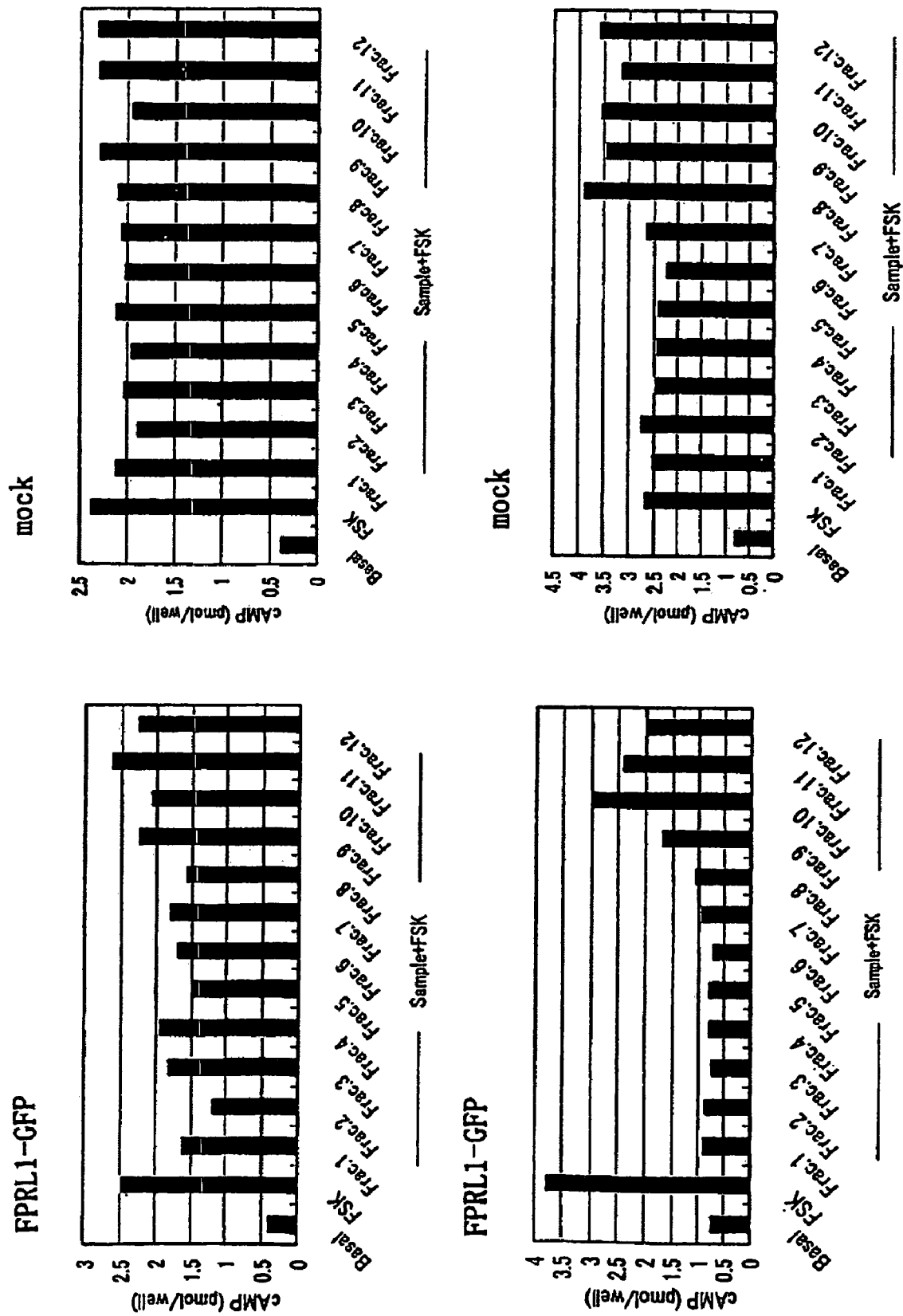
FIG. 1 shows a result obtained by measuring a level of intracellular cAMP compared to the state not stimulated with forskolin (Basal) after incubation of swine-derived extract fraction 1-12 (Frac. 1-12), which is represented in the figure, together with 1 μM forskolin (FSK). Upper shows a result in the case where the extract equivalent to 0.05 g/well was added, and lower shows a result in the case where the extract equivalent to 0.5 g/well was added. Right column (mock) shows a result in the case where mock cells expressing no human FPRL1-GFP were used, and left column shows CHO cells expressing human FPRL1-GFP (FPRL1-GFP) were used. Vertical axis represents a concentration of intracellular cAMP (pmol/well).

As a result, when it is compared to CHO cells (mock), in which a vector was solely introduced, dose dependent- and specific- reduction of a level of intracellular cAMP, which had been increased by addition of forskolin, by fraction of porcine stomach extract (0.05 g/well and 0.5 g/well) was specifically detected for CHO cells, in which FPRL1-GFP gene was introduced (FIG. 1).

Example 2

Purification of Intrinsic FPRL1 Ligand P3 From Porcine Stomach

Human FPRL1-GFP expressing CHO cell-specific inhibiting activity for intracellular cAMP production, which is found in Example 1, was purified from crude peptide fraction of porcine stomach.

Figure 2:
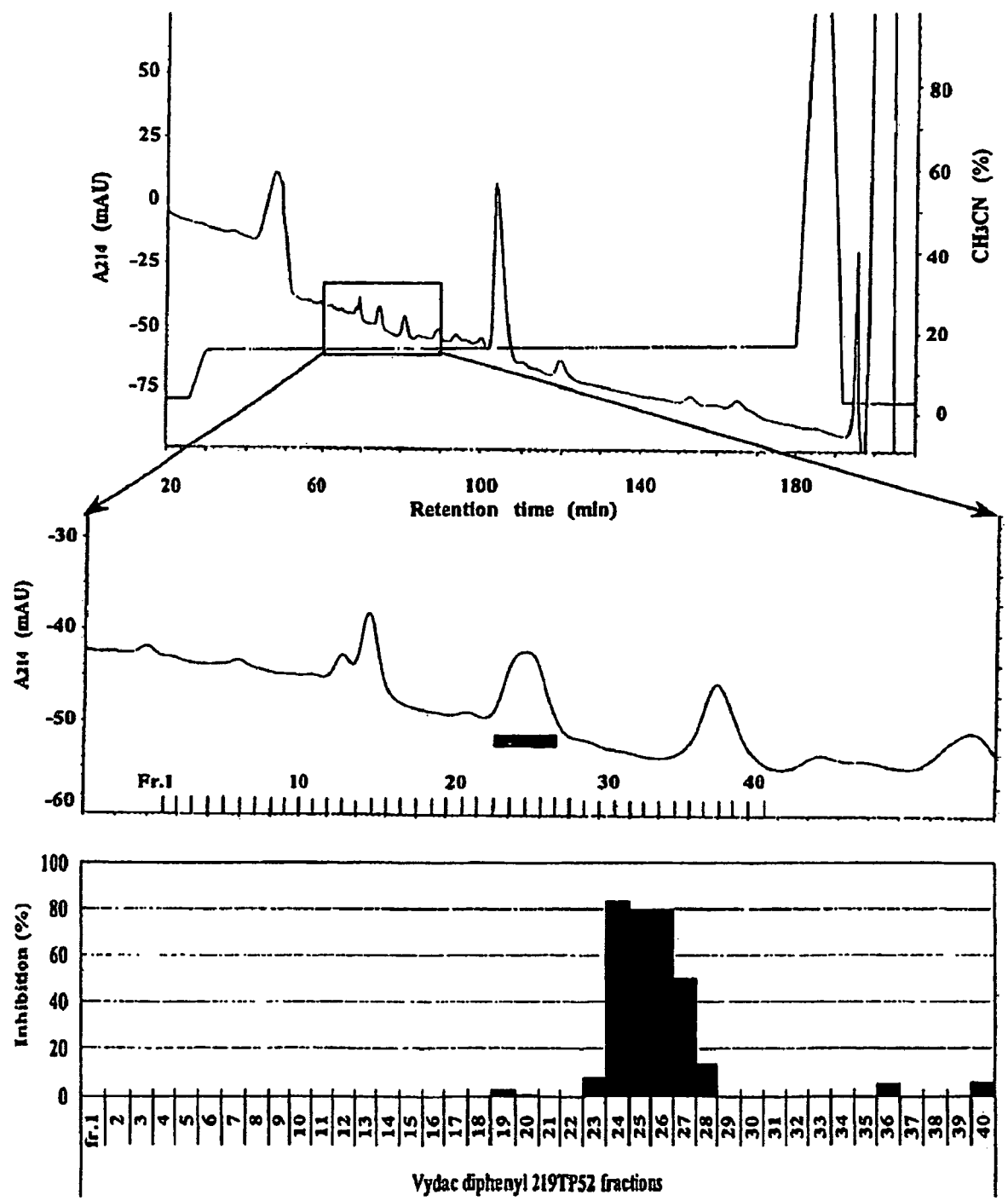
FIG. 2 shows a result for final purification step of intrinsic FPRL1 ligand from porcine stomach by reverse column diphenyl 219TP52 (Vydac). Upper shows a pattern of chromatogram. Solid line in the figure represents absorbance at 214 nm (A214 (mAU)) and a concentration of acetonitrile in eluate ($CH_2CN$ (%)). Middle shows an enlarged view of a portion wherein the eluate having an activity was fractionated in upper column. Absorbance at 214 nm (A214 (mAU)) and fractions (Fr.) are represented. In addition, a peak corresponding to activity is marked. Lower shows a human FPRL1-GFP expressing CHO cells-specific inhibitory activity for intracellular cAMP production (Inhibition (%)) in each fraction fractionated in middle column (Vydac diphenyl 219TP52 fraction 1-40).

Firstly, 4 kg of porcine stomach was boiled in 8 L of milliQ water and after addition of acetic acid to be 1 M, homogenized by Polytoron. After stirring for overnight, a supernatant was obtained by centrifugation. Trifluoroacetic acid (TFA) was added to the supernatant to be 0.05%, and the supernatant was applied to C18 column (Prep C18 125A; Waters). Peptide bound to the column was eluted by stepwise method of 30% and 50% acetonitrile containing 0.5% TFA. Fraction at 30% acetonitrile was diluted with two volume of 20 mM ammonium acetate (pH4.7) and was applied to ion-exchange column HiPrep CM-Sepharose FF (Pharmacia). Peptide bound to ion-exchange column was eluted with a gradient of 0-1.0 M NaCl in 20 mM ammonium acetate (pH4.7) containing 10% acetonitrile. To the fractions at 0.1-0.2 M NaCl, in which most of human FPRL1-GFP expressing CHO cell-specific inhibiting activity for intracellular cAMP production was contained, three volume of cold acetone was added. After discarding precipitates by centrifugation, a supernatant was concentrated by evaporation. To the concentrated supernatant, TFA was added to be 0.1%. Subsequently, further isolation was carried out with reverse phase HPLC column SOURCE 15RPC 20 ml (Pharmacia). Isolation using RESOURCE RPC was done with a gradient of 10% to 30% acetonitrile. Human FPRL1-GFP expressing CHO cell-specific inhibiting activity for intracellular cAMP production was eluted with multiple peaks. Among them, fraction at 26% acetonitrile was isolated using YMC-Pack Pro C18 column. Isolation using YMC-Pack Pro C18 column was performed with a gradient of 22% to 26% acetonitrile. Active fraction was eluted at the concentration of 24% acetonitrile. Further, this active fraction was applied to cation-exchange column TSK gel CM-SW (TOSO) and eluted with a gradient of 0 to 0.5 M NaCl in 20 mM ammonium acetate (pH4.7) containing 10% acetonitrile. Major activity was eluted at the concentration of 0.2 M NaCl. To the active fraction of CM-2SW column, TFA was added to be 0.1%. Final purification with reverse phase column diphenyl 219TP52 (Vydac) was done using a gradient of 20% to 22% acetonitrile. As a result, single peak coincident with human FPRL1-GFP expressing CHO cell-specific inhibiting activity for intracellular cAMP production was obtained (FIG. 2).

Example 3

Mass Spectrometry for Porcine Intrinsic FPRL1 Ligand P3

Figure 3:
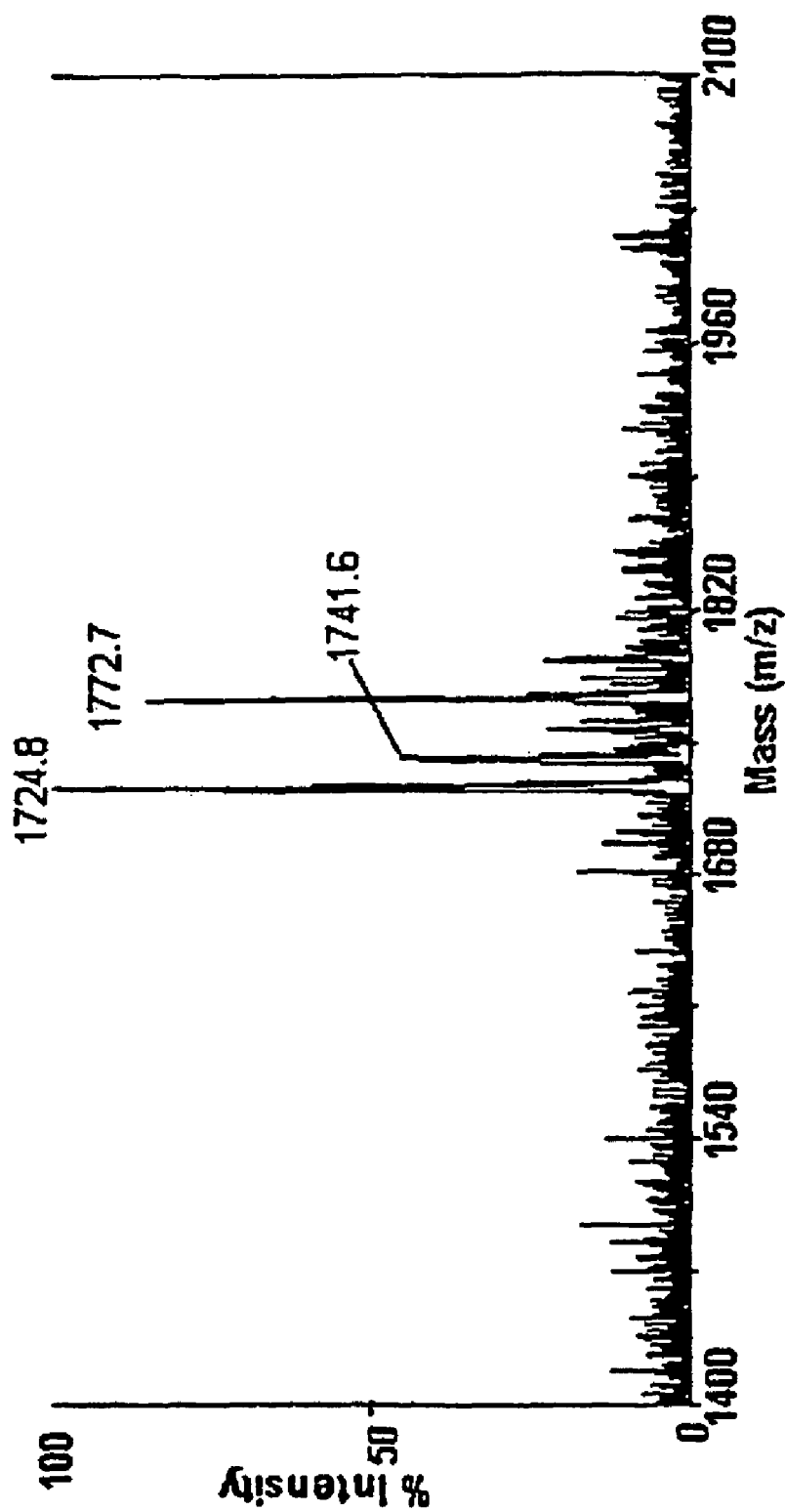
FIG. 3 shows a mass spectrum of porcine intrinsic FPRL1 ligand P3 by matrix assisted laser desorption ionization time-of-flight mass spectrometer. Horizontal axis (Mass) and vertical axis (% Intensity) represent mass/electric charge (m/z) and relative intensity in the case where the highest signal is referred to as 100%, respectively. In the figure, numeric value labeled with signal indicates a value of m/z for molecular-associated ion ($M+H^+$) of each signal.

When porcine intrinsic FPRL1 ligand P3 fraction purified in Example 2 was analyzed by matrix assisted laser desorbtion ionization time of flight mass spectrometry using Voyager-DE PRO (ABI) (FIG. 3), m/z 1724.8, 1741.6, 1772.7 was obtained.

Figure 4:
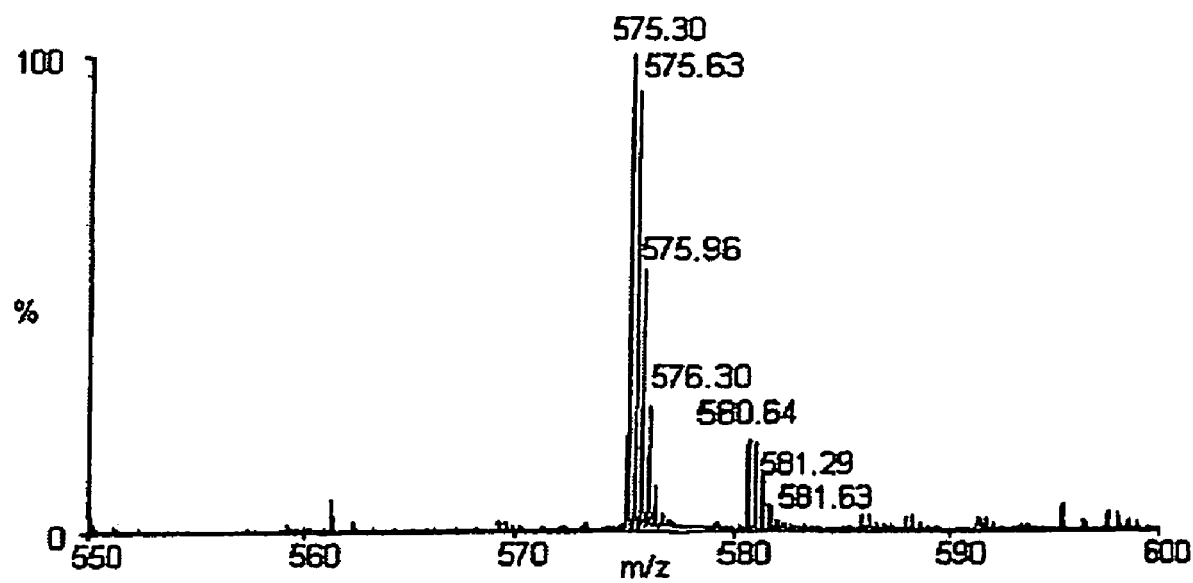
FIG. 4 shows a mass spectrum of porcine intrinsic FPRL1 ligand P3 by electrospray ionization mass spectrometer in which a mixture of polyvalent ions, trivalent ion m/z 575.30, 580.64 is shown. Horizontal axis and vertical axis represent mass/electric charge (m/z) and relative intensity in the case where the highest signal is referred to as 100%, respectively. In the figure, each of the numeric values associated with the labeled peaks indicates a value of m/z.

Then FPRL1 ligand P3 fraction was examined by electrospray ionization mass spectrometry using Q-Tof Ultima API (Micromass) and analyzed by analysis software MassLynx attached to the above equipment. In raw data (FIG. 4), which shows a mixture of polyvalent ion, trivalent ion m/z 575.30, 580.64 was mainly appeared. When these values were converted to monovalent ion by treatment of "MaxEnt 3", one of MassLynx functions (data not shown), m/z 1723.88 and m/z 1739.89 were obtained. From these results, it was considered that molecular-associated ion $(M+H^+)$ of FPRL1 ligand is m/z 1723.88, and m/z 1739.89 is an oxidant of m/z 1723.88.

Figure 5:
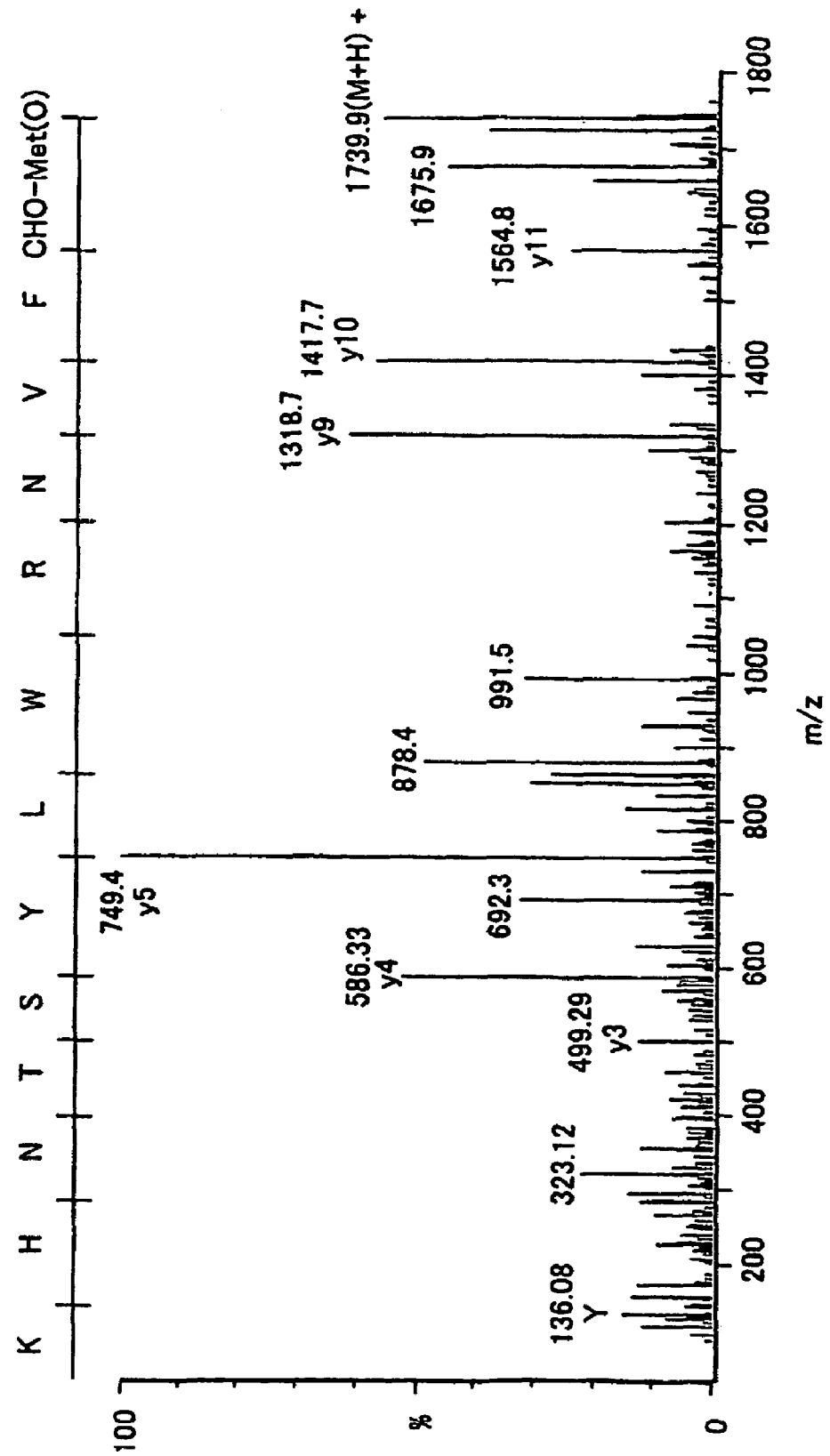
FIG. 5 shows a conversion to monovalence of MS/MS spectrum wherein m/z is 580.6 as parent ion by using MaxEnt 3, analysis software attached with mass spectrometer. Horizontal axis and vertical axis represent mass/electric charge (m/z) and relative intensity in the case where the highest signal is referred to as 100%, respectively. In the figure, numeric value labeled with signal indicates a value of m/z.

Next, using Q-Tof Ultima API, MS/MS measurement was performed. When it was measured using m/z 575.3, 580.6 as a parent ion, in both spectrums, many fragment ion was appeared in common. Due to ease of analysis, the spectrum measured using trivalent ion m/z 580.6 of oxidant as a parent ion was treated with MaxEnt 3 (FIG. 5). From the result, a sequence analysis was carried out. Based on the result, a search of database was done. Subsequently, it was deduced that the sequence of the substance is 13 residues at the N-terminus of N-formylated porcine cytochrome c oxidase. The sequence is as follows: CHO-Met(O)-Phe-Val-Asn-Arg-Trp-Leu-Tyr-Ser-Thr-Asn-His-Lys. It is estimated that in non-oxidant, Met at first position of the deduced structure is not oxidized.

Example 4

Analysis for Internal Sequence of Porcine Intrinsic FPRL1 Ligand P3

To confirm the structure of porcine intrinsic FPRL1 ligand P3 deduced in Example 3, after tryptic digestion, a sequence of the N-terminus was analyzed (FIG. 6). As a result, a sequence of peptide fragment, which is produced by cleaving $Arg^5$ from deduced structure at the C-terminus, was confirmed.

Reference Example 1

Cloning of cDNA Encoding Mouse Spleen-Derived FPRL2 and Construction of an Expression Vector Using mouse spleen-derived cDNA (Marathon-Ready™ cDNA, Clontech) as a template and two primers designed on the basis of the sequence information of mouse FPRL2 (Accession #071180, NCBI), namely, primer 1 (SEQ ID NO: 8) and primer 2 (SEQ ID NO: 9), PCR was carried out. Using Pyrobest DNA polymerase (Takara Shuzo CO., LTD), the PCR reaction was carried out by (1) reaction at 98° C. for 1 minute, (2) 35 cycles each consisting of reaction at 98° C. for 10 seconds, at 55° C. for 30 seconds and at 72° C. for 60 seconds, and (3) extension reaction at 72° C. for 2 minutes. After the reaction, the amplified product was cleaved with restriction enzymes Sal I and Xba I and then inserted into plasmid vector pAKKO-111H to construct an expression vector. As a result of analysis of the nucleotide sequence thereof, a cDNA sequence (SEQ ID NO: 7) encoding mouse FPRL2 consisting of the amino acid sequence represented by SEQ ID NO: 6 was obtained.

Example 5

Cloning of cDNA Encoding Rat Spleen-Derived FPRL1, Determination of its Base Sequence, and Construction of an Expression Vector From rat spleen mRNA, cDNA was synthesized by using Marathon™ cDNA Amplification Kit (Clontech), and an adapter was added to the terminal thereof. Using this cDNA as a template and two primers, namely, primer 3 (SEQ ID NO: 10) and primer 4 (SEQ ID NO: 11), PCR was carried out. Using Advantage 2 Polymerase mix (Clontech), the PCR reaction was carried out by (1) reaction at 96° C. for 1 minute, (2) 5 cycles each consisting of reaction at 96° C. for 10 seconds and at 72° C. for 2 minutes, (3) 5 cycles each consisting of reaction at 96° C. for 10 seconds and at 70° C. for 2 minutes, (4) 25 cycles each consisting of reaction at 96° C. for 10 seconds and at 68° C. for 2 minutes, and (5) extension reaction at 72° C. for 5 minutes. After the reaction, the amplified product was inserted into plasmid vector pCR2.1TOPO (Invitrogen, Inc.) according to a protocol of TOPO TA Cloning Kit (Invitrogen, Inc.), and the resulting vector was cloned into *Escherichia coli* JM109 (Takara Shuzo CO., LTD). As a result of analysis for sequence of each clone, a cDNA sequence encoding a part of the novel G protein-coupled receptor protein was obtained. On the basis of this sequence information, two primers, namely, primer 5 (SEQ ID NO: 12) and primer 6 (SEQ ID NO: 13) were designed. Using the primers and the above cDNA as a template synthesized from rat spleen mRNA, 5'-RACE and 3'-RACE were carried out respectively according to a protocol of Marathon™ cDNA Amplification Kit (Clontech). The PCR was carried out in the same manner as above, and after the reaction, the amplified product was inserted into plasmid vector pCR2.1TOPO (Invitrogen, Inc.) according to a protocol of TOPO TA Cloning Kit (Invitrogen, Inc.), and the resulting vector was cloned into *Escherichia coli* JM109 (Takara Shuzo CO., LTD). As a result of analysis for sequence of each clone, a cDNA sequence encoding a part of the novel G protein-coupled receptor protein was obtained. On the basis of this sequence information, two primers, namely, primer 7 (SEQ ID NO: 14) and primer 8 (SEQ ID NO: 15) were designed. Using the primers and the above cDNA as a template synthesized from rat spleen mRNA, PCR was carried out. Using Pyrobest DNA Polymerase (Takara Shuzo Co., Ltd.), the PCR reaction was carried out by (1) reaction at 96° C. for 1 minute, (2) 35 cycles each consisting of reaction at 98° C. for 10 seconds, at 55° C. for 30 seconds and at 72° C. for 60 seconds, and (3) extension reaction at 72° C. for 2 minutes. After the reaction, the amplified product was cleaved with restriction enzymes Sal I and Xba I and then inserted into plasmid vector pAKKO-111H to construct an expression vector. The inserted fragment was cut off by cleaving the expression vector with restriction enzymes Sal I and Nhe I and then inserted into plasmid vector pUC119. As a result of analysis for its nucleotide sequence, a cDNA sequence encoding the novel rat G protein-coupled receptor protein consisting of the amino acid sequence represented by SEQ ID NO: 4 was obtained (SEQ ID NO: 5). The novel protein comprising the amino acid sequence (SEQ ID NO: 4) derived from the cDNA was designated rat FPRL1. The transformant harboring this plasmid was designated *Escherichia coli* JM109/pUC119-rFPRL1.

Example 6

Preparation of a Plasmid Harboring cDNA Encoding Rat Spleen-Derived FPRL1

The expression vector obtained in Example 5 was cleaved with restriction enzymes Sal I and Nhe I to cut off the inserted fragment which was then inserted into plasmid vector pUC18. As a result of analysis for its base sequence, it could be confirmed that this sequence, similar to the cDNA sequence in Example 5, is a cDNA sequence (SEQ ID NO: 5) encoding the novel rat G protein-coupled receptor protein consisting of the amino acid sequence represented by SEQ ID NO: 4. A transformant harboring this plasmid was designated *Escherichia coli* JM109/pUC18-rFPRL1.

Example 7

Purification of Intrinsic FPRL1 Ligand P1 from Porcine Stomach

Human FPRL1-GFP expressing CHO cell-specific inhibiting activity for ntracellular cAMP production, which is found in Example 1, was purified from crude peptide fraction of porcine stomach.

Firstly, 12 kg of porcine stomach was boiled in 8 L of milliQ water and after addition of acetic acid to be 1 M, homogenized by Polytoron. After stirring for overnight, a supernatant was obtained by centrifugation. Trifluoroacetic acid (TFA) was added to the supernatant to be 0.05%, and the supernatant was applied to C18 column (Prep C18 125A; Waters). Peptide bound to the column was eluted by stepwise method of 30% and 50% acetonitrile containing 0.5% TFA. Fraction at 30% acetonitrile was diluted with two volume of 20 mM ammonium acetate (pH4.7) and was applied to ion-exchange column HiPrep CM-Sepharose FF (Pharmacia). Peptide bound to ion-exchange column was eluted with a gradient of 0-1.0 M NaCl in 20 mM ammonium acetate (pH4.7) containing 10% acetonitrile. To the fractions at 0.1-0.2 M NaCl, in which most of human FPRL1-GFP expressing CHO cell-specific inhibiting activity for intracellular cAMP production was contained, three volume of cold acetone was added. After discarding precipitates by centrifugation, a supernatant was concentrated by evaporation. To the concentrated supernatant, TFA was added to be 0.1%. Subsequently, further isolation was carried out with reverse phase HPLC column SOURCE 15RPC 20 ml (Pharmacia). Isolation using RESOURCE RPC was done with a gradient of 10% to 30% acetonitrile. Human FPRL1-GFP expressing CHO cell-specific inhibiting activity for intracellular cAMP production was eluted with multiple peaks. Among them, fraction at 22% acetonitrile was isolated using YMC-Pack Pro C18 column. Isolation using YMC-Pack Pro C18 column was performed with a gradient of 18% to 22% acetonitrile. Active fraction was eluted at the concentration of 21% acetonitrile. Further, this active fraction was applied to cation-exchange column TSK gel CM-SW (TOSO) and eluted with a gradient of 0.05 to 0.3 M NaCl in 20 mM ammonium acetate (pH4.7) containing 10% acetonitrile. Major activity was eluted at the concentration of 0.17 M NaCl. To the active fraction of CM-2SW column, TFA was added to be 0.1%. Purification with reverse phase column diphenyl 219TP52 (Vydac) was done using a gradient of 15% to 17% acetonitrile. Finally, the active fraction eluted at 16.5% acetonitrile was purified with μRPC C2/C18 SC2.1/10 (Amersham Biosciences). As a result, single peak coincident with human FPRL1-GFP expressing CHO cell-specific inhibiting activity for intracellular cAMP production was obtained (FIG. 7).

Example 8

Mass Spectrometry for Porcine Intrinsic FPRL1 Ligand P1

When porcine intrinsic FPRL1 ligand P1 fraction purified in Example 7 was analyzed by matrix assisted laser desorbtion ionization time of flight mass spectrometry using Voyager-DE PRO (ABI) (FIG. 8), m/z 1921, 1937, 1952 was obtained.

Then FPRL1 ligand P1 fraction was examined by electrospray ionization mass spectrometry using Q-Tof Ultima API (Micromass) and analyzed by analysis software MassLynx attached to the above equipment. In raw data (FIG. 9 and FIG. 10), which shows a mixture of polyvalent ion, M+2H$^{2+}$ (m/z 960.52), M+3H$^{3+}$ (m/z 640.99) and M+4H$^{4+}$ (m/z 481.00) were appeared. When these values were converted to monovalent ion by treatment of "MaxEnt 3", m/z 1920.0 was obtained.

Next, using Q-Tof Ultima API, MS/MS measurement was performed. From the spectrum measured using M+2H$^{2+}$ and M+4H$^{4+}$ as a parent ion, which was treated with MaxEnt 3, a sequence analysis was carried out (FIG. 11 and FIG. 12).

Based on the result, a search of database was done. Subsequently, it was deduced that the sequence of the substance is a peptide at the N-terminus of N-formylated porcine cytochrome b. The sequence is CHO-Met-Thr-Asn-Ile-Arg-Lys-Ser-His-Pro-Leu-Met-Lys-Ile-Ile-Asn (SEQ ID NO: 17).

Example 9

Analysis for Internal Sequence of Porcine Intrinsic FPRL1 Ligand P1

To confirm the structure of porcine intrinsic FPRL1 ligand P1 deduced in Example 8, after treatment of cleaving N-formyl group (25% TFA, 55° C., 2 hours), a sequence of the N-terminus was analyzed (FIG. 13). As a result, a sequence of nine residues from Met$^1$ of the deduced structure, was confirmed.

Example 10

Comparison of Activity Between Intrinsic FPRL1 Ligand P1 from Porcine Stomach and Chemical Preparation Activity of porcine intrinsic FPRL1 ligand P1, which was purified in Example 7, and activity of 16 amino acid-peptide (formyl-MTNIRKSHPLMKIINN, SEQ ID NO: 18), comprising 15 amino acids at N-terminus of N-terminally formylated porcine cytochrome B, wherein the sequence was deduced from structure analysis, were compared using an inhibiting activity for intracellular cAMP production in human DPRL1-expressing CHO cells as an index (FIG. 14). As a result, it was found that both activities are equivalent.

Example 11

Purification of Intrinsic FPRL1 Ligand P4 from Porcine Stomach

Human FPRL1-GFP expressing CHO cell-specific inhibiting activity for intracellular cAMP production, which is found in Example 1, was purified from crude peptide fraction of porcine stomach.

Firstly, 8 kg of porcine stomach was boiled in 16 L of milliQ water and after addition of acetic acid to be 1 M, homogenized by Polytoron. After stirring for overnight, a supernatant was obtained by centrifugation. Trifluoroacetic acid (TFA) was added to the supernatant to be 0.05%, and the supernatant was applied to C18 column (Prep C18 125A; Waters). Peptide bound to the column was eluted by stepwise method of 10%, 30% and 50% acetonitrile containing 0.5% TFA. Fraction at 30% acetonitrile was diluted with two volume of 20 mM ammonium acetate (pH4.7) and was applied to ion-exchange column HiPrep CM-Sepharose FF (Pharmacia). Peptide bound to ion-exchange column was eluted with a gradient of 0-1.0 M NaCl in 20 mM ammonium acetate (pH4.7) containing 10% acetonitrile. To the fractions at 0.1-0.2 M NaCl, in which most of human FPRL1-GFP expressing CHO cell-specific inhibiting activity for intracellular cAMP production was contained, three volume of cold acetone was added. After discarding precipitates by centrifugation, a supernatant was concentrated by evaporation. To the concentrated supernatant, TFA was added to be 0.1%. Subsequently, further isolation was carried out with reverse phase HPLC column SOURCE 15RPC 20 ml (Pharmacia). Isolation using RESOURCE RPC was done with a gradient of 10% to 30% acetonitrile. Human FPRL1-GFP expressing CHO cell-specific inhibiting activity for intracellular cAMP production was eluted with multiple peaks. Among them, fraction at 28% acetonitrile was isolated using YMC-Pack Pro C18 column. Isolation using YMC-Pack Pro C18 column was performed with a gradient of 24% to 28% acetonitrile. Active fraction was eluted at the concentration of 26% acetonitrile. Further, this active fraction was applied to cation-exchange column TSK gel CM-SW (TOSO) and eluted with a gradient of 0.05 to 0.3 M NaCl in 20 mM ammonium acetate (pH4.7) containing 10% acetonitrile. Major activity was eluted at the concentration of 0.18 M NaCl. To the active fraction of CM-2SW column, TFA was added to be 0.1%. Final purification with reverse phase column diphenyl 219TP52 (Vydac) was done using a gradient of 20% to 22% acetonitrile. As a result, single peak coincident with human FPRL1-GFP expressing CHO cell-specific inhibiting activity for intracellular cAMP production was obtained (FIG. 15).

Example 12

Mass Spectrometry for Porcine Intrinsic FPRL1 Ligand P4

Porcine intrinsic FPRL1 ligand P4 fraction purified in Example 11 was examined by electrospray ionization mass spectrometry using Q-Tof Ultima API (Micromass) and analyzed by analysis software MassLynx attached to the above equipment. In raw data, which shows a mixture of polyvalent ion, trivalent ion was appeared (FIG. 16). Monoisotopic ion was m/z 660.2485. In addition, ions derived from oxidized molecule were appeared.

Next, using Q-Tof Ultima API, MS/MS measurement was performed. From the spectrum measured using trivalent ion 665.60 and divalent ion m/z 989.88 of oxidant as a parent ion, which was treated with MaxEnt 3, a sequence analysis was carried out (FIG. 17 and FIG. 18). As a result of the analysis, the deduced sequence coincided with a sequence of 15 amino acid residues at the N-terminus of porcine cytochrome c oxidase, which is N-formylated. The sequence is as follows: formyl Met-Phe-Val-Asn-Arg-Trp-Leu-Tyr-Ser-Thr-Asn-His-Lys-Asp-Ile-X (SEQ ID NO: 21 -X; X means an undetermined structure.)

Example 13

Analysis for Internal Sequence of Porcine Intrinsic FPRL1 Ligand P4

To confirm the structure of porcine intrinsic FPRL1 ligand P4 deduced in Example 12, after treatment for removing N-formyl group under the conditions of hydrolytic cleavage, a sequence of the N-terminus was analyzed. That is, 35 µl of FPRL1 ligand P4 fraction #40 was collected, and fraction volume was reduced with SAVANT. To the fraction, 100 µl of 25% TFA-water was added, and a reaction was performed at 55° C. for two hours. Then, after reducing the volume with SAVANT, a sequence of the N-terminus was analyzed for all samples (FIG. 19). As a result, a sequence for 13 amino acid residues following Met at first position of the deduced structure was confirmed.

Example 14

Competitive Inhibition Test for Human FPRL1

By the lactoperoxidase method, $^{125}$I-labeled porcine FPRL ligand P3 (pfCYOX-1(1-13)) and human FPRL ligand P3 (hfCYOX-1(1-13)), wherein both were synthesized in Peptide Institute, Inc., were prepared. To 20 µl of 0.1 mM peptide solution, 20 µl of 10 µg/ml lactoperoxidase (Sigma) dissolved in 0.1 M HEPES-NaOH/pH7.0, 20 µl of Iodine-125 (Amersham, IMS-30, 74 MBq) and 20 µl of 6000-fold diluted 30% hydrogen peroxide solution (Wako Pure Chemicals) were added. After mixing with Vortexmixer, the mixture was incubated at room temperature for 10 minutes. By adding 600 µl of distilled water containing 0.1% TFA, the reaction was terminated. Then, by reverse phase HPLC using TSKgel ODS-80TM CTR 4.6×100 mm column, a peak of labeled form, which was produced by the reaction, was fractionated. The fraction was mixed with an equal volume of assay buffer (50 mM Tris-HCl/pH7.5, 5 mM EDTA, 0.5 mM PMSF, 20 µg/ml leupeptine, 0.1 µg/ml pepstatin A, 4 µg/ml E-64 (Peptide Institute), and 0.1% bovine serum albumin) and stored at −30° C. until use.

Human FPRL1-expressing CHO cells (No. 8) were cultivated, collected using PBS containing 5 mM EDTA from culture vessel, and suspended in assay buffer containing no bovine serum albumin, which is described above. Homogenization using Polytron homogenizer (Kinematica) at 18,000 rpm for 40 seconds was performed three times. After centrifugation (1000×g, 4° C., 10 minutes), supernatant was recovered. To precipitation, the same operation was repeated and supernatant was recovered again. Then, by the centrifugation (100,000×g, 4° C., 1 hour), precipitation (membrane fraction) was recovered. The membrane fraction was re-suspended in a small amount of buffer, homogenized using Tefron homogenizer, and stored at −80° C. until use.

Competitive inhibition test was carried out under the following conditions. In 96-well polypropyrene plate, 200 µl of solution containing 0.25 µg of the membrane fraction, 25 pM (final concentration) $^{125}$I-labeled compound, a test sample and assay buffer were prepared and incubated at room temperature for 1 hour. For determining a level of non-specific binding, 1 µM non-labeled compound instead of a test sample in the well was used for assay. After completion of incubation, The membrane fraction was isolated using cell harvester corresponding to 96-well (Packard) and filter unit (GF/C, Packard) treated with polyethyleneimine (Wako Pure Chemicals), and trapped on the filter. After completely drying the filter, Microcinti 0 (Packard) was added to the filter, and a level of labeled form co-trapped with the membrane fraction on the filter was measured using Topcount (Pakard). Non-specific binding level was subtracted from each measured value. Then the ratio of reduced binding level by addition of test sample to the well with notest sample (total binding level), that is, the inhibition rate was calculated. Further, from dosage of test sample-inhibition curve, $IC_{50}$ was calculated (Table 1).

TABLE 1

| Sample | IC50 (nM) |
| --- | --- |
| pfCYOX-1(1-13) | 0.15 ± 0.01 |
| hfCYOX-1(1-13) | 1.1 ± 0.01 |

Example 15

Purification of Intrinsic FPRL1 Ligand P4 from Porcine Stomach

Human FPRL1-GFP expressing CHO cell-specific inhibiting activity for intracellular cAMP production, which is found in Example 1, was purified from crude peptide fraction of porcine stomach.

Firstly, 14 kg of porcine stomach was boiled in 28 L of milliQ water and after addition of acetic acid to be 1 M, homogenized by Polytoron. After stirring for overnight, a supernatant was obtained by centrifugation. Trifluoroacetic acid (TFA) was added to the supernatant to be 0.05%, and the supernatant was applied to C18 column (Prep C18 125A; Waters). Peptide bound to the column was eluted by stepwise method of 10%, 30% and 50% acetonitrile containing 0.5% TFA. Fraction at 30% acetonitrile was diluted with two volume of 20 mM ammonium acetate (pH4.7) and was applied to ion-exchange column HiPrep CM-Sepharose FF (Pharmacia). Peptide bound to ion-exchange column was eluted with a gradient of 0-1.0 M NaCl in 20 mM ammonium acetate (pH4.7) containing 10% acetonitrile. To the fractions at 0.1-0.2 M NaCl, in which most of human FPRL1-GFP expressing CHO cell-specific inhibiting activity for intracellular cAMP production was contained, three volume of cold acetone was added. After discarding precipitates by centrifugation, a supernatant was concentrated by evaporation. To the concentrated supernatant, TFA was added to be 0.1%. Subsequently, further isolation was carried out with reverse phase HPLC column SOURCE 15RPC 20 ml (Pharmacia). Isolation using RESOURCE RPC was done with a gradient of 10% to 30% acetonitrile. Human FPRL1-GFP expressing CHO cell-specific inhibiting activity for intracellular cAMP production was eluted with multiple peaks. Among them, fraction at 25% acetonitrile was isolated using YMC-Pack Pro C18 column. Isolation using YMC-Pack Pro C18 column was performed with a gradient of 20% to 26% acetonitrile. Active fraction was eluted at the concentration of 25% acetonitrile. Further, this active fraction was applied to cation-exchange column TSK gel CM-SW (TOSO) and eluted with a gradient of 0.05 to 0.3 M NaCl in 20 mM ammonium acetate (pH4.7) containing 10% acetonitrile. Major activity was eluted at the concentration of 0.14 M NaCl. To the active fraction of CM-2SW column, TFA was added to be 0.1%. Final purification with reverse phase column diphenyl 219TP52 (Vydac) was done using a gradient of 20% to 24% acetonitrile. As a result, 120 pmol of single peak coincident with human FPRL1-GFP expressing CHO cell-specific inhibiting activity for intracellular cAMP production was obtained (FIG. 20).

Example 16

Mass Spectrometry for Porcine Intrinsic FPRL1 Ligand P2

Porcine intrinsic FPRL1 ligand P2 fraction purified in Example 15 was examined by electrospray ionization mass spectrometry using Q-Tof Ultima API (Micromass) and analyzed by analysis software MassLynx attached to the above equipment. FIG. 21 shows $M+3H^{3+}$ (value for monoisotopic peak: m/z 719.38). Then, MS/MS was measured with the same equipment. The spectrum measured using $M+2H^{2+}$ as a parent ion was treated with MaxEnt 3. From the result, a sequence analysis was carried out (FIG. 22, -PLMKLLNNAF: The symbol "-" means an undetermined amino acid. Mass number of L and I is the same.) Based on the result, a search of database was done. Subsequently, it was deduced that the sequence of the substance is peptides at the N-terminus of N-formylated porcine cytochrome b. Considering a result of mass spectorum and the amino acid sequence of cytochrome b, it is presumed that the sequence of the preparation is as follows:

CHO-Met-Thr-Asn-Ile-Arg-Lys-Ser-His-Pro-Leu-Met-Lys-Ile-Ile-Asn-Asn-Ala-Phe.    (SEQ ID NO: 23)

Calculated value for $M+3H^{3+}$ monoisotopic peak of the deduced structure is m/z 719.39, which is well coincided with measured value (m/z 719.38).

Example 17

Analysis for Internal Sequence of Porcine Intrinsic FPRL1 Ligand P2

To confirm the structure of porcine intrinsic FPRL1 ligand P2 deduced in Example 16, after treatment of cleaving N-formyl group (25% TFA, 55° C., 2 hours), a sequence of the N-terminus was analyzed as follows:
FPRL1 ligand P2 HPLC fraction
↓SAVANT
↓+100 µl of 25% TFA-DW
↓55° C., 2 hours
↓The volume was reduced with SAVANT.
Analysis for the N-terminal Sequence (ABI 491 cLC)
As a result, a sequence of 13 residues following Met at first position of the deduced structure.

Example 18

Intracellular Transition of FPRL1-GFP Fusion Protein, which is Expressed in CHO Cells, by Addition of Formylated Peptide (Porcine FPRL Ligand P3 (pfCYOX-1(1-13)) and Human FPRL Ligand P3 (hfCYOX-1(1-13)))

CHO cell line, in which a protein, wherein GFP (Green Fluorescent Protein) is fused to the C-terminus of human FPRL1, is stably expressed, was established using an expression plasmid for animal cells by publicly known method. For assay of intracellular transition of the protein, the cells at growth phase was seeded at the concentration of 40000 cells/well on 96-well plate (Packard, View-Plate™-96, Black), and cultured for overnight at 37° C. under 5% $CO_2$. Firstly, the cells into the well were washed with assay buffer (HBSS (GibcoBRL) supplemented with 0.1% bovine serum albumin (BSA)). Then, 100 µl of the assay buffer containing a test sample were added to the well and incubated at 37° C. under 5% $CO_2$ for one hour. Subsequently, 100 µl/well of cell fixation solution (PBS containing 4% paraformaldehyde (Ca/Mg free)) were added to the well and stood at room temperature for 30 minutes. After removing the cell fixation solution and washing the cells with Ca/Mg free PBS, a labeling solution (3.13 µg/ml of wheat germ aggulutinin (Molecular Probe, W-849) and 5 µg/ml of Hoechst-containing Ca/Mg free PBS) was added (50 µl/well) and stood at room temperature for 20 minutes. After removing the labeling solution, the cells were washed with Ca/Mg free PBS (200 µl/well) to replace the same (200 µl/well). Then the surface of the plate was sealed, and immediately analysis using Cellomics ArrayScan System (Cellomics) was carried out. Estimation for intracellular localization of FPRL1-GFP fusion protein was optimized according to GPCR Signaling assay Protocol attached to the above system, and done using MemCyto Above Threshold (cell ratio (unit %) over specific parameter (MemCyto Intensity Ratio) representing the ratio of membrane/cytoplasmic localization of the protein to all cells in the well).

As a result, when formylated peptide (porcine FPRL ligand P3 (pfCYOX-1(1-13)) and human FPRL ligand P3 (hf- CYOX-1(1-13))) was added, concentration-dependent transition of FPRL1-GFP protein from cell membrane to cytoplasm, that is, induction of internalization (decrease of value for MemCyto Above Threshold) was detected.

Example 19

Cell Migration Stimulating Activity of Formylated Peptide (Porcine FPRL Ligand P3 (pfCYOX-1(1-13)) and Human FPRL Ligand P3 (hfCYOX-1(1-13))) to FPRL1-GFP Fusion Protein-Expressing CHO Cells Using FPRL1-GFP fusion protein-expressing CHO cells, which are described in Example 18, a cell migration activity of the above cells by stimulation using formylated peptide was investigated.

The 96-well disposable chemotaxis chamber (ChemoTx-96, Neuro Probe) was used for assay. Firstly, to bottom well of the chamber, a test sample diluted with DMEM (Invitrogen) containing 0.5% BSA was added. Then, a polycarbonate filter, which is precoated with 10 µg/ml bovine fibronectin (Yagai) on both sides, was fixed on the chamber, and contacted with the test sample. Next, suspension for FPRL1-GFP fusion protein-expressing CHO cells was put onto the filter at 96-well site as a droplet. The chamber was covered, and cultured at 37° C. for 4 hours under conditions of 5% $CO_2$.

The cell suspension was prepared as follows: the aforementioned CHO cells at growth phase, which had been precultured in 150 $cm^2$ flask for culture, were peal off using trypsin/EDTA; the cell suspension obtained was centrifuged to get cell precipitation; and after washing with PBS once, the cells were resuspended in DMEM medium containing 0.5% BSA at the concentration of $3.6 \times 10^6$ cells/ml. The cells were cultivated on the chamber, and then after removing non-migrating cells present onto the filter, the cells migrated underneath the filter were fixed and stained according to the protocol of accompanying instructions using Diff-Quick (International Reagents Corporation). The filter other than the underside was sufficiently washed and air-dried. For this filter, absorbance at 595 nm was measured using microplate reader. As a result, porcine FPRL ligand P3 (pfCYOX-1(1-13)) and human FPRL ligand P3 (hfCYOX-1(1-13)) exhibited a bell-shaped dose-dependent cell migration stimulating activity (FIG. 24).

INDUSTRIAL APPLICABILITY

FPRL1 ligand of the present invention, FPRL1 of the present invention, or DNA encoding FPRL1 of the present invention can be used as, for example, an anti-inflammatory agent.

By using FPRL1 ligand and FPRL1 of the present invention, a compound that alters binding property between FPRL1 ligand and FPRL1 can efficiently be screened.

The invention claimed is:

1. A peptide consisting of the amino acid sequence of SEQ ID NO:1 or SEQ ID NO:16 or an amino acid sequence having at least 90% homology to the amino acid sequence of SEQ ID NO:1 or SEQ ID NO:16, its amide or ester, or salts thereof, wherein the peptide has a ligand activity or a signal transduction activity, and a methionine residue at the N-terminus, if any, is formylated.

2. A peptide consisting of the amino acid sequence of SEQ ID NO:21 or SEQ ID NO:22 or an amino acid sequence having at least 90% homology to the amino acid sequence of SEQ ID NO:21 or SEQ ID NO:22, its amide or ester, or salts thereof, wherein the peptide has a ligand activity or a signal transduction activity, and a methionine residue at the N-terminus, if any, is formylated.

3. A peptide consisting of the amino acid sequence of SEQ ID NO:21 or SEQ ID NO:22 or an amino acid sequence having at least 90% homology to the amino acid sequence of SEQ ID NO:21 or SEQ ID NO:22, its amide or ester, or salts thereof, wherein the peptide has a ligand activity or a signal transduction activity, and a methionine residue at the N-terminus, if any, is formylated and an isoleucine residue at the C-terminus, if any, is modified.

4. A peptide consisting of the amino acid sequence of SEQ ID NO:17, SEQ ID NO:18, SEQ ID NO:19 or SEQ ID NO:20 or an amino acid sequence having at least 90% homology to the amino acid sequence of SEQ ID NO:17, SEQ ID NO:18, or SEQ ID NO:20, its amide or ester, or salts thereof, wherein the peptide has a ligand activity or a signal transduction activity, and a methionine residue at the N-terminus, if any, is formylated.

5. A peptide consisting of the amino acid sequence of SEQ ID NO:23 or SEQ ID NO:24 or an amino acid sequence having at least 90% homology to the amino acid sequence of SEQ ID NO:23 or SEQ ID NO:24, its amide or ester, or salts thereof, wherein the peptide has a ligand activity or a signal transduction activity, and a methionine residue at the N-terminus, if any, is formylated.

6. An isolated antibody against a peptide consisting of the amino acid sequence of SEQ ID NO:1 or SEQ ID NO:21, its amide or ester, or salts thereof, wherein a methionine residue at the N terminus of the peptide is formylated or unformylated.

7. An isolated antibody against a peptide consisting of the amino acid sequence of SEQ ID NO:17 or SEQ ID NO:23, its amide or ester, or salts thereof, wherein a methionine residue at the N terminus of the peptide is formylated or unformylated.

8. An isolated antibody against a peptide consisting of the amino acid sequence of SEQ ID NO:16 or SEQ ID NO:22, its amide or ester, or salts thereof, wherein a methionine residue at the N-terminus of the peptide is formylated.

9. A method for inhibiting a cell stimulation, or a method for preventing/treating infectious disease, which comprises administrating to a mammal an effective dose of an antibody selected from the group consisting of: (i) the antibody according to claim 6, (ii) the antibody according to claim 7, and (iii) the antibody according to claim 8.

10. A peptide consisting of the amino acid sequence of SEQ ID NO:1 or SEQ ID NO:21 or an amino acid sequence having at least 90% homology to the amino acid sequence of SEQ ID NO:1 or SEQ ID NO:21, its amide or ester, or salts thereof, wherein the peptide has a ligand activity or a signal transduction activity, and a methionine residue at the N-terminus, if any, is formylated or unformylated.

11. The peptide consisting of SEQ ID NO:1 or an amino acid sequence having at least 90% homology to the amino acid sequence of SEQ ID NO:1 according to claim 10, its amide or ester, or salts thereof, wherein the peptide has a ligand activity or a signal transduction activity, and a methionine residue at the N-terminus, if any, is formylated or unformylated.

12. A method for screening a compound or a salt thereof that alters a binding property or a signal transduction between a G protein-coupled receptor protein or salts thereof, and the peptide according to claim 10, its amide or ester, or salts thereof, which comprises;

(A)
(a) contacting (1) the receptor protein comprising the amino acid sequence of SEQ ID NO:2 or an amino acid sequence having at least 90% homology to the amino acid sequence of SEQ ID NO:2, a partial peptide of the receptor protein or salts thereof wherein the peptide has a ligand activity or a signal transduction activity, with (2) (i) the peptide according to claim 10, its amide or ester, or salts thereof, or (ii) the compound or a salt thereof that alters a binding property between the receptor protein or a salt thereof, and the peptide according to claim 10, its amide or ester, or salts thereof,
and
(b) measuring a binding level of 2(i) said peptide, its amide or ester, or salts thereof, to (1) said receptor protein;

(B)
(a) contacting (1) the receptor protein comprising the amino acid sequence of SEQ ID NO:2 or an amino acid sequence having at least 90% homology to the amino acid sequence of SEQ ID NO:2, a partial peptide of the receptor protein or salts thereof, wherein the peptide has a ligand activity or a signal transduction activity and a test compound, with 2(i) the peptide according to claim 1, its amide or ester or salts thereof, or (ii) the compound or a salt thereof, that alters a binding property between the receptor protein or a salt thereof, and the peptide according to claim 10, its amide or ester, or salts thereof, to (1) said receptor protein; and (C) comparing the binding level of step (A) with the binding level of step (B).

13. A kit for screening a compound or a salt thereof that alters a binding property or a signal transduction between a G protein-coupled receptor protein or salts thereof, and the peptide according to claim 10, its amide or ester, or salts thereof, which comprises;

(A) (1) the receptor protein comprising the amino acid sequence of SEQ ID NO:2 or an amino acid sequence having at least 90% homology to the amino acid sequence of SEQ ID NO:2, a partial peptide of the receptor protein or salts thereof wherein the peptide has a ligand activity or a signal transduction activity, or (2) a cell producing the receptor protein comprising the amino acid sequence of SEQ ID NO:2 or an amino acid sequence having at least 90% homolog to the amino acid sequence of SEQ ID NO:2, a partial peptide of the receptor protein or salts thereof wherein the peptide has a ligand activity or a signal transduction activity, and (B)(1) (i) the peptide according to claim 10, its amide or ester, or salts thereof, or (ii) the compound or a salt thereof that alters a binding property between the receptor protein or a salt thereof, and the peptide according to claim 10, its amide or ester, or salts thereof or (2) (i) a labeled peptide according to claim 10, its amide or ester, or salts thereof, or (ii) the compound or a salt thereof that alters a binding property between the receptor protein or a salt thereof, and a labeled peptide according to claim 10, its amide, or ester, or salts thereof.

14. A method for screening a compound or a salt thereof that alters a binding property or a signal transduction between a G protein-coupled receptor protein or salts thereof, and the peptide according to claim 10, its amide or ester, or salts thereof, which comprises:

(A)
  (a) contacting (1) a cell producing the receptor protein comprising the amino acid sequence of SEQ ID NO:2 or an amino acid sequence having at least 90% homology to the amino acid sequence of SEQ ID NO:2, a partial peptide of the receptor protein or its salts thereof wherein the peptide has a ligand activity or a signal transduction activity, with (2)(i) the peptide according to claim 10, its amide or ester, or salts thereof, or (ii) the compound or a salt thereof that alters a binding property between the receptor protein or a salt thereof, and the peptide according to claim 10, its amide or ester, or salts thereof, and
  (b) measuring a cell stimulating activity;
(B)
  (a) contacting (1) a cell producing the receptor protein comprising the amino acid sequence of SEQ ID NO:2 or an amino acid sequence having at least a 90% homology to the amino acid sequence of SEQ ID NO:2, a partial peptide of the receptor protein or salts thereof wherein the peptide has a ligand activity or a signal transduction activity and a test compound with (2)(i) the peptide according to claim 10, its amide or ester, or salts thereof, or (ii) the compound or a salt thereof that alters a binding property between the receptor protein or a salt thereof, and the peptide according to claim 10, its amide or ester, or salts thereof, and
  (b) measuring a cell stimulating activity; and
(C) comparing the cell stimulating activity of step (A) with the cell stimulating activity of step (B).

15. A peptide consisting of the amino acid sequence of SEQ ID NO:17 or SEQ ID NO:23 or an amino acid sequence having at least 90% homology to the amino acid sequence of SEQ ID NO:17 or SEQ ID NO:23, its amide or ester, or salts thereof, wherein the peptide has a ligand activity or a signal transduction activity, and a methionine residue at the N-terminus, if any, is formylated or unformylated.

16. The peptide consisting of the amino acid sequence of SEQ ID NO:17 or an amino acid sequence having at least 90% homology to the amino acid sequence of SEQ ID NO:17 according to claim 15, its amide or ester, or salts thereof, wherein the peptide has a ligand activity or a signal transduction activity, and a methionine residue at the N-terminus, if any, is formylated or unformylated.

17. A method for screening a compound or a salt thereof that alters a binding property or a signal transduction between a G protein-coupled receptor protein or salts thereof, and the peptide according to claim 15, its amide or ester, or salts thereof, which comprises;

(A)
  (a) contacting (1) the receptor protein comprising the amino acid sequence of SEQ ID NO:2 or an amino acid sequence having at least 90% homology to the amino acid sequence of SEQ ID NO:2, a partial peptide of the receptor protein or salts thereof, wherein the peptide has a ligand activity or a signal transduction activity, with (2) (i) the peptide according to claim 15, its amide or ester, or salts thereof, or (ii) the compound or a salt thereof that alters a binding property between the receptor protein or a salt thereof, and the peptide according to claim 15, its amide or ester, or salts thereof,
  and
  (b) measuring a binding level of (2)(i) said peptide, its amide or ester, or salts thereof, to (1) said receptor protein;
(B)
  (a) contacting (1) the receptor protein comprising the amino acid sequence of SEQ ID NO:2 or an amino acid sequence having at least 90% homology to the amino acid sequence of SEQ ID NO:2, a partial peptide of the receptor protein or salts thereof, wherein the peptide has a ligand activity or a signal transduction activity and a test compound, with (2)(i) the peptide according to claim 15, its amide or ester, or salts thereof, or (ii) the compound or a salt thereof, that alters a binding property between the receptor protein or a salt thereof, and the peptide according to claim 15, its amide or ester, or salts thereof,
  and
  (b) measuring a binding level of (2) (i) said peptide, its amide or ester, or salts thereof, to (1) said protein receptor; and
(C) comparing the binding level of step (A) with the binding level of step (B).

18. A kit for screening a compound or a salt thereof that alters a binding property or a signal transduction between a G protein-coupled receptor protein or salts thereof, and the peptide according to claim 15, its amide or ester, or salts thereof, which comprises;

(A) (1) the receptor protein comprising the amino acid sequence of SEQ ID NO:2 or an amino acid sequence having at least 90% homology to the amino acid sequence of SEQ ID NO:2, a partial peptide of the receptor protein or salts thereof wherein the peptide has a ligand activity or a signal transduction activity, or (2) a cell producing the receptor protein comprising the amino acid sequence of SEQ ID NO:2 or an amino acid sequence having at least 90% homology to the amino acid sequence of SEQ ID NO:2, a partial peptide of the receptor protein or salts thereof wherein the peptide has a ligand activity or a signal transduction activity, and (B)(1) (i) the peptide according to claim 15, its amide or ester, or salts thereof, or (ii) the compound or a salt thereof that alters a binding property between the receptor protein or a salt thereof, and the peptide according to claim 15, its amide or ester, or salts thereof, or (2) (i) a labeled peptide according to claim 15, its amide or ester or salts thereof, or (ii) the compound or salt thereof that alters a binding property between the receptor protein or a salt thereof, and a labeled peptide according to claim 15, its amide or ester, or salts thereof.

19. A method for screening a compound or a salt thereof that alters a binding property or a signal transduction between a G protein-coupled receptor protein or salts thereof, and the peptide according to claim 15, its amide or ester, or salts thereof, which comprises:

(A)
  (a) contacting (1) a cell producing the receptor protein comprising the amino acid of SEQ ID NO:2 or an amino acid sequence having at least 90% homology to the amino acid sequence of SEQ ID NO:2, a partial peptide of the receptor protein or salts thereof wherein the peptide has a ligand activity or a signal transduction activity, with (2) (i) the peptide according to claim 15, its amide or ester, or salts thereof, or (ii) the compound or salt thereof that alters a binding property between the receptor protein or a salt thereof, and the peptide according to claim 15, its amide or ester, or salts thereof,
  and
  (b) measuring a cell stimulating activity;
(B)
  (a) contacting (1) a cell producing the receptor protein comprising the amino acid sequence of SEQ ID NO:2 or an amino acid sequence having at least 90% homology to the amino acid sequence of SEQ ID NO:2, a partial peptide of the receptor protein or salts thereof wherein the peptide has a ligand activity or a signal transduction activity and a test compound, with (2) (i) the peptide according to claim 15, its amide or ester, or salts thereof, or (ii) the compound or a salt thereof that alters a binding property between the receptor protein or a salt thereof, and the peptide according to claim 15, its amide or ester, or salts thereof,
  and
  (b) measuring a cell stimulating activity; and
(C) comparing the cell stimulating activity of step (A) with the cell stimulating activity of step (B).

20. A peptide consisting of the amino acid sequence of SEQ ID NO:16 or SEQ ID NO:22 or an amino acid sequence having at least 90% homology to the amino acid sequence of SEQ ID NO:16 or SEQ ID NO:22, its amide or ester, or salts thereof, wherein the peptide has a ligand activity or a signal transduction activity, and a methionine residue at the N-terminus, if any, is formylated or unformylated.

21. The peptide consisting of the amino acid sequence of SEQ ID NO:16 or SEQ ID NO:22 or an amino acid sequence having at least 90% homology to the amino acid sequence of SEQ ID NO:16 or SEQ ID NO:22 according to claim 20, its amide or ester, or salts thereof, wherein the peptide has a ligand activity or signal transduction activity, and a methionine residue at the N-terminus, if any, is formylated.

22. The peptide consisting of the amino acid sequence of SEQ ID NO:16 or SEQ ID NO:22 or an amino acid sequence having at least 90% homology to the amino acid sequence of SEQ ID NO:16 or SEQ ID NO:22 according to claim 20, its amide or ester, or salts thereof, wherein the peptide has a ligand activity or a signal transduction activity, and a methionine residue at the N-terminus, if any, is formylated and an isoleucine residue at the C-terminus, if any, is modified.

23. A method for screening a compound or a salt thereof that alters a binding property or a signal transduction between a G-protein-coupled receptor protein or salts thereof, and the peptide according to claim 20, its amide or ester, or salts thereof, which comprises:

(A)
  (a) contacting (1) the receptor protein comprising the amino acid sequence of SEQ ID NO:2 or an amino acid sequence having at least 90% homology to the amino acid sequence of SEQ ID NO:2, a partial peptide of the receptor protein or salts thereof wherein the peptide has a ligand activity or a signal transduction activity, with (2) (i) the peptide according to claim 20, its amide or salts thereof, or (ii) the compound or a salt thereof that alters a binding property between the receptor protein or a salt thereof, and the peptide according to claim 20, its amide or ester, or salts thereof,
  and
  (b) measuring a binding level of (2) (i) said peptide, its amide or ester, or salts thereof, to (1) said receptor protein;
(B)
  (a) contacting (1) the receptor protein comprising the amino acid sequence of SEQ ID NO:2 or an amino acid sequence having at least 90% homology to the amino acid sequence of SEQ ID NO:2, a partial peptide of the receptor protein or salts thereof wherein the peptide has a ligand activity or a signal transduction activity and a test compound with (2) (i) the peptide according to claim 20, its amide or ester, or salts thereof, or (ii) the compound or a salt thereof that alters a binding property between the receptor protein or a salt thereof, and the peptide according to claim 20, its amide or ester, or salts thereof,
  and
  (b) measuring a binding level of (2) (i) said peptide, its amide or ester, or salts thereof, to (1) said receptor protein; and
(C) comparing the binding level of step (A) with the binding level of step (B).

24. A method for screening a compound or a salt thereof that alters a binding property or a signal transduction between a G protein-coupled receptor protein or salts thereof, and the peptide according to claim 20, its amide or ester, or salts thereof, which comprises:

(A)
  (a) contacting (1) a cell producing the receptor protein comprising the amino acid sequence of SEQ ID NO:2 or an amino acid sequence having at least 90% homology to the amino acid sequence of SEQ ID NO:2, a partial peptide of the receptor protein or its salts thereof wherein the peptide has a ligand activity or a signal transduction activity, with (2)(i) the peptide according to claim 20, its amide or ester, or salts thereof, or (ii) the compound or a salt thereof that alters a binding property between the receptor protein or a salt thereof, and the peptide according to claim 20, its amide or ester, or salts thereof, and (b) measuring a cell stimulating activity;

(B)

(a) contacting (1) a cell producing the receptor protein comprising the amino acid sequence of SEQ ID NO:2 or an amino acid sequence having at least a 90% homology to the amino acid sequence of SEQ ID NO:2, a partial peptide of the receptor protein or salts thereof wherein the peptide has a ligand activity or a signal transduction activity and a test compound with (2)(i) the peptide according to claim 20, its amide or ester, or salts thereof, or (ii) the compound or a salt thereof that alters a binding property between the receptor protein or a salt thereof, and the peptide according to claim 20, its amide or ester, or salts thereof, and (b) measuring a cell stimulating activity; and (C) comparing the cell stimulating activity of step (A) with the cell stimulating activity of step (B).

25. A kit for screening a compound or a salt thereof that alters a binding property or a signal transduction between a G protein-coupled receptor protein or salts thereof, and the peptide according to claim 20, its amide or ester, or salts thereof, which comprises:

(A)

(1) the receptor protein comprising the amino acid sequence of SEQ ID NO:2 or an amino acid sequence having at least 90% homology to the amino acid sequence of SEQ ID NO:2, a partial peptide of the receptor protein or salts thereof wherein the peptide has a ligand activity or a signal transduction activity, or (2) a cell producing the receptor protein comprising the amino acid sequence of SEQ ID NO:2 or an amino acid sequence having at least 90% homology to the amino acid sequence of SEQ ID NO:2, a partial peptide of the receptor protein or salts thereof wherein the peptide has a ligand activity or a signal transduction activity;

(B)

(1)

(i) the peptide according to claim 20, its amide or ester, or salts thereof, or (ii) the compound or a salt thereof that alters a binding property between the receptor protein or a salt thereof, and the peptide according to claim 20, its amide or ester, or salts thereof, or (2)

(i) a labeled peptide according to claim 20, its amide or ester, or salts thereof, or (ii) the compound or a salt thereof that alters a binding property between the receptor protein or a salt thereof, and a labeled peptide according to claim 20, its amide or ester, or salts thereof.

26. The screening method according to any one of claims 12, 17, 24, 14 and 19, wherein the G protein-coupled receptor protein comprising the amino acid sequence of SEQ ID NO:2 or an amino acid sequence having at least 90% homology to the amino acid sequence of SEQ ID NO:2, is a G protein-coupled receptor protein consisting of the amino acid sequence of SEQ ID NO:2, SEQ ID NO:4 or SEQ ID NO:6.

* * * * *